(12) United States Patent
Machatha et al.

(10) Patent No.: US 12,029,735 B2
(45) Date of Patent: Jul. 9, 2024

(54) POLYMORPHIC COMPOUNDS AND USES THEREOF

(71) Applicant: Aldeyra Therapeutics, Inc., Lexington, MA (US)

(72) Inventors: Stephen Gitu Machatha, Wilmington, MA (US); Charles Montgomery, Bolton, MA (US); Steven Krausert, Medford, MA (US); Jonathan James Loughrey, Edinburgh (GB); Hannah Ruth McLachlan, Edinburgh (GB); Gregor Sneddon, Stirlingshire (GB)

(73) Assignee: Aldeyra Therapeutics, Inc., Lexington, MA (US)

(*) Notice: Subject to any disclaimer, the term of this patent is extended or adjusted under 35 U.S.C. 154(b) by 272 days.

(21) Appl. No.: 17/334,094

(22) Filed: May 28, 2021

(65) Prior Publication Data

US 2021/0393612 A1 Dec. 23, 2021

Related U.S. Application Data

(63) Continuation of application No. PCT/US2020/031138, filed on May 1, 2020.

(60) Provisional application No. 62/841,900, filed on May 2, 2019.

(51) Int. Cl.
*A61K 31/47* (2006.01)
*C07D 215/38* (2006.01)

(52) U.S. Cl.
CPC .......... *A61K 31/47* (2013.01); *C07D 215/38* (2013.01)

(58) Field of Classification Search
CPC ...... A61K 31/47; A61K 45/06; C07D 215/38; A61P 1/00; A61P 1/04; A61P 3/00; A61P 3/10; A61P 9/00; A61P 9/10; A61P 17/00; A61P 17/06; A61P 25/00; A61P 25/28; A61P 27/02; A61P 27/04; A61P 27/12; A61P 35/00; A61P 37/00; A61P 37/02; A61P 37/04; A61P 37/08
USPC ........................................................ 514/313
See application file for complete search history.

(56) References Cited

U.S. PATENT DOCUMENTS

| 2,086,186 A | 7/1937 | Messer |
| 3,912,748 A | 10/1975 | Evans et al. |
| 4,668,626 A | 5/1987 | Kobayashi et al. |
| 4,956,351 A | 9/1990 | Mesens et al. |

(Continued)

FOREIGN PATENT DOCUMENTS

| CA | 3032609 A1 | 3/2018 |
| CN | 1830964 A | 9/2006 |

(Continued)

OTHER PUBLICATIONS

Aldeyra Press Release—Aldeyra Therapeutics Schedules Conference Call and Webcast to Announce Results from Allergic Conjunctivitis Phase 2b Clinical Trial, Jun. 13, 2017 (1 page).

(Continued)

*Primary Examiner* — Taylor V Oh
(74) *Attorney, Agent, or Firm* — Dechert LLP; Andrea L. C. Reid; Joseph W. Arico

(57) ABSTRACT

The present invention relates to free-base and salt forms, and compositions thereof of small molecule therapeutics acting as a scavenger for toxic aldehydes. The present invention further relates to use of the free-base and salt forms, and compositions thereof for treating diseases, disorders, or conditions in which aldehyde toxicity is implicated in their pathogenesis.

21 Claims, 46 Drawing Sheets

(56) References Cited

U.S. PATENT DOCUMENTS

| | | |
|---|---|---|
| 5,024,998 A | 6/1991 | Bodor |
| 5,032,392 A | 7/1991 | Varma |
| 5,364,637 A | 11/1994 | De et al. |
| 5,376,645 A | 12/1994 | Stella et al. |
| 5,419,898 A | 5/1995 | Ikejiri et al. |
| 5,472,954 A | 12/1995 | Loftsson |
| 5,493,027 A | 2/1996 | Nichols et al. |
| 5,576,311 A | 11/1996 | Guy |
| 5,668,117 A | 9/1997 | Shapiro |
| 5,767,109 A | 6/1998 | Sanchez et al. |
| 5,998,488 A | 12/1999 | Shinohara et al. |
| 6,107,300 A | 8/2000 | Bakthavatchalam et al. |
| 6,191,127 B1 | 2/2001 | Holscher et al. |
| 6,358,948 B1 | 3/2002 | Zhang et al. |
| 6,444,221 B1 | 9/2002 | Shapiro |
| 6,492,520 B1 | 12/2002 | Chen |
| 6,498,154 B1 | 12/2002 | Grubb et al. |
| 6,515,010 B1 | 2/2003 | Franchini et al. |
| 6,525,056 B2 | 2/2003 | Arvanitis et al. |
| 6,569,879 B2 | 5/2003 | Liu et al. |
| 7,083,803 B2 | 8/2006 | Peyman |
| 7,297,709 B2 | 11/2007 | Dai et al. |
| 7,531,564 B2 | 5/2009 | Malamas et al. |
| 7,563,906 B2 | 7/2009 | Hagihara et al. |
| 7,842,312 B2 | 11/2010 | Burgermeister et al. |
| 7,956,189 B2 | 6/2011 | Chen et al. |
| 7,973,025 B2 | 7/2011 | Jordan et al. |
| 7,982,071 B2 | 7/2011 | Scott et al. |
| 8,158,609 B1 | 4/2012 | Marsh et al. |
| 8,435,965 B2 | 5/2013 | Tabuchi et al. |
| 8,490,764 B2 | 7/2013 | Simester |
| 8,575,221 B2 | 11/2013 | Masse et al. |
| 8,722,669 B2 | 5/2014 | Palczewski et al. |
| 8,791,154 B2 | 7/2014 | Gamache et al. |
| 8,940,721 B2 | 1/2015 | Jordan et al. |
| 8,940,764 B2 | 1/2015 | Jordan et al. |
| 9,067,963 B2 | 6/2015 | Thompson et al. |
| 9,084,730 B2 | 7/2015 | Bedos et al. |
| 9,259,427 B2 | 2/2016 | Tierney et al. |
| 9,265,759 B2 | 2/2016 | Jordan et al. |
| 9,364,430 B2 | 6/2016 | Babul |
| 9,364,471 B2 | 6/2016 | Jordan et al. |
| 9,375,408 B2 | 6/2016 | Singh |
| 9,562,039 B2 | 2/2017 | Julia Jane et al. |
| 9,604,997 B2 | 3/2017 | Jordan et al. |
| 9,650,342 B2 | 5/2017 | Jordan et al. |
| 9,663,526 B2 | 5/2017 | Fensome et al. |
| 9,687,481 B2 | 6/2017 | Brady et al. |
| 9,814,701 B2 | 11/2017 | Jordan et al. |
| 9,817,701 B2 | 11/2017 | Baptist et al. |
| 9,896,419 B2 | 2/2018 | Jordan et al. |
| 10,058,095 B2 | 8/2018 | Czarnik |
| 10,098,894 B2 | 10/2018 | Amadio et al. |
| 10,111,862 B2 | 10/2018 | Chabala et al. |
| 10,202,348 B2 | 2/2019 | Jordan et al. |
| 10,213,395 B2 | 2/2019 | Brady et al. |
| 10,414,732 B2 | 9/2019 | Buist et al. |
| 10,426,790 B2 | 10/2019 | Young et al. |
| 10,463,687 B2 | 11/2019 | Rodriguez-Boulan et al. |
| 10,543,181 B2 | 1/2020 | Brady et al. |
| 10,550,085 B2 | 2/2020 | Brady et al. |
| 10,588,874 B2 | 3/2020 | Brady et al. |
| 10,736,842 B2 | 8/2020 | Misra |
| 10,744,144 B2 | 8/2020 | Shah |
| 10,781,158 B2 | 9/2020 | Singh |
| 10,864,166 B2 | 12/2020 | Venkatesh et al. |
| 10,913,722 B2 | 2/2021 | Jordan et al. |
| 11,007,157 B2 | 5/2021 | Brady et al. |
| 11,040,039 B2 | 6/2021 | Macdonald et al. |
| 11,046,650 B2 | 6/2021 | Brady et al. |
| 11,129,823 B2 | 9/2021 | Brady et al. |
| 11,197,821 B2 | 12/2021 | Clark et al. |
| 11,312,692 B1 | 4/2022 | Machatha et al. |
| 11,459,300 B2 | 10/2022 | Brady et al. |
| 11,583,529 B2 | 2/2023 | Macdonald et al. |
| 11,701,331 B2 | 7/2023 | Brady et al. |
| 11,724,987 B2 | 8/2023 | Jordan et al. |
| 11,786,518 B2 | 10/2023 | Clark et al. |
| 11,845,722 B2 | 12/2023 | Brady et al. |
| 2004/0132636 A1 | 7/2004 | Dooley et al. |
| 2004/0198828 A1 | 10/2004 | Abelson et al. |
| 2004/0235892 A1 | 11/2004 | Dai et al. |
| 2005/0020603 A1 | 1/2005 | Dai et al. |
| 2005/0090553 A1 | 4/2005 | Shapiro |
| 2005/0130906 A1 | 6/2005 | Matier et al. |
| 2005/0197292 A1 | 9/2005 | Smithson et al. |
| 2005/0234018 A1 | 10/2005 | Lyons et al. |
| 2006/0014786 A1 | 1/2006 | Raut |
| 2006/0111318 A1 | 5/2006 | Okamoto |
| 2006/0183909 A1 | 8/2006 | Schmitt et al. |
| 2006/0189608 A1 | 8/2006 | Bingaman |
| 2006/0257488 A1 | 11/2006 | Hubbard |
| 2007/0129404 A1 | 6/2007 | Hagihara et al. |
| 2007/0135481 A1 | 6/2007 | Jordan et al. |
| 2007/0243257 A1 | 10/2007 | Bedos et al. |
| 2007/0297981 A1 | 12/2007 | Ousler et al. |
| 2008/0108818 A1 | 5/2008 | Chen et al. |
| 2008/0241256 A1 | 10/2008 | Kuhn |
| 2009/0118503 A1 | 5/2009 | Sprott et al. |
| 2009/0182009 A1 | 7/2009 | Jordan et al. |
| 2010/0160304 A1 | 6/2010 | Katayama |
| 2010/0240624 A1 | 9/2010 | Chapin et al. |
| 2010/0331315 A1 | 12/2010 | Haddach et al. |
| 2011/0071091 A1 | 3/2011 | Chowhan et al. |
| 2011/0105450 A1 | 5/2011 | Chapin et al. |
| 2011/0257271 A1 | 10/2011 | Masse et al. |
| 2011/0263645 A1 | 10/2011 | Jordan et al. |
| 2012/0108585 A1 | 5/2012 | Vu |
| 2012/0295967 A1 | 11/2012 | Gamache et al. |
| 2012/0302601 A1 | 11/2012 | Jordan et al. |
| 2013/0165419 A1 | 6/2013 | Lindstrom et al. |
| 2013/0190500 A1 | 7/2013 | Greiner et al. |
| 2014/0038918 A1 | 2/2014 | Rodriguez-Boulan et al. |
| 2014/0050797 A1 | 2/2014 | Venkatesh et al. |
| 2014/0235604 A1 | 8/2014 | Palczewski et al. |
| 2014/0235722 A1 | 8/2014 | Jordine et al. |
| 2015/0209333 A1 | 7/2015 | Jordan et al. |
| 2015/0209345 A1 | 7/2015 | Jordan et al. |
| 2015/0258120 A1 | 9/2015 | Zarnitsyn et al. |
| 2015/0335632 A1 | 11/2015 | Brady et al. |
| 2015/0344432 A1 | 12/2015 | Jordan et al. |
| 2015/0344447 A1 | 12/2015 | Chabala et al. |
| 2016/0009698 A1 | 1/2016 | Julia Jane et al. |
| 2016/0030449 A1 | 2/2016 | Persicaner et al. |
| 2016/0052930 A1 | 2/2016 | Fensome et al. |
| 2016/0136231 A1 | 5/2016 | Gadek |
| 2016/0151381 A1 | 6/2016 | Blackburn et al. |
| 2016/0168098 A1 | 6/2016 | Jordan et al. |
| 2017/0029354 A1 | 2/2017 | Singh |
| 2017/0095449 A1 | 4/2017 | Winters et al. |
| 2017/0143627 A1 | 5/2017 | Misra |
| 2017/0239196 A1 | 8/2017 | Brady et al. |
| 2017/0266220 A1 | 9/2017 | Young et al. |
| 2017/0320829 A1 | 11/2017 | Jordan et al. |
| 2017/0354655 A1 | 12/2017 | Beaupre et al. |
| 2018/0050989 A1 | 2/2018 | Machatha et al. |
| 2018/0092882 A1 | 4/2018 | Jordan et al. |
| 2018/0194733 A1 | 7/2018 | Jordan et al. |
| 2018/0235980 A1 | 8/2018 | Shah |
| 2018/0250306 A1 | 9/2018 | Brady et al. |
| 2018/0265474 A1 | 9/2018 | Buist et al. |
| 2018/0354905 A1 | 12/2018 | Brady et al. |
| 2019/0054023 A1 | 2/2019 | Seaman et al. |
| 2019/0087646 A1 | 3/2019 | Goulden et al. |
| 2019/0105322 A1 | 4/2019 | Macdonald et al. |
| 2019/0125729 A1 | 5/2019 | Chabala et al. |
| 2019/0183878 A1 | 6/2019 | Brady et al. |
| 2019/0210971 A1 | 7/2019 | Jordan et al. |
| 2019/0231715 A1 | 8/2019 | Brady et al. |
| 2019/0247334 A1 | 8/2019 | Brady et al. |
| 2020/0038392 A1 | 2/2020 | Brady et al. |
| 2020/0062712 A1 | 2/2020 | Machatha et al. |
| 2020/0121591 A1 | 4/2020 | Clark et al. |
| 2020/0199075 A1 | 6/2020 | Brady et al. |

(56) References Cited

U.S. PATENT DOCUMENTS

| | | |
|---|---|---|
| 2020/0246345 A1 | 8/2020 | Brady et al. |
| 2020/0323841 A1 | 10/2020 | Clark et al. |
| 2020/0368182 A1 | 11/2020 | Brady et al. |
| 2021/0269402 A1 | 9/2021 | Jordan et al. |
| 2021/0275469 A1 | 9/2021 | Brady et al. |
| 2021/0317385 A1 | 10/2021 | Macdonald et al. |
| 2021/0347735 A1 | 11/2021 | Brady et al. |
| 2021/0353628 A1 | 11/2021 | Macdonald et al. |
| 2021/0393527 A1 | 12/2021 | Brady et al. |
| 2021/0393612 A1 | 12/2021 | Machatha et al. |
| 2022/0017475 A1 | 1/2022 | Machatha et al. |
| 2022/0089542 A1 | 3/2022 | Machatha et al. |
| 2022/0133629 A1 | 5/2022 | Clark et al. |
| 2022/0133697 A1 | 5/2022 | Machatha et al. |
| 2022/0184057 A1 | 6/2022 | Brady et al. |
| 2022/0202745 A1 | 6/2022 | Brady et al. |
| 2022/0211691 A1 | 7/2022 | Brady et al. |
| 2022/0354857 A1 | 11/2022 | Brady et al. |
| 2023/0041335 A1 | 2/2023 | Jordan et al. |
| 2023/0131929 A1 | 4/2023 | Machatha et al. |
| 2023/0149383 A1 | 5/2023 | Brady et al. |
| 2023/0174491 A1 | 6/2023 | Brady et al. |
| 2023/0228744 A1 | 7/2023 | Brady et al. |
| 2023/0248727 A1 | 8/2023 | Macdonald et al. |
| 2023/0293527 A1 | 9/2023 | Macdonald et al. |

FOREIGN PATENT DOCUMENTS

| | | |
|---|---|---|
| CN | 1882339 A | 12/2006 |
| CN | 101048384 A | 10/2007 |
| CN | 101321742 A | 12/2008 |
| CN | 101534826 A | 9/2009 |
| CN | 101611009 A | 12/2009 |
| CN | 104884049 A | 9/2015 |
| CN | 105120866 A | 12/2015 |
| CN | 105704440 A | 6/2016 |
| CN | 108135867 A | 6/2018 |
| CN | 109640983 A | 4/2019 |
| CN | 111527530 A | 8/2020 |
| CN | 112541870 A | 3/2021 |
| CN | 112800947 A | 5/2021 |
| CN | 113168511 A | 7/2021 |
| EP | 0186367 A2 | 7/1986 |
| EP | 0245054 A1 | 11/1987 |
| EP | 0483881 A1 | 5/1992 |
| EP | 1621199 A1 | 2/2006 |
| EP | 1679308 A1 | 7/2006 |
| EP | 1888548 A1 | 2/2008 |
| EP | 2301549 A1 | 3/2011 |
| GB | 2327672 A | 2/1999 |
| JP | H04264422 A | 9/1992 |
| JP | H06239748 A | 8/1994 |
| JP | H07025758 A | 1/1995 |
| JP | H08175985 A | 7/1996 |
| JP | H09169647 A | 6/1997 |
| JP | H09285529 A | 11/1997 |
| JP | H10306022 A | 11/1998 |
| JP | 2001041757 A | 2/2001 |
| JP | 2001318350 A | 11/2001 |
| JP | 2002003364 A | 1/2002 |
| JP | 2003519698 A | 6/2003 |
| JP | 2005132834 A | 5/2005 |
| JP | 2005187407 A | 7/2005 |
| JP | 3736916 B2 | 1/2006 |
| JP | 2006008568 A | 1/2006 |
| JP | 2007532648 A | 11/2007 |
| JP | 2008542291 A | 11/2008 |
| JP | 4466875 B2 | 5/2010 |
| JP | 4748289 B2 | 8/2011 |
| JP | 2011203665 A | 10/2011 |
| JP | 2012506449 A | 3/2012 |
| JP | 5194218 B2 | 5/2013 |
| JP | 2014515355 A | 6/2014 |
| JP | 2015057437 A | 3/2015 |
| JP | 2015535293 A | 12/2015 |
| JP | 2016508994 A | 3/2016 |
| JP | 2018523700 A | 8/2018 |
| JP | 2018530524 A | 10/2018 |
| JP | 2019507756 A | 3/2019 |
| KR | 20180073554 A | 7/2018 |
| RU | 2010137842 A | 3/2012 |
| RU | 2565448 C2 | 10/2015 |
| SU | 50906 A1 | 11/1936 |
| SU | 50906 A1 | 11/1936 |
| SU | 509046 A1 | 6/1984 |
| WO | 199507274 A1 | 3/1995 |
| WO | 1996022992 A1 | 8/1996 |
| WO | 1998005645 A1 | 2/1998 |
| WO | 1999046237 A1 | 9/1999 |
| WO | 2001041757 A1 | 6/2001 |
| WO | WO0151919 A2 | 7/2001 |
| WO | 2004082622 A2 | 9/2004 |
| WO | 2004091630 A1 | 10/2004 |
| WO | 2005035506 A1 | 4/2005 |
| WO | 2005040151 A1 | 5/2005 |
| WO | WO-2005051328 A2 | 6/2005 |
| WO | 2005079774 A2 | 9/2005 |
| WO | WO-2005105067 A2 | 11/2005 |
| WO | 2006002473 A1 | 1/2006 |
| WO | WO-2006000421 A2 | 1/2006 |
| WO | WO-2006049968 A1 | 5/2006 |
| WO | 2006077821 A1 | 7/2006 |
| WO | 2006127945 A1 | 11/2006 |
| WO | 2007118276 A1 | 10/2007 |
| WO | WO-2008014602 A1 | 2/2008 |
| WO | WO2008052086 A1 | 5/2008 |
| WO | 2009045479 A1 | 4/2009 |
| WO | 2009102418 A1 | 8/2009 |
| WO | 2010048332 A2 | 4/2010 |
| WO | 2010133672 A1 | 11/2010 |
| WO | 2011008202 A1 | 1/2011 |
| WO | 2011071995 A2 | 6/2011 |
| WO | 2011078204 A1 | 6/2011 |
| WO | WO-2011072141 A1 | 6/2011 |
| WO | 2012097173 A2 | 7/2012 |
| WO | 2012105887 A1 | 8/2012 |
| WO | WO-2014100425 A1 | 6/2014 |
| WO | 2014116593 A1 | 7/2014 |
| WO | 2014116836 A2 | 7/2014 |
| WO | WO-2015002893 A1 | 1/2015 |
| WO | 2015187942 A1 | 12/2015 |
| WO | 2016085939 A2 | 6/2016 |
| WO | 2016165626 A1 | 10/2016 |
| WO | 2017035077 A1 | 3/2017 |
| WO | 2017035082 A1 | 3/2017 |
| WO | 2017147617 A1 | 8/2017 |
| WO | 2017196881 A1 | 11/2017 |
| WO | WO-2017214201 A1 | 12/2017 |
| WO | 2018039192 A1 | 3/2018 |
| WO | 2018039197 A1 | 3/2018 |
| WO | 2018067860 A1 | 4/2018 |
| WO | WO-2018064354 A1 | 4/2018 |
| WO | WO2018071619 A1 | 4/2018 |
| WO | WO2018091859 A1 | 5/2018 |
| WO | 2018170476 A1 | 9/2018 |
| WO | 2019075136 A1 | 4/2019 |
| WO | 2020018498 A1 | 1/2020 |
| WO | 2020028820 A1 | 2/2020 |
| WO | 2020033344 A1 | 2/2020 |
| WO | 2020068986 A1 | 4/2020 |
| WO | 2020072621 A1 | 4/2020 |
| WO | 2020118045 A1 | 6/2020 |
| WO | 2020198064 A1 | 10/2020 |
| WO | 2020223685 A1 | 11/2020 |
| WO | 2020223717 A1 | 11/2020 |
| WO | WO-2021051003 A1 | 3/2021 |
| WO | 2021195211 A1 | 9/2021 |
| WO | WO-2021211625 A1 | 10/2021 |
| WO | 2021231792 A1 | 11/2021 |
| WO | 2021248031 A1 | 12/2021 |

(56) References Cited

FOREIGN PATENT DOCUMENTS

| WO | WO-2022150580 A1 | 7/2022 |
|----|------------------|--------|
| WO | WO-2023278816 A1 | 1/2023 |

OTHER PUBLICATIONS

Aldeyra Press Release—Aldeyra Therapeutics Schedules Conference Call to Present Results of a Randomized, Double-Blind, Vehicle-Controlled Clinical Trial in Sjogren-Larsson Syndrome, Aug. 8, 2016 (2 pages).
Aldeyra Press Release—Aldeyra Therapeutics Schedules Webcast and Conference Call to Announce Results from Dry Eye Disease Phase 2a Clinical Trial, Sep. 11, 2017 (1 page).
Aldeyra Press Release—Aldeyra Therapeutics Selected for Podium Presentation of Phase 2a Dry Eye Disease Results at the 2018 Association for Research in Vision and Ophthalmology (ARVO) Annual Meeting, Feb. 21, 2018 (3 pages).
Aldeyra Press Release—Aldeyra Therapeutics Submits FDA IND Filing for Noninfectious Anterior Uveitis, Dec. 18, 2014 (2 pages).
Aldeyra Press Release—Aldeyra Therapeutics Submits IND Filing to FDA for Clinical Testing of NS2 in Patients With Sjogren-Larsson Syndrome, Jan. 5, 2015 (2 pages).
Aldeyra Press Release—Aldeyra Therapeutics to Host 2019 Research & Development Day, Feb. 12, 2019 (1 page).
Aldeyra Press Release—Aldeyra Therapeutics to Present at the 2016 SSADH Symposium, Mar. 24, 2016 (1 page).
Aldeyra Press Release—Aldeyra Therapeutics to Present Novel Data on a Potential Treatment for Sjogren-Larsson Syndrome at the 2015 Society for Inherited Metabolic Disorders Annual Meeting, Jan. 29, 2015 (2 pages).
Aldeyra Press Release—Aldeyra Therapeutics to Present Novel Data on a Potential Treatment for Succinic Semi-Aldehyde Dehydrogenase Deficiency at the 2015 American Society of Human Genetics (ASHG) Annual Meeting, Sep. 9, 2015 (2 pages).
Aldeyra Press Release—Aldeyra Therapeutics' Data on Lead Candidate NS2 to be Presented at Society for Investigative Dermatology 2014 Annual Meeting, May 8, 2014 (2 pages).
Aldeyra Press Release—Aldeyra Therapeutics, Inc. Announces Last Patient Dosed in Allergic Conjunctivitis Phase 2b Clinical Trial, Apr. 18, 2017 (2 pages).
Aldeyra Press Release—Aldeyra Therapeutics, Inc. Announces Last Patient Dosed in Phase II Clinical Trial of Topical Dermatologic NS2 in Patients With Sjögren-Larsson Syndrome Jun. 7, 2016 (2 pages).
Aldeyra Press Release—Aldeyra Therapeutics, Inc. Receives Orphan Drug Designation from the U.S. Food and Drug Administration for ADX-102 in Sjögren-Larsson Syndrome, Apr. 20, 2017 (2 pages).
Aldeyra Press Release—Phase II Allergic Conjunctivitis, Feb. 29, 2016 (3 pages).
Aldeyra Therapeutics Press Release, "Aldeyra Therapeutics Announces Positive Results from Dry Eye Disease Phase 2a Clinical Trial," Sep. 12, 2017, retrieved from the internet on Aug. 4, 2021 at <https://ir.aldeyra.com/static-files/28479cb4-8d0f-468b-a0d8-a28250062d63>.
Aldeyra Press Release—Positive Results From Phase II Clinical Trial in Subjects With Noninfectious Anterior Uveitis, May 9, 2016 (4 pages).
Aldini et al., "Lipoxidation-Derived Reactive Carbonyl Species as Potential Drug Targets in Preventing Protein Carbonylation and Related Cellular Dysfunction," ChemMedChem, 1(10): 1045-1058 (2006).
Aldini et al., "The carbonyl scavenger carnosine ameliorates dyslipidaemia and renal function in Zucker obese rats," The Journal of Cellular and Molecular Medicine, 15(6):1339-1354 (2011).
Amara et al., "Autoantibodies to malondialdehyde-modified epitope in connective tissue disease and vasculitides," Clinical and Experimental Immunology, 101(2):233-238 (1995).
Anonymous, "Aldeyra Therapeutics Reaches Agreement with the Food and Drug Administration for the Use of RASP as an Objective Sign for the Treatment of Dry Eye Disease," BusinessWire, Jun. 4, 2020, p. 1.
Ao et al., "Methyl-β-Cyclodextrin Impairs the Monocyte-Adhering Ability of Endothelial Cells by Down-Regulating Adhesion Molecules and Caveolae and Reorganizing the Actin Cytoskeleton," Biol Pharm Bull, 39(6):1029-1034 (2016).
Apparsundaram, S et al., "Molecular cloning of a human, hemicholinium-3-sensitive choline transporter," Biochem. Biophys. Res. Commun., 276(3):862-867 (2000).
Ardati, A. et al., "Interaction of [3H]orphanin FQ and 125I-Tyr14-orphanin FQ with the orphanin FQ receptor: kinetics and modulation by cations and guanine nucleotides," Mol. Pharmacol., 51:816-824 (1997).
Ashton et al., "Location of penetration and metabolic barriers to levobunolol in the corneal epithelium of the pigmented rabbit," The Journal of Pharmacology and Experimental Therapeutics, 259(2):719-724 (1991).
Atkinson et al., "Triazaphenanthrenes. Part VI.* Further Observations on the Widman-Stoermer and Brosche Reactions," J. Chem. Soc. (C) pp. 2053-2060 (1966).
Augustin et al., "Oxidative reactions in the tear fluid of patients suffering from dry eyes," Graefe's Archive for Clinical and Experimental Ophthalmology, 233(11):694-698 (1995).
Axelsson et al., "Experimental colitis induced by dextran sulphate sodium in mice: beneficial effects of sulphasalazine and olsalazine," Aliment Pharmacol Ther, 12:925-934 (1998).
Bachman, G.B et al., "Quinoline derivatives from 3-nitro-4-hydroxyquinoline," Am. Chem. Soc., 69:365-371 (1947).
Badii, "Allergic Conjunctivitis," Apr. 28, 2016, retrieved on Nov. 22, 2019 from https://www.healthline.com/health/allergic-conjunctivitis; entire document, especially p. 2 last para.
Balci et al., "Effects of computer monitor-emitted radiation on oxidant/antioxidant balance in cornea and lens from rats," Molec Vis, 15:2521-2525 (2009).
Balci et al., "Investigation of oxidative stress in pterygium tissue," Molecular Vision, 17:443-447 (Feb. 2011).
Ballard, S.A et al., "Effects of sildenafil on the relaxation of human corpus cavernosum tissue in vitro and on the activities of cyclic nucleotide phosphodiesterase isozymes," J. Urol., 159(6):2164-2171 (1998).
Baltatzis et al., "Mycophenolate mofetil as an immunomodulatory agent in the treatment of chronic ocular inflammatory disorders," Ophthalmology, 110(5):1061-5 (May 2003).
Bardwell, A.J. et al., "Docking sites on mitogen-activated protein kinase (MAPK) kinases, MAPK phosphatases and the Elk-1 transcription factor compete for MAPK binding and are crucial for enzymic activity," Biochem. J., 370:1077-1085 (2003).
Baron, B.M. et al., "[3H]MDL 105,519, a high-affinity radioligand for the N-methyl-D-aspartate receptor-associated glycine recognition site," J. Pharmacol. Exp. Ther., 279:62-68 (1996).
Bartoli et al., "Malondialdehyde in Exhaled Breath Condensate as a Marker of Oxidative Stress in Different Pulmonary Diseases," Mediators of Inflammation, vol. 2011, Article ID 891752 (2011) (7 pages).
Batista et al., "Age-dependent changes in rat lacrimal gland antioxidant and vesicular related protein expression profiles," Molecular Vision, 18:194-202 (2012).
Batista et al., "Short-term treatment with bisphenol-A leads to metabolic abnormalities in adult male mice," PLOS One, vol. 7, No. 3, (2012).
Baum et al., "Omega 3 fatty acid inhibition of inflammatory cytokine-mediated Connexin43 regulation in the heart," Front. Physiol. 3:272 doi: 10.3389/fphys.2012.00272. eCollection 2012 (2012).
Baz et al., "Plasma reactive oxygen species activity and antioxidant potential levels in rosacea patients: correlation with seropositivity to Helicobacter pylori," International Journal of Dermatology, 43(7):494-497 (2004).
Berge et al., "Pharmaceutical salts," The Journal of Pharmaceuticals Sciences, 66(1):1-19 (1977).

(56) References Cited

OTHER PUBLICATIONS

Berkhout, T.A. et al., "Cloning, in vitro expression, and functional characterization of a novel human CC chemokine of the monocyte chemotactic protein (MCP) family (MCP-4) that binds and signals through the CC chemokine receptor 2B," J. Biol. Chem., 272:16404-16413 (1997).
Bermudez et al., "Thermosensitive poloxamer-based injectables as controlled drug release platforms for veterinary use: Development and in-vitro evaluation," Intl Res J Pharmacy Pharmacol, 1(6):109-118 (Sep. 2011).
Bernstein et al., "Mechanism of Action of Aromatic Amines that Short-Circuit the Visual Cycle," Biochemistry, 25 (11):3370-3377 (1986).
Bernstein et al., "Retinal Toxicity Associated with Occupational Exposure to the Fish Anesthetic MS-222," Am J Ophthalmol, 124(6):843-844 (1997).
Bernstein et al., "Short-Circuiting the Visual Cycle with Retinotoxic Aromatic Amines," Proc Natl Acad Sci USA, 83(6):1632-1635 (1986).
Bernstein et al., The Specific Inhibition of 11-cis-retinyl Palmitate Formation in the Frog Eye by Diaminophenoxypentane, an Inhibitor of Rhodopsin Regeneration, Vision Research, 25(6):741-748 (1985).
Bickett, D.A. et al., "A high throughput fluorogenic substrate for interstitial collagenase (MMP-1) and gelatinase (MMP-9)," Anal. Biochem., 212:58-64 (1993).
Bignon, E. et al., "SR146131: a new potent, orally active, and selective nonpeptide cholecystokinin subtype 1 receptor agonist. I. In vitro studies," J. Pharmacol. Exp. Ther. 289:742-751 (1999).
Roat, "Ocular Mucous Membrane Pemphigoid," Merck Manual Professional Version, 3 pages (2016), Available at: https://www.merckmanuals.com/professional/eye-disorders/conjunctival-and-scleral-disorders/ocular-mucous-membrane-pemphigoid.
Roat, "Scleritis," Merck Manual Professional Version, 3 pages (2016), Available at: https://www.merckmanuals.com/professional/eye-disorders/conjunctival-and-scleral-disorders/scleritis.
Roberts et al., "Basic Principles of Organic Chemistry," 2nd edition, copyright 1977 W. A. Benjamin, Inc., pp. 580-582.
Sandikci et al., "Lipid Peroxidation and Antioxidant Defence System in Patients with Active or Inactive Behcet's Disease," Acta Derm Venereol, 83:342-346 (2003).
Sasaki et al., "Retinal drug delivery using eyedrop preparations of poly-L-lysine-modified liposomes," Eur J Pharm Biopharm, 83(3):364-9 (2013).
Schaumberg et al., "Prevalence of Dry Eye Disease among US Men: Estimates from the Physicians' Health Studies," Arch Ophthalmol, 127(6):763-768 (Jun. 2009).
Schaumberg et al., "Prevalence of Dry Eye Syndrome Among US Women," Am J Ophthalmol, 136(2):318-326 (Aug. 2003).
Sheppard et al., "Targeting Anterior Uveitis: A Focus on Iontophoresis . . . ", Sep. 1, 2018, Retrieved from Internet URL: https://www.nyee.edu/files/NYEE/Health%20Professionals/Continuing%20Medical%20Education/Enduring%20CME%20Activities/158_supplement.small_v1_FINAL%20082818.pdf.
Shoemaker et al., "[3H]diltiazem binding to calcium channel antagonists recognition sites in rat cerebral cortex," Eur. J. Pharmacol., 111:273-277 (1985).
Smith et al., "Basic pathogenic mechanisms operating in experimental models of acute anterior uveitis," Immunol Cell Biol, 76:497-512 (1998).
Sus et al., "Uber die Lichtreaktion der o-Chinondiazide V. Mitteilung1) Ubergange heterocyclischer 6-Ringe in heterocyclische 5-Ringe," Liebigs Ann. Chem. 583:150 (1953).
Tang-Liu et al., "Effects of four penetration enhancers on corneal permeability of drugs in vitro," Journal of Pharmaceutical Sciences, 83(1):85-90 (1994).
Tian et al., "First total synthesis and determination of the absolute configuration of 1-N-methyl-3-methylamino-[N-butanoicacid-3-(9-methyl-8-propen-7-one)-amide]-benzo[f][1,7]naphthyridine-2-one, a novel benzonaphthyridine alkaloid," Tetrahedron Letters, 53:4892-4895 (2012).
Westphal et al., "Reactions with Pryridinium Pyruvic Acid Esters," Pharmazie, 31(11)770-773 (1976).
Zarkovic "4-hydroxynonenal and neurodegenerative diseases," Molecular Aspects of Medicine, 24(4-5):293-303 (2003).
Abelson et al., "Combined analysis of two studies using the conjunctival allergen challenge model to evaluate olopatadine hydrochloride, a new ophthalmic antiallergic agent with dual activity," American Journal of Ophthalmology, 125(6):797-804 (Jun. 1998).
Abelson et al., "Conjunctival allergen challenge. A clinical approach to studying allergic conjunctivitis," Archives of Ophthalmology, 108(1):84-88 (1990).
Abelson et al., "Conjunctival allergen challenge: models in the investigation of ocular allergy," Current Allergy and Asthma Reports, 3(4):363-368 (2003).
Abelson et al., The conjunctival provocation test model of ocular allergy: utility for assessment of an ocular corticosteroid, loteprednol etabonate, J Ocul Pharmacol Ther, 14(6):533-42 (Dec. 1998).
Abramovitz, M. et al., "The utilization of recombinant prostanoid receptors to determine the affinities and selectivities of prostaglandins and related analogs," Biochem. Biophys. Acta., 1483(2):285-293 (2000).
Acland et al., "Gene Therapy Restores Vision in a Canine Model of Childhood Blindness," Nature Genetics, 28 (1):92-95 (2001).
Aharony, D. et al., "Pharmacological characterization of cloned human NK-2 (neurokinin A) receptor expressed in a baculovirus/Sf-21 insect cell system," Molecular Pharmacology, 44(2):356-363 (1993).
Akturk, S. et al., "Nitric oxide and malondialdehyde levels in plasma and tissue of psoriasis patients," Journal of the European Academy of Dermatology and Venereology, 26(7):833-837 (2012).
Al-Essa et al., "Clinical, fluorine-18 labeled 2-fluoro-2-deoxyglucose positron emission tomography (FDG PET), MRI of the brain and biochemical observations in a patient with 4-hydroxy butyric aciduria; a progressive neurometabolic disease," Brain Dev., 22(2):127-31 (2000).
Al-Hasani, H. et al., "Phosphoryl exchange is involved in the mechanism of the insulin receptor kinase," FEBS Lett., 349:17-22 (1994).
Albano et al., "Immune response towards lipid peroxidation products as a predictor of progression of non-alcoholic fatty liver disease to advanced fibrosis," Gut 54:987-93 (2005).
Aldeyra Press Release—Aldeyra Therapeutics Abstract Accepted at 2015 American Academy of Allergy Asthma & Immunology Annual Meeting, Dec. 16, 2014 (2 pages).
Aldeyra Press Release—Aldeyra Therapeutics Abstract Accepted for Presentation at the 2015 Multinational Association of Supportive Care in Cancer—International Society of Oral Oncology (Masccisoo) Annual Meeting, Apr. 23, 2015 (2 pages).
Aldeyra Press Release—Aldeyra Therapeutics Abstracts Accepted for Presentation at the 2015 Annual Meeting of the Association for Research in Vision and Ophthalmology, Feb. 2, 2015 (2 pages).
Aldeyra Press Release—Aldeyra Therapeutics Announces Agreement with Johnson & Johnson Innovation to Advance Novel Immune-Modulating Drugs for Systemic Inflammatory Diseases, Feb. 27, 2018 (2 pages).
Aldeyra Press Release—Aldeyra Therapeutics Announces Clinical Development Update for Phase 3 Programs, Jan. 25, 2017 (2 pages).
Aldeyra Press Release—Aldeyra Therapeutics Announces Collaboration With the National Organization for Rare Disorders to Enhance Awareness for Sjogren-Larsson Syndrome Patients, Dec. 4, 2014 (2 pages).
Aldeyra Press Release—Aldeyra Therapeutics Announces Development Programs at 2018 Research Day, Jun. 26, 2018 (2 pages).
Aldeyra Press Release—Aldeyra Therapeutics Announces First Patient Enrolled in Allergic Conjunctivitis Phase 2b Clinical Trial, Feb. 7, 2017 (2 pages).
Aldeyra Press Release—Aldeyra Therapeutics Announces First Patient Enrolled in Allergic Conjunctivitis Phase 3 Clinical Trial, Apr. 24, 2018 (2 pages).
Aldeyra Press Release—Aldeyra Therapeutics Announces First Patient Enrolled in Allergic Conjunctivitis Phase IIa Clinical Trial, Sep. 29, 2015 (2 pages).

(56) References Cited

OTHER PUBLICATIONS

Aldeyra Press Release—Aldeyra Therapeutics Announces First Patient Enrolled in Dry Eye Disease Phase 2a Clinical Trial, Jun. 6, 2017 (2 pages).
Aldeyra Press Release—Aldeyra Therapeutics Announces First Patient Enrolled in Dry Eye Disease Phase 2b Clinical Trial, Jan. 30, 2018 (2 pages).
Aldeyra Press Release—Aldeyra Therapeutics Announces First Patient Enrolled in Noninfectious Anterior Uveitis Phase 3 Clinical Trial, Apr. 27, 2017 (2 pages).
Aldeyra Press Release—Aldeyra Therapeutics Announces First Patient Enrolled in Noninfectious Anterior Uveitis Phase II Clinical Trial, Apr. 16, 2015 (2 pages).
Aldeyra Press Release—Aldeyra Therapeutics Announces First Patient Enrolled in Sjogren-Larsson Syndrome Phase II Clinical Trial, Mar. 24, 2015 (2 pages).
Aldeyra Press Release—Aldeyra Therapeutics Announces First Patient Enrolled in Sjögren-Larsson Syndrome Pivotal Phase 3 Clinical Trial, Jul. 24, 2018 (2 pages).
Aldeyra Press Release—Aldeyra Therapeutics Announces Last Patient Dosed in Dry Eye Disease Phase 2a Clinical Trial, Jul. 18, 2017 (2 pages).
Aldeyra Press Release—Aldeyra Therapeutics Announces Last Patient Dosed in Dry Eye Disease Phase 2b Clinical Trial, Jul. 12, 2018 (2 pages).
Aldeyra Press Release—Aldeyra Therapeutics Announces Last Patient Dosed in Phase II Trial of NS2 in Patients with Allergic Conjunctivitis, Dec. 16, 2015 (2 pages).
Aldeyra Press Release—Aldeyra Therapeutics Announces Last Patient Dosed in the Alleviate Phase 3 Clinical Trial, Dec. 20, 2018 (2 pages).
Aldeyra Press Release—Aldeyra Therapeutics Announces Positive Mesothelioma Investigator-Sponsored Clinical Trial Results Presented at the International Association for The Study of Lung Cancer 19th World Conference on Lung Cancer, Sep. 25, 2018 (2 pages).
Aldeyra Press Release—Aldeyra Therapeutics Announces Positive Results from Dry Eye Disease Phase 2a Clinical Trial, Sep. 12, 2017 (3 pages).
Aldeyra Press Release—Aldeyra Therapeutics Announces Positive Results from Phase 2b Dry Eye Disease Clinical Trial, Sep. 26, 2018 (2 pages).
Aldeyra Press Release—Aldeyra Therapeutics Announces Positive Top-Line Results from the Phase 3 Alleviate Trial in Patients with Allergic Conjunctivitis, Mar. 26, 2019 (2 pages).
Aldeyra Press Release—Aldeyra Therapeutics Announces Presentation of Novel Data on the Efficacy of ADX-102 in a Model of Succinic Semialdehyde Dehydrogenase Activity at the 2017 American Society of Human Genetics Annual Meeting, Oct. 5, 2017 (2 pages).
Aldeyra Press Release—Aldeyra Therapeutics Announces Presentation of Phase 2 Allergic Conjunctivitis Results at the 2016 American College of Allergy, Asthma and Immunology Annual Scientific Meeting, Nov. 7, 2016 (2 pages).
Aldeyra Press Release—Aldeyra Therapeutics Announces Presentation of Results on the Efficacy of ADX-102 in Noninfectious Anterior Uveitis at the American Uveitis Society Held at the American Academy of Ophthalmology 2017 Annual Meeting, Oct. 25, 2017 (2 pages).
Aldeyra Press Release—Aldeyra Therapeutics Announces Results from Allergic Conjunctivitis Phase 2b Clinical Trial and Plans for Phase 3 Clinical Testing, Jun. 14, 2017 (3 pages).
Aldeyra Press Release—Aldeyra Therapeutics Announces Third Quarter 2017 Financial Results, Nov. 9, 2017 (4 pages).
Aldeyra Press Release—Aldeyra Therapeutics Launches the Aldeyra Registry for Patients with Sjögren-Larsson Syndrome, Feb. 22, 2017 (2 pages).
Aldeyra Press Release—Aldeyra Therapeutics Opens Enrollment in Noninfectious Anterior Uveitis Phase II Clinical Trial, Mar. 26, 2015 (2 pages).
Aldeyra Press Release—Aldeyra Therapeutics Opens Enrollment in Sjogren-Larsson Syndrome Clinical Trial and Finalizes Noninfectious Anterior Uveitis Clinical Trial Protocol, Mar. 17, 2015 (2 pages).
Aldeyra Press Release—Aldeyra Therapeutics Presents Dry Eye Disease Phase 2a Clinical Trial Results at the Association for Research in Vision and Ophthalmology 2018 Annual Meeting, May 1, 2018 (2 pages).
Aldeyra Press Release—Aldeyra Therapeutics Presents Evidence for Aldehyde Sequestration as a Potential Therapeutic Approach in Succinic Semialdehyde Dehydrogenase Deficiency at the American Society of Human Genetics 2017 Annual Meeting, Oct. 24, 2017 (2 pages).
Aldeyra Press Release—Aldeyra Therapeutics Presents Noninfectious Anterior Uveitis Phase 2 Clinical Trial Data at the Association for Research in Vision and Ophthalmology 2017 Annual Meeting, May 17, 2017 (3 pages).
Aldeyra Press Release—Aldeyra Therapeutics Presents Noninfectious Anterior Uveitis Phase 2 Clinical Trial Data to the American Uveitis Society Held at the American Academy of Ophthalmology 2017 Annual Meeting, Nov. 29, 2017 (2 pages).
Aldeyra Press Release—Aldeyra Therapeutics Provides Update on Late-Stage Clinical Trials at 2016 Research and Development Day, Sep. 26, 2016 (2 pages).
Aldeyra Press Release—Aldeyra Therapeutics Provides Update on NS2 Clinical Program, Mar. 2, 2015 (2 pages).
Aldeyra Press Release—Aldeyra Therapeutics Provides Update on Ophthalmic Programs at 2019 Research & Development Day, Feb. 28, 2019 (2 pages).
Abelson and Loeffler, "Conjunctival allergen challenge: models in the investigation of ocular allergy," Curr Allergy Asthma Rep. 2003;3(4):363-8.
Ackerman et al., "Ocular itch associated with allergic conjunctivitis: latest evidence and clinical management," Ther Adv Chronic Dis. 2016;7(1):52-67.
Al-Bari, "Chloroquine analogues in drug discovery: new directions of uses, mechanisms of actions and toxic manifestations from malaria to multifarious diseases," J Antimicrob Chemother. 2015;70(6):1608-21.
Aldeyra Therapeutics, "Aldeyra Therapeutics Announces Positive Top-Line Symptom and Sign Results from Run-In Cohort of Phase 3 Tranquility Trial in Dry Eye Disease," Jan. 7, 2021.
Aldeyra Therapeutics, Inc., "A Randomized, Double Masked, Clinical Study of Subjects with Dry Eye Syndrome," ClinicalTrials.gov identifier NCT03162783. First Posted May 22, 2017; https://clinicaltrials.gov/ct2/show/NCT03162783.
Allergan, "Restasis® Prescribing Information," copyright 2016, revised 2017.
Bacsi et al., "Effect of pollen-mediated oxidative stress on immediate hypersensitivity reactions and late-phase inflammation in allergic conjunctivitis," J Allergy Clin Immunol. 2005;116(4):836-43.
Balci et al., "Effects of computer monitor-emitted radiation on oxidant/antioxidant balance in cornea and lens from rats," Mol Vis. 2009;15:2521-5.
Bastin et al., "Salt Selection and Optimisation Procedures for Pharmaceutical New Chemical Entities," Org Proc Res Dev. 2000;4(5):427-35.
Berge et al., "Pharmaceutical salts," J Pharm Sci. 1977;66(1):1-19.
Blindauer et al., "A randomized controlled trial of etilevodopa in patients with Parkinson disease who have motor fluctuations," Arch Neurol. 2006;63(2):210-6.
Boldogh et al., "ROS generated by pollen NADPH oxidase provide a signal that augments antigen-induced allergic airway inflammation," J Clin Invest. 2005;115(8):2169-79.
Boner et al., "Bronchodilating activity of oral clenbuterol in asthmatic children after single administration of different dosages," Pediatr Pulmonol. 1987;3(1):34-7.
Brandt et al., "The Prevalence of Non-Alcoholic Fatty Liver Disease in Patients With Inflammatory Bowel Disease," American Journal of Gastroenterology 2017;112:S542,S544.
Buddi et al., "Evidence of oxidative stress in human corneal diseases," J Histochem Cytochem. 2002;50(3):341-51.

(56) References Cited

OTHER PUBLICATIONS

Chao et al., "Co-existence of non-alcoholic fatty liver disease and inflammatory bowel disease: A review article," World J Gastroenterol. 2016;22(34): 7727-7734.
Davies, "Biopharmaceutical considerations in topical ocular drug delivery," Clin Exp Pharmacol Physiol, 2000; 27(7):558-62.
Devillier et al., "The allergen challenge chamber: A valuable tool for optimizing the clinical development of pollen immunotherapy," Allergy, 2011; 66(2):163-9.
Division of AIDS, National Institute of Allergy and Infectious Diseases, National Institutes of Health, US Department of Health and Human Services, Division of AIDS (DAIDS) Table for Grading the Severity of Adult and Pediatric Adverse Events, V2.0, 33 pages. (Nov. 2014).
Ellis et al., "Multiple Doses of Trodusquemine Improve Glucose Tolerance in Type 2 Diabetic Subjects," 69th Scientific Sessions of the American Diabetes Association, Abstract No. 2071-PO (2009).
Esterbauer et al., "Chemistry and Biochemistry of 4-Hydroxynonenal, Malonaldehyde and Related Aldehydes," Free Radic Biol Med, 1991; 11:81-128.
Farid et al., "Detection of corneal fibrosis by imaging second harmonic-generated signals in rabbit corneas treated with mitomycin C after excimer laser surface ablation," Invest Ophthalmol Vis Sci. 2008;49(10):4377-83.
Goldstein et al., "A Phase 2 Exploratory Study of a Novel Interleukin-1 Receptor Inhibitor (EBI-005) in the Treatment of Moderate-to-Severe Allergic Conjunctivitis," Eye Contact Lens, 2015; 41(3):145-55.
Hessen et al., "Dry Eye: an Inflammatory Ocular Disease," J Ophthalmic Vis Res, 2014; 9(2):240-250.
Highlights of Prescribing Information, Bridion® (sugammadex) Injection, for intravenous use, Initial U.S. Approval: 2015, Last Revised Dec. 2015 (19 pages).
Hom et al., "Allergic conjunctivitis and dry eye syndrome," Ann Allergy Asthma Immunol, 2012; 108(3):163-6.
Hong et al., "Laboratory Scale Production of Injectable Liposomes By Using Cell Disruptor . . . ," Journal of Pharmaceutical Investigation, 2015, vol. 45, pp. 73-78.
Irons, "Fluvoxamine in the treatment of anxiety disorders," Neuropsychiatr Dis Treat. 2005;1(4):289-99.
Jacobs et al., "Responses to ragweed pollen in a pollen challenge chamber versus seasonal exposure identify allergic rhinoconjunctivitis endotypes," J. Allergy Clin. Immunol., 2012; 130(1):122-7.
Jellinger et al., "American Association of Clinical Endocrinologists and American College of Endocrinology Guidelines for Management of Dyslipidemia and Prevention of Cardiovascular Disease," Endocr Pract. 2017;23(Suppl 2):1-87.
Keister et al., "Inflammatory Bowel Disease and Irritable Bowel Syndrome Similarities and Differences," Crohn's & Colitis Foundation of America 2014.
Levey et al., "A new equation to estimate glomerular filtration rate," Ann Intern Med. 2009;150(9):604-12.
Liang et al., "Ocular safety of cationic emulsion of cyclosporine in an in vitro corneal wound-healing model and an acute in vivo rabbit model," Mol Vis, 2012; 18:2195-204.
Lopachin et al., "Molecular mechanisms of aldehyde toxicity: a chemical perspective," Chem Res Toxicol, 2014; 27(7):1081-91.
Malondialdehyde, Wikipedia. Edited 2020; Accessed 2021: https://en.wikipedia.org/w/index.php?title=Malondialdehyde&oldid=993228459.
Mathew et al., "Updates in the management of diabetic macular edema," J Diabetes Res. 2015; 2015:794036.
Merck Sharp & Dohme Corp., "Bridion® (sugammadex) Injection Prescribing Information, for intravenous use," Highlights of Prescribing Information. 2015.
Mishra et al., "Recent Patents and Emerging Therapeutics in the Treatment of Allergic Conjunctivitis," Recent Pat. Inflamm. Allergy Drug Discov.; 2011; 5(1):26-36.
Na et al., "Molecular profiling of a 6-hydroxydopamine model of Parkinson's disease," Neurochem Res. 2010;35(5):761-72.
Nagai et al., Improved corneal toxicity and permeability of tranilast by the preparation of ophthalmic formulations containing its nanoparticles, J Oleo Sci, 2014; 63(2):177-86.
Nerurkar et al., "Beta-Arylglutaconic Acids. II. Imides of Certain Beta-Arylglutaconic and Glutaric Acids," J Org Chem, 24(12):2055-2056 (1959).
O'Regan et al., "Filaggrin in atopic dermatitis," J Allergy Clin Immunol. 2009; 124(3 Suppl 2):R2-6.
Okayasu et al., "A novel method in the induction of reliable experimental acute and chronic ulcerative colitis in mice," Gastroenterology. 1990;98(3):694-702.
Park et al., "Homogeneous proximity tyrosine kinase assays: scintillation proximity assay versus homogeneous time-resolved fluorescence," Anal. Biochem., 269:94-104 (1999).
Patel C.Y., "Subtype selectivity of peptide analogs for all five cloned human somatostatin receptors (hsstr 1-5)," Endocrinology, 135:2814-2817 (1994).
Pellock, "Balancing clinical benefits of vigabatrin with its associated risk of vision loss," Acta Neurologica. Scandinavica. Supplementum., 124(s192):83-91 (2011).
Petroski et al., "Selective labeling of embryonic neurons cultured on astrocyte monolayers with 5(6)-carboxyfluorescein diacetate (CFDA)," Journal of Neuroscience Methods, 52(1):23-32 (1994).
Pfaar et al., "Perspectives in allergen immunotherapy: 2017 and beyond," Allergy, 2018; 73(Suppl 104):5-23.
Pontikis et al., "Cyclodextrin alleviates neuronal storage of cholesterol in Niemann-Pick C disease without evidence of detectable blood-brain barrier permeability," Journal of Inherited Metabolic Disease, 2013; 36(3):491-498.
Pozzi et al., "Modification of Collagen IV by Glucose or Methylglyoxal Alters Distinct Mesangial Cell Function," Journal of the American Society of Nephrology, 20:2119-2125 (2009).
Pred Forte Prescribing Information, Allergan, 5 pages (2017).
Pristupa et al., "Pharmacological heterogeneity of the cloned and native human dopamine transporter: disassociation of [3H]WIN 35,428 and [3H]GBR 12,935 binding.," Mol. Pharmacol., 45:125-135 (1994).
Pruneau et al., "LF 16.0335, a novel potent and selective nonpeptide antagonist of the human bradykinin B2 receptor," Brit. J. Pharmacol., 125:365-372 (1998).
Pubchem, 1824609-67-7, SID 333824451, Apr. 24, 2017 (6 pages).
Pubchem, 2-(3-Aminoquinolin-2-yl)propan-2-ol, CID 117758222, Feb. 23, 2016, modified Jun. 13, 2020 (11 pages).
Pubchem, SCHEMBL16316728, CID 117758222, Feb. 23, 2016, modified Sep. 30, 2017 (13 pages).
Roberts et al., "Experimental Organic Chemistry—A Miniscale Approach," copyright 1994 by Saunders College Publishing, pp. 580-581 and 584-586.
Roche, "Tween 20," Sigma-Aldrich Datasheet. Retrieved Nov. 19, 2020: https://www.sigmaaldrich.com/catalog/product/roche/11332465001?lang=en&region=US#:~:text=Tween%2020%>.
Rohrer et al., "Cloning and characterization of a fourth human somatostatin receptor," Proc. Natl. Acad. Sci. U.S.A., 90:4196-4200 (1993).
Roumen et al., "Serum Lipofuscin as a Prognostic Indicator of Adult Respiratory Distress Syndrome and Multiple Organ Failure," British Journal of Surgery, 1994, vol. 81, pp. 1300-1305.
Rønborg et al., "Exposure chamber for allergen challenge. The development and validation of a new concept," Allergy, 1996; 51(2):82-8.
Sahi et al., "Hepatocytes as a tool in drug metabolism, transport and safety evaluations in drug discovery." Current Drug Discov. Technol., 7(3):188-198 (2010).
Salvatore et al., "Molecular cloning and characterization of the human A3 adenosine receptor," Proc. Natl. Acad. Sci. U.S.A., 90:10365-10369 (1993).
Samsonov et al., "Impact of Atherosclerosis- and Diabetes-Related Dicarbonyls on Vascular Endothelial Permeability: A Comparative Assessment," Oxid. Med. Cell Longev. Article 1625130 (2017).
Sanchez et al., "Allergic Conjunctivitis," J Investig Allergol Clin Immunol., 2011; 21(2):1-19.

(56) References Cited

OTHER PUBLICATIONS

Sandikci et al., "Lipid Peroxidation and Antioxidant Defence System in Patients with Active or Inactive Behcet's Disease," Acta Derm Venereol, 2003; 83:342-346.
Sarafian et al., "Synergistic cytotoxicity of Delta(9)-tetrahydrocannabinol and butylated hydroxyanisole," Toxicology Letters, 133(2-3):171-179 (2002).
Sarfare et al., "Biocompatibility of a Synthetic Biopolymer for the Treatment of Rhegmatogenous Retinal Detachment," J Clin Exp Ophthalmol. 2015;6(5):475.
Sarup et al., "Resolution of high and low affinity progesterone receptors from human breast carcinoma T47D cells," J. Biol. Chem., 263:5624-5633 (1988).
Sasaki et al., "Retinal drug delivery using eyedrop preparations of poly-L-lysine-modified liposomes," Eur J Pharm Biopharm, 2013; 83(3):364-9.
Satici et al., "Malondialdehyde and antioxidant enzyme levels in the aqueous humor of rabbits in endotoxin-induced uveitis," Eur J Ophthalmol, 2003; 13(9-10):779-83.
Sayed et al., "Metabolic Activation of R,S-1-(Tetrahydro-2-turanyl)-5-fluorouracil (Ftorafur) to 5-fluorouracil by Soluble Enzymes," Cancer Research, 43:4039-4044 (1983).
Schaumberg et al., "Prevalence of dry eye syndrome among US women," Am J Ophthalmol. 2003;136(2):318-26.
Schaumberg et al., "Epidemiology of dry eye syndrome," Lacrimal Gland, Tear Film, and Dry Eye Syndromes 3, Kluwer Academic/Plenum Publishers, pp. 989-998 (2002).
Schaumberg et al., "Prevalence of Dry Eye Disease among US Men: Estimates from the Physicians' Health Studies," Arch Ophthalmol, 2009; 127(6):763-768.
Schioth et al., "Characterization of the binding of MSH-B, HB-228, GHRP-6 and 153N-6 to the human melanocortin receptor subtypes," Neuropeptides, 31:565-571 (1997).
Schramm et al., "The Cross-linked Biopolymer Hyaluronic Acid as an Artificial Vitreous Substitute," Invest Ophthalmol Vis Sci, 53(2):613-621 (Feb. 2012).
Schwartz and Work, "Measurement and estimation of GFR in children and adolescents," Clin J Am Soc Nephrol. 2009;4(11):1832-43.
Schwartz et al., "Tamponade in surgery for retinal detachment associated with proliferative vitreoretinopathy," Cochrane Database Syst Rev. 2020;5(5):CD006126.
Schwinn et al., "Molecular cloning and expression of the cDNA for a novel alpha 1-adrenergic receptor subtype," J. Biol. Chem., 265:8183-8189 (1990).
Sciuto et al., "Therapeutic Treatments of Phosgene-Induced Lung Injury," Inhal Toxicol, 16(8):565-580 (2004).
Search Report and Written Opinion issued by the Intellectual Property Office of Singapore for Singapore Patent Application No. 11201504859Y dated Aug. 1, 2016 (12 pages).
Serbecic et al., "Anti-oxidative vitamins prevent lipid-peroxidation and apoptosis in corneal endothelial cells," Cell Tissue Res, 320(3):465-75 (Jun. 2005).
Shank et al., "Ion and temperature effects on the binding of gamma-aminobutyrate to its receptors and the high-affinity transport system," J. Neurochem., 54:2007-2015 (1990).
Shen et al., "Molecular cloning and expression of a 5-hydroxytryptamine7 serotonin receptor subtype," J. Biol. Chem., 268:18200-18204 (1993).
Sheppard et al., "Targeting Anterior Uveitis: A Focus on Iontophoresis . . . ", Sep. 1, 2018, Retrieved from Internet URL: https://www.nyee.edu/files/NYEE/Health%20Professionals/Continuing%20Medical%20Education/Enduring%20CME%20Activities/158_supplement.small_v1_FINAL%20082818.pdf.
Sheppard et al., "A Randomized, Comparator-Controlled Phase 2 Clinical Trial of ADX-102 Ophthalmic Solution in Noninfectious Anterior Uveitis," ARVO Annual Meeting Abstract, Invest Ophth Vis Sci. 2017; 58(8):1231.

Sherman et al., "Cellular Defenses Against Unfolded Proteins: A Cell Biologist Thinks about Neurodegenerative Diseases," Neuron, 29(1):15-32 (2001).
Shipp et al., "Common acute lymphoblastic leukemia antigen (CALLA) is active neutral endopeptidase 24.11 ("enkephalinase"): direct evidence by cDNA transfection analysis," Proc Natl Acad Sci USA. 86:297 (1989).
Schoemaker et al., "[3H]diltiazem binding to calcium channel antagonists recognition sites in rat cerebral cortex," Eur. J. Pharmacol., 111:273-277 (1985).
Siegrist et al., "Radioreceptor assay for alpha-MSH using mouse B16 melanoma cells+.," J. Recep. Res., 8:323-343 (1988).
Sieving et al., "Inhibition of the Visual Cycle in vivo by 13-cis Retinoic Acid Protects from Light Damage and Provides a Mechanism for Night Blindness in Isotretinoin Therapy," Proc Natl Acad Sci USA, 98(4):1835-1840 (2001).
Sills et al., "[3H]CGP 39653: a new N-methyl-D-aspartate antagonist radioligand with low nanomolar affinity in rat brain," Eur. J. Pharmacol., 192:19-24 (1991).
Simeone et al., "Modification of the Pyridine Moiety of Non-peptidyl Indole GnRH Receptor Antagonists," Bioorganic & Medicinal Chemistry Letters, 12(22):3329-3332 (2002).
Simonin et al., "The human delta-opioid receptor: genomic organization, cDNA cloning, functional expression, and distribution in human brain," Mol. Pharmacol., 46:1015-1021 (1994).
Singh et al., "The epidemiology of ocular and nasal allergy in the United States, 1988-1994," J. Allergy Clin. Immunol., 2010; 126(4):778-783.
Smit et al., "Regulation of the human histamine H1 receptor stably expressed in Chinese hamster ovary cells," Brit. J. Pharmacol., 117:1071-1080 (1996).
Smith and Cass, "Oxidative stress and dopamine depletion in an intrastriatal 6-hydroxydopamine model of Parkinson's disease," Neuroscience. 2007;144(3):1057-66.
Smith et al., "Basic pathogenic mechanisms operating in experimental models of acute anterior uveitis," Immunol Cell Biol, 1998; 76:497-512.
Snead et al., "Gamma-hydroxybutyric acid," New England Journal of Medicine, 352(26):2721-2732 (2005).
Snell et al., "Novel structure having antagonist actions at both the glycine site of the N-Methyl-D-Aspartate receptor and neuronal voltage-sensitive sodium channels. Biochemical, electrophysiological, and behavioral characterization," J Pharmacol Exp Ther, 292(1):215-227 (2000).
Spadea et al., "Corneal wound healing after laser vision correction," Br J Ophthalmol. 2016; 100:28-33.
Spagnol et al., "Efficient synthesis of tricyclic benzobisoxazines by silica gel catalysis," J Org Chem, 2;72(5):1867-1869 (Mar. 2007).
Sparrow et al. "Phospholipid meets all-trans-retinal: the making of RPE bisretmoids," Journal of Lipid Research, 51: 247-261 (2010).
Speth et al., "Benzodiazepine receptors: temperature dependence of [3H]flunitrazepam binding," Life Sci., 24:351-358 (1979).
Stefánsson and Loftsson, "Cyclodextrins in Eye Drop Formulations," J Incl Phenom Macrocycl Chem. 2002;44:23-27 (abstract).
Stehle et al., "Molecular cloning and expression of the cDNA for a novel A2-adenosine receptor subtype," Mol. Endocrinol., 6:384-393 (1992).
Stevenson et al., "Dry eye disease: an immune-mediated ocular surface disorder," Arch Ophthalmol. 2012; 130(1): 90-100.
Struys et al., "Determination of the GABA analogue succinic semialdehyde in urine and cerebrospinal fluid by dinitrophenylhydrazine derivatization and liquid chromatography-tandem mass spectrometry: application to SSADH deficiency," J Inherit Metab Dis., 28(6):913-20 (2005).
Struys et al., "Metabolism of gamma-hydroxybutyrate to d-2-hydroxyglutarate in mammals: further evidence ford-2-hydroxyglutarate transhydrogenase," Metabolism, 55(3):353-8 (2006).
Study showing effect of ADX-102 on Fibrotic Changes in Cardiac Fibroblasts Following Cell Stress, American Society for Cell Biology Annual Meeting, Dec. 3-7, 2016 (2 pages).
Sus et al., "Uber die Lichtreaktion der o-Chinondiazide V Mitteilungl) Ubergange heterocyclischer 6-Ringe in heterocyclische 5-Ringe," Liebigs Ann. Chem. 583:150 (1953).

(56) References Cited

OTHER PUBLICATIONS

Tahara et al., "Pharmacological characterization of the human vasopressin receptor subtypes stably expressed in Chinese hamster ovary cells," Brit. J. Pharmacol., 125:1463-1470 (1998).
Tang-Liu et al., "Effects of four penetration enhancers on corneal permeability of drugs in vitro," Journal of Pharmaceutical Sciences, 1994; 83(1):85-90.
Tatsumi et al., "Pharmacological profile of neuroleptics at human monoamine transporters," Eur. J. Pharmacol., 368: 277-283 (1999).
Tayeh et al., "Macrophage oxidation of L-arginine to nitric oxide, nitrite, and nitrate. Tetrahydrobiopterin is required as a cofactor," J. Biol. Chem., 264:19654-19658 (1989).
Tempest-Roe et al., "Local therapies for inflammatory eye disease in translation: past, present and future," BMC Ophthalmol., 2013; 13(1):39.
Tewari-Singh et al., "Silibinin attenuates sulfur mustard analog-induced skin injury by targeting multiple pathways connecting oxidative stress and inflammation," PLoS One 7(9):e46149 (2012).
Tian et al., "First total synthesis and determination of the absolute configuration of 1-N-methyl-3-methylamino- [N-butanoicacid-3-(9-methyl-8-propen-7-one)-amide]-benzo [f][1,7]naphthyridine-2-one, a novel benzonaphthyridine alkaloid," Tetrahedron Letters, 53:4892-4895 (2012).
Tikly et al., "Lipid peroxidation and trace elements in systemic sclerosis," Clinical Rheumatology, 25(3):320-324 (2006).
Torkildsen et al., "Efficacy and safety of olopatadine hydrochloride 0.77% in patients with allergic conjunctivitis using a conjunctival allergen-challenge model," Clinical Ophthalmology, 9:1703-1713 (2015).
Toth et al., "A simple, continuous fluorometric assay for HIV protease," Int. J. Pept. Protein Res., 36:544-550 (1990).
Tsugeno et al., "Regions of the molecule responsible for substrate specificity of monoamine oxidase A and B: a chimeric enzyme analysis," J. Biochem., 118 (5) 974-80 (1995).
Tsuzuki et al., "Molecular cloning and expression of the gene encoding human angiotensin II type 2 receptor.," Biochem. Biophys. Res. Commun., 200:1449-1454 (1994).
Tukozkan et al., "Measurement of Total Malondialdehyde in Plasma and tissues by High-Performance Liquid Chromatography and Thiobarbituric Acid Assay," Firat Tip Dergisi, 11 (2):88-92 (2006).
Turk et al., "Serum anti-carbonic anhydrase antibodies and oxidant-antioxidant balance in patients with acute anterior uveitis," Ocul Immunol Inflamm, 22(2):127-32 (Apr. 2014).
Ueda et al., "Evaluation of a Sulfobutyl Ether 13-Cyclodextrin as a Solubilizing/Stabilizing Agent for Several Drugs," Drug Dev Ind Pharm, 24(9):863-867(1998).
Upadhyaya et al., "The sphingolipid degradation product trans-2-hexadecenal forms adducts with DNA," Biochem Biophy Res Comm., 424(1):18-21 (2012).
Vanachayangkul et al., "Inhibition of heme peroxidases by melamine," Enzyme Research, 2012:416062 (2012).
Vignon et al., "[3H]thienyl-phencyclidine ([3H]TCP) binds to two different sites in rat brain. Localization by autoradiographic and biochemical techniques," Brain Res., 378:133-141 (1986).
Vlaskina et al., "Novel Synthesis of Substituted Benzimidazoles by Reduction of Esters of 4-Alkylamino-3,5-dinitrobenzoic Acids by Tin Chloride," Chemistry of Heterocyclic Compounds, vol. 40(4):523-524 (2004).
Vogel et al., "Thirty years beyond discovery-clinical trials in succinic semialdehyde dehydrogenase deficiency, a disorder of GABA metabolism," J Inherit Metab Dis., 36(3):401-10 (2013).
Voziyan et al., "A Post-Amadori Inhibitor Pyridoxamine also Inhibits Chemical Modification of Proteins by Scavenging Carbonyl Intermediates for Carbohydrate and Lipid Degradation," J Biol Chem, 277(5):3397-3403 (2002).
Wagner et al., "Omega-conotoxin GVIA binding to a high-affinity receptor in brain: characterization, calcium sensitivity, and solubilization," J. Neurosci., 8:3354-3359 (1988).
Wakamatsu et al., "Evaluation of lipid oxidative stress status and inflammation in atopic ocular surface disease," Mol Vis, 16:2465-75 (Nov. 2010).
Wall et al., "Plant Antitumor Agents. 30. Synthesis and Structure Activity of Novel Camptothecin Analogs," J. Med. Chem., 36(18):2689-2700 (1993).
Walter et al., "Novel Complex N-Heterocycles via Intramolecular 1,5-Electrocyclizations: 1,2,3,4,4a,5,5a, 10-Octahydropyrido-[4",3":2',3']cyclobuta[1',2':4,5]pyrrolo[2,3-b]pyridines," Heterocycles, 48(8):1581-1591 (1998).
Wang et al., "A facile one-pot synthesis of 2-substituted-3-aminoquinolines: Preparation of benzo[b]naphthyridine-3-carbonitriles," Tetrahedron, 60(13):2937-2942 (2004).
Wang et al., "Human mu opiate receptor. cDNA and genomic clones, pharmacologic characterization and chromosomal assignment," FEBS Lett., 338:217-222 (1994).
Wang et al., "Markers of oxidative and nitrosative stress in systemic lupus erythematosus: correlation with disease activity," Arthritis and Rheumatism, 62(7):2064-2072 (2010).
Wang, X.K., "Pharmacological study on recombinant human GABA-A receptor complex containing alphas (leucine 155 to valine) combined with beta3gamma2s subunits," Acta. Pharmacol. Sin., 22:521-523 (2001).
Waslidge et al., "A colorimetric method for the determination of lipoxygenase activity suitable for use in a high throughput assay format," Anal. Biochem., 231:354-358 (1995).
Weaver et al., "The Th17 pathway and inflammatory diseases of the intestines, lungs, and skin," Annu. Rev. Pathol., 8:477-512 (2013).
Webb et al., "Intralesional cytokines in chronic oxazolone-induced contact sensitivity suggest roles for tumor necrosis factor alpha and interleukin-4," J Invest Dermatol, 111(1):86-92 (Jul. 1998).
Weishaar et al., "Multiple molecular forms of cyclic nucleotide phosphodiesterase in cardiac and smooth muscle and in platelets. Isolation, characterization, and effects of various reference phosphodiesterase inhibitors and cardiotonic agents," Biochem. Pharmacol., 35:787-800 (1986).
Weng et al., "Insights into the Function of Rim Protein in Photoreceptors and Etiology of Stargardt's Disease from the Phenotype in abcr Knockout Mice," Cell, 98(1):13-23 (1999).
Westphal et al., "Reactions with Pryridinium Pyruvic Acid Esters," Pharmazie, 31(11)770-773 (1976) [English Translation].
Wieland et al., "Subtype selectivity and antagonistic profile of the nonpeptide Y1 receptor antagonist BIBP 3226," J. Pharmacol. Exp. Ther., 275:143-149 (1995).
Winfield and Richards, "Ophthalmic products," Pharmaceutical Practice, Churchill Livingstone. 2004;265-268.
Witt-Enderby et al., "Characterization and regulation of the human ML1A melatonin receptor stably expressed in Chinese hamster ovary cells," Mol. Pharmacol., 50:166-174 (1996).
Wolkenberg et al., "Design, synthesis, and evaluation of novel 3,6-diaryl-4-aminoalkoxyquinolines as selective agonists of somatostatin receptor subtype 2," J Med Chem, 54(7):2351-2358 (2011).
Wood et al., "Aldehyde Load in Ischemia-Reperfusion Brain Injury: Neuroprotection by Neutralization of reactive Aldehydes with Phenelzine," Brain Res, 1122(1):184-190 (2006).
Wood et al., "The concept of "aldehyde load" in neurodegenerative mechanisms: cytotoxicity of the polyamine degradation products hydrogen peroxide, acrolein, 3-aminopropanal, 3-acetamidiorioanal and 4-aminobutanal in a retinal ganglion cell line," Brain Research, 1145:150-156 (2007).
Wurch et al., "Sequence and functional analysis of cloned guinea pig and rat serotonin 5-HT1D receptors: common pharmacological features within the 5-HT1D receptor subfamily," J. Neurochem., 68:410-418 (1997).
Wynn, "Cellular and molecular mechanisms of fibrosis," J Pathol. 2008;214(2):199-210.
Yadav et al., "Regulation of NF-κB-Induced Inflammatory Signaling by Lipid Peroxidation-Derived Aldehydes," Oxidative Med & Cell Longev, 2013, Art ID 690545, 11 pages (2013).
Yarnell, "Light Flips the Lipid Switch: Palmitoylation—the reversible attachment of palmitate to proteins—gets a new role in vision," C&EN, 82(29):22-23 (2004).

(56) References Cited

OTHER PUBLICATIONS

Yokomizo et al., "Hydroxyeicosanoids bind to and activate the low affinity leukotriene B4 receptor, BLT2," J. Biol. Chem., 276:12454-12459 (2001).
Yu et al., "Injectable Chemically Crosslinked Hydrogel for the Controlled Release of Bevacizumab in Vitreous: A 6-Month In Vivo Study," Transl Vis Sci Technol, 4(2,5):1-11 (2015).
Zagol-Ikapitte et al., "Characterization of scavengers of γ-ketoaldehydes that do not inhibit prostaglandin biosynthesis," Chem Res Toxicol, 23(1):240-250 (2010).
Zarkovic "4-hydroxynonenal and neurodegenerative diseases," Molecular Aspects of Medicine, 2003; 24(4-5):293-303.
Zava et al., "Androgen receptor assay with [3H]methyltrienolone (R1881) in the presence of progesterone receptors," Endocrinology, 104:1007-1012 (1979).
Zhang et al., "Potent nonsteroidal progesterone receptor agonists: synthesis and SAR study of 6-aryl benzoxazines," Bioorg Med Chem Lett, 12(5):787-90 (Mar. 2002).
Zhang et al., "Practical ophthalmic pharmacology," People's Military Medical Press, 2015; p. 590.
Zhou et al., "Chemical and biological evidence for base propenals as the major source of the endogenous M1dG adduct in cellular DNA," J Biol Chem., 280(27):25377-82 (2005).
Zhou et al., "Cloning and expression of human and rat D1 dopamine receptors," Nature, 347:76-80 (1990).
Zhou et al., "Mechanisms for the induction of HNE- MDA- and AGE-adducts, RAGE and VEGF in retinal pigment epithelial cells," Exp Eye Res., 80(4):567-80 (2005).
PCT International Search Report of PCT Application No. PCTUS2014/012762, mailed by the U.S. Patent and Trademark Office dated Jul. 18, 2014.
PCT International Search Report of PCT Application No. PCT/US2016/048054, mailed by the U.S. Patent and Trademark Office dated Nov. 4, 2016.
PCT International Search Report of PCT Application No. PCT/US2016/040064, mailed by the U.S. Patent and Trademark Office dated Nov. 15, 2016.
PCT International Search Report of PCT Application No. PCT/US2021/023884, mailed by the U.S. Patent and Trademark Office dated Jul. 28, 2021.
PCT International Search Report of PCT Application No. PCT/US2022/035898, mailed by the U.S. Patent and Trademark Office dated Nov. 16, 2022.
PCT International Search Report of PCT Application No. PCT/US2018/023000, mailed by the U.S. Patent and Trademark Office dated Jun. 1, 2018.
PCT International Search Report of PCT Application No. PCT/US2017/47945, mailed by the U.S. Patent and Trademark Office dated Oct. 20, 2017.
PCT International Search Report of PCT Application No. PCTUS2019/052961, mailed by the U.S. Patent and Trademark Office dated Dec. 10, 2019.
PCT International Search Report of PCT Application No. PCT/US2019/054263, mailed by the U.S. Patent and Trademark Office dated Jan. 6, 2020.
PCT International Search Report of PCT Application No. PCT/US2019/064669, mailed by the U.S. Patent and Trademark Office dated Feb. 27, 2020.
PCT International Search Report of PCT Application No. PCT/US2018/055310, mailed by the U.S. Patent and Trademark Office dated Jan. 29, 2019.
PCT International Search Report of PCT Application No. PCT/US2020/031138, mailed by the U.S. Patent and Trademark Office dated Jul. 13, 2020.
PCT International Search Report of PCT Application No. PCT/US2020/031219, mailed by the U.S. Patent and Trademark Office dated Aug. 31, 2020.
PCT International Search Report of PCT Application No. PCT/US2019/045206, mailed by the U.S. Patent and Trademark Office dated Oct. 17, 2019.
PCT International Search Report of PCT Application No. PCT/US2017/020020, mailed by the U.S. Patent and Trademark Office dated May 24, 2017.
PCT International Search Report of PCT Application No. PCT/US2021/032335, mailed by the U.S. Patent and Trademark Office dated Jul. 27, 2021.
PCT International Search Report of PCT Application No. PCT/US2017/031808, mailed by the U.S. Patent and Trademark Office dated Aug. 11, 2017.
PCT International Search Report of PCT Application No. PCT/US2021027148, mailed by the U.S. Patent and Trademark Office dated Jun. 28, 2021.
PCT International Search Report of PCT Application No. PCT/US2021/035948, mailed by the U.S. Patent and Trademark Office dated Oct. 26, 2021.
PCT International Search Report of PCT Application No. PCT/US2006/020320, mailed by the European Patent Office dated Sep. 26, 2006.
PCT International Search Report of PCT Application No. PCT/US2010/59719, mailed by the U.S. Patent and Trademark Office dated Feb. 8, 2011.
Pearl et al., "Inherited disorders of gamma-aminobutyric acid metabolism and advances in ALDH5A1 mutation identification," Dev Med Child Neurol., 57(7):611-617 (2015).
Peralta et al., "Distinct primary structures, ligand-binding properties and tissue-specific expression of four human muscarinic acetylcholine receptors," EMBO. J., 6:3923-3929 (1987).
Pickering, D.S., "Pharmacological characterization of melatonin binding sites in Syrian hamster hypothalamus," Eur. J. Pharmacol., 175:71-77 (1990).
Pontikis et al., "Cyclodextrin alleviates neuronal storage of cholesterol in Niemann-Pick C disease without evidence of detectable blood-brain barrier permeability," Journal of Inherited Metabolic Disease, 36(3):491-498 (2013).
Pubchem, Substance Record for SID 333824451, Available Date: Apr. 24, 2017 [retrieved on Jun. 17, 2020]. Retrieved from Internet: <URL: https://pubchem.ncbi.nlm.nih.gov/substance/333824451>. entire document.
Pufahl et al., "Development of a fluorescence-based enzyme assay of human 5-lipoxygenase," Anal. Biochem., 364:204-212 (2007).
Radu et al., "Isotretinoin treatment inhibits lipofuscin accumulation in a mouse model of recessive Stargardt's macular degeneration," Novartis Foundation Symposium, 255(51-63):177-178 (2004).
Radu et al., "Treatment with Isotretinoin Inhibits Lipofuscin Accumulation in a Mouse Model of Recessive Stargardt's Macular Degeneration," Proc Natl Acad Sci USA, 100(8):4742-4747(2003).
Rapp et al., "The Effects of Local Anaesthetics on Retinal Function," Vision Res, 22(9):1097-1103 (1982).
Rauli et al., "Validation of Malondialdehyde and 4-Hydroxy-2-trans-Nonenal Measurement in Plasma by NICI-GC-MS1," J Biochem, 123:918-923 (1998).
Reed, "Lipid peroxidation and neurodegenerative disease," Free Radical Biology and Medicine, 51(7):1302-1319 (2011).
Rees et al., "Cloning and characterisation of the human 5-HT5A serotonin receptor," FEBS Lett., 355:242-246 (1994).
Reynolds et al., "(-)-[3H] desmethoxyverapamil labels multiple calcium channel modulator receptors in brain and skeletal muscle membranes: differentiation by temperature and dihydropyridines," J. Pharmacol. Exp. Ther., 237:731-738 (1986).
Rinaldi-Carmona et al., "Characterization of two cloned human CB1 cannabinoid receptor isoforms," J. Pharmacol. Exp. Ther., 278:871-878 (1996).
Rivkees et al., "Identification of domains of the human A1 adenosine receptor that are important for binding receptor subtype-selective ligands using chimeric A1/A2a adenosine receptors," J. Biol. Chem., 270:20485-20490 (1995).
Rizzo et al., "Endogenous antioxidants and radical scavengers," Advances in Experimental Medicine and Biology, 698:52-6 (2010).
Rizzo et al., "Ichthyosis in Sjögren-Larsson syndrome reflects defective barrier function due to abnormal lamellar body structure and secretion," Arch Dermatol Res, 302(6):443-451 (2010).

(56) References Cited

OTHER PUBLICATIONS

Rizzo et al., "Sjögren-Larsson syndrome: molecular genetics and biochemical pathogenesis of fatty aldehyde dehydrogenase deficiency," Mol Genet Metab. 90(1):1-9 (2007).
Rizzo, "The role of fatty aldehyde dehydrogenase in epidermal structure and function" Dermato-Endocrinol, 3(2):91-99 (2011).
Roat, "Allergic Conjunctivitis," Merck Manual Professional Version, 3 pages (2016), Available at: https://www.merckmanuals.com/professional/eye-disorders/conjunctival-and-scleral-disorders/allergic-conjunctivitis.
Roat, "Keratoconjunctivitis Sicca," Merck Manual Professional Version, 5 pages (2016), Available at: https://www.merckmanuals.com/professional/eye-disorders/corneal-disorders/keratoconjunctivitis-sicca.
Luthin et al., "Characterization of two affinity states of adenosine A2a receptors with a new radioligand, 2-[2-(4-amino-3-[125I]iodophenyl)ethylamino]adenosine," Mol. Pharmacol., 47:307-313 (1995).
MacDonald et al., "ADX-102, a novel aldehyde trap, reduces nociceptive behavior in mouse models of carrageenan and CFA induced pain," Int'l Conference on Pain Research & Management Abstract, J Pain Relief, 5 (5 Suppl):50 (Oct. 2016).
MacDonald et al., "Inhibition of fibroblast activation to the myofibroblast phenotype in neonatal rat cardiac fibroblasts using a small molecule aldehyde trap," ASCB Annual Meeting Abstract, p. 2 (Dec. 2016).
MacDonald et al., "Molecular characterization of the melanin-concentrating hormone/receptor complex: identification of critical residues involved in binding and activation," Mol. Pharmacol., 58:217-225 (2000).
MacDonald et al., "Novel Small Molecule Aldehyde Sequestering Agents Demonstrate Broad Therapeutic Potential for Ocular Inflammation," ARVO Annual Meeting Abstract, 2 pages (Jul. 2018).
MacDonald et al., "The novel aldehyde trap, ADX-102, reduces inflammation-mediated lung infiltrate in a mouse model of LPS-induced acute lung injury," 13th World Congress on Inflammation Abstract, p. 192 (Jul. 2017).
MacKenzie et al., "Characterization of the human dopamine D3 receptor expressed in transfected cell lines," Eur. J. Pharmacol., 266:79-85 (1994).
Maeda et al., "Involvement of All-trans-retinal in Acute Light-induced Retinopathy of Mice," J Biol Chem, 284 (22):15173-83 (May 2009).
Maeda et al., "Primary amines protect against retinal degeneration in mouse models of retinopathies," Nat Chem Biol, 8(2):170-178 (Dec. 2011).
Maguire et al., "Orphan-receptor ligand human urotensin II: receptor localization in human tissues and comparison of vasoconstrictor responses with endothelin-1," Brit. J. Pharmacol., 131:441-446 (2000).
Malondialdehyde, Wikipedia, 2008, retrieved from the internet on Aug. 4, 2021 at https://en.wikipedia.org/wiki/Malondialdehyde, pp. 1-2.
Mandell et al., "The Aldehyde Trap NS2 Reduces Ocular Inflammation in an Endotoxin-Induced Model in Rats," Investigative ophthalmology & visual science. 2015; 56(7):3095.
Mantey et al., "Discovery of a high affinity radioligand for the human orphan receptor, bombesin receptor subtype 3, which demonstrates that it has a unique pharmacology compared with other mammalian bombesin receptors," J. Biol. Chem., 272:26062-26071 (1997).
Marnett, "Oxy radicals, lipid peroxidation and DNA damage," Toxicology, 181-182:219-222 (2002).
Martin et al., "Molecular cloning and functional characterization of murine cysteinyl-leukotriene 1 (CysLT(1)) receptors.," Biochem. Pharmacol., 62:1193-1200 (2001).
Matern et al., "Seizures in a boy with succinic semialdehyde dehydrogenase deficiency treated with vigabatrin (gamma-vinyl-GABA)," J Inherit Metab Dis., 19(3):313-8 (1996).
Maurice et al., "Advances in targeting cyclic nucleotide phosphodiesterases," Nat Rev Drug Discov., 13:290-314 (2014).

McCord et al., "Superoxide dismutase. An enzymic function for erythrocuprein (hemocuprein).," J. Biol. Chem., 244: 6049-6055 (1969).
McGinnity et al., "Evaluation of fresh and cryopreserved hepatocytes as in vitro drug metabolism tools for the prediction of metabolic clearance." Drug Metab. Dispos., 32(11):1247-1253 (2004).
McLaurin et al., "Phase 3 Randomized Double-Masked Study of Efficacy and Safety of Once-Daily 0.77% Olopatadine Hydrochloride Ophthalmic Solution in Subjects with Allergic Conjunctivitis Using the Conjunctival Allergen Challenge Model," Clinical Science, 34(10):1245-1251 (2015).
Medline Plus. Macular Degeneration—age-related. (6 pages) (2013).
Meijer et al., "Biochemical and cellular effects of roscovitine, a potent and selective inhibitor of the cyclin-dependent kinases cdc2, cdk2 and cdk5," Eur. J. Biochem., 243:527-536 (1997).
Meng et al., "Cloning and pharmacological characterization of a rat kappa opioid receptor," Proc. Natl. Acad. Sci. U.S.A., 90:9954-9958 (1993).
Mialet et al., "Isolation oftheserotoninergic 5-HT4(e) receptor from human heart and comparative analysis of its pharmacological profile in C6-glial and CHO cell lines," Brit. J. Pharmacol., 129:771-781 (2000).
Miceli et al., "Efficacy of keratinocyte growth factor-2 in dextran sulfate sodium-induced murine colitis," J Pharmacol Exp Ther, 290(1):464-71 (Jul. 1999).
Mittl et al., "Structure of recombinant human CPP32 in complex with the tetrapeptide acetyl-Asp-Val-Ala-Asp fluoromethyl ketone," J. Biol. Chem., 272:6539-6547 (1997).
Monaghan et el., "The distribution of [3H]kainic acid binding sites in rat CNS as determined by autoradiography," Brain Res., 252:91-100 (1982).
Monsma et al., "Cloning and expression of a novel serotonin receptor with high affinity for tricyclic psychotropic drugs," Mol. Pharmacol., 43:320-327 (1993).
Mulheron et al., "Human 5-HT1A receptor expressed in insect cells activates endogenous G(o)-like G protein(s)," J. Biol. Chem., 269:12954-12962 (1994).
Muller-Enoch et al., "[6.7-Dihydroxycoumarin (Aesculetin) as a substrate for catechol-o-methyltransferase (author's transl)]," Z. Naturforsch., 31:280-284 (1976).
Munro et al., "Molecular characterization of a peripheral receptor for cannabinoids," Nature, 365:61-65 (1993).
Murphy et al., "Characterization of quisqualate recognition sites in rat brain tissue using DL-[3H]alpha-amino-3-hydroxy-5-methylisoxazole-4-propionic acid (AMPA) and a filtration assay," Neurochem. Res., 12:775-781 (1987).
Nagase et al., "Design and characterization of a fluorogenic substrate selectively hydrolyzed by stromelysin 1 (matrix metalloproteinase-3),"J. Biol. Chem., 269:20952-20957 (1994).
Nakamura et al., "Involvement of Oxidative Stress on Corneal Epithelial Alterations in a Blink-Suppressed Dry Eye," Investigative Ophthalmology and Visual Science, 48(4):1552-1558 (2007).
Negre-Salvayre et al., "Advanced Lipid Peroxidation End Products in Oxidative Damage to Proteins. Potential Role in Diseases and Therapeutic Prospects for the Inhibitors," Br J Pharmacol, 153(1):6-20 (2008).
Nema et al., "Excipients and Their Use in injectable Products," PDA J Pharm Sci Technol, 51(4):166-171 (1997).
Niwa et al., "Protein oxidative damage in the stratum corneum: Evidence for a link between environmental oxidants and the changing prevalence and nature of atopic dermatitis in Japan," Br J Dermatol., 149:248 (2003).
Nociari et al., "Beta cyclodextrins bind, stabilize, and remove lipofuscin bisretinoids from retinal pigment epithelium," Proc Natl Acad Sci U.S.A E1402-E1408 (2014).
Noorwez et al., "Pharmacological Chaperone-mediated in Vivo Folding and Stablization of the P23H-Opsin Mutant Associated with Autosomal Dominant Retinitis Pigmentosa," J Biol Chem, 278:14442-14450 (2003).
O'Brien et al., "Aldehyde Sources, Metabolism, Molecular Toxicity Mechanisms, and Possible Effects on Human Health," Crit Rev Toxicol, 35:609-662 (2005).

(56) References Cited

OTHER PUBLICATIONS

Obourn et al., "Hormone- and DNA-binding mechanisms of the recombinant human estrogen receptor," Biochemistry 32(24):6229 (1993).
Organisciak et al., "Susceptibility to Retinal Light Damage in Transgenic Rats with Rhodopsin Mutations," Invest Ophthalmol Vis Sci, 44(2):486-492 (2003).
Ousler et al., "Use of the Controlled Adverse Environment (CAE) in Clinical Research: A Review," Opthalmology and Therapy, Sep. 27, 2017, vol. 6, pp. 263-276.
Pacholczyk et al., "Expression cloning of a cocaine- and antidepressant-sensitive human noradrenaline transporter," Nature, 350:350-354 (1991).
Pal et al., "Sulfur mustard analog induces oxidative stress and activates signaling cascades in the skin of SKH-1 hairless mice," Free Radic Biol Med., 47(11):1640-51 (2009).
Palchaudhuri et al., "Corticotropin-releasing factor receptor type 1 from Tupaia belangeri-cloning, functional expression and tissue distribution," Eur. J. Biochem., 258:78-84 (1998).
Parish et al., "Isolation and One-Step Preparation of A2E and iso-A2E, Fluorophores from Human Retinal Pigment Epithelium," Proc Natl Acad Sci USA, 95(25):14609-14613 (1998).
Parracho et al., "Differences between the gut microflora of children with autistic spectrum disorders and that of healthy children," Journal of Medical Microbiology, 54:987-991 (2005).
Dente et al., "Modified phage peptide libraries as a tool to study specificity of phosphorylation and recognition of tyrosine containing peptides," J. Mol. Biol., 269:694-703 (1997).
Devedjian et al., "Further characterization of human alpha 2-adrenoceptor subtypes: [3H]RX821002 binding and definition of additional selective drugs," Eur. J. Pharmacol., 252:43-49 (1994).
Dolmotova et al., "Cardiomyocyte ATP release through pannexin 1 aids in early fibroblast activation," Am. J. Physiol Heart Circ Physiol 303(10):H1208-1218 (2012).
Dorje et al., "Antagonist binding profiles of five cloned human muscarinic receptor subtypes," J. Pharmacol. Exp. Ther., 256:727-733 (1991).
Dowling, "Neural and Photochemical Mechanisms of Visual Adaptation in the Rat," Journal of General Physiology, 46 (6):1287-1291 (1963).
Drysdale et al., "Complex Promoter and Coding Region Beta 2-adrenergic Receptor Haplotypes Alter Receptor Expression and Predict in vivo Responsiveness," Proc Natl Acad Sci USA, 97(19):10483-10488 (2000).
Egger, et al., "Keratinocyte growth factor ameliorates dextran sodium sulfate colitis in mice," Dig Dis Sci, 44(4): 836-44 (Apr. 1999).
Ellman et al., "A new and rapid colorimetric determination of acetylcholinesterase activity," Biochem. Pharmacol., 7: 88-95 (1961).
Erdos et al., "Neutral endopeptidase 24.11 (enkephalinase) and related regulators of peptide hormones," FASEB J. 3:145 (1989).
Ermolieff et al., "Proteolytic activation of recombinant pro-memapsin 2 (pro-beta-secretase) studied with new fluorogenic substrates," Biochemistry, 39:12450-12456 (2000).
Escalera et al., "Succinic semialdehyde dehydrogenase deficiency: decrease in 4-OH-butyric acid levels with low doses of vigabatrin," An Pediatr (Barc). 72(2):128-32 (2010).
Esterbauer et al., "Chemistry and Biochemistry of 4-Hydroxynonenal, Malonaldehyde and Related Aldehydes," Free Radic Biol Med, 11:81-128 (1991).
European Supplementary Partial Search Report issued by the European Patent Office for European Patent Application No. 13865015.5 dated Mar. 31, 2016 (9 pages).
European Supplementary Partial Search Report issued by the European Patent Office for European Patent Application No. 14743711.5 dated Jul. 20, 2016 (14 pages).
Everest-Todd, "Topical Application of Cyclodextrin Ethers in the Control of Pain," Proceedings of the Eighth International Symposium on Cyclodextrins, pp. 495-498 (1998).
FDA, "Bam R59: Phosphate-Buffered Saline (PBS), pH 7.4," Jan. 2001, retrieved online at <http://www.fda.gov/Food/FoodScienceR.esearch/LaboratoxyMethods/ucm062268.htm> on Apr. 18, 2015 (1 page).
Feighner et al., "Receptor for motilin identified in the human gastrointestinal system," Science, 284:2184-2188 (1999).
Fernandes et al., "Characterization of angiotensin-converting enzymes 1 and 2 in the soleus and plantaris muscles of rats," Braz J Med Biol Res., 43:837-842 (2010).
Ferry et al., "Binding of prostaglandins to human PPAR?: Tool assessment and new natural ligands," Eur. J. Pharmacol., 417:77-89 (2001).
Feve et al., "Transcriptional down-regulation by insulin of the beta 3-adrenergic receptor expression in 3T3-F442A adipocytes: a mechanism for repressing the cAMP signaling pathway," Proc Natl Acad Sci USA. 91:5677 (1994).
Fiske et al., "The Colormetric Determination of Phosphorus," J. Biol. Chem., 66:375-400 (1925).
Fitzmaurice et al., "Aldehyde dehydrogenase inhibition as a pathogenic mechanism in Parkinson disease," Proc. Natl Acad Sci U.S.A, 110(2):636-641 (2013).
Ford et al., "Pharmacological pleiotropism of the human recombinant alpha1A-adrenoceptor: implications for alphal-adrenoceptor classification," Brit. J. Pharmacol., 121:1127-1135 (1997).
Fowler et al., "Coloured Complexes of all-trans-retinal with Benzocaine and Other Local Anesthetics," J Photochem Photobiol B, 8(2):183-188 (1991).
Frantz et al., "The Activation State of p38 Mitogen-Activated Protein Kinase Determines the Efficiency of ATP Competition for Pyridinylimidazole Inhibitor Binding," Biochemistry, 37:13846-13853 (1998).
Friesen et al., "Optimization of a Tertiary Alcohol Series of Phosphodiesterase-4 (PDE4) Inhibitors: Structure-Activity Relationship Related to PDE4 Inhibition and Human Ether-a-go-go Related Gene Potassium Channel Binding Affinity," J. Med. Chem., 46(12):2413-2426 (2003).
Fuchs et al., "Functional characterization of three mutations of the endothelin B receptor gene in patients with Hirschsprung's disease: evidence for selective loss of Gi coupling," Mol. Med., 7:115-124 (2001).
Fukunaga et al., "Single nucleotide polymorphism of human platelet-activating factor receptor impairs G-protein activation," J. Biol. Chem., 276:43025-43030 (2001).
Full 1H NMR assignment for RAL-NS2 in CDCIJ, submitted to Japanese Patent Office Mar. 1, 2012.
Ganapathy et al., "Molecular and ligand-binding characterization of the sigma-receptor in the Jurkat human T lymphocyte cell line," JPET, 289:251-260 (1999).
Gasper et al., "2-Hydroxypropyl-beta-cyclodextrin (HP?CD) reduces age-related lipofuscin accumulation through a cholesterol-associated pathway," Scientific Reports, 7(2197):1-7 (2017).
Gibson et al., "Stable isotope dilution analysis of 4-hydroxybutyric acid: an accurate method for quantification in physiological fluids and the prenatal diagnosis of 4-hydroxybutyric aciduria," Biomed Environ Mass Spectrom., 19 (2):89-93 (1990).
Gibson et al., "Stable-isotope dilution analysis of D- and L-2-hydroxyglutaric acid: application to the detection and prenatal diagnosis of D- and L-2-hydroxyglutaric acidemias," Pediatr Res., 34(3):277-80 (1993).
Gibson et al., "The Aldehyde Trap NS2 Mitigates Dense Haze in a Rabbit Model of Photorefractive Keratectomy" ARVO Annual Meeting Abstract, 1 page (Jun. 2015).
Godard et al., "Sur les orthoamino formyl quinoleines, nouveaux synthons heterocycliques," J Heterocyclic Chem, 17 (3):465-473 (1980).
Gole et al., "Plasma Proteins Modified by Tyrosine Nitration in Acute Respiratory Distress Syndrome," Am J Physiol Lung Cell Mol Physiol, 2000, vol. 278, pp. L961-L967.
Gomez, "Dimethyltin(IV) 2,6-disubstituted pyridine complexes," J. Organometallic Chemistry, 672(2):115-122 (2003).
Good, "Measuring field loss in children administered vigabatrin: a problem in search of a solution," J AAPOS. 15 (5):411-2 (2011).

(56) References Cited

OTHER PUBLICATIONS

Gopalakrishnan et al., "Stable expression, pharmacologic properties and regulation of the human neuronal nicotinic acetylcholine alpha 4 beta 2 receptor," J. Pharmacol. Exp. Ther., 276:289-297 (1996).
Gould et al., "[3H]nitrendipine-labeled calcium channels discriminate inorganic calcium agonists and antagonists," Proc. Natl. Acad. Sci. U.S.A., 79:3656-3660 (1982).
Grandy et al., "Cloning of the cDNA and gene for a human D2 dopamine receptor," Proc. Natl. Acad. Sci. U.S.A., 86:9762-9766 (1989).
Green et al., "Characterization of [(3)H]-CGP54626A binding to heterodimeric GABA(B) receptors stably expressed in mammalian cells," Brit. J. Pharmacol., 131:1766-1774 (2000).
Green et al., "Influence of Various Agents on Corneal Permeability," American Journal of Ophthalmology, 72 (5):897-905 (1971).
Grob et al., "Die Synthese von 5-Oxy-benz(cd)indolin and dessen Umpagerung in 5-Keto-1,3,4,5-tetrahydro-benz(cd) indol," Helvetica Chimica Acta, Verlag Helvetica Chimica Acta, CH, 33(6):1796-1808 (1950) [Machine Translation].
Grob et al., "Die Synthese von 5-Oxy-benz(cd)indolin and dessen Umpagerung in 5-Keto-1,3,4,5-tetrahydro-benz(cd) indol," Helvetica Chimica Acta, Verlag Helvetica Chimica Acta, CH, 33(6):1796-1808 (1950).
Gromachevskaya et al., "4H-3,1-benzoxazines. 2. Synthesis of 2,4-substituted 1 2-dihydro-4H-3, 1-benzoxazines," Chemistry of Heterocyclic Compounds, 24(6):692-697 (Jun. 1988).
Grotto et al., "Importance of the lipid peroxidation biomarkers and methodological aspects for malondialdehyde quantification," Quim Nova, 32(1):169-174 (2009).
Halilovic et al., "ADX-103, a Novel Small Molecule Aldehyde Sequestering Agent, Decreases Retinal Edema and Inflammation in a Rat Model of Diabetic Macular Edema," ARVO Annual Meeting Abstract, 2 pages (Jul. 2018).
Hampson et al., "Cannabidiol and (-)Delta9-tetrahydrocannabinol are neuroprotective antioxidants," Proc. Nat. Acad. Sci 95:8268-8273 (1998).
Hassan et al., "Oxidative stress in systemic lupus erythematosus and rheumatoid arthritis patients: relationship to disease manifestations and activity," International Journal of Rheumatic Diseases, 14(1):325-331 (2011).
Bousquet et al., "Howto Design and Evaluate Randomized Controlled Trials in Immunotherapy for Allergic Rhinitis: An ARIA-GA2 Len Statement," Allergy, 66(6):765-774 (2011).
Boyer et al., "Lipofuscin and N-Retinylidene-N-Retinylethanolamine (A2E) Accumulate in Retinal Pigment Epithelium in Absence of Light Exposure," J Biol Chem, 287(26):22276-22286 (Jun. 2012).
Bozkir et al., "Effect of hydroxypropyl-beta-cyclodextrin on the solubility, stability and in-vitro release of ciprofloxacin for ocular drug delivery," Acta Poloniae Pharmaceutica, 69(4):719-24 (2012).
Bragagni et al., "Cyclodextrin complexation highly enhances efficacy of arylsulfonylureido benzenesulfonamide carbonic anhydrase inhibitors as atopical antiglaucoma agents," Bioorganic & Medicinal Chemistry, 23(18):6223-6227 (2015).
Brenneman et al., "Cannabidiol Provides Protection from Ethanol and Ammonium toxicity in a Hippocampal Model of Hepatic Encephalopathy," 24th Annual Symposium of the International Cannabinoid Research Society, Baveno, Italy, Jun. 28-Jun. 3, 2014 (p. 73).
Brenneman et al., "Small Molecule Anticonvulsant Agents with Potent In Vitro Neuroprotection," Journal of Molecular Neuroscience, 47(2):368-379 (2012).
Brewitt et al., "Dry Eye Disease—The Scale of the Problem," Survey of Ophthalmol, 45(Suppl 2):S199-S2 (Mar. 2001).
Bridion® (sugammadex) Injection Prescribing Information, for intravenous use, Initial U.S. Approval: 2015, Last Revised Dec. 2015 (19 pages).
Brockhaus, M. et al., "Identification of two types of tumor necrosis factor receptors on human cell lines by monoclonal antibodies," Proc. Natl. Acad. Sci. U.S.A., 87:3127-3131 (1990).
Brown, G.B., "3H-batrachotoxinin—A benzoate binding to voltage-sensitive sodium channels: inhibition by the channel blockers tetrodotoxin and saxitoxin," J. Neurosci., 6:2064-2070 (1986).
Brozek et al., "Grading quality of evidence and strength of recommendations in clinical practice guidelines: Part 2 of 3. The GRADE approach to grading quality of evidence about diagnostic tests and strategies," Allergy, 64(8):1109-1116 (2009).
Bryant, H.U. et al., "A novel class of 5-HT2A receptor antagonists: aryl aminoguanidines," Life Sci., 59(15): 1259-1268 (1996).
Bucciantini et al., "Inherent Toxicity of Aggregates Implies a Common Mechanism for Protein Misfolding Diseases," Nature, 416(6880):507-511 (2002).
Buchan, K.W. et al., "Characterization of three non-peptide endothelin receptor ligands using human cloned ETA and ETB receptors," Brit. J. Pharmacol., 112:1251-1257 (1994).
Buddi et al., "Evidence of oxidative stress in human corneal diseases," The Journal of Histochemistry and Cytochemistry: official journal of the Histochemistry Society, 50(3):341-351 (2002).
Bundgaard et al., "Glycolamide esters as biolabile prodrugs of carboxylic acid agents: Synthesis, Stability, bioconversion, and physicochemical properties," Journal of Pharmaceutical Sciences, 77(4):285-298 (1988).
Bundgaard, "Means to enhance penetration: (1) Prodrugs as a means to improve the delivery of peptide drugs," Advanced Drug Delivery Reviews, 8(1):1-38 (1992).
Burcham et al., "Aldehyde-Sequestering Drugs: Tools for Studying Protein Damage by Lipid Peroxidation Products," Toxicology, 181-182:229-236 (2002).
Burstein, "Preservative cytotoxic threshold for benzalkonium chloride and chlorhexidine digluconate in cat and rabbit corneas," Investigative Ophthalmology and Visual Science, 19(3):308-313 (1980).
Burstein, "The effects of topical drugs and preservatives on the tears and corneal epithelium in dry eye," Transactions of the Ophthalmological Societies of the United Kingdom, 104:402-409 (1985).
Canonica et al., "Recommendations for standardization of clinical trials with Allergen Specific Immunotherapy for respiratory allergy. A statement of a World Allergy Organization (WAO) taskforce," Allergy, 62(3):317-324 (2007).
Canonica et al., "Sub-lingual immunotherapy: World Allergy Organization Position Paper 2009," Allergy, 64(Suppl 91:1-59 (2009).
Casanaro et al., "A convenient solvent system for cellulose dissolution and derivatization: Mechanistic aspects of the acylation of the biopolymer in tetraallylammonium fluoride/dimethyl sulfoxide," Carbohydrate Polymers, 8(3):1395-1402 (2011).
Casanaro et al., "Efficacy of vigabatrin intervention in a mild phenotypic expression of succinic semialdehyde dehydrogenase deficiency," JIMD Rep. 2:119-23 (2011).
Cejkova et al., "The role of conjunctival epithelial cell xanthine oxidoreductase/xanthine oxidase in oxidative reactions on the ocular surface of dry eye patients with Sjogren's syndrome," Histol Histopathol 22(9):997-1003 (Sep. 2007).
Cesura et al., "Characterization of the binding of [3H]Ro 41-1049 to the active site of human monoamine oxidase-A," Mol. Pharmacol., 37:358-366 (1990).
Chapple et al., "Unfolding Retinal Dystrophies: a Role for Molecular Chaperones?" Trends Mol Med, 7(9):414-421 (2001).
Chen et al., "Methazolamide Calcium Phosphate Nanoparticles in an Ocular Delivery System," Pharm Soc Japan, 130 (3):419-24 (2010).
Cheng et al., "A synthetic peptide derived from p34cdc2 is a specific and efficient substrate of src-family tyrosine kinases," J. Biol. Chem., 267:9248-9256 (1992).
Chiarpotto et al., "Role of 4-hydroxy-2,3-nonenal in the pathogenesis of fibrosis," Biofactors, 24(1-4):229-36 (2005).
Chicchi et al., "Alterations in receptor activation and divalent cation activation of agonist binding by deletion of intracellular domains of the glucagon receptor," J. Biol. Chem., 272:7765-7769 (1997).
Choi et al., "Expression of Lipid Peroxidation Markers in the Tear Film and Ocular Surface of Patients with Non-Sjogren Syndrome: Potential Biomarkers for Dry Eye Disease," Curr Eye Res, 41(9):1143-11 (2016).

(56) References Cited

OTHER PUBLICATIONS

Choi et al., "The human serotonin 5-HT2B receptor: pharmacological link between 5-HT2 and 5-HT1D receptors," FEBS Lett., 352:393-399 (1994).
Ciolino et al., "Effect of alcaftadine 0.25% on ocular itch associated with seasonal or perennial allergic conjunctivitis: a pooled analysis of two multicenter randomized clinical trials," Clin Ophthalmol, 9:765-72 (May 2015).
Clark et al., "Inhibition of dexamethasone-induced cytoskeletal changes in cultured human trabecular meshwork cells by tetrahydrocortisol," Invest. Ophtalmol. Vis. Sci., 37:805-813 (1996).
Clinical Trials Results for Outcome Measures of Ocular Itching and Ocular Tearing (1 page) (2016).
Clinical Trials Results of Treatment with Aldehyde Trapping Compound NS2 (1 page) (2015).
Clinical Trials Results of Treatment with NS2 Topical Formulation (1 page) (2015).
ClinicalTrials.gov identifier NCT02402309, "A Study of Topical NS2 Cream to Treat Ichthyosis in Sjogren-Larsson Syndrome (SLS)," https://clinicaltrials.gov/ct2/show/NCT02402309 (3 pages) (2015).
ClinicalTrials.gov identifier NCT02406209, "A Safety and Efficacy Study of NS2 in Patients with Anterior Uveitis," https://clinicaltrials.gov/ct2/show/NCT02406209 (4 pages) (2015).
ClinicalTrials.gov identifier NCT02578914, "A Safety and Activity Study of NS2 in Subjects with Allergic Conjunctivitis," https://clinicaltrials.gov/ct2/show/NCT02578914 (6 pages) (2015).
Conover et al., "Thiazole Analogs of Pyridoxine," Journal of the American Chemical Society, 72(11):5221-5225 (1950).
Cooper et al., "Clinicopathologic study of dextran sulfate sodium experimental murine colitis," Lab Invest, 69(2):238-49 (Aug. 1993).
Couvineau et al., "Molecular identification and structural requirement of vasoactive intestinal peptide (VIP) receptors in the human colon adenocarcinoma cell line, HT-29," Biochem. J., 231:139-143 (1985).
Cullen et al., "Administration of the small molecule aldehyde trap NS2 in a hamster model of radiation-induced oral mucositis," ISOO 2015 Annual Meeting Abstract, Support Care Cancer, 23 (Suppl 1):S107 (Jun. 2015).
Cullen et al., "The small molecule aldehyde trap NS2 exhibits potent anti-inflammatory activity in three murine models of inflammation," AAAAI Annual Meeting Abstract, 1 page (Feb. 2015).
De Jong, "Age-Related Macular Degeneration," N Engl J Med, 355(14):1474-1485 (2006).
Del Valle, "Cyclodextrins and their uses: a review," Process Biochemistry, 39(9):1033-1046 (2004).
Demir et al., "Oxidative stress of intracameral lidocaine and levobupivacaine on ocular tissues," Br J Ophthalmol, 94 (8):1083-7 (Aug. 2010).
Demir et al., "The protective effect of alpha-lipoic acid against oxidative damage in rabbit conjunctiva and cornea exposed to ultraviolet radiation," Ophthalmologica, 219(1):49-53 (Jan.-Feb. 2005).
Herbort et al., "Endotoxin-induced uveitis in the rat," Graefe's Arch Clin Exp Ophthalmol, 226:553-8 (1988).
Heuillet et al., "Characterization of a Human NK1 Tachykinin Receptor in the Astrocytoma Cell Line U 373 MG," J. Neurochem., 60:868-876 (1993).
Hogema et al., "Pharmacologic rescue of lethal seizures in mice deficient in succinate semialdehyde dehydrogenase," Nat Genet. 29:212-16 (2001).
Hope et al., "Characterization of a human 5-hydroxytryptamine3 receptor type A (h5-HT3R-AS) subunit stably expressed in HEK 293 cells," Brit. J. Pharmacol., 118:1237-1245 (1996).
Horner et al., "Analogs of 3-Amino-7-chloro-1,2,4-benzotriazine 1-Oxide as Antimalarial Agents," J. Med. Chem., 11 (5):946-949 (1968).
Hoyer et al., "Characterization of the 5-HT1B recognition site in rat brain: binding studies with (-)[125I] iodocyanopindolol," Eur. J. Pharmacol., 118:1-12 (1985).

Huang et al., "Characterization of Calcium Phosphate Nanoparticles Based on a PEGylated Chelator for Gene Delivery," ACS Appl Mater Interfaces, 9:10435?10445 (Mar. 2017).
Huang et al., "Identification of human Ether-a-go-go related gene modulators by three screening platforms in an academic drug-discovery setting," Assay Drug Dev Technol., 8(6):727-42 (2010).
Huang et al., "Novel peptide inhibitors of angiotensin-converting enzyme 2," J. Biol. Chem., 278:15532-15540 (2003).
Hubbard, "Geometrical Isomerization of Vitamin A, Retinene and Retinene Oxime," Journal of the American Chemical Society, 78(18):4662-4667 (1956).
Hugues et al., "Preparation of a pure monoiodo derivative of the bee venom neurotoxin apamin and its binding properties to rat brain synaptosomes," J. Biol. Chem., 257:2762-2769 (1982).
Hurd et al., "Reaction of Propiolactone with Aniline Derivatives," Journal of the American Chemical Society, 74 (23):5889-5893 (1952).
Inoue et al., "Filter-binding assay procedure for thyroid hormone receptors," Anal Biochem. 134(1):176 (1983).
Iriyama et al., "A2E, a pigment of the lipofuscin of retinal pigment epithelial cells, is an endogenous ligand for retinoic acid receptor," J Biol Chem., 283(18):11947-53 (2008) Epub Mar. 6, 2008.
Ishida et al., "Stabilization of calmodulin-dependent protein kinase II through the autoinhibitory domain," J. Biol. Chem., 270:2163-2170 (1995).
Ito et al., "A Medium-Term Rat Liver Bioassay for Rapid in vivo Detection of Carcinogenic Potential of Chemicals," Cancer Science, 94(1):3-8 (2003).
Itokawa et al., "Antiangiogenic effect by SU5416 is partly attributable to inhibition of Flt-1 receptor signaling," Mol. Cancer Ther., 1:295-302 (2002).
Jafari et al., "Evaluation of plasma, erythrocytes, and bronchoalveolar lavage fluid antioxidant defense system in sulfur mustard-injured patients," Clin Toxicol (Phila)., 48(3):184-92 (2010).
Janowski et al., "Structural requirements of ligands for the oxysterol liver X receptors LXRalpha and LXRbeta," Proc. Natl. Acad. Sci. USA, 96:266-271 (1999).
Jarrett et al., "Mitochondrial DNA damage and impaired base excision repair during epileptogenesis," Neurobiology of Disease, 30(1):130-138 (2008).
Ji et al., "Exploration of diverse hinge-binding scaffolds for selective Aurora kinase inhibitors," Bioorg. & Med. Chem. Let. 22:4528 (2012).
Johannsdottir et al., "Development of a Cyclodextrin-Based Aqueous Cyclosporin A Eye Drop Formulations," International Journal of Pharmaceutics, 493(1-2):86-95 (2015).
Johnson et al., "2-Hydroxypropyl-ß-Cyclodextrin Removes All-Trans Retinol from Frog Rod Photoreceptors in a Concentration-Dependent Manner," Journal of Ocular Pharmacology and Therapeutics, 26(3):245-248 (2010).
Joseph et al., "Binding of (-)-[3H]-CGP12177 at two sites in recombinant human beta 1-adrenoceptors and interaction with beta-blockers," Naun.-Sch. Arch. Pharm., 369:525-532 (2004).
Kam et al., "Topical Cyclodextrin Reduces Amyloid Beta and Inflammation Improving Retinal Function in Ageing Mice," Experimental Eye Research, 135:59-66 (2015).
Kamino et al., "Deficiency in mitochondrial aldehyde dehydrogenase increases the risk for late-onset Alzheimer's disease in the Japanese population," Biochemical and Biophysical Research Communications, 273(1):192-196 (2000).
Karahashi et al., "Changes of caspase activities involved in apoptosis of a macrophage-like cell line J774.1/JA-4 treated with lipopolysaccharide (LPS) and cycloheximide," Biol. Pharm. Bull., 23:140-144 (2000).
Karan et al., Lipofuscin Accumulation, Abnormal Electrophysiology, and Photoreceptor Degeneration in Mutant ELOVL4 Transgenic Mice: A Model for Macular Degeneration, Proc Natl Acad Sci USA, 102(11):4164-4169 (2005).
Katugampola et al., "[(125)I]-(Pyr(1))Apelin-13 is a novel radioligand for localizing the APJ orphan receptor in human and rat tissues with evidence for a vasoconstrictor role in man," Brit. J. Pharmacol., 132:1255-1260 (2001).

(56) References Cited

OTHER PUBLICATIONS

Kenney et al., "The Cascade Hypothesis of Keratoconus," Contact Lens & Ant Eye, 26:139-146 (2003).
Keri, "Rosacea," Merck Manual, Professional Version, https://www.merckmanuals.com/professional/dermatologic-disorders/acne-and-related-disorders/rosacea, 7 pages (2017).
Knapp et al., "Intraocular Availability of Topically Applied Mycophenolate Mofetil in Rabbits," J. Ocul. Pharmacol. Ther., 19(2):181-192 (2003).
La Rosa et al., "Allergic conjunctivitis: a comprehensive review of the literature," Ital J Pediatr, 39:18 (2013).
Landor et al., "Allenes. Part 49, 4-Amino-2-(1-hydroxyalkyl)quinolones from Phenylhydroxylamine and Allenic Nitrites," J Chem Soc Perkin Trans 1, pp. 251-254 (1989).
Langin et al., "[3H]RX821002: a new tool for the identification of alpha 2A-adrenoceptors," Eur. J. Pharmacol., 167:95-104 (1989).
Lankin et al., "Role of Oxidative Stress in the Genesis of Atherosclerosis and Diabetes Mellitus: A Personal Look Back on 50 Years of Research," Curr. Aging Sci. 10:18 (2017).
Le et al., "Ligand binding and functional properties of human angiotensin AT1 receptors in transiently and stably expressed CHO-K1 cells," Eur. J. Pharmacol., 513:35-45 (2005).
Lee et al., "Human recombinant soluble guanylyl cyclase: expression, purification, and regulation," Proc. Natl. Acad. Sci. USA, 97(20):10763-10768 (2000).
Lee et al., "The human brain cholecystokinin-B/gastrin receptor. Cloning and characterization," J. Biol. Chem., 268:8164-8169 (1993).
Leibundgut et al., "Oxidation-specific epitopes and immunological responses: Translational biotheranostic implications for atherosclerosis," Current Opinion in Pharmacology, 13(2):168-179 (2013).
Leonardi et al., "Correlation Between Conjunctival Provocation Test (CPT) and Systemic Allergometric Tests in Allergic Conjunctivitis," Eye, 4:760-764 (1990).
Leurs et al., "Pharmacological characterization of the human histamine H2 receptor stably expressed in Chinese hamster ovary cells," Brit. J. Pharmacol., 112: 847-854 (1994).
Levin et al., "The myocardium-protective Gly-49 variant of the beta 1-adrenergic receptor exhibits constitutive activity and increased desensitization and down-regulation," J. Biol.Chem., 277:30429-30435 (2002).
Lewin et al., "meta- and para-isothiocyanato-t-butylbicycloorthobenzoate: irreversible ligands of the gamma-aminobutyric acid-regulated chloride ionophore," Mol. Pharmacol., 35:189-194 (1989).
Li et al., "Effect of Vitamin A Supplementation on Rhodopsin Mutants Threonine-17 -> Methionine and Proline-347 -> Serine in Transgenic Mice and in Cell Cultures," Proc Natl Acad Sci USA, 95(20):11933-11938 (1998).
Liu et al., "Comparison of human, mouse, rat, and guinea pig histamine H4 receptors reveals substantial pharmacological species variation," J. Pharmacol. Exp. Ther., 299:121-130 (2001).
Loftsson et al., "Cyclodextrin Microparticles for Drug Delivery to the Posterior Segment of the Eye: Aqueous Dexamethasone Eye Drops," Journal of Pharmacy and Pharmacology, 59(5):629-635 (2007).
Loftsson et al., "Cyclodextrins in Eye Drop Formulations: Enhanced Topical Delivery of Corticosteroids to the Eye," Acta Ophthalmologica Scandinavica, 80(2):144-150 (2002).
Lovenberg et al., "Cloning and functional expression of the human histamine H3 receptor," Mol. Pharmacol., 55:1101-1107 (1999).
Lukas, R.J., "Characterization of curaremimetic neurotoxin binding sites on membrane fractions derived from the human medulloblastoma clonal line, TE671," J. Neurochem., 46:1936-1941 (1986).
"Shin iyakuhin no kikaku oyobi shaken houhou no settei nituite nituite (Regarding the setting of the standard and test method of a new medical product" PMSB/ELD Notification No. 568, May 2001, 46 pages (Only Official Copy).
Aldeyra Therapeutics, "Positive Results from Phase IIa Clinical Trials in Subjects with Allergic Conjunctivitis", Press Release, Feb. 29, 2016, 3 pages.

Caira, "Crystalline Polymorphism of Organic Compounds", Topics in Current Chemistry, Jan. 1999, 198:163-208.
Ellis et al., "Multiple Doses of Trodusquemine Improve Glucose Tolerance in Type 2 Diabetic Subjects," 69th Scientific Sessions of the American Diabetes Association, Abstract No. 2071-PO, 2009, 2 pages.
Kawaguchi et al., "Drug and crystal polymorphism," Journal of human environmental engineering, 2002, 4(2):310-317.
Leonardi, "Allergy and allergic mediators in tears," Exp. Eye Res., 2013, 117:106-117.
Maghsoodi et al., "Physicomechanical Properties of Naproxen-Loaded Microparticles Prepared from Eudragit L100", AAPS PharmSciTech., Mar. 2009, 10(1):120-128.
*Neptune Generics, LLC* v. *Auspex Pharmaceuticals, Inc.*, IPR2015-01313, Paper No. 25, Dec. 9, 2015, 23 pages.
Nielsen and Bundgaard, "Glycolamide esters as biolabile prodrugs of carboxylic acid agents: synthesis, stability, bioconversion, and physicochemical properties," J Pharm Sci. 1988, 77(4):285-298.
Noriyuki Takada "Souyaku dankai ni okeru genyaku Form sukuri ningu to sentaku (Bulk drug screening and selection in a drug development phase," Pharm Stage, Jan. 2007, 6(10):20-25.
Ono, "Analysis of Salt Selection of Current Active Pharmaceutical Ingredients (API)," Journal of Pharmaceutical Science and Technology, 2013, 73(3):176-182.
Park et al., "Modulation of Acute Inflammation and Keratocyte Death by Suturing, Blood, and Amniotic Membrane in PRK," Invest. Opthalmol Vis Sci. 2000, 41(10):2906-2914.
Pubchem CID 149143404, Aug. 12, 2020, 2 pages.
Pubchem CID 4391047, Sep. 14, 2005, 2 pages.
Quinlan et al., "4-Hydroxy-2-Nonenal Levels Increase in the Plasma of Patients with Adult Respiratory Distress Syndrome as Linoleic Acid Appears to Fall," Free Radic Res. 1994, 21(2):95-106.
Rajewski et al., "Pharmaceutical applications of cyclodextrins. 2. In vivo drug delivery," J Pharm Sci, 1996; 85(11):1142-1169.
Reproxalap (Medchem Express), 2013, 3 pages.
Ricca et al., "Amphetamine derivatives and obesity," Appetite, Apr. 2009, 52(2):405-409.
Rizzo et al., "Aldehyde Trapping Agent NS2 Blocks Formation of Fatty Aldehyde Adducts with Phosphatidylethanolamine and Suggests Potential Therapeutic Approach for Sjogren-Larsson Syndrome," Mol Genet and Metab, 114(3):362A (Mar. 2015) [Abstract Only].
Rizzo, Fatty aldehyde and fatty alcohol metabolism: review and importance for epidermal structure and function, Biochim Biophys Acta, Mar. 2014, 1841(3):377-389.
Rizzo, "Genetics and prospective therapeutic targets for Sjogren-Larsson Syndrome," Expert Ooin Orphan Druos. 2016, 4(4):395-406.
Saal, et al. "Pharmaceutical salts: A summary on doses of salt formers from the Orange Book", European Journal of Pharmaceutical Sciences, Jul. 16, 2013, 49(4):614-623.
Serajuddin, "Salt formation to improve drug solubility," Adv Drug Deliv Rev., 2007, 59(7):603-616.
Smalley, Science of Synthesis, 2002, 11:289.
Tanna et al., "Stargardt disease: clinical features, molecular genetics, animal models and therapeutic options," Br J Ophthalmol. 2017; 101 (1):25-30.
Tripathi et al., "Monoamine oxidase-B inhibitors as potential neurotherapeutic agents: An overview and update", Med Res Rev. Sep. 2019, 39(5):1603-1706.
Wermuth, "The Practice of Medicinal Chemistry," Elsevier, Second vol. 1999, pp. 347-365.
Yamano, "Approach to Crystal Polymorph in Process Research of New Drug," Journal of Synthetic Organic Chemistry, 2007, 65:907-913.
Yoko et al., "Drug and Crystal Polymorphism", Journal of Human Environmental Engineering, 2002, 4(2):310-317.
Young et al., "NS2, a novel aldehyde trap, decreases aldehyde levels in dry skin and eye models," Aldeyra therapeutics, 2014, 1 page.
Extended European Search Report received for European Patent Application No. 13865015.5 dated Mar. 31, 2016, 9 pages.
Extended European Search Report received for European Patent Application No. 19891719.7 dated Jul. 27, 2022, 9 pages.

(56) References Cited

OTHER PUBLICATIONS

Partial Supplementary European Search Report received for European Patent Application No. 14743711.5 dated Jul. 20, 2016, 14 pages.
PCT International Preliminary Report on Patentability received for PCT/US2013/076592, dated Jul. 2, 2015, 7 pages.
PCT International Preliminary Report on Patentability received for PCT/US2014/012356, dated Jul. 28, 2015, 7 pages.
PCT International Preliminary Report on Patentability received for PCT/US2014/012762, dated Aug. 6, 2015, 9 pages.
PCT International Preliminary Report on Patentability received for PCT/US2016/048054, dated Mar. 8, 2018, 6 pages.
PCT International Preliminary Report on Patentability received for PCT/US2016/048064, dated Mar. 8, 2018, 7 pages.
PCT International Preliminary Report on Patentability received for PCT/US2017/020020, dated Sep. 7, 2018, 10 pages.
PCT International Preliminary Report on Patentability received for PCT/US2017/047945, dated Mar. 7, 2019, 7 pages.
PCT International Preliminary Report on Patentability received for PCT/US2017/047958, dated Mar. 7, 2019, 08 pages.
PCT International Preliminary Report on Patentability received for PCT/US2018/023000, dated Sep. 26, 2019, 7 pages.
PCT International Preliminary Report on Patentability received for PCT/US2018/055310, dated Apr. 23, 2020, 6 pages.
PCT International Preliminary Report on Patentability received for PCT/US2019/052961, dated Apr. 8, 2021, 9 pages.
PCT International Preliminary Report on Patentability received for PCT/US2019/054263, dated Apr. 15, 2021, 11 pages.
PCT International Preliminary Report on Patentability received for PCT/US2019/064669, dated Jun. 17, 2021, 10 pages.
PCT International Preliminary Report on Patentability received for PCT/US2020/024022, dated Oct. 7, 2021, 9 pages.
PCT International Preliminary Report on Patentability received for PCT/US2020/031138, dated Nov. 11, 2021, 6 pages.
PCT International Preliminary Report on Patentability received for PCT/US2020/031219, dated Nov. 11, 2021, 11 pages.
PCT International Preliminary Report on Patentability received for PCT/US2021/023884, dated Oct. 6, 2022, 8 pages.
PCT International Preliminary Report on Patentability received for PCT/US2021/027148, dated Oct. 27, 2022, 7 pages.
PCT International Preliminary Report on Patentability received for PCT/US2021/032335, dated Nov. 24, 2022, 9 pages.
PCT International Preliminary Report on Patentability received for PCT/US2021/035948, dated Dec. 15, 2022, 8 pages.
PCT International Search Report and Written Opinion received for PCT/CN2022/113284, dated Nov. 2, 2022, 6 pages.
PCT International Search Report and Written Opinion received for PCT/US2006/020320, dated Sep. 26, 2006, 10 pages.
PCT International Search Report and Written Opinion received for PCT/US2010/059719, dated Feb. 8, 2011, 8 pages.
PCT International Search Report and Written Opinion received for PCT/US2013/076592, dated Apr. 30, 2014, 10 pages.
PCT International Search Report and Written Opinion received for PCT/US2014/012356, dated May 30, 2014, 11 pages.
PCT International Search Report and Written Opinion received for PCT/US2016/048064, dated Nov. 15, 2016, 8 pages.
PCT International Search Report and Written Opinion received for PCT/US2017/047958, dated Oct. 31, 2017, 10 pages.
PCT International Search Report and Written Opinion received for PCT/US2019/041942, dated Sep. 30, 2019, 18 pages.
PCT International Search Report and Written Opinion received for PCT/US2019/044929, dated Nov. 20, 2019, 15 pages.
PCT International Search Report and Written Opinion received for PCT/US2020/024022, dated Jun. 17, 2020, 11 pages.
PCT International Search Report and Written Opinion received for PCT/US2020/050565, dated Dec. 22, 2020, 9 pages.
PCT International Search Report and Written Opinion received for PCT/US2022/011604, dated Mar. 25, 2022, 12 pages.
PCT International Search Report and Written Opinion received for PCT/US2019/069097 dated Apr. 30, 2020, 9 pages.
Search Report and Written Opinion received by the Intellectual Property Office of Singapore for Singapore Patent Application No. 11201504859Y dated Aug. 1, 2016, 12 pages.
Search Report and Written Opinion received by the Intellectual Property Office of Singapore for Singapore Patent Application No. 11201505587Y, dated Jul. 12, 2016 (12 pages).
Search Report and Written Opinion received by the Intellectual Property Office of Singapore for Singapore Patent Application No. 11201505599Y dated Sep. 14, 2016 (5 pages).
U.S. Appl. No. 15/437,699 of Jordan et al., filed Feb. 21, 2017.
U.S. Appl. No. 16/547,930 of Buist et al., filed Aug. 22, 2019.
U.S. Appl. No. 17/305,915 of Machatha et al., filed Jul. 16, 2021.

POLYMORPHIC COMPOUNDS AND USES THEREOF

CROSS-REFERENCE TO RELATED APPLICATIONS

This application is a continuation of PCT International Application No. PCT/US2020/031138, filed May 1, 2020, which claims the benefit under 35 U.S.C. § 119(e) of U.S. Provisional Application No. 62/841,900, filed May 2, 2019, the contents of each of which are incorporated herein by reference in its entirety.

FIELD OF THE INVENTION

The present disclosure relates to various forms and compositions of small molecule therapeutics acting as a scavenger for toxic aldehydes, and their use for treating diseases, disorders, or conditions in which aldehyde toxicity is implicated in their pathogenesis.

BACKGROUND OF THE INVENTION

Metabolic and inflammatory processes in cells generate toxic aldehydes, such as malondialdehyde (MDA), 4-hydroxyl-2-nonenal (4-HNE), glyoxal, and methylglyoxal. These aldehydes are highly reactive with proteins, carbohydrates, lipids and DNA, leading to chemically modified biological molecules, activation of inflammatory mediators such as NF-kappa B, and damage in diverse organs. For example, retinaldehyde can react with phosphatidylethanolamine (PE) to form a highly toxic compound called A2E, which is a component of lipofuscin that is believed to be involved in the development and progression of Age-Related Macular Degeneration (AMD). Many bodily defense mechanisms function to remove or lower the levels of toxic aldehydes, including metabolism by aldehyde dehydrogenases, buffering by molecules such as glutathione (GSH) and removal from sites of potential toxicity by transporters such as ABCA4. Novel small molecule therapeutics can be used to scavenge "escaped" retinaldehyde in the retina, thus reducing A2E formation and lessening the risk of AMD (see, e.g., WO2006127945 by Jordan et al.).

Aldehydes are implicated in diverse pathological conditions such as dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., systemic lupus erythematosus (SLE) and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents (Negre-Salvayre et al., British J Pharmacol., 2008; 153:6-20; Nakamura et al., Investigative Ophthalmology & Visual Sci., 2007; 48(4):1552-1558; Batista et al., PLoS ONE, 2022 7(3):e33814; Kenney et al., Contact Lens & Anterior Eye, 2003, 26:139-146; Baz et al., Int J Dermatol., 2004; 43(7): 494-7; Nakamura et al., Invest Ophthalmol Vis Sci., 2007; 48(4):1552-8; Augustiin et al., Graefe's Arch Clin Exp Ophthalmol., 1994; 233:694-698; Batista et al., Molecular Vision., 2012; 18:194-202). Decreasing or eliminating aldehydes should thus ameliorate the symptoms and slow the progression of these pathological conditions.

MDA, 4-HNE and other toxic aldehydes are generated by a myriad of metabolic mechanisms involving fatty alcohols, sphingolipids, glycolipids, phytol, fatty acids, arachidonic acid metabolism (Rizzo, Mol Genet Metab., 2007; 90(1):1-9), polyamine metabolism (Wood et al., Brain Res., 2006; 1122:134-190), lipid peroxidation, oxidative metabolism (Buddi et al., J Histochem Cytochem., 2002; 50(3):341-351; Zhou et al., J Biol Chem., 2005; 280(27):25377-25382), and glucose metabolism (Pozzi et al., J Am Soc Nephrol, 2009; 20(10):2119-2125). Aldehydes can cross link with primary amino groups and other chemical moieties on proteins, phospholipids, carbohydrates, and DNA, leading in many cases to toxic consequences, such as mutagenesis and carcinogenesis (Marnett, Toxicology, 2002; 181-182:219-222). MDA is associated with diseased corneas in conditions such as keratoconus, bullous and other keratopathy, and Fuchs' endothelial dystrophy (Buddi et al., J Histochem Cytochem., 2002; 50(3):341-351). Also, a dysfunctional dermal water barrier in skin disorders such as Sjögren-Larsson Syndrome, are likely connected with the accumulation of fatty aldehydes, including octadecanal and hexadecanal (Rizzo et al., Arch Dermatol Res., 2010; 302:443-451). Further, increased lipid peroxidation and resultant aldehyde generation are associated with the toxic effects of blister agents (Sciuto et al., Inhalation Tech., 2004; 16:565-580) and Pal et al., Free Radic Biol Med., 2009; 47(11):1640-1651).

Thus, there is a need for treating, preventing, and/or reducing a risk of a disease, disorder or condition in which aldehyde toxicity is implicated in the pathogenesis.

SUMMARY OF THE INVENTION

It has now been found that compounds of the present invention, and compositions thereof, are useful for treating, preventing, and/or reducing a risk of a disease, disorder, or condition in which aldehyde toxicity is implicated in the pathogenesis. In general, salt forms or free base forms, and pharmaceutically acceptable compositions thereof, are useful for treating or lessening the severity of a variety of diseases, disorders, or conditions as described in detail herein. Such compounds are represented by the chemical structure below, denoted as Compound A:

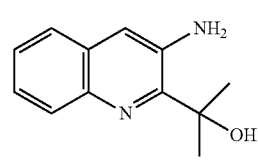

or a pharmaceutically acceptable salt thereof.

Compounds of the present invention, and pharmaceutically acceptable compositions thereof, are useful for treating a variety of diseases, disorders or conditions, associated with toxic aldehydes. Such diseases, disorders, or conditions include those described herein.

Compounds provided by this invention are also useful for the study of certain aldehydes in biological and pathological phenomena.

DETAILED DESCRIPTION OF THE INVENTION

Figure 1:
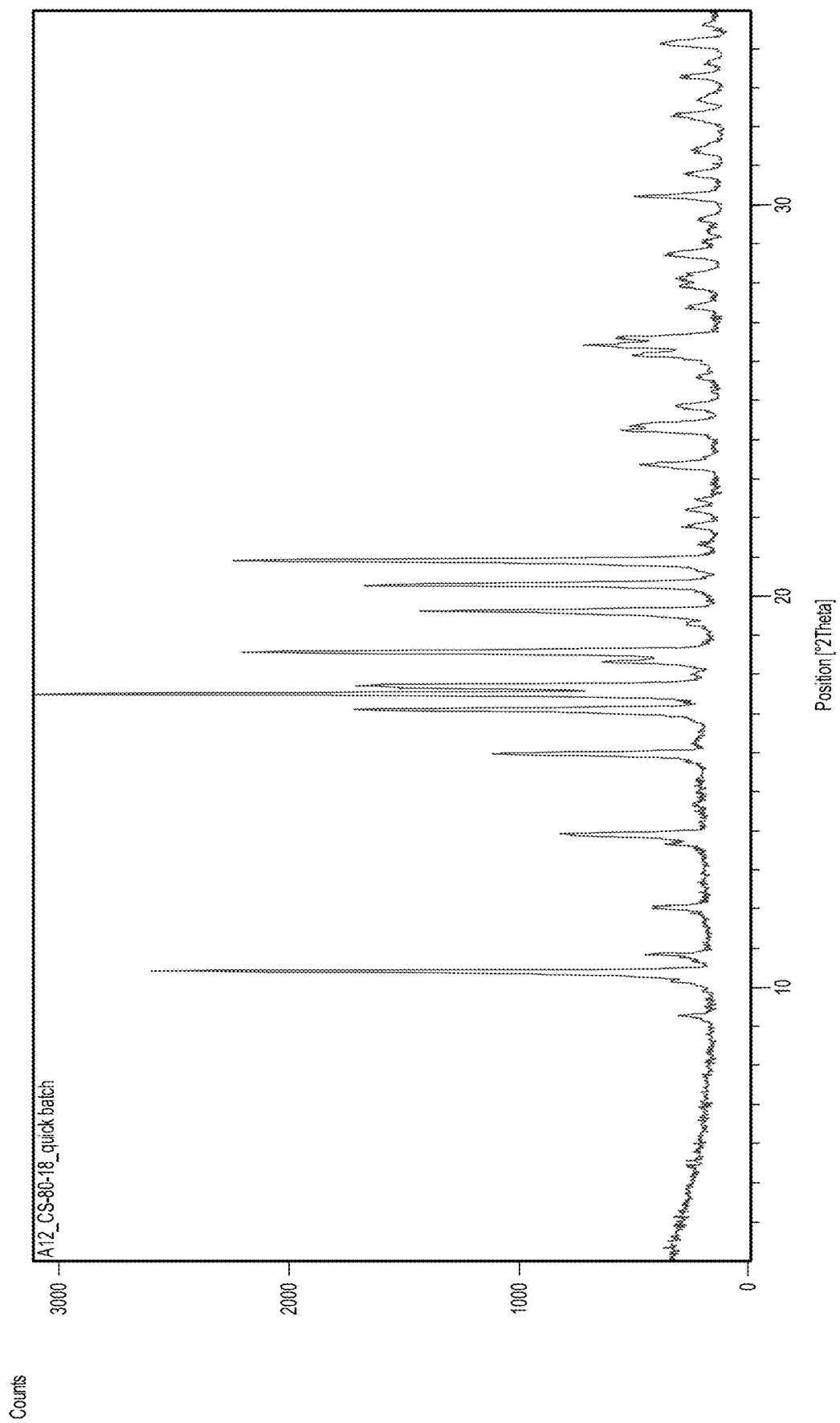
FIG. 1 depicts the XRPD pattern of Compound A, Form A.

I. General Description of Certain Aspects of the Invention

It would be desirable to provide a solid form of Compound A (e.g., as a free base thereof or salt thereof) that imparts characteristics such as improved aqueous solubility, stability and ease of formulation. Accordingly, the present invention provides both free base forms and salt forms of Compound A:

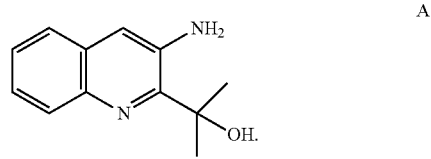

A

1. Free Base Forms of Compound A

It is contemplated that Compound A can exist in a variety of physical forms. For example, Compound A can be in solution, suspension, or in solid form. In certain embodiments, Compound A is in solid form. When Compound A is in solid form, the compound may be amorphous, crystalline, or a mixture thereof. Exemplary solid forms are described in more detail below.

In some embodiments, the present invention provides a form of Compound A substantially free of impurities. As used herein, the term "substantially free of impurities" means that the compound contains no significant amount of extraneous matter. Such extraneous matter may include different forms of Compound A, residual solvents, or any other impurities that may result from the preparation of, and/or isolation of, Compound A. In some embodiments, the "impurities" and their levels can be determined by HPLC according to the procedures set forth in the Examples for the relevant solid forms of Compound A.

In some embodiments, at least about 95% by weight of a form of Compound A is present. In still other embodiments of the invention, at least about 99% by weight of a form of Compound A is present.

In some embodiments, a form of Compound A is present in an amount of at least about 97, 97.5, 98.0, 98.5, 99, 99.5, 99.8 weight percent where the percentages are based on the total weight of the composition. In some embodiments, a form of Compound A contains no more than about 3.0 area percent HPLC of total organic impurities and, in certain embodiments, no more than about 1.5 area percent HPLC total organic impurities relative to the total area of the HPLC chromatogram. In some embodiments, a form of Compound A contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for a form of Compound A is also meant to include all tautomeric forms of Compound A. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

As used herein, the term "polymorph" refers to the different crystal structures into which a compound, or a salt or solvate thereof, can crystallize.

In certain embodiments, Compound A is a crystalline solid. In some embodiments, Compound A is a crystalline solid substantially free of amorphous Compound A. As used herein, the term "substantially free of amorphous Compound A" means that the compound contains no significant amount of amorphous Compound A. In some embodiments, at least about 95% by weight of crystalline Compound A is present. In still other embodiments of the invention, at least about 99% by weight of crystalline Compound A is present.

It has been found that Compound A can exist in a variety of solid forms. Exemplary such forms include polymorphs such as those described herein.

In some embodiments, Compound A is amorphous. In some embodiments, Compound A is amorphous, and is substantially free of crystalline Compound A.

a. Form A of Compound A

In some embodiments, Form A of Compound A has at least 1, 2, 3, 4, 5 or more spectral peak(s) selected from the peaks listed in Table 1 below. In some embodiments, the peak(s) with relatively highest intensity peak(s) are selected.

TABLE 1

XRPD Peak Positions for Form A of Compound A

| Pos. [°2Th.] | d-spacing [Å] | Rel. Int. [%] |
|---|---|---|
| 9.3 | 9.55 | 4.35 |
| 10.4 | 8.49 | 81.69 |
| 10.9 | 8.15 | 9.83 |
| 12.1 | 7.33 | 8.44 |
| 13.7 | 6.48 | 6.51 |
| 13.9 | 6.35 | 21.39 |
| 16.0 | 5.54 | 31.73 |
| 17.1 | 5.18 | 52.98 |
| 17.5 | 5.07 | 100 |
| 17.6 | 5.03 | 41.77 |
| 17.7 | 5.01 | 49.62 |
| 18.3 | 4.84 | 16.55 |
| 18.6 | 4.78 | 68.6 |
| 19.7 | 4.53 | 43.7 |
| 20.3 | 4.38 | 51.66 |
| 20.9 | 4.25 | 70.46 |
| 21.3 | 4.17 | 1.67 |
| 21.8 | 4.08 | 4.36 |
| 22.2 | 4.0 | 4.18 |
| 22.5 | 3.96 | 2.83 |
| 23.4 | 3.81 | 11.17 |
| 24.2 | 3.67 | 13.97 |
| 24.4 | 3.65 | 11.26 |
| 24.9 | 3.58 | 5.29 |
| 25.6 | 3.48 | 2.46 |
| 26.1 | 3.41 | 12.02 |
| 26.4 | 3.37 | 19.22 |
| 26.6 | 3.35 | 14.25 |
| 27.4 | 3.26 | 3.65 |
| 27.9 | 3.20 | 5.23 |
| 28.2 | 3.17 | 4.55 |
| 28.7 | 3.11 | 7.49 |
| 29.0 | 3.08 | 1.59 |
| 29.6 | 3.02 | 2.61 |
| 30.2 | 2.96 | 12.62 |
| 30.8 | 2.91 | 4.75 |
| 31.3 | 2.86 | 3.27 |
| 32.3 | 2.77 | 5.82 |
| 32.7 | 2.74 | 2.93 |
| 33.3 | 2.69 | 4.66 |
| 33.6 | 2.66 | 1.56 |
| 34.1 | 2.63 | 5.84 |
| 34.6 | 2.59 | 2.15 |

[1] In this and all subsequent tables, the position 2θ is within ± 0.2.

In some embodiments, Form A of Compound A is characterized in that it has one or more peaks in its X-ray powder diffraction (XRPD) pattern selected from those at about 10.4, about 17.5, and about 20.9 degrees 2-theta. In some embodiments, Form A of Compound A is characterized in that it has two or more peaks in its X-ray powder diffraction pattern selected from those at about 10.4, about 17.5, and about 20.9 degrees 2-theta. In some embodiments, Form A of Compound A is characterized in that it has all three peaks in its X-ray powder diffraction pattern at about 10.4, about 17.5, and about 20.9 degrees 2-theta. In some embodiments, Form A of Compound A is further characterized by additional 1, 2, 3, 4 or 5 peak(s) selected from Table 1. As used herein, the term "about", when used in reference to a degree 2-theta value, refers to the stated value±0.2 degree 2-theta.

In some embodiments, the X-ray powder diffraction pattern is substantially similar to the XRPD provided in FIG. 1.

Figure 2:
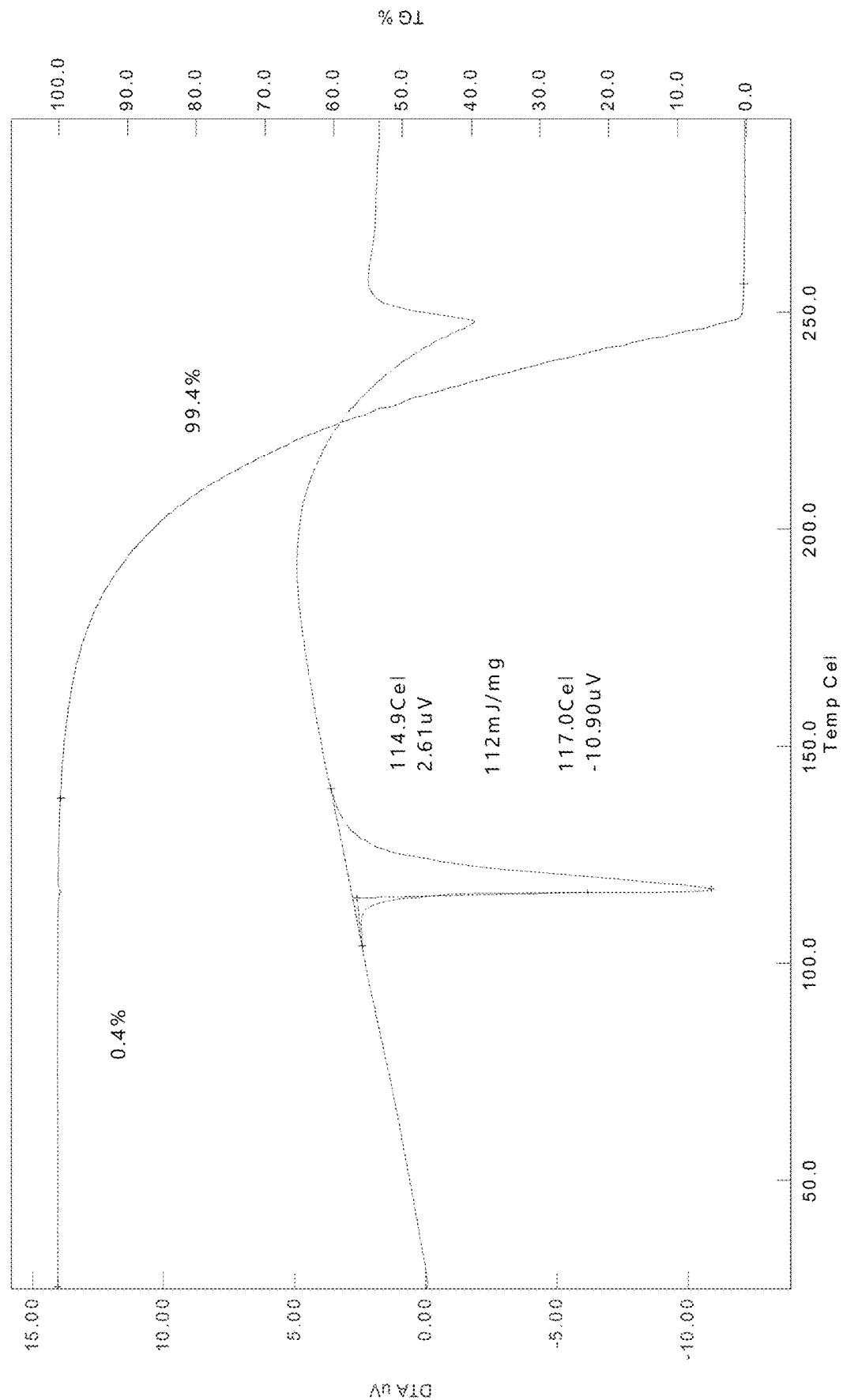
FIG. 2 depicts a DSC thermogram and TGA trace of Compound A, Form A.

In some embodiments, Form A of Compound A is characterized by a differential scanning calorimetry (DSC) thermogram having the endothermic peak(s) as shown in FIG. 2. In some embodiments, Form A of Compound A has a DSC thermogram substantially the same as that shown in FIG. 2.

Methods for preparing Form A of Compound A are described infra.

In some embodiments, the present invention provides Compound A:

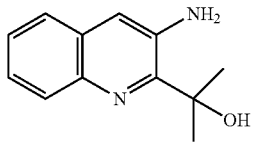

Compound A wherein the compound is crystalline.

In some embodiments, the present invention provides Compound A, wherein the compound is substantially free of amorphous Compound A.

In some embodiments, the present invention provides Compound A, wherein the compound is substantially free of impurities. In some embodiments, the "impurities" are determined by HPLC according to the procedures set forth in the Examples for the relevant solid forms of Compound A.

In some embodiments, the present invention provides Compound A, wherein the compound has one or more peaks in its XRPD selected from those at about 10.4, about 17.5, and about 20.9 degrees 2-theta. In some such embodiments, the present invention provides Compound A, wherein the compound has at least two peaks in its XRPD selected from those at about 10.4, about 17.5, and about 20.9 degrees 2-theta. In some such embodiments, the present invention provides Compound A, wherein the compound is of Form A.

In some embodiments, the present invention provides Compound A, wherein the compound has an XRPD substantially similar to that depicted in FIG. 1.

In some embodiments, the present invention provides a composition comprising Compound A and a pharmaceutically acceptable carrier or excipient.

In some embodiments, the present invention provides a method of inhibiting or preventing the accumulation of A2E in a patient, comprising administering Compound A or composition thereof to the patient.

In some embodiments, the present invention provides a method of treating various conditions in a patient in which aldehyde toxicity is implicated in the pathogenesis, comprising administering of Compound A or composition thereof to the patient. In some such embodiments, the various conditions, in a patient in which aldehyde toxicity is implicated in the pathogenesis, may include dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., SLE and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents.

2. Salt Forms of Compound A

In some embodiments, an acid and Compound A are ionically bonded to form one of compounds 1 through 11, described below. It is contemplated that compounds 1 through 11 can exist in a variety of physical forms. For example, compounds 1 through 11 can be in solution, suspension, or in solid form. In certain embodiments, compounds 1 through 11 are in solid form. When compounds 1 through 11 are in solid form, the compounds may be amorphous, crystalline, or a mixture thereof. Exemplary such solid forms of compounds 1 through 11 are described in more detail below.

a. Compound 1—Mesylate Salts of Compound A

In some embodiments, the present invention provides a mesylate salt of Compound A, represented by Compound 1:

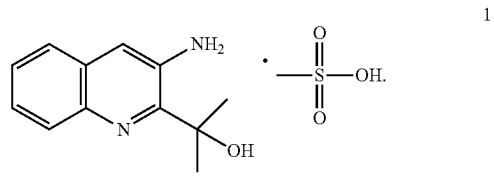

1

It will be appreciated by one of ordinary skill in the art that the methanesulfonic acid and Compound A are ionically bonded to form Compound 1. It is contemplated that Compound 1 can exist in a variety of physical forms. For example, Compound 1 can be in solution, suspension, or in solid form. In certain embodiments, Compound 1 is in solid form. When Compound 1 is in solid form, the compound may be amorphous, crystalline, or a mixture thereof. Exemplary solid forms are described in more detail below.

In some embodiments, the present invention provides Compound 1 substantially free of impurities. As used herein, the term "substantially free of impurities" means that the compound contains no significant amount of extraneous matter. In some embodiments, the "impurities" can be determined by HPLC according to the procedures set forth in the Examples for the relevant solid forms of Compound 1. Such extraneous matter may include excess methanesulfonic acid, excess Compound A, residual solvents, or any other impurities that may result from the preparation of, and/or isolation of, Compound 1.

In some embodiments, at least about 95% by weight of Compound 1 is present. In still other embodiments of the invention, at least about 99% by weight of Compound 1 is present.

In some embodiments, Compound 1 is present in an amount of at least about 97, 97.5, 98.0, 98.5, 99, 99.5, 99.8 weight percent where the percentages are based on the total weight of the composition. In some embodiments, Compound 1 contains no more than about 3.0 area percent HPLC of total organic impurities and in certain embodiments, no more than about 1.5 area percent HPLC total organic impurities relative to the total area of the HPLC chromatogram. In other embodiments, Compound 1 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 1 is also meant to include all tautomeric forms of Compound 1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that Compound 1 can exist in a variety of solid forms. Exemplary such forms include polymorphs such as those described herein.

In some embodiments, Compound 1 is a crystalline solid. In some embodiments, Compound 1 is a crystalline solid substantially free of amorphous Compound 1. As used herein, the term "substantially free of amorphous Compound 1" means that the compound contains no significant amount of amorphous Compound 1. In certain embodiments, at least about 95% by weight of crystalline Compound 1 is present. In still other embodiments of the invention, at least about 99% by weight of crystalline Compound 1 is present.

It has been found that Compound 1 can exist in at least two distinct polymorphic forms. In some embodiments, the present invention provides a polymorphic form of Compound 1 referred to herein as Form A. In some embodiments, the present invention provides a polymorphic form of Compound 1 referred to herein as Form B.

In some embodiments, Compound 1 is amorphous. In some embodiments, Compound 1 is amorphous, and is substantially free of crystalline Compound 1.

i. Form A of Compound 1

In some embodiments, Form A of Compound 1 has at least 1, 2, 3, 4, 5, or more spectral peak(s) selected from the peaks listed in Table 2 below. In some embodiments, the peak(s) with relatively highest intensity peak(s) are selected.

TABLE 2

XRPD Peak Positions for Form A of Compound 1

| Pos. [°2θ] | d-spacing [Å] | Rel. Int. [%] |
|---|---|---|
| 9.7 | 9.10 | 21.52 |
| 10.4 | 8.51 | 23.71 |
| 12.2 | 7.25 | 12.22 |
| 13.7 | 6.47 | 43.53 |
| 14.5 | 6.09 | 5.00 |
| 14.8 | 5.99 | 12.51 |
| 16.8 | 5.28 | 7.23 |
| 17.2 | 5.14 | 10.42 |
| 17.8 | 5.00 | 9.84 |
| 18.0 | 4.93 | 69.59 |
| 19.8 | 4.48 | 7.43 |
| 20.9 | 4.26 | 11.84 |
| 22.2 | 4.01 | 28.47 |
| 22.8 | 3.90 | 4.34 |
| 24.6 | 3.63 | 14.88 |
| 26.5 | 3.36 | 100.00 |
| 27.8 | 3.21 | 5.39 |
| 28.3 | 3.15 | 14.34 |
| 29.3 | 3.05 | 11.60 |
| 33.2 | 2.70 | 5.33 |

[1] In this and all subsequent tables, the position 2θ is within ± 0.2.

In some embodiments, Form A of Compound 1 is characterized in that it has one or more peaks in its X-ray powder diffraction pattern selected from those at about 13.7, about 18.0, and about 26.5 degrees 2-theta. In some embodiments, Form A of Compound 1 is characterized in that it has two or more peaks in its X-ray powder diffraction pattern selected from those at about 13.7, about 18.0, and about 26.5 degrees 2-theta. In some embodiments, Form A of Compound 1 is characterized in that it has all three peaks in its X-ray powder diffraction pattern at about 13.7, about 18.0, and about 26.5 degrees 2-theta. In some embodiments, Form A of Compound 1 is further characterized by additional 1, 2, 3, 4 or 5 peak(s) selected from Table 2.

Figure 3:
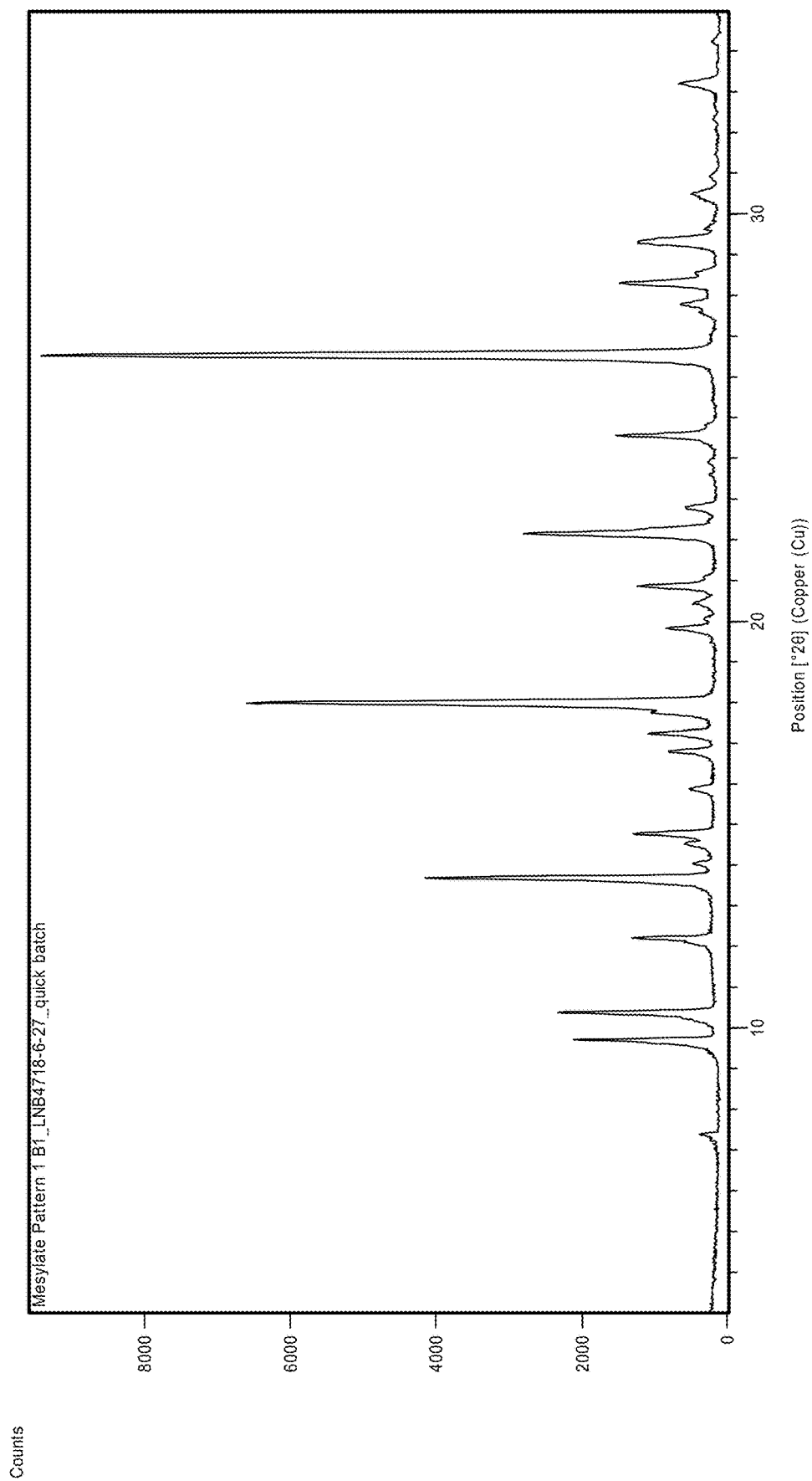
FIG. 3 depicts the XRPD pattern of Compound 1, Form A.

In certain embodiments, the X-ray powder diffraction pattern is substantially similar to the XRPD provided in FIG. 3.

Figure 4:
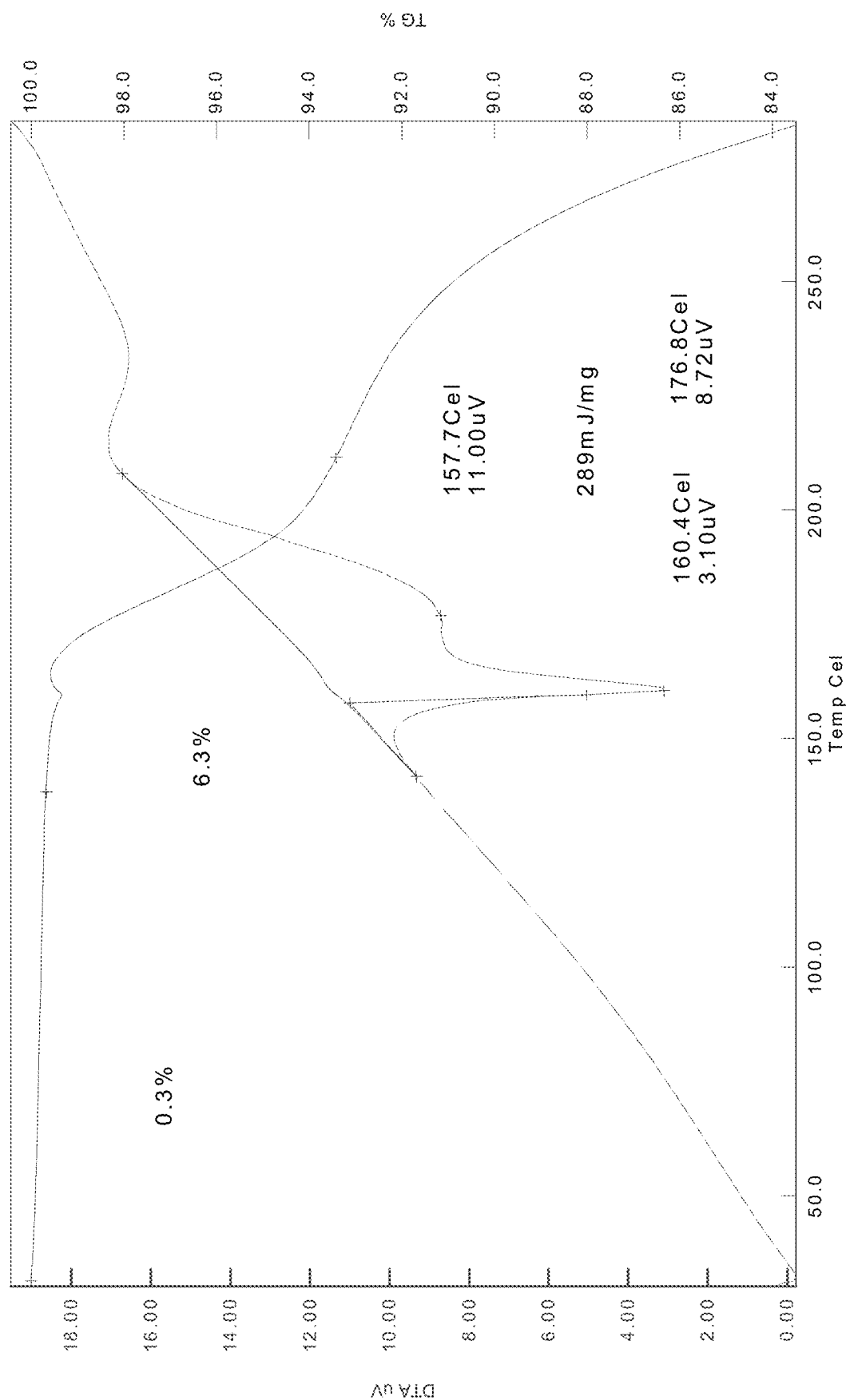
FIG. 4 depicts a DSC thermogram and TGA trace of Compound 1, Form A.

In some embodiments, Form A of Compound 1 is characterized by a differential scanning calorimetry (DSC) thermogram having the endothermic peak(s) as shown in FIG. 4. In some embodiments, Form A of Compound 1 has a DSC thermogram substantially the same as that shown in FIG. 4.

Methods for preparing Form A of Compound 1 are described infra.

ii. Form B of Compound 1

In some embodiments, Form B of Compound 1 has at least 1, 2, 3, 4, 5, or more spectral peak(s) selected from the peaks listed in Table 3 below. In some embodiments, the peak(s) with relatively highest intensity peak(s) are selected.

TABLE 3

XRPD Peak Positions for Form B of Compound 1

| Pos. [°2θ] | d-spacing [Å] | Rel. Int. [%] |
|---|---|---|
| 8.4 | 10.52 | 29.49 |
| 11.5 | 7.72 | 13.76 |
| 13.0 | 6.80 | 40.87 |
| 14.6 | 6.08 | 23.63 |
| 15.8 | 5.60 | 23.94 |
| 17.9 | 4.94 | 100.00 |
| 19.4 | 4.58 | 8.37 |
| 20.9 | 4.24 | 23.67 |
| 21.2 | 4.19 | 11.35 |
| 21.8 | 4.07 | 17.53 |
| 22.4 | 3.98 | 15.58 |
| 23.6 | 3.77 | 9.23 |
| 25.6 | 3.48 | 8.32 |
| 25.6 | 3.48 | 8.81 |
| 26.2 | 3.40 | 33.35 |
| 26.2 | 3.40 | 32.56 |
| 27.2 | 3.28 | 12.44 |
| 27.9 | 3.20 | 16.72 |
| 28.0 | 3.18 | 17.35 |
| 31.9 | 2.80 | 11.58 |

[1] In this and all subsequent tables, the position 2θ is within ± 0.2.

In some embodiments, Form B of Compound 1 is characterized in that it has one or more peaks in its X-ray powder diffraction pattern selected from those at about 13.0, about 17.9, and about 26.2 degrees 2-theta. In some embodiments, Form B of Compound 1 is characterized in that it has two or more peaks in its X-ray powder diffraction pattern selected from those at about 13.0, about 17.9, and about 26.2 degrees 2-theta. In some embodiments, Form B of Compound 1 is characterized in that it has all three peaks in its X-ray powder diffraction pattern at about 13.0, about 17.9, and about 26.2 degrees 2-theta. In some embodiments, Form B of Compound 1 is further characterized by additional 1, 2, 3, 4 or 5 peak(s) selected from Table 3.

Figure 5:
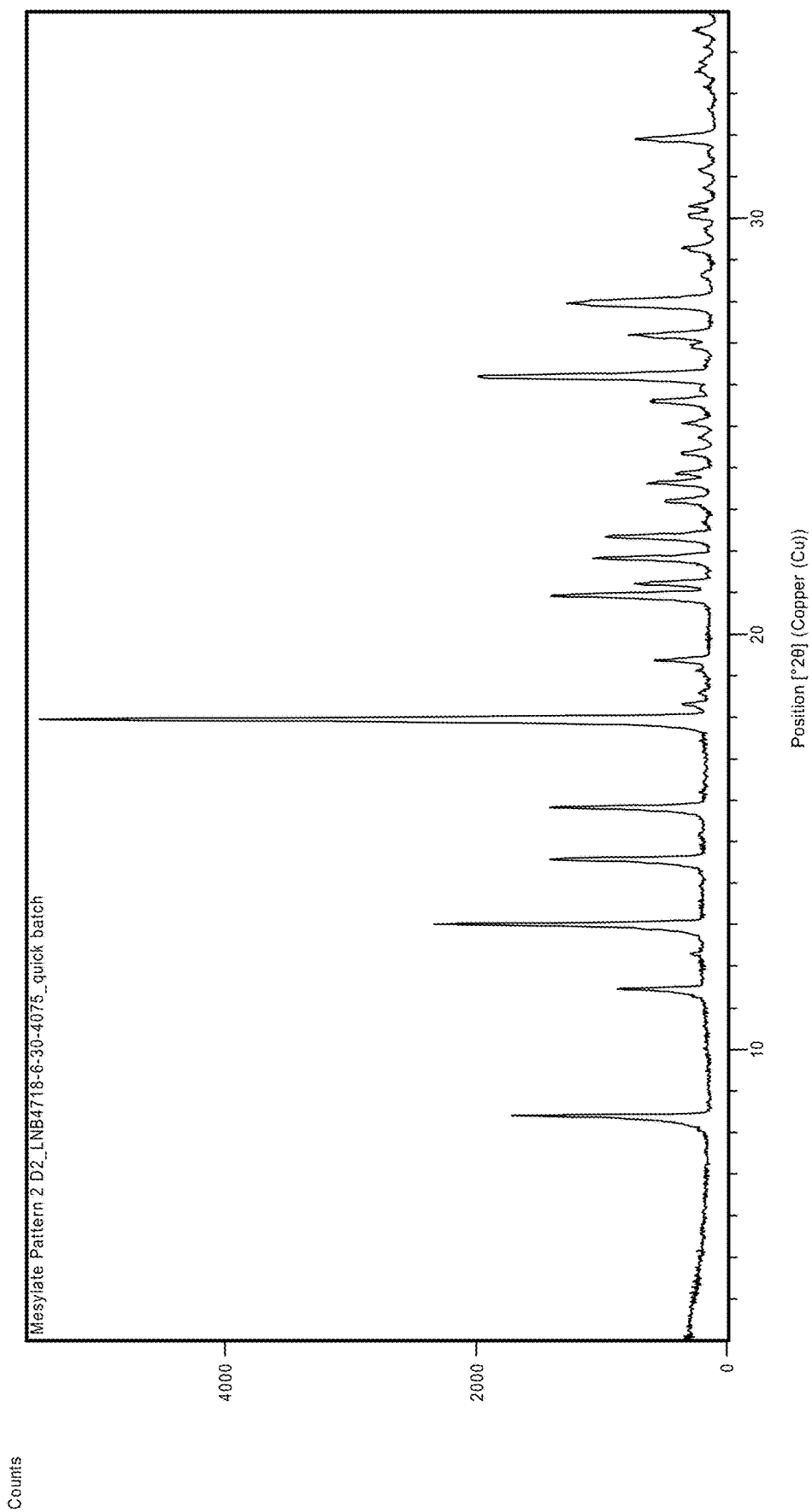
FIG. 5 depicts the XRPD pattern of Compound 1, Form B.

In certain embodiments, the X-ray powder diffraction pattern is substantially similar to the XRPD provided in FIG. 5.

Figure 6:
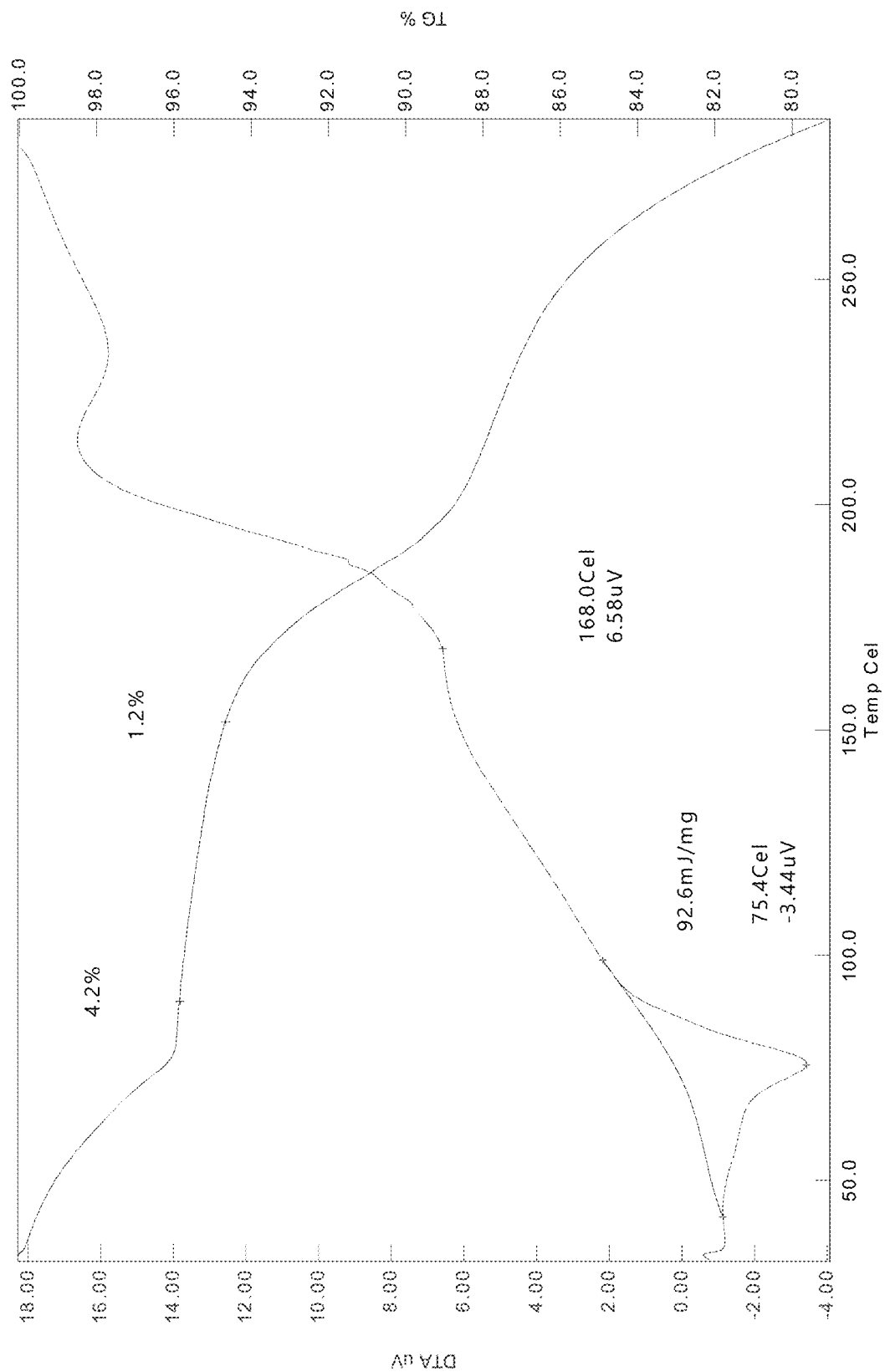
FIG. 6 depicts a DSC thermogram and TGA trace of Compound 1, Form B.

In some embodiments, Form B of Compound 1 is characterized by a differential scanning calorimetry (DSC) thermogram having the endothermic peak(s) as shown in FIG. 6. In some embodiments, Form B of Compound 1 has a DSC thermogram substantially the same as that shown in FIG. 6.

Methods for preparing Form B of Compound 1 are described infra.

In some embodiments, the present invention provides Compound 1:

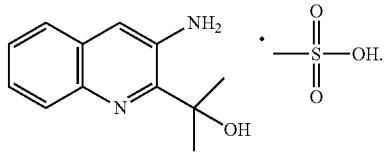

In some embodiments, the present invention provides Compound 1, wherein the compound is crystalline.

In some embodiments, the present invention provides Compound 1, wherein the compound is a crystalline solid substantially free of amorphous Compound 1.

In some embodiments, the present invention provides Compound 1, wherein the compound is substantially free of impurities.

In some embodiments, the present invention provides Compound 1, wherein the compound has one or more peaks in its XRPD selected from those at about 13.7, about 18.0, and about 26.5 degrees 2-theta. In some such embodiments, the present invention provides Compound 1, wherein the compound has at least two peaks in its XRPD selected from those at about 13.7, about 18.0, and about 26.5 degrees 2-theta. In some such embodiments, the present invention provides Compound 1, wherein the compound is of Form A.

In some embodiments, the present invention provides Compound 1, wherein the compound has an XRPD substantially similar to that depicted in FIG. 3.

In some embodiments, the present invention provides Compound 1, wherein the compound has one or more peaks in its XRPD selected from those at about 13.0, about 17.9, and about 26.2 degrees 2-theta. In some such embodiments, the present invention provides Compound 1, wherein the compound has at least two peaks in its XRPD selected from those at about 13.0, about 17.9, and about 26.2 degrees 2-theta. In some such embodiments, the present invention provides Compound 1, wherein the compound is of Form B.

In some embodiments, the present invention provides Compound 1, wherein the compound has an XRPD substantially similar to that depicted in FIG. 5.

In some embodiments, the present invention provides a composition comprising Compound 1 and a pharmaceutically acceptable carrier or excipient.

In some embodiments, the present invention provides a method of inhibiting or preventing the accumulation of A2E in a patient comprising administering to the patient Compound 1 or composition thereof.

In some embodiments, the present invention provides a method of treating various conditions in a patient in which aldehyde toxicity is implicated in the pathogenesis, comprising administering of Compound 1 or composition thereof to the patient. In some such embodiments, the various conditions, in a patient, in which aldehyde toxicity is implicated in the pathogenesis may include dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., SLE and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents.

b. Compound 2—Besylate Salts of Compound A

In some embodiments, the present invention provides a besylate salt of Compound A, represented by Compound 2:

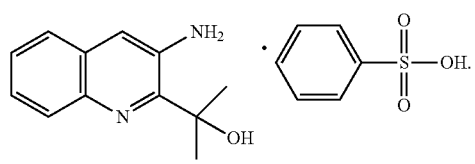

It will be appreciated by one of ordinary skill in the art that the benzenesulfonic acid and Compound A are ionically bonded to form Compound 2. It is contemplated that Compound 2 can exist in a variety of physical forms. For example, Compound 2 can be in solution, suspension, or in solid form. In certain embodiments, Compound 2 is in solid form. When Compound 2 is in solid form, the compound may be amorphous, crystalline, or a mixture thereof. Exemplary solid forms are described in more detail below.

In some embodiments, the present invention provides Compound 2 substantially free of impurities. As used herein, the term "substantially free of impurities" means that the compound contains no significant amount of extraneous matter. In some embodiments, the "impurities" can be determined by HPLC according to the procedures set forth in the Examples for the relevant solid forms of Compound 2. Such extraneous matter may include excess benzenesulfonic acid, excess Compound A, residual solvents, or any other impurities that may result from the preparation of, and/or isolation of, Compound 2.

In certain embodiments, at least about 95% by weight of Compound 2 is present. In still other embodiments of the invention, at least about 99% by weight of Compound 2 is present.

In some embodiments, Compound 2 is present in an amount of at least about 97, 97.5, 98.0, 98.5, 99, 99.5, 99.8 weight percent where the percentages are based on the total weight of the composition. In some embodiments, Compound 2 contains no more than about 3.0 area percent HPLC of total organic impurities and, in certain embodiments, no more than about 1.5 area percent HPLC total organic impurities relative to the total area of the HPLC chromatogram. In other embodiments, Compound 2 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 2 is also meant to include all tautomeric forms of Compound 2. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that Compound 2 can exist in a variety of solid forms. Exemplary such forms include polymorphs such as those described herein.

In certain embodiments, Compound 2 is a crystalline solid. In other embodiments, Compound 2 is a crystalline solid substantially free of amorphous Compound 2. As used herein, the term "substantially free of amorphous Compound 2" means that the compound contains no significant amount of amorphous Compound 2. In certain embodiments, at least about 95% by weight of crystalline Compound 2 is present. In still other embodiments of the invention, at least about 99% by weight of crystalline Compound 2 is present.

It has been found that Compound 2 can exist in a variety of solid forms. Exemplary such forms include polymorphs such as those described herein.

In some embodiments, Compound 2 is amorphous. In some embodiments, Compound 2 is amorphous, and is substantially free of crystalline Compound 2.

i. Form A of Compound 2

In some embodiments, Form A of Compound 2 has at least 1, 2, 3, 4 5 or more spectral peak(s) selected from the peaks listed in Table 4 below. In some embodiments, the peak(s) with relatively highest intensity peak(s) are selected.

TABLE 4

XRPD Peak Positions for Form A of Compound 2

| Pos. [°2θ] | d-spacing [Å] | Rel. Int. [%] |
|---|---|---|
| 11.2 | 7.89 | 80.98 |
| 13.4 | 6.60 | 55.12 |
| 13.6 | 6.51 | 37.52 |
| 15.0 | 5.90 | 65.91 |
| 15.1 | 5.85 | 55.93 |
| 16.9 | 5.26 | 33.60 |
| 18.1 | 4.91 | 41.70 |
| 19.7 | 4.50 | 23.90 |
| 20.4 | 4.36 | 40.50 |
| 21.9 | 4.05 | 19.49 |
| 22.5 | 3.95 | 17.69 |
| 22.8 | 3.90 | 16.92 |
| 23.7 | 3.76 | 83.16 |
| 25.1 | 3.54 | 100.00 |
| 25.2 | 3.54 | 59.31 |
| 26.4 | 3.38 | 88.05 |
| 26.6 | 3.35 | 31.34 |
| 27.0 | 3.30 | 19.68 |
| 27.5 | 3.24 | 34.38 |
| 27.6 | 3.24 | 24.82 |

[1] In this and all subsequent tables, the position 2θ is within ± 0.2.

In some embodiments, Form A of Compound 2 is characterized in that it has one or more peaks in its X-ray powder diffraction pattern selected from those at about 23.7, about 25.1, and about 26.4 degrees 2-theta. In some embodiments, Form A of Compound 2 is characterized in that it has two or more peaks in its X-ray powder diffraction pattern selected from those at about 23.7, about 25.1, and about 26.4 degrees 2-theta. In some embodiments, Form A of Compound 2 is characterized in that it has all three peaks in its X-ray powder diffraction pattern at about 23.7, about 25.1, and about 26.4 degrees 2-theta. In some embodiments, Form A of Compound 2 is further characterized by additional 1, 2, 3, 4 or 5 peak(s) selected from Table 4.

Figure 7:
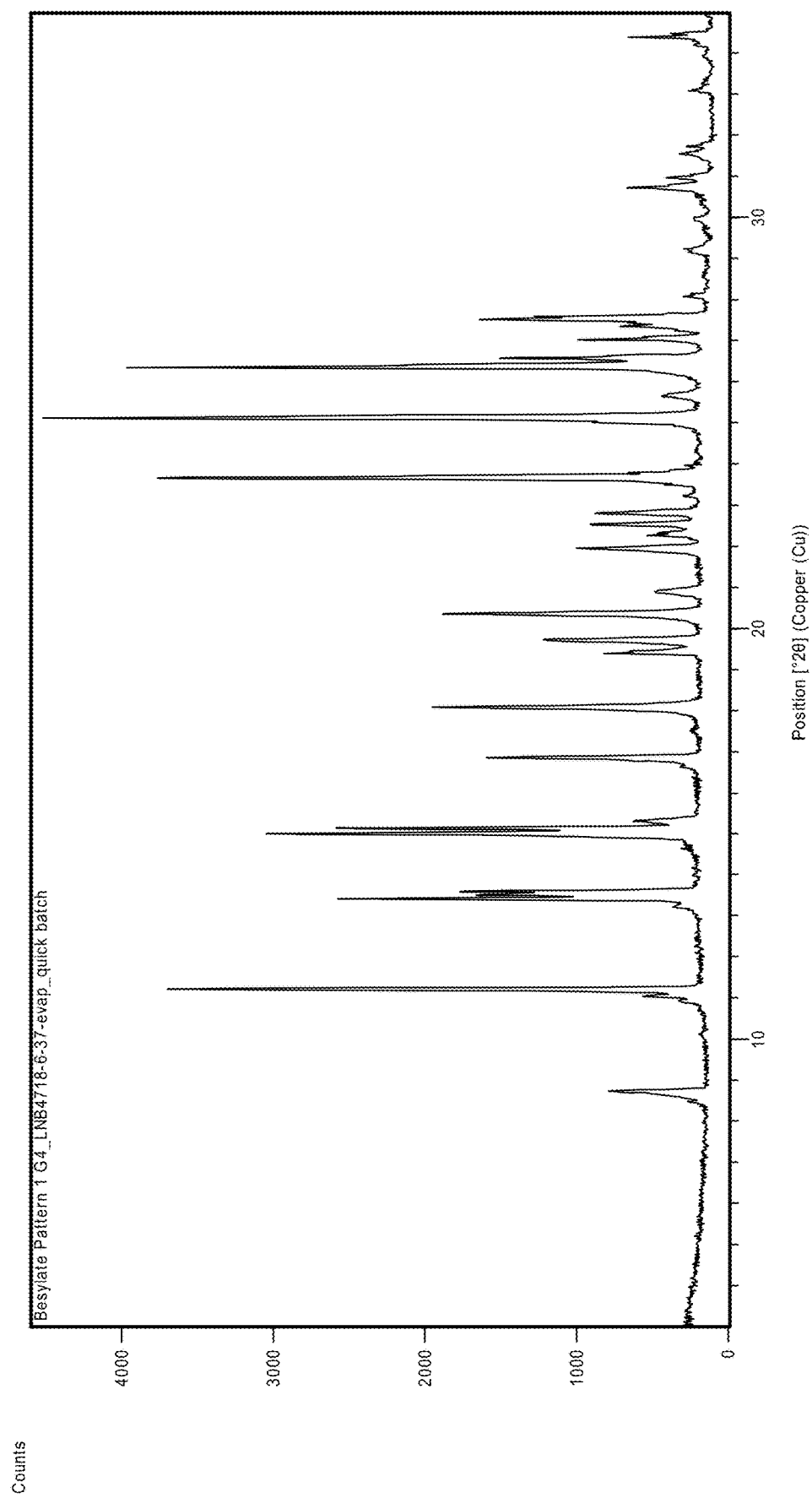
FIG. 7 depicts the XRPD pattern of Compound 2, Form A.

In certain embodiments, the X-ray powder diffraction pattern is substantially similar to the XRPD provided in FIG. 7.

Figure 8:
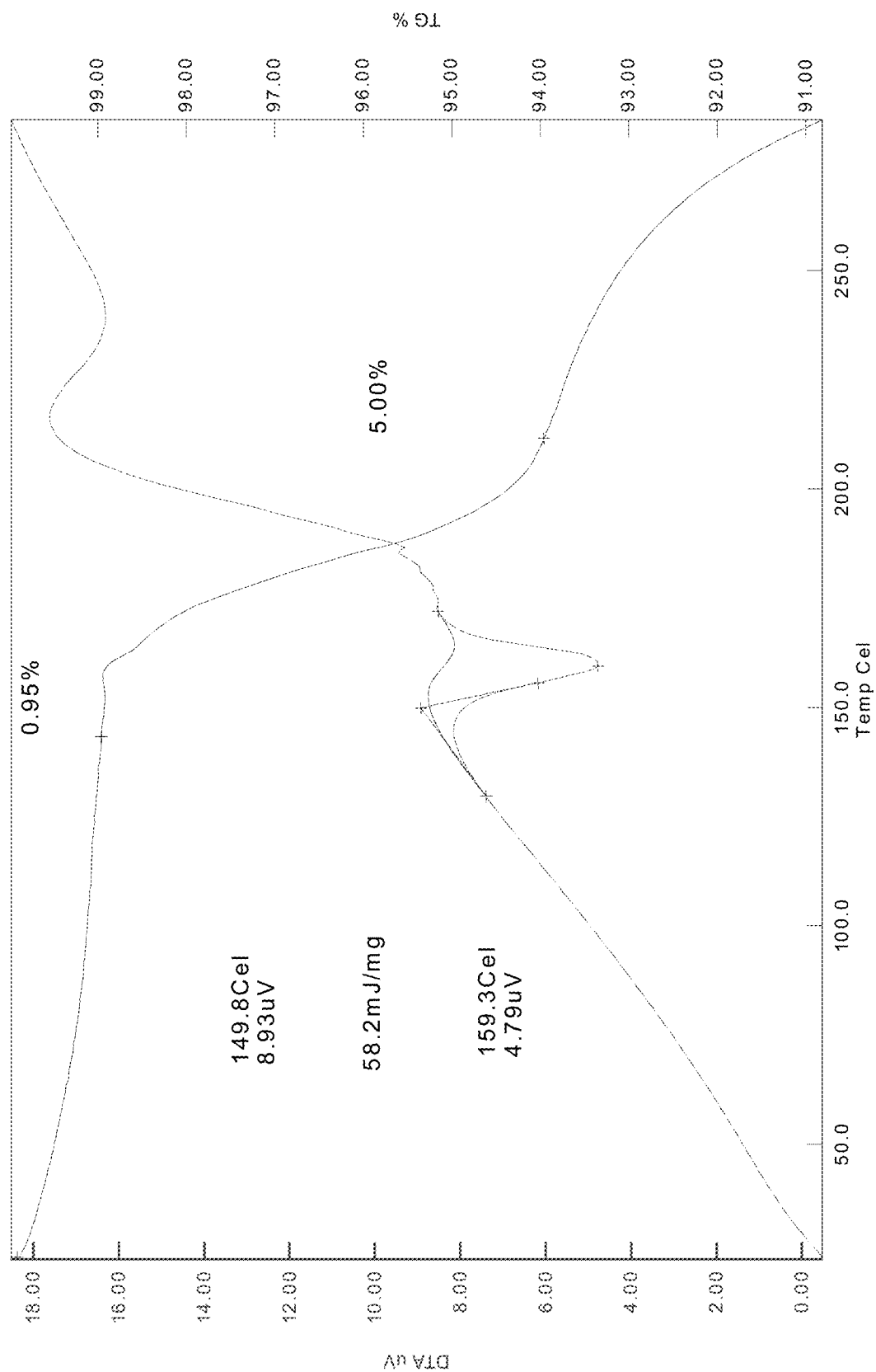
FIG. 8 depicts a DSC thermogram and TGA trace of Compound 2, Form A.

In some embodiments, Form A of Compound 2 is characterized by a differential scanning calorimetry (DSC) thermogram having the endothermic peak(s) as shown in FIG. 8. In some embodiments, Form A of Compound 2 has a DSC thermogram substantially the same as that shown in FIG. 8.

Methods for preparing Form A of Compound 2 are described infra.

In some embodiments, the present invention provides Compound 2:

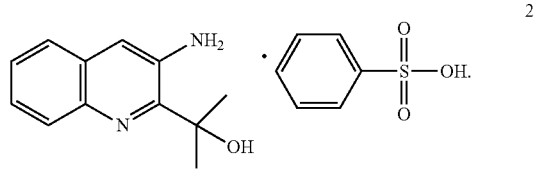

In some embodiments, the present invention provides Compound 2, wherein the compound is crystalline.

In some embodiments, the present invention provides Compound 2, wherein the compound is a crystalline solid substantially free of amorphous Compound 2.

In some embodiments, the present invention provides Compound 2, wherein the compound is substantially free of impurities.

In some embodiments, the present invention provides Compound 2, wherein the compound has one or more peaks in its XRPD selected from those at about 23.7, about 25.1, and about 26.4 degrees 2-theta. In some such embodiments, the present invention provides Compound 2, wherein the compound has at least two peaks in its XRPD selected from those at about 23.7, about 25.1, and about 26.4 degrees 2-theta. In some such embodiments, the present invention provides Compound 2, wherein the compound is of Form A.

In some embodiments, the present invention provides Compound 2, wherein the compound has an XRPD substantially similar to that depicted in FIG. 7.

In some embodiments, the present invention provides a composition comprising Compound 2 and a pharmaceutically acceptable carrier or excipient.

In some embodiments, the present invention provides a method of inhibiting or preventing the accumulation of A2E in a patient comprising administering to the patient Compound 2 or composition thereof.

In some embodiments, the present invention provides a method of treating various conditions in a patient in which aldehyde toxicity is implicated in the pathogenesis, comprising administering of Compound 2 or composition thereof to the patient. In some such embodiments, the various conditions, in a patient, in which aldehyde toxicity is implicated in the pathogenesis may include dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., SLE and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents.

c. Compound 3—Sulfate Salts of Compound A

In some embodiments, the present invention provides a sulfate salt of Compound A, represented by Compound 3:

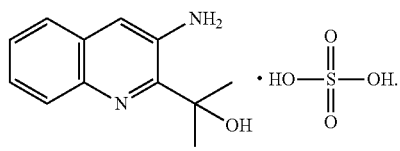

It will be appreciated by one of ordinary skill in the art that the sulfuric acid and Compound A are ionically bonded to form Compound 3. It is contemplated that Compound 3 can exist in a variety of physical forms. For example, Compound 3 can be in solution, suspension, or in solid form. In certain embodiments, Compound 3 is in solid form. When Compound 3 is in solid form, the compound may be amorphous, crystalline, or a mixture thereof. Exemplary solid forms are described in more detail below.

In some embodiments, the present invention provides Compound 3 substantially free of impurities. As used herein, the term "substantially free of impurities" means that the compound contains no significant amount of extraneous matter. In some embodiments, the "impurities" can be determined by HPLC according to the procedures set forth in the Examples for the relevant solid forms of Compound 3. Such extraneous matter may include excess sulfuric acid, excess Compound A, residual solvents, or any other impurities that may result from the preparation of, and/or isolation of, Compound 3.

In certain embodiments, at least about 95% by weight of Compound 3 is present. In still other embodiments of the invention, at least about 99% by weight of Compound 3 is present.

In some embodiments, Compound 3 is present in an amount of at least about 97, 97.5, 98.0, 98.5, 99, 99.5, 99.8 weight percent where the percentages are based on the total weight of the composition. In some embodiments, Compound 3 contains no more than about 3.0 area percent HPLC of total organic impurities and, in certain embodiments, no more than about 1.5 area percent HPLC total organic impurities relative to the total area of the HPLC chromatogram. In other embodiments, Compound 3 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 3 is also meant to include all tautomeric forms of Compound 3. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that Compound 3 can exist in at least four distinct polymorphic forms. In some embodiments, the present invention provides a polymorphic form of Compound 3 referred to herein as Form A. In some embodiments, the present invention provides a polymorphic form of Compound 3 referred to herein as Form B. In some embodiments, the present invention provides a polymorphic form of Compound 3 referred to herein as Form C. In some embodiments, the present invention provides a polymorphic form of Compound 3 referred to herein as Form D.

In certain embodiments, Compound 3 is a crystalline solid. In other embodiments, Compound 3 is a crystalline solid substantially free of amorphous Compound 3. As used herein, the term "substantially free of amorphous Compound 3" means that the compound contains no significant amount of amorphous Compound 3. In certain embodiments, at least about 95% by weight of crystalline Compound 3 is present. In still other embodiments of the invention, at least about 99% by weight of crystalline Compound 3 is present.

In some embodiments, Compound 3 is amorphous. In some embodiments, Compound 3 is amorphous, and is substantially free of crystalline Compound 3.

i. Form A of Compound 3

In some embodiments, Form A of Compound 3 has at least 1, 2, 3, 4, 5, or more spectral peak(s) selected from the peaks listed in Table 5 below. In some embodiments, the peak(s) with relatively highest intensity peak(s) are selected.

TABLE 5

XRPD Peak Positions for Form A of Compound 3

| Pos. [°2θ] | d-spacing [Å] | Rel. Int. [%] |
| --- | --- | --- |
| 8.6 | 10.33 | 11.59 |
| 13.2 | 6.69 | 99.09 |
| 13.5 | 6.56 | 11.90 |
| 14.4 | 6.17 | 17.80 |
| 14.7 | 6.03 | 14.16 |
| 17.7 | 5.01 | 84.48 |
| 18.6 | 4.78 | 21.33 |
| 19.2 | 4.63 | 22.31 |
| 19.8 | 4.49 | 44.88 |
| 21.6 | 4.11 | 30.97 |
| 22.2 | 4.01 | 51.90 |
| 24.3 | 3.66 | 17.55 |
| 25.3 | 3.53 | 11.98 |
| 27.1 | 3.28 | 100.00 |
| 27.2 | 3.28 | 80.05 |
| 27.7 | 3.22 | 11.34 |
| 28.0 | 3.18 | 12.49 |
| 28.9 | 3.09 | 20.40 |
| 29.0 | 3.07 | 28.49 |
| 29.7 | 3.01 | 13.66 |

[1] In this and all subsequent tables, the position 2θ is within ± 0.2.

In some embodiments, Form A of Compound 3 is characterized in that it has one or more peaks in its X-ray powder diffraction pattern selected from those at about 13.2, about 17.7, and about 27.1 degrees 2-theta. In some embodiments, Form A of Compound 3 is characterized in that it has two or more peaks in its X-ray powder diffraction pattern selected from those at about 13.2, about 17.7, and about 27.1 degrees 2-theta. In some embodiments, Form A of Compound 3 is characterized in that it has all three peaks in its X-ray powder diffraction pattern at about 13.2, about 17.7, and about 27.1 degrees 2-theta. In some embodiments, Form A of Compound 3 is further characterized by additional 1, 2, 3, 4 or 5 peak(s) selected from Table 5.

Figure 9:
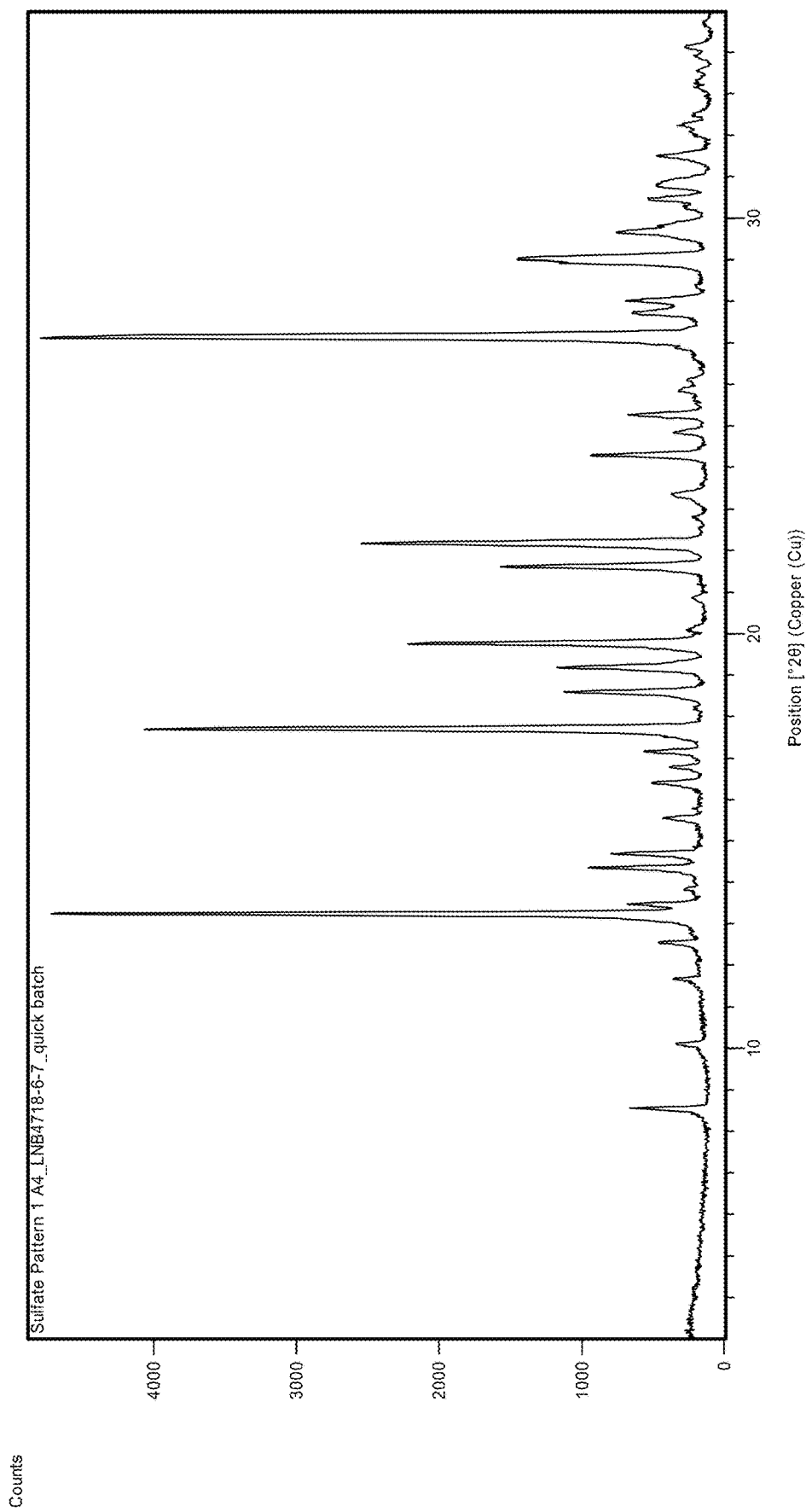
FIG. 9 depicts the XRPD pattern of Compound 3, Form A.

In certain embodiments, the X-ray powder diffraction pattern is substantially similar to the XRPD provided in FIG. 9.

Figure 10:
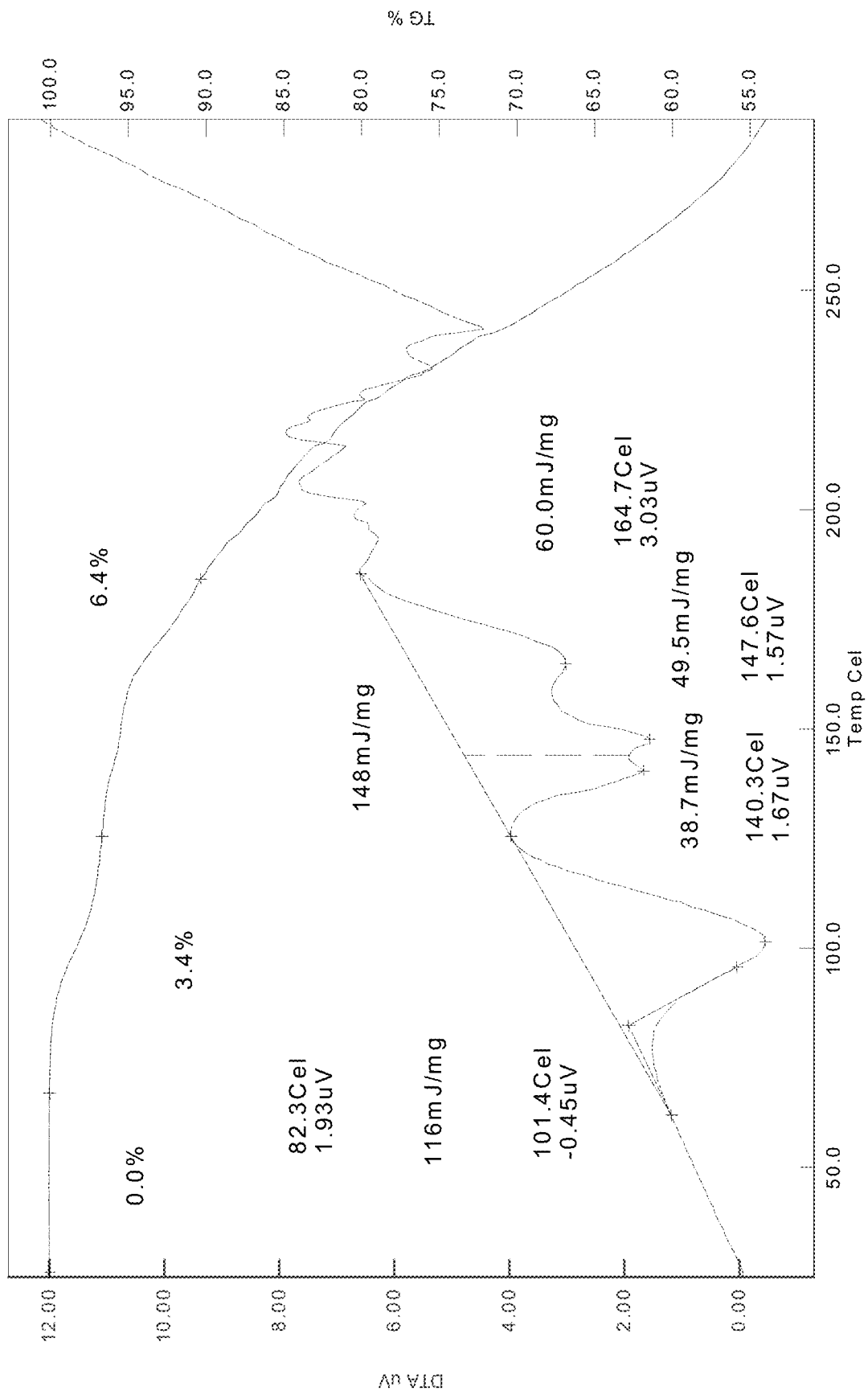
FIG. 10 depicts a DSC thermogram and TGA trace of Compound 3, Form A.

In some embodiments, Form A of Compound 3 is characterized by a differential scanning calorimetry (DSC) thermogram having the endothermic peak(s) as shown in FIG. 10. In some embodiments, Form A of Compound 3 has a DSC thermogram substantially the same as that shown in FIG. 10.

Methods for preparing Form A of Compound 3 are described infra.

ii. Form B of Compound 3

In some embodiments, Form B of Compound 3 has at least 1, 2, 3, 4, 5, or more spectral peak(s) selected from the peaks listed in Table 6 below. In some embodiments, the peak(s) with relatively highest intensity peak(s) are selected.

TABLE 6

XRPD Peak Positions for Form B of Compound 3

| Pos. [°2θ] | d-spacing [Å] | Rel. Int. [%] |
|---|---|---|
| 9.9 | 8.93 | 29.22 |
| 10.1 | 8.73 | 23.13 |
| 12.6 | 7.04 | 23.63 |
| 13.3 | 6.68 | 68.31 |
| 15.8 | 5.61 | 28.48 |
| 17.5 | 5.08 | 38.70 |
| 17.7 | 5.01 | 100.00 |
| 18.6 | 4.77 | 31.45 |
| 19.2 | 4.62 | 25.63 |
| 19.8 | 4.49 | 57.57 |
| 20.1 | 4.41 | 62.25 |
| 20.2 | 4.40 | 43.73 |
| 20.9 | 4.25 | 32.58 |
| 21.6 | 4.11 | 65.94 |
| 22.2 | 4.00 | 50.49 |
| 23.3 | 3.81 | 62.22 |
| 24.3 | 3.65 | 20.78 |
| 25.5 | 3.49 | 20.30 |
| 27.1 | 3.28 | 79.55 |
| 29.1 | 3.07 | 38.25 |

[1] In this and all subsequent tables, the position 2θ is within ± 0.2.

In some embodiments, Form B of Compound 3 is characterized in that it has one or more peaks in its X-ray powder diffraction pattern selected from those at about 13.3, about 17.7, and about 27.1 degrees 2-theta. In some embodiments, Form B of Compound 3 is characterized in that it has two or more peaks in its X-ray powder diffraction pattern selected from those at about 13.3, about 17.7, and about 27.1 degrees 2-theta. In some embodiments, Form B of Compound 3 is characterized in that it has all three peaks in its X-ray powder diffraction pattern at about 13.3, about 17.7, and about 27.1 degrees 2-theta. In some embodiments, Form B of Compound 3 is further characterized by additional 1, 2, 3, 4 or 5 peak(s) selected from Table 6.

Figure 11:
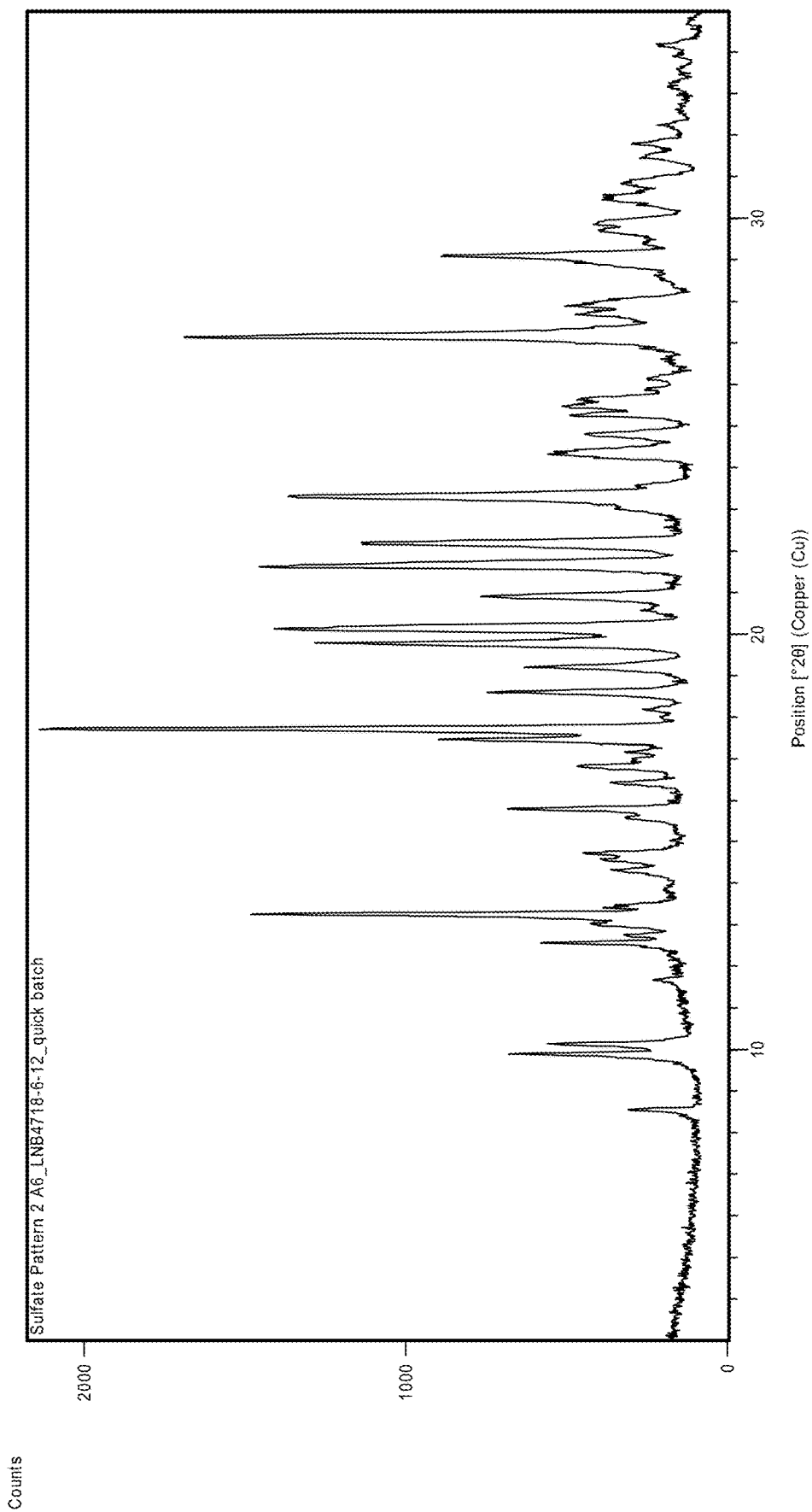
FIG. 11 depicts the XRPD pattern of Compound 3, Form B.

In certain embodiments, the X-ray powder diffraction pattern is substantially similar to the XRPD provided in FIG. 11.

Figure 12:
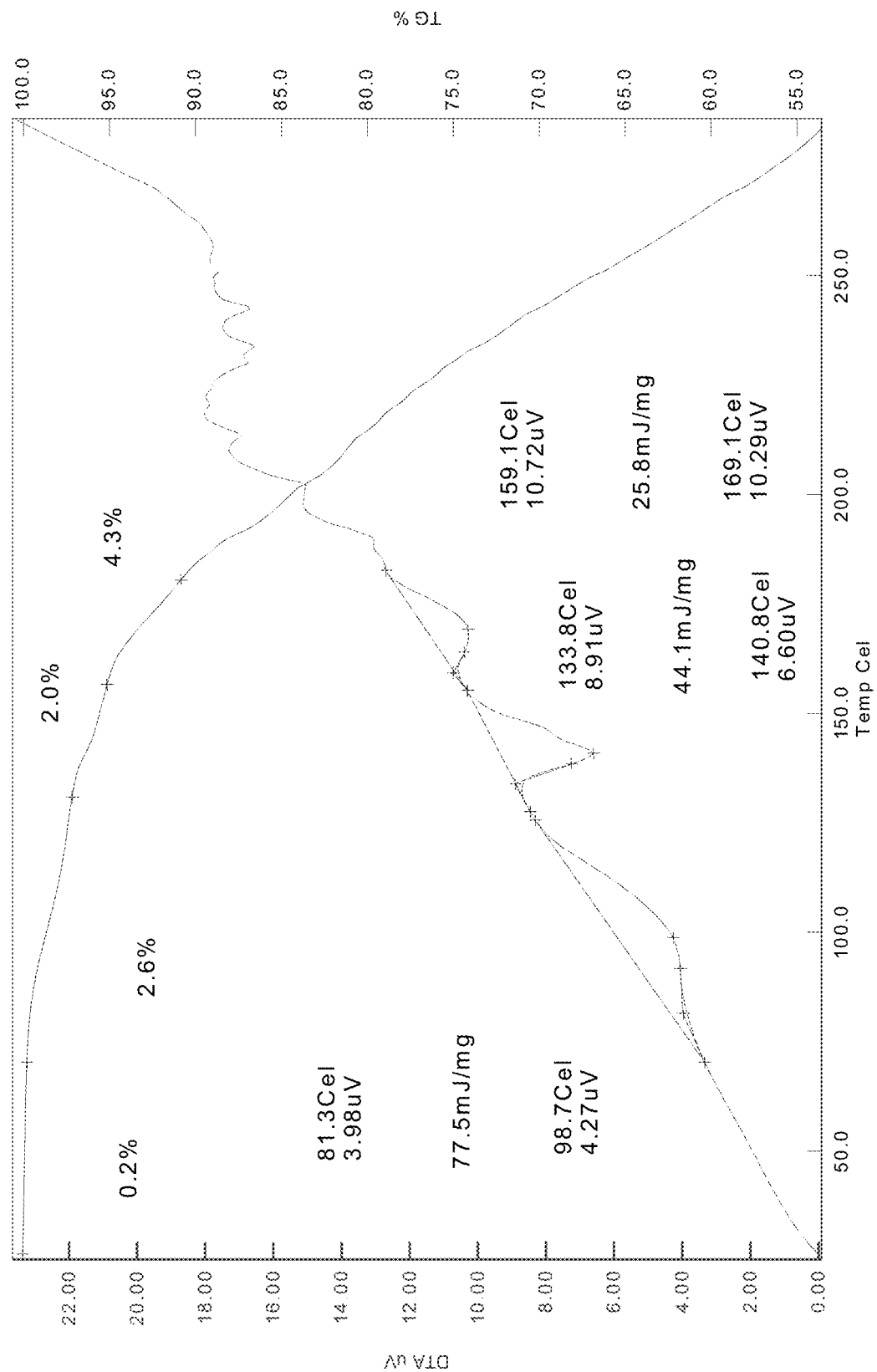
FIG. 12 depicts a DSC thermogram and TGA trace of Compound 3, Form B.

In some embodiments, Form B of Compound 3 is characterized by a differential scanning calorimetry (DSC) thermogram having the endothermic peak(s) as shown in FIG. 12. In some embodiments, Form B of Compound 3 has a DSC thermogram substantially the same as that shown in FIG. 12.

Methods for preparing Form B of Compound 3 are described infra.

iii. Form C of Compound 3

In some embodiments, Form C of Compound 3 has at least 1, 2, 3, 4, 5, or more spectral peak(s) selected from the peaks listed in Table 7 below. In some embodiments, the peak(s) with relatively highest intensity peak(s) are selected.

TABLE 7

XRPD Peak Positions for Form C of Compound 3

| Pos. [°2θ] | d-spacing [Å] | Rel. Int. [%] |
|---|---|---|
| 8.8 | 10.00 | 6.39 |
| 12.2 | 7.25 | 4.36 |
| 12.7 | 6.99 | 3.87 |
| 13.0 | 6.83 | 1.66 |
| 13.2 | 6.69 | 3.22 |
| 16.5 | 5.38 | 20.50 |
| 16.6 | 5.34 | 24.05 |
| 16.8 | 5.28 | 61.67 |
| 16.9 | 5.26 | 100.00 |
| 17.7 | 5.01 | 5.02 |
| 18.5 | 4.80 | 4.27 |
| 19.1 | 4.65 | 2.23 |
| 19.8 | 4.47 | 49.51 |
| 21.6 | 4.12 | 1.47 |
| 22.1 | 4.01 | 2.18 |
| 22.8 | 3.90 | 1.74 |
| 23.9 | 3.73 | 3.74 |
| 25.5 | 3.49 | 3.12 |
| 27.1 | 3.29 | 5.11 |
| 34.1 | 2.63 | 2.17 |

[1] In this and all subsequent tables, the position 2θ is within ± 0.2.

In some embodiments, Form C of Compound 3 is characterized in that it has one or more peaks in its X-ray powder diffraction pattern selected from those at about 16.8, about 16.9, and about 19.8 degrees 2-theta. In some embodiments, Form C of Compound 3 is characterized in that it has two or more peaks in its X-ray powder diffraction pattern selected from those at about 16.8, about 16.9, and about 19.8 degrees 2-theta. In some embodiments, Form C of Compound 3 is characterized in that it has all three peaks in its X-ray powder diffraction pattern at about 16.8, about 16.9, and about 19.8 degrees 2-theta. In some embodiments, Form C of Compound 3 is further characterized by additional 1, 2, 3, 4 or 5 peak(s) selected from Table 7.

Figure 13:
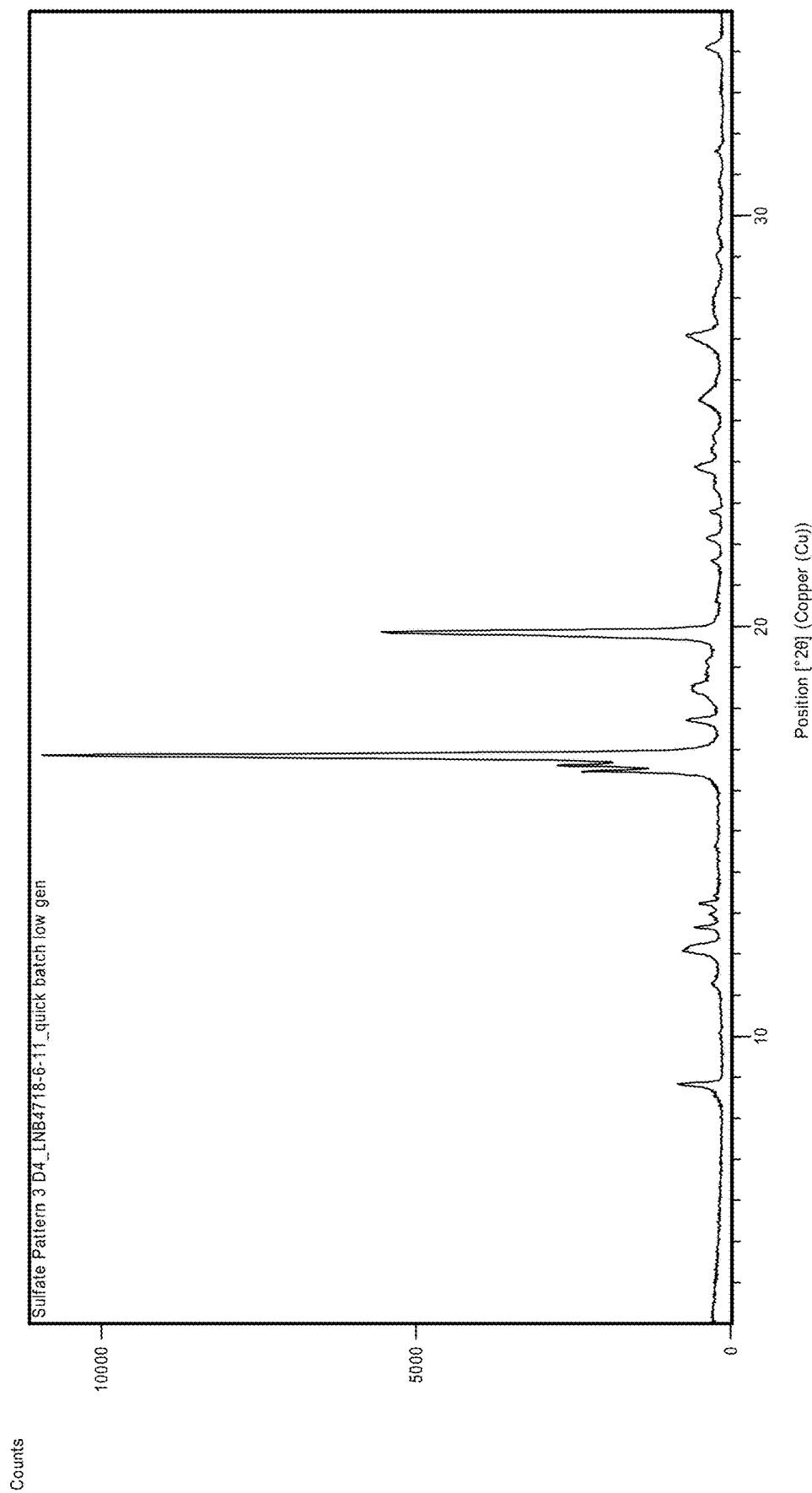
FIG. 13 depicts the XRPD pattern of Compound 3, Form C.

In certain embodiments, the X-ray powder diffraction pattern is substantially similar to the XRPD provided in FIG. 13.

Figure 14:
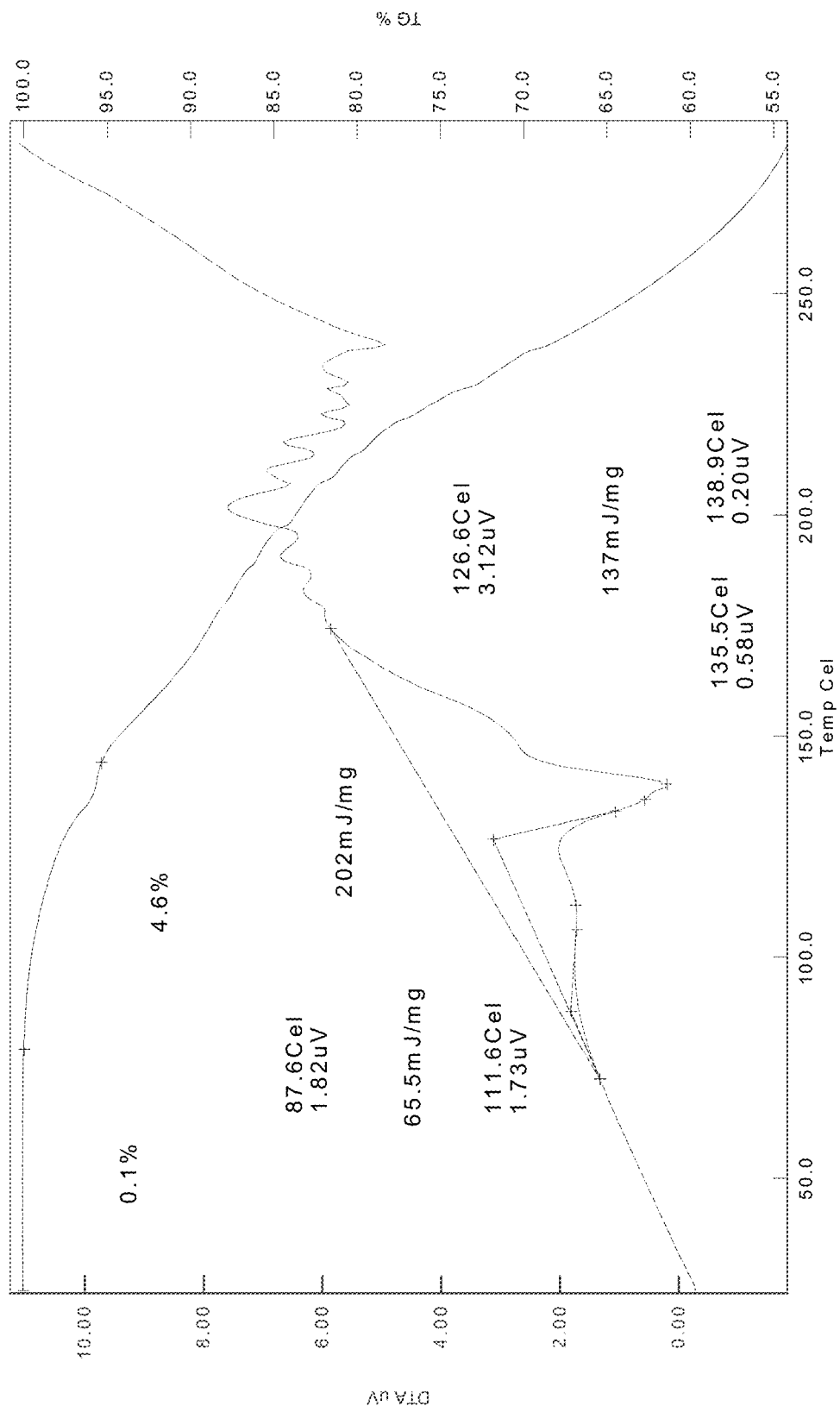
FIG. 14 depicts a DSC thermogram and TGA trace of Compound 3, Form C.

In some embodiments, Form C of Compound 3 is characterized by a differential scanning calorimetry (DSC) thermogram having the endothermic peak(s) as shown in FIG. 14. In some embodiments, Form C of Compound 3 has a DSC thermogram substantially the same as that shown in FIG. 14.

Methods for preparing Form C of Compound 3 are described infra.

iv. Form D of Compound 3

In some embodiments, Form D of Compound 3 has at least 1, 2, 3, 4, 5, or more spectral peak(s) selected from the peaks listed in Table 8 below. In some embodiments, the peak(s) with relatively highest intensity peak(s) are selected.

TABLE 8

XRPD Peak Positions for Form D of Compound 3

| Pos. [°2θ] | d-spacing [Å] | Rel. Int. [%] |
|---|---|---|
| 9.1 | 9.67 | 23.98 |
| 12.3 | 7.17 | 20.98 |
| 12.4 | 7.12 | 27.62 |
| 13.1 | 6.74 | 12.41 |
| 15.0 | 5.90 | 15.13 |
| 15.4 | 5.75 | 12.18 |
| 15.5 | 5.72 | 12.65 |
| 16.2 | 5.47 | 100.00 |

TABLE 8-continued

XRPD Peak Positions for Form D of Compound 3

| Pos. [°2θ] | d-spacing [Å] | Rel. Int. [%] |
|---|---|---|
| 18.3 | 4.84 | 48.40 |
| 19.9 | 4.46 | 21.99 |
| 20.2 | 4.40 | 38.48 |
| 20.4 | 4.35 | 14.01 |
| 20.6 | 4.31 | 34.56 |
| 21.4 | 4.16 | 14.48 |
| 25.7 | 3.47 | 17.18 |
| 25.8 | 3.45 | 25.53 |
| 27.0 | 3.30 | 30.53 |
| 28.0 | 3.19 | 13.39 |
| 28.7 | 3.11 | 22.90 |
| 29.1 | 3.07 | 12.07 |

[1] In this and all subsequent tables, the position 2θ is within ± 0.2.

In some embodiments, Form D of Compound 3 is characterized in that it has one or more peaks in its X-ray powder diffraction pattern selected from those at about 16.2, about 18.3 and about 20.2 degrees 2-theta. In some embodiments, Form D of Compound 3 is characterized in that it has two or more peaks in its X-ray powder diffraction pattern selected from those at about 16.2, about 18.3 and about 20.2 degrees 2-theta. In some embodiments, Form D of Compound 3 is characterized in that it has all three peaks in its X-ray powder diffraction pattern selected from those at about 16.2, about 18.3 and about 20.2 degrees 2-theta. In some embodiments, Form D of Compound 3 is further characterized by additional 1, 2, 3, 4 or 5 peak(s) selected from Table 8.

Figure 15:
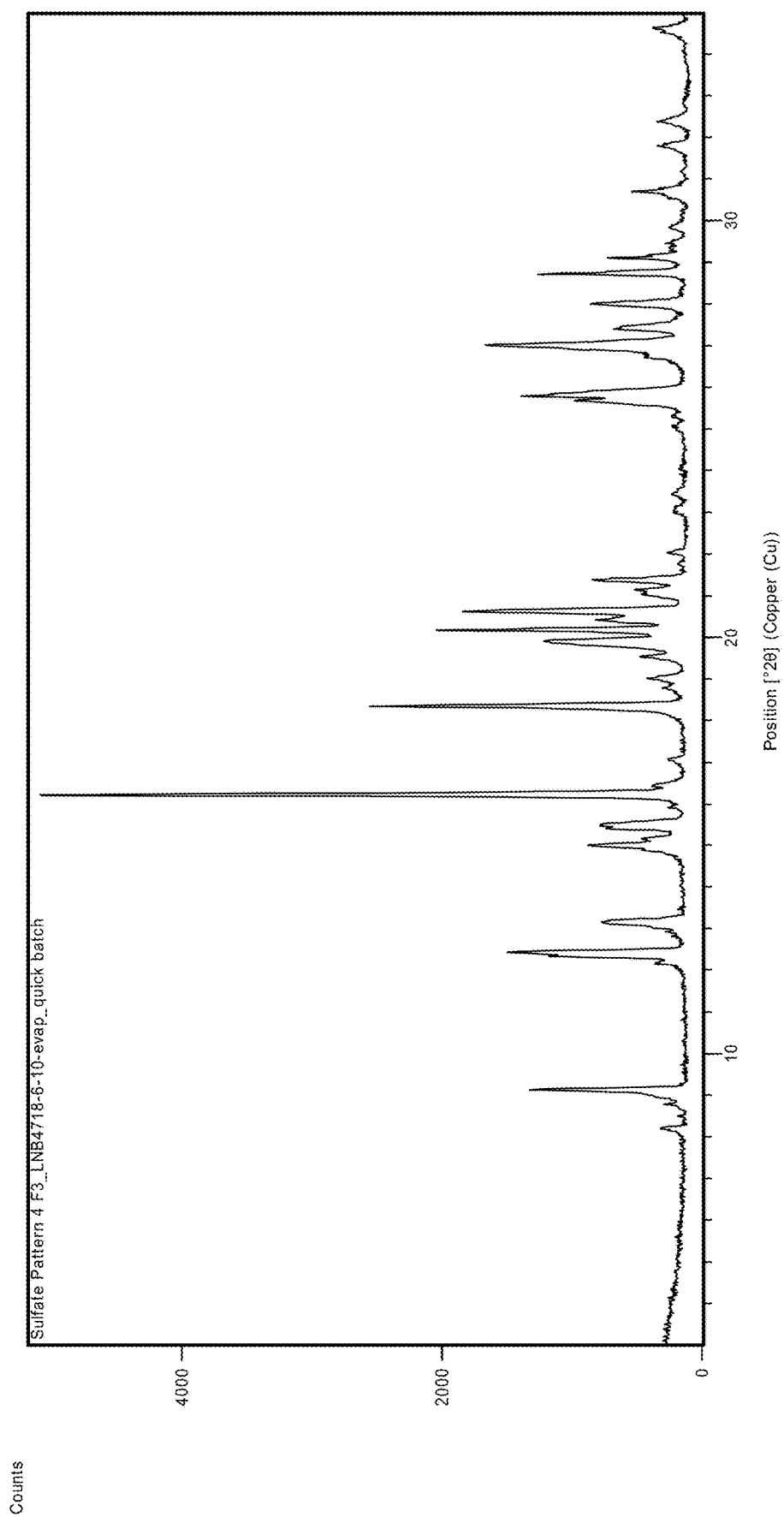
FIG. 15 depicts the XRPD pattern of Compound 3, Form D.

In certain embodiments, the X-ray powder diffraction pattern is substantially similar to the XRPD provided in FIG. 15.

Figure 16:
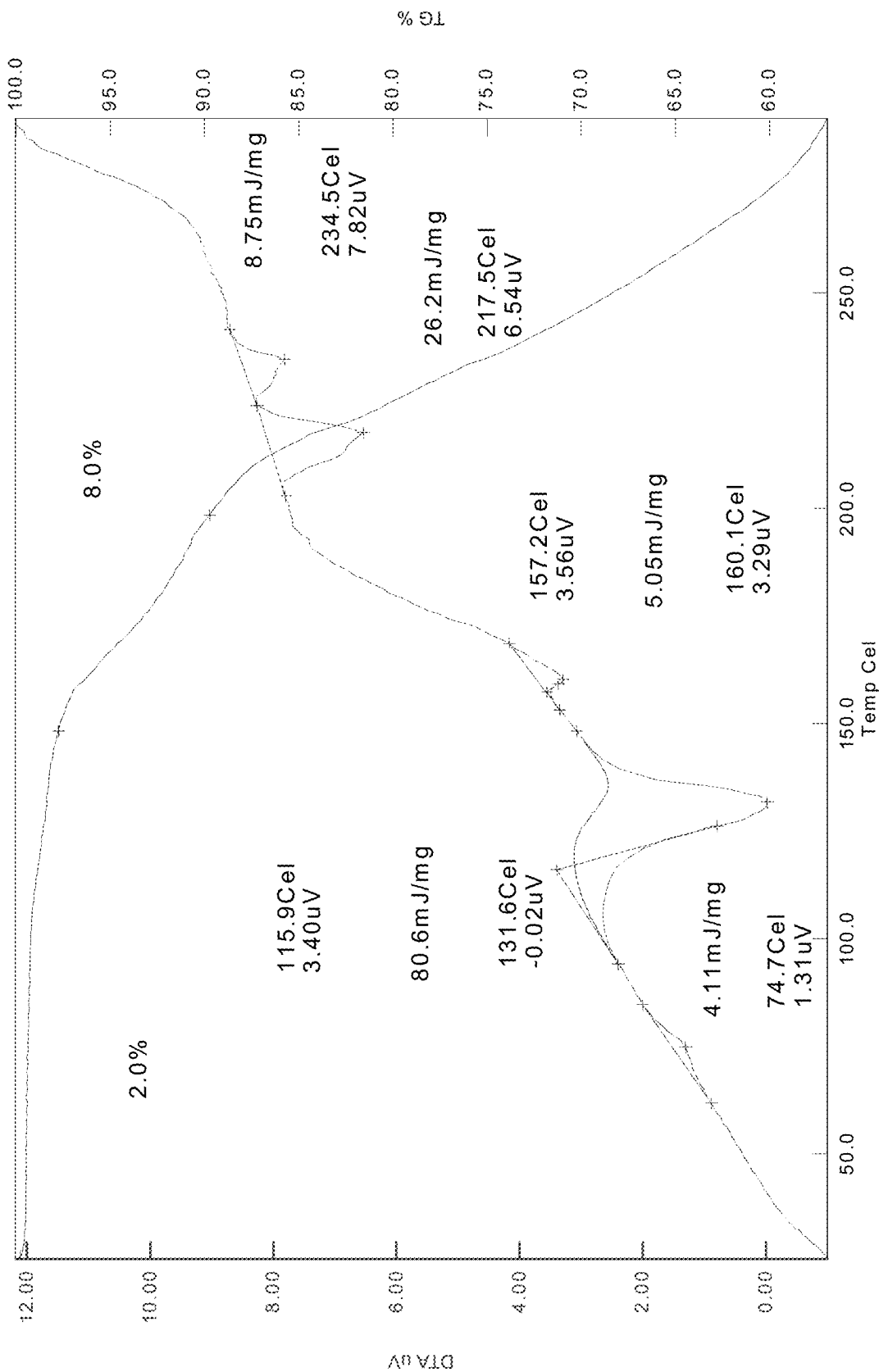
FIG. 16 depicts a DSC thermogram and TGA trace of Compound 3, Form D.

In some embodiments, Form D of Compound 3 is characterized by a differential scanning calorimetry (DSC) thermogram having the endothermic peak(s) as shown in FIG. 16. In some embodiments, Form D of Compound 3 has a DSC thermogram substantially the same as that shown in FIG. 16.

Methods for preparing Form D of Compound 3 are described infra.

In some embodiments, the present invention provides Compound 3:

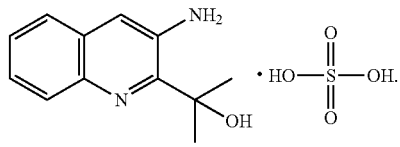

3

In some embodiments, the present invention provides Compound 3, wherein the compound is crystalline.

In some embodiments, the present invention provides Compound 3, wherein the compound is a crystalline solid substantially free of amorphous Compound 3.

In some embodiments, the present invention provides Compound 3, wherein the compound is substantially free of impurities.

In some embodiments, the present invention provides Compound 3, wherein the compound has one or more peaks in its XRPD selected from those at about 13.2, about 17.7, and about 27.1 degrees 2-theta. In some such embodiments, the present invention provides Compound 3, wherein the compound has at least two peaks in its XRPD selected from those at about 13.2, about 17.7, and about 27.1 degrees 2-theta. In some such embodiments, the present invention provides Compound 3, wherein the compound is of Form A.

In some embodiments, the present invention provides Compound 3, wherein the compound has an XRPD substantially similar to that depicted in FIG. 9.

In some embodiments, the present invention provides Compound 3, wherein the compound has one or more peaks in its XRPD selected from those at about 13.3, about 17.7, and about 27.1 degrees 2-theta. In some such embodiments, the present invention provides Compound 3, wherein the compound has at least two peaks in its XRPD selected from those at about 13.3, about 17.7, and about 27.1 degrees 2-theta. In some such embodiments, the present invention provides Compound 3, wherein the compound is of Form B.

In some embodiments, the present invention provides Compound 3, wherein the compound has an XRPD substantially similar to that depicted in FIG. 11.

In some embodiments, the present invention provides Compound 3, wherein the compound has one or more peaks in its XRPD selected from those at about 16.8, about 16.9, and about 19.8 degrees 2-theta. In some such embodiments, the present invention provides Compound 3, wherein the compound has at least two peaks in its XRPD selected from those at about 16.8, about 16.9, and about 19.8 degrees 2-theta. In some such embodiments, the present invention provides Compound 3, wherein the compound is of Form C.

In some embodiments, the present invention provides Compound 3, wherein the compound has an XRPD substantially similar to that depicted in FIG. 13.

In some embodiments, the present invention provides Compound 3, wherein the compound has one or more peaks in its XRPD selected from those at about 16.2, about 18.3, and about 20.2 degrees 2-theta. In some such embodiments, the present invention provides Compound 3, wherein the compound has at least two peaks in its XRPD selected from those at about 16.2, about 18.3, and about 20.2 degrees 2-theta. In some such embodiments, the present invention provides Compound 3, wherein the compound is of Form D.

In some embodiments, the present invention provides Compound 3, wherein the compound has an XRPD substantially similar to that depicted in FIG. 15.

In some embodiments, the present invention provides a composition comprising Compound 3 and a pharmaceutically acceptable carrier or excipient.

In some embodiments, the present invention provides a method of inhibiting or preventing the accumulation of A2E in a patient comprising administering to the patient Compound 3 or composition thereof.

In some embodiments, the present invention provides a method of treating various conditions in a patient in which aldehyde toxicity is implicated in the pathogenesis, comprising administering of Compound 3 or composition thereof to the patient. In some such embodiments, the various conditions, in a patient, in which aldehyde toxicity is implicated in the pathogenesis may include dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents.

d. Compound 4—Tosylate Salts of Compound A

In some embodiments, the present invention provides a tosylate salt of Compound A, represented by Compound 4:

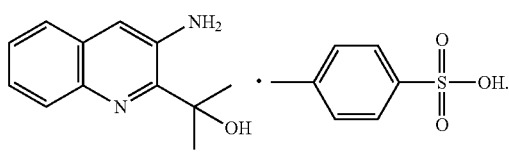

By "tosylate" is meant p-toluene sulfonate, i.e., the ionic form of p-toluenesulfonic acid. It will be appreciated by one of ordinary skill in the art that the p-toluenesulfonic acid and Compound A are ionically bonded to form Compound 4. It is contemplated that Compound 4 can exist in a variety of physical forms. For example, Compound 4 can be in solution, suspension, or in solid form. In certain embodiments, Compound 4 is in solid form. When Compound 4 is in solid form, the compound may be amorphous, crystalline, or a mixture thereof. Exemplary solid forms are described in more detail below.

In some embodiments, the present invention provides Compound 4 substantially free of impurities. As used herein, the term "substantially free of impurities" means that the compound contains no significant amount of extraneous matter. In some embodiments, the "impurities" can be determined by HPLC according to the procedures set forth in the Examples for the relevant solid forms of Compound 4. Such extraneous matter may include excess p-toluenesulfonic acid, excess Compound A, residual solvents, or any other impurities that may result from the preparation of, and/or isolation of, Compound 4.

In certain embodiments, at least about 95% by weight of Compound 4 is present. In still other embodiments of the invention, at least about 99% by weight of Compound 4 is present.

In some embodiments, Compound 4 is present in an amount of at least about 97, 97.5, 98.0, 98.5, 99, 99.5, 99.8 weight percent where the percentages are based on the total weight of the composition. In some embodiments, Compound 4 contains no more than about 3.0 area percent HPLC of total organic impurities and, in certain embodiments, no more than about 1.5 area percent HPLC total organic impurities relative to the total area of the HPLC chromatogram. In other embodiments, Compound 4 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 4 is also meant to include all tautomeric forms of Compound 4. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that Compound 4 can exist in at least two distinct polymorphic forms. In some embodiments, the present invention provides a polymorphic form of Compound 4 referred to herein as Form A. In some embodiments, the present invention provides a polymorphic form of Compound 4 referred to herein as Form B.

In certain embodiments, Compound 4 is a crystalline solid. In other embodiments, Compound 4 is a crystalline solid substantially free of amorphous Compound 4. As used herein, the term "substantially free of amorphous Compound 4" means that the compound contains no significant amount of amorphous Compound 4. In certain embodiments, at least about 95% by weight of crystalline Compound 4 is present. In still other embodiments of the invention, at least about 99% by weight of crystalline Compound 4 is present.

In some embodiments, Compound 4 is amorphous. In some embodiments, Compound 4 is amorphous, and is substantially free of crystalline Compound 4.

i. Form A of Compound 4

In some embodiments, Form A of Compound 4 has at least 1, 2, 3, 4, 5, or more spectral peak(s) selected from the peaks listed in Table 9 below. In some embodiments, the peak(s) with relatively highest intensity peak(s) are selected.

TABLE 9

XRPD Peak Positions for Form A of Compound 4

| Pos. [°2θ] | d-spacing [Å] | Rel. Int. [%] |
|---|---|---|
| 8.7 | 10.21 | 43.02 |
| 13.1 | 6.78 | 34.27 |
| 13.3 | 6.64 | 10.07 |
| 13.6 | 6.52 | 21.56 |
| 15.1 | 5.87 | 8.78 |
| 15.9 | 5.58 | 9.30 |
| 16.3 | 5.43 | 16.59 |
| 17.4 | 5.09 | 7.17 |
| 18.7 | 4.75 | 5.78 |
| 20.0 | 4.45 | 22.49 |
| 20.2 | 4.40 | 22.35 |
| 20.5 | 4.33 | 9.60 |
| 21.8 | 4.08 | 24.01 |
| 22.0 | 4.04 | 9.51 |
| 22.4 | 3.97 | 24.66 |
| 22.9 | 3.88 | 18.07 |
| 23.5 | 3.79 | 4.96 |
| 24.2 | 3.68 | 100.00 |
| 26.5 | 3.36 | 21.60 |
| 28.7 | 3.11 | 9.24 |

[1] In this and all subsequent tables, the position 2θ is within ± 0.2.

In some embodiments, Form A of Compound is characterized in that it has one or more peaks in its X-ray powder diffraction pattern selected from those at about 8.7, about 13.1 and about 24.2 degrees 2-theta. In some embodiments, Form A of Compound 4 is characterized in that it has two or more peaks in its X-ray powder diffraction pattern selected from those at about 8.7, about 13.1 and about 24.2 degrees 2-theta. In some embodiments, Form A of Compound 4 is characterized in that it has all three peaks in its X-ray powder diffraction pattern at about 8.7, about 13.1, and about 24.2 degrees 2-theta. In some embodiments, Form A of Compound 4 is further characterized by additional 1, 2, 3, 4 or 5 peak(s) selected from Table 9.

Figure 17:
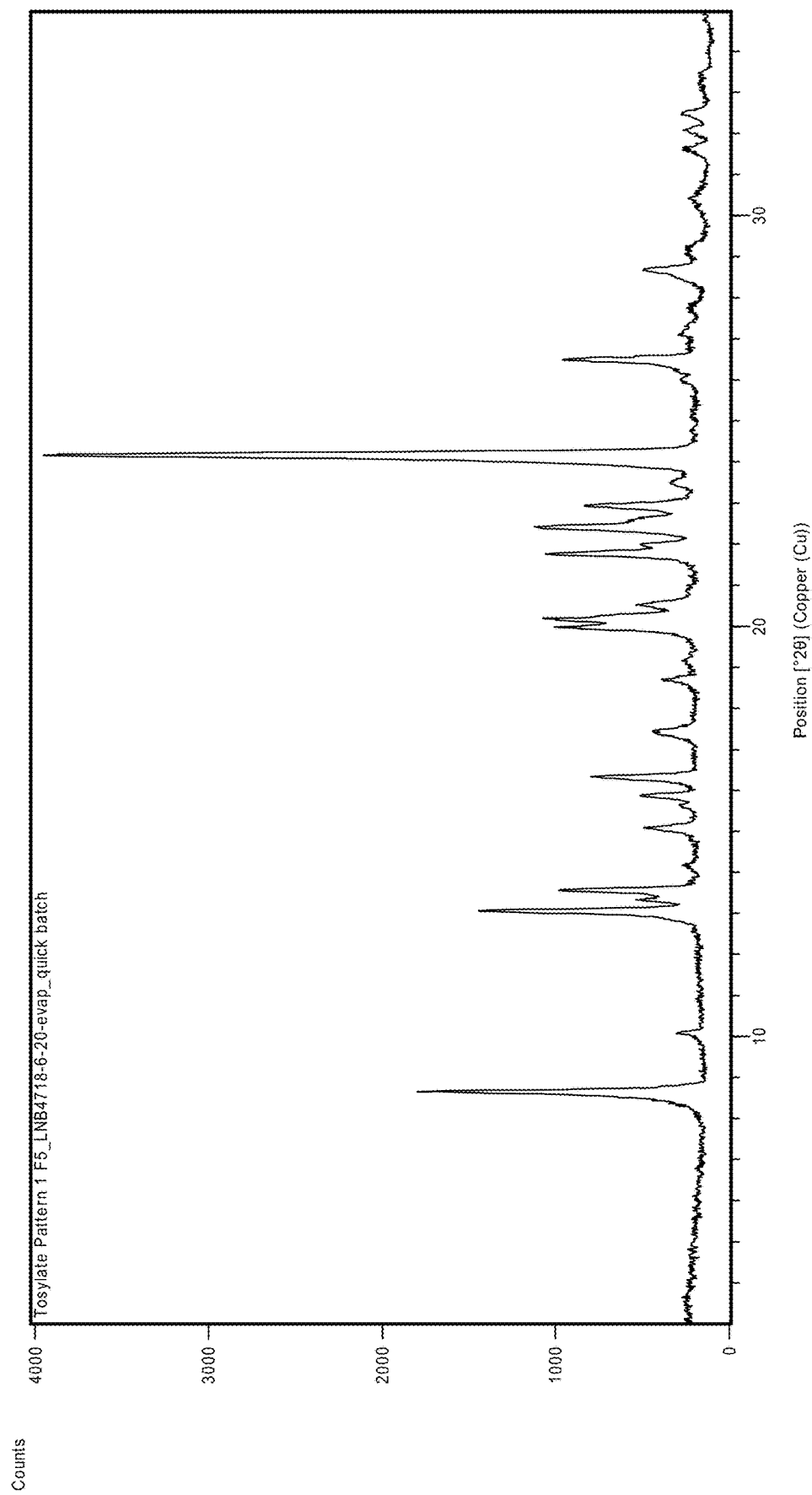
FIG. 17 depicts the XRPD pattern of Compound 4, Form A.

In certain embodiments, the X-ray powder diffraction pattern is substantially similar to the XRPD provided in FIG. 17.

Figure 18:
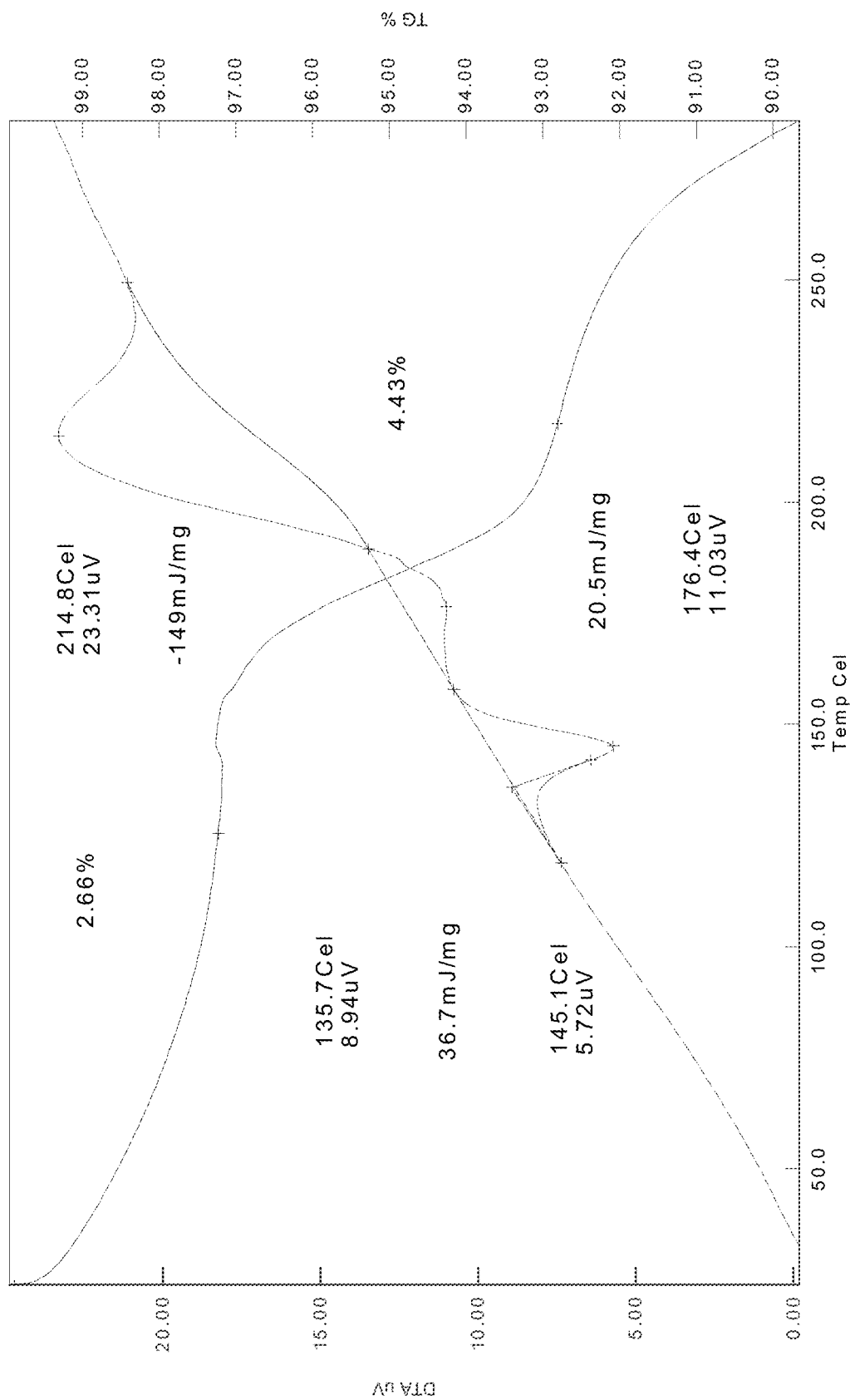
FIG. 18 depicts a DSC thermogram and TGA trace of Compound 4, Form A.

In some embodiments, Form A of Compound 4 is characterized by a differential scanning calorimetry (DSC) thermogram having the endothermic peak(s) as shown in FIG. 18. In some embodiments, Form A of Compound 4 has a DSC thermogram substantially the same as that shown in FIG. 18.

Methods for preparing Form A of Compound 4 are described infra.

ii. Form B of Compound 4

In some embodiments, Form B of Compound 4 has at least 1, 2, 3, 4, 5, or more spectral peak(s) selected from the peaks listed in Table 10 below. In some embodiments, the peak(s) with relatively highest intensity s are selected.

TABLE 10

XRPD Peak Positions for Form B of Compound 4

| Pos. [°2θ] | d-spacing [Å] | Rel. Int. [%] |
|---|---|---|
| 8.7 | 10.17 | 11.38 |
| 8.8 | 10.01 | 28.41 |
| 13.3 | 6.64 | 100.00 |
| 13.8 | 6.42 | 9.72 |
| 14.1 | 6.26 | 26.86 |
| 15.6 | 5.67 | 21.68 |
| 19.2 | 4.62 | 7.20 |
| 20.1 | 4.42 | 32.77 |
| 20.3 | 4.38 | 16.46 |
| 20.5 | 4.33 | 29.77 |
| 21.9 | 4.05 | 62.53 |
| 22.2 | 4.00 | 14.46 |
| 22.4 | 3.96 | 17.84 |
| 23.4 | 3.80 | 33.85 |
| 23.8 | 3.73 | 30.33 |
| 24.1 | 3.69 | 7.52 |
| 25.9 | 3.43 | 50.89 |
| 26.7 | 3.34 | 10.18 |
| 27.2 | 3.28 | 9.55 |
| 28.5 | 3.13 | 22.60 |

[1] In this and all subsequent tables, the position 2θ is within ± 0.2.

In some embodiments, Form B of Compound 4 is characterized in that it has one or more peaks in its X-ray powder diffraction pattern selected from those at about 13.3, about 21.9, and about 25.9 degrees 2-theta. In some embodiments, Form B of Compound 4 is characterized in that it has two or more peaks in its X-ray powder diffraction pattern selected from those at about 13.3, about 21.9, and about 25.9 degrees 2-theta. In some embodiments, Form B of Compound 4 is characterized in that it has all three peaks in its X-ray powder diffraction pattern at about 13.3, about 21.9 and about 25.9 degrees 2-theta. In some embodiments, Form B of Compound 4 is further characterized by additional 1, 2, 3, 4 or 5 peak(s) selected from Table 10.

Figure 19:
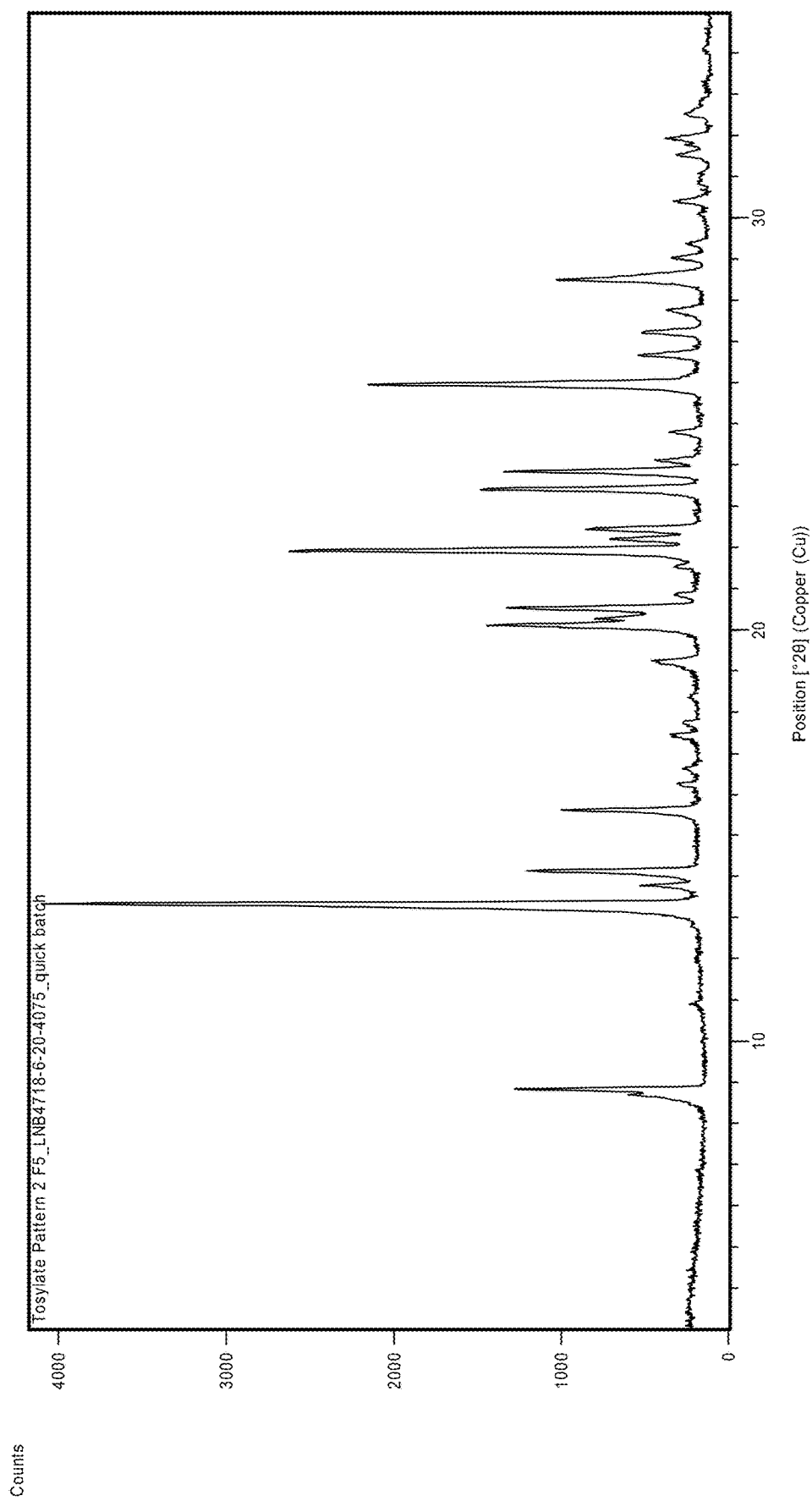
FIG. 19 depicts the XRPD pattern of Compound 4, Form B.

In certain embodiments, the X-ray powder diffraction pattern is substantially similar to the XRPD provided in FIG. 19.

Figure 20:
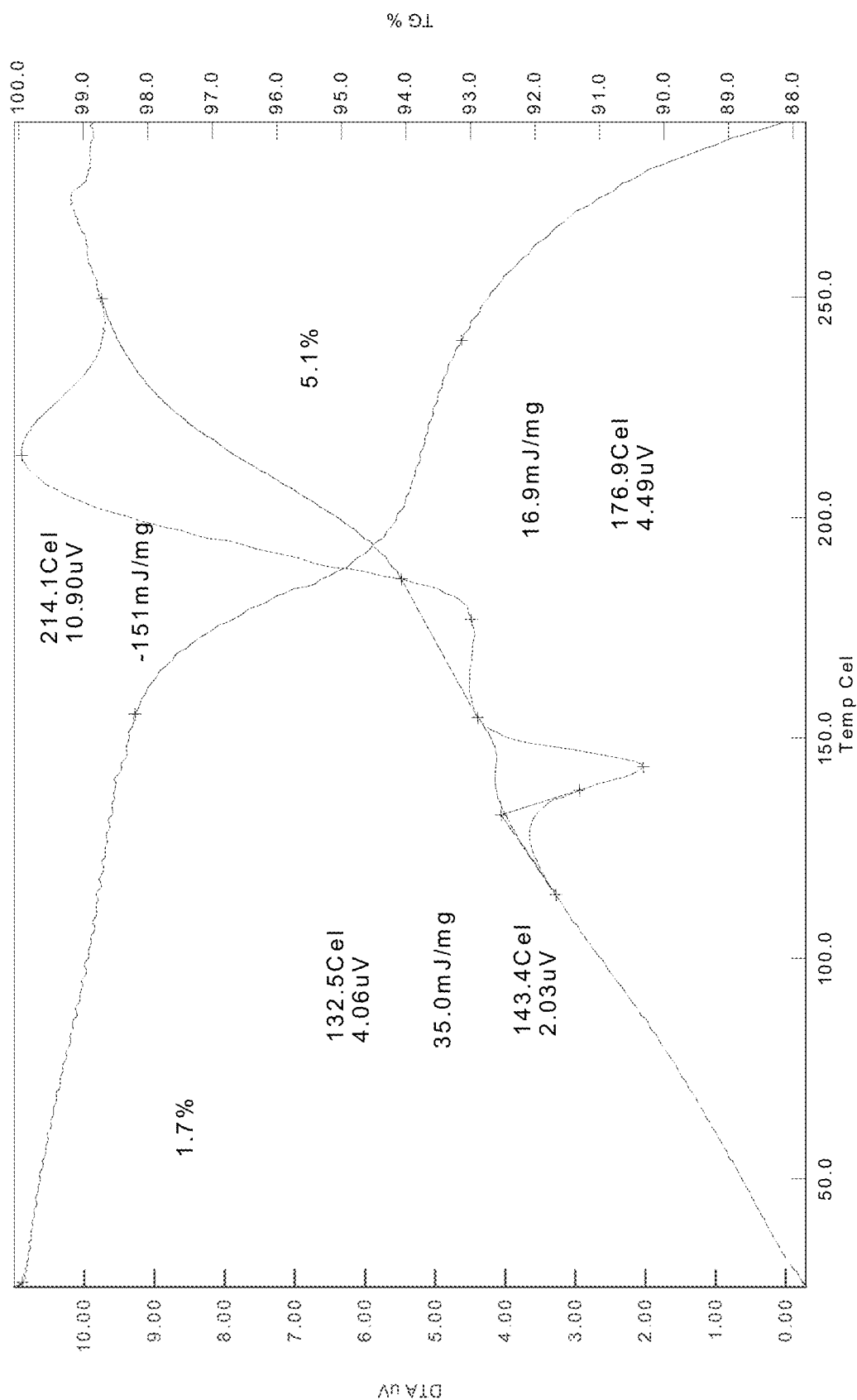
FIG. 20 depicts a DSC thermogram and TGA trace of Compound 4, Form B.

In some embodiments, Form B of Compound 4 is characterized by a differential scanning calorimetry (DSC) thermogram having the endothermic peak(s) as shown in FIG. 20. In some embodiments, Form B of Compound 4 has a DSC thermogram substantially the same as that shown in FIG. 20.

Methods for preparing Form B of Compound 4 are described infra.

In some embodiments, the present invention provides Compound 4:

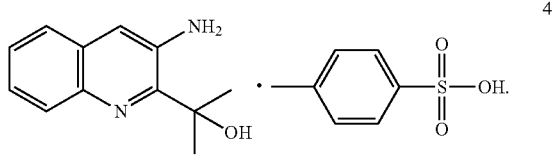

In some embodiments, the present invention provides Compound 4, wherein the compound is crystalline.

In some embodiments, the present invention provides Compound 4, wherein the compound is a crystalline solid substantially free of amorphous Compound 4.

In some embodiments, the present invention provides Compound 4, wherein the compound is substantially free of impurities.

In some embodiments, the present invention provides Compound 4, wherein the compound has one or more peaks in its XRPD selected from those at about 8.7, about 13.1, and about 24.2 degrees 2-theta. In some such embodiments, the present invention provides Compound 4, wherein the compound has at least two peaks in its XRPD selected from those at about 8.7, about 13.01, and about 24.2 degrees 2-theta. In some such embodiments, the present invention provides Compound 4, wherein the compound is of Form A.

In some embodiments, the present invention provides Compound 4, wherein the compound has an XRPD substantially similar to that depicted in FIG. 17.

In some embodiments, the present invention provides Compound 4, wherein the compound has one or more peaks in its XRPD selected from those at about 13.3, about 21.9 and about 25.9 degrees 2-theta. In some such embodiments, the present invention provides Compound 4, wherein the compound has at least two peaks in its XRPD selected from those at about 13.3, about 21.9 and about 25.9 degrees 2-theta. In some such embodiments, the present invention provides Compound 4, wherein the compound is of Form B.

In some embodiments, the present invention provides Compound 4, wherein the compound has an XRPD substantially similar to that depicted in FIG. 19.

In some embodiments, the present invention provides a composition comprising Compound 4 and a pharmaceutically acceptable carrier or excipient.

In some embodiments, the present invention provides a method of inhibiting or preventing the accumulation of A2E in a patient comprising administering to the patient Compound 4 or composition thereof.

In some embodiments, the present invention provides a method of treating various conditions in a patient in which aldehyde toxicity is implicated in the pathogenesis, comprising administering of Compound 4 or composition thereof to the patient. In some such embodiments, the various conditions, in a patient, in which aldehyde toxicity is implicated in the pathogenesis may include dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents.

e. Compound 5—Hydrochloride Salts of Compound A

In some embodiments, the present invention provides a hydrochloride salt of Compound A, represented by Compound 5:

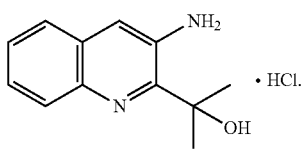

It will be appreciated by one of ordinary skill in the art that the hydrochloric acid and Compound A are ionically bonded to form Compound 5. It is contemplated that Compound 5 can exist in a variety of physical forms. For example, Compound 5 can be in solution, suspension, or in solid form. In certain embodiments, Compound 5 is in solid form. When Compound 5 is in solid form, the compound may be amorphous, crystalline, or a mixture thereof. Exemplary solid forms are described in more detail below.

In some embodiments, the present invention provides Compound 5 substantially free of impurities. As used herein, the term "substantially free of impurities" means that the compound contains no significant amount of extraneous matter. In some embodiments, the "impurities" can be determined by HPLC according to the procedures set forth in the Examples for the relevant solid forms of Compound 5. Such extraneous matter may include excess hydrochloric acid, excess Compound A, residual solvents, or any other impurities that may result from the preparation of, and/or isolation of, Compound 5.

In certain embodiments, at least about 95% by weight of Compound 5 is present. In still other embodiments of the invention, at least about 99% by weight of Compound 5 is present.

In some embodiments, Compound 5 is present in an amount of at least about 97, 97.5, 98.0, 98.5, 99, 99.5, 99.8 weight percent where the percentages are based on the total weight of the composition. In some embodiments, Compound 5 contains no more than about 3.0 area percent HPLC of total organic impurities and, in certain embodiments, no more than about 1.5 area percent HPLC total organic impurities relative to the total area of the HPLC chromatogram. In other embodiments, Compound 5 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 5 is also meant to include all tautomeric forms of Compound 5. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that Compound 5 can exist in at least two distinct polymorphic forms. In some embodiments, the present invention provides a polymorphic form of Compound 5 referred to herein as Form A. In some embodiments, the present invention provides a polymorphic form of Compound 5 referred to herein as Form B.

In certain embodiments, Compound 5 is a crystalline solid. In other embodiments, Compound 5 is a crystalline solid substantially free of amorphous Compound 5. As used herein, the term "substantially free of amorphous Compound 5" means that the compound contains no significant amount of amorphous Compound 5. In certain embodiments, at least about 95% by weight of crystalline Compound 5 is present. In still other embodiments of the invention, at least about 99% by weight of crystalline Compound 5 is present.

In some embodiments, Compound 5 is amorphous. In some embodiments, Compound 5 is amorphous, and is substantially free of crystalline Compound 5.

i. Form A of Compound 5

In some embodiments, Form A of Compound 5 has at least 1, 2, 3, 4, 5, or more spectral peak(s) selected from the peaks listed in Table 11 below. In some embodiments, the peak(s) with relatively highest intensity peak(s) are selected.

TABLE 11

XRPD Peak Positions for Form A of Compound 5

| Pos. [°2θ] | d-spacing [Å] | Rel. Int. [%] |
|---|---|---|
| 10.0 | 8.85 | 13.64 |
| 10.2 | 8.64 | 33.20 |
| 12.7 | 6.97 | 40.44 |
| 13.9 | 6.37 | 79.47 |
| 15.8 | 5.61 | 100.00 |
| 18.2 | 4.86 | 33.01 |
| 18.5 | 4.80 | 39.33 |
| 20.4 | 4.35 | 15.26 |
| 20.8 | 4.27 | 14.96 |
| 21.7 | 4.09 | 27.67 |
| 23.3 | 3.82 | 35.73 |
| 24.3 | 3.66 | 94.78 |
| 24.8 | 3.59 | 18.42 |
| 25.5 | 3.50 | 36.21 |
| 28.0 | 3.19 | 48.63 |
| 28.5 | 3.13 | 17.72 |
| 28.8 | 3.10 | 27.58 |
| 30.0 | 2.98 | 12.41 |
| 30.3 | 2.95 | 57.23 |
| 31.9 | 2.80 | 19.17 |

[1] In this and all subsequent tables, the position 2θ is within ± 0.2.

In some embodiments, Form A of Compound 5 is characterized in that it has one or more peaks in its X-ray powder diffraction pattern selected from those at about 13.9, about 15.8, and about 24.3 degrees 2-theta. In some embodiments, Form A of Compound 5 is characterized in that it has two or more peaks in its X-ray powder diffraction pattern selected from those at about 13.9, about 15.8, and about 24.3 degrees 2-theta. In some embodiments, Form A of Compound 5 is characterized in that it has all three peaks in its X-ray powder diffraction pattern at about 13.9, about 15.8, and about 24.3 degrees 2-theta. In some embodiments, Form A of Compound 5 is further characterized by additional 1, 2, 3, 4 or 5 peak(s) selected from Table 11.

Figure 21:
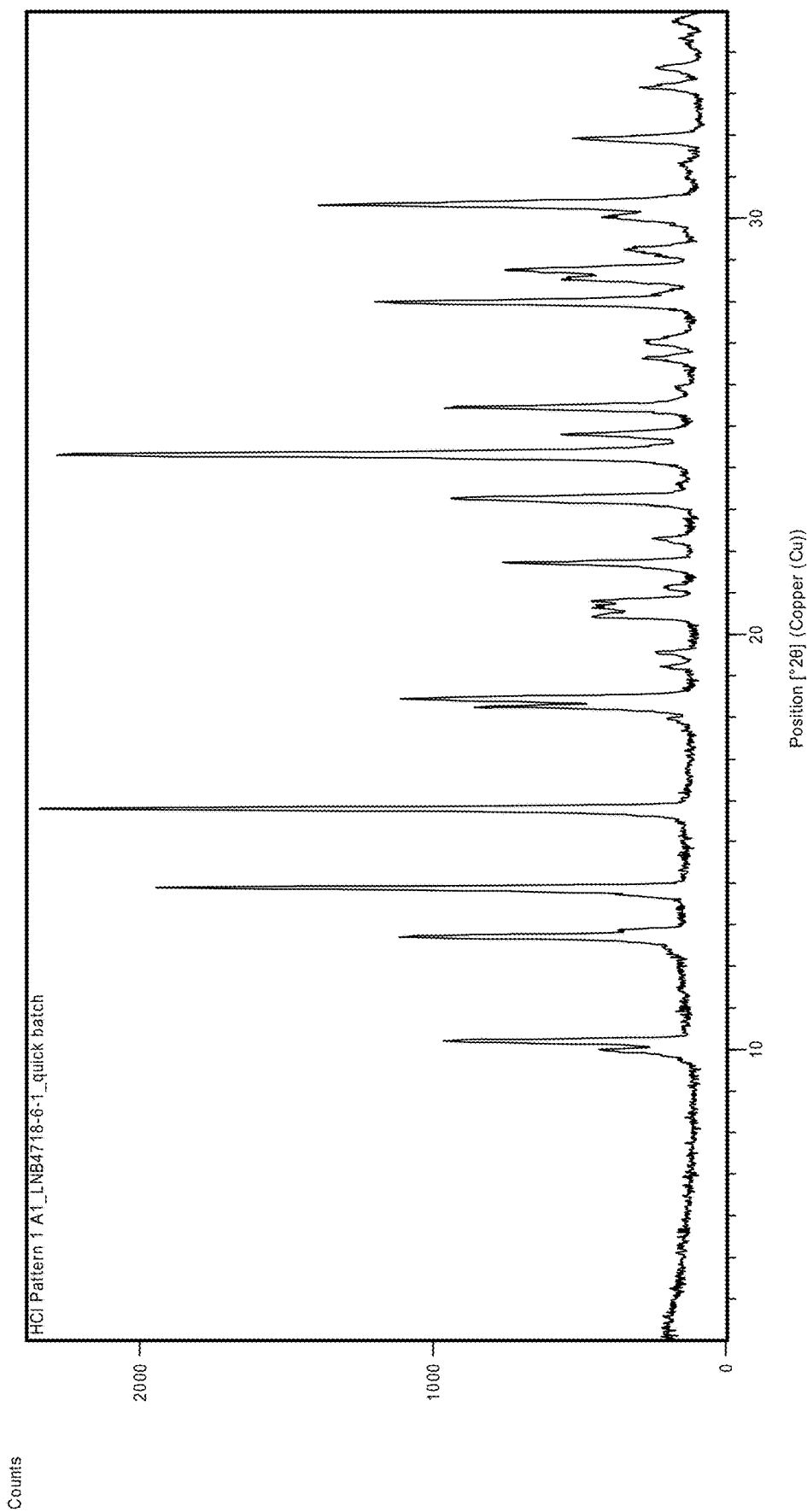
FIG. 21 depicts the XRPD pattern of Compound 5, Form A.

In certain embodiments, the X-ray powder diffraction pattern is substantially similar to the XRPD provided in FIG. 21.

In some embodiments, Form A of Compound 5 is characterized by a differential scanning calorimetry (DSC) thermogram having the endothermic peak(s) as shown in FIG.

22. In some embodiments, Form A of Compound 5 has a DSC thermogram substantially the same as that shown in FIG. 22.

Methods for preparing Form A of Compound 5 are described infra.

ii. Form B of Compound 5

In some embodiments, Form B of Compound 5 has at least 1, 2, 3, 4, 5, or more spectral peak(s) selected from the peaks listed in Table 12 below. In some embodiments, the peak(s) with relatively highest intensity peak(s) are selected.

TABLE 12

XRPD Peak Positions for Form B of Compound 5

| Pos. [°2θ] | d-spacing [Å] | Rel. Int. [%] |
|---|---|---|
| 10.0 | 8.86 | 28.40 |
| 10.2 | 8.71 | 100.00 |
| 11.2 | 7.90 | 11.02 |
| 15.4 | 5.75 | 25.60 |
| 17.0 | 5.21 | 75.77 |
| 17.5 | 5.06 | 16.26 |
| 19.1 | 4.65 | 12.93 |
| 19.9 | 4.47 | 32.12 |
| 20.1 | 4.42 | 7.00 |
| 22.6 | 3.93 | 6.96 |
| 23.5 | 3.79 | 12.62 |
| 23.7 | 3.75 | 15.34 |
| 24.2 | 3.67 | 25.53 |
| 24.3 | 3.66 | 42.05 |
| 26.4 | 3.38 | 23.72 |
| 28.3 | 3.15 | 28.13 |
| 28.8 | 3.10 | 42.83 |
| 28.9 | 3.10 | 21.99 |
| 29.7 | 3.01 | 11.83 |
| 30.5 | 2.93 | 7.93 |

[1] In this and all subsequent tables, the position 2θ is within ± 0.2.

In some embodiments, Form B of Compound 5 is characterized in that it has one or more peaks in its X-ray powder diffraction pattern selected from those at about 10.2, about 17.0, and about 28.8 degrees 2-theta. In some embodiments, Form B of Compound 5 is characterized in that it has two or more peaks in its X-ray powder diffraction pattern selected from those at about 10.2, about 17.0, and about 28.8 degrees 2-theta. In some embodiments, Form B of Compound 5 is characterized in that it has all three peaks in its X-ray powder diffraction pattern selected from those at about 10.2, about 17.0, and about 28.8 degrees 2-theta. In some embodiments, Form B of Compound 5 is further characterized by additional 1, 2, 3, 4 or 5 peak(s) selected from Table 12.

Figure 23:
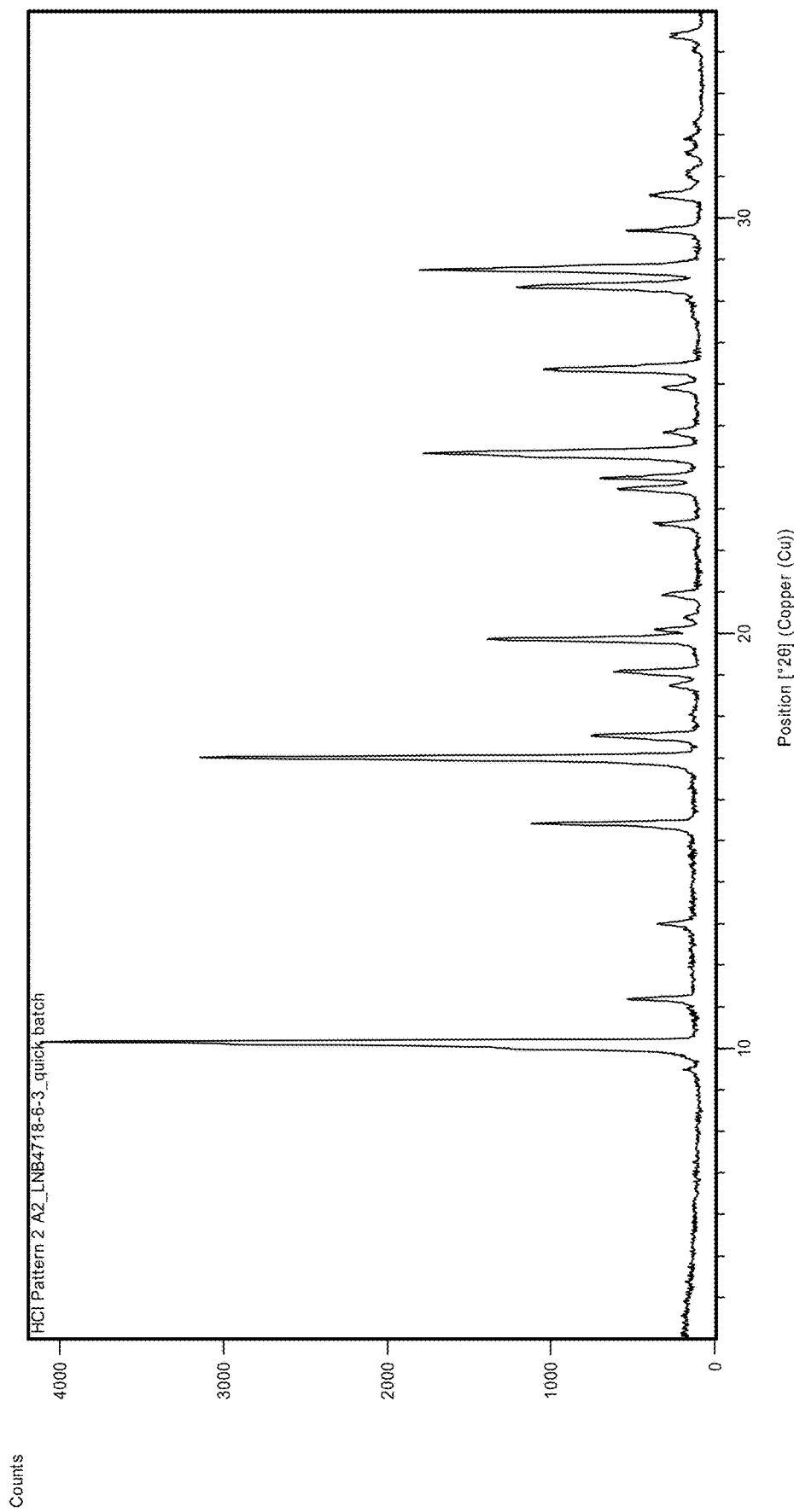
FIG. 23 depicts the XRPD pattern of Compound 5, Form B.

In certain embodiments, the X-ray powder diffraction pattern is substantially similar to the XRPD provided in FIG. 23.

Figure 24:
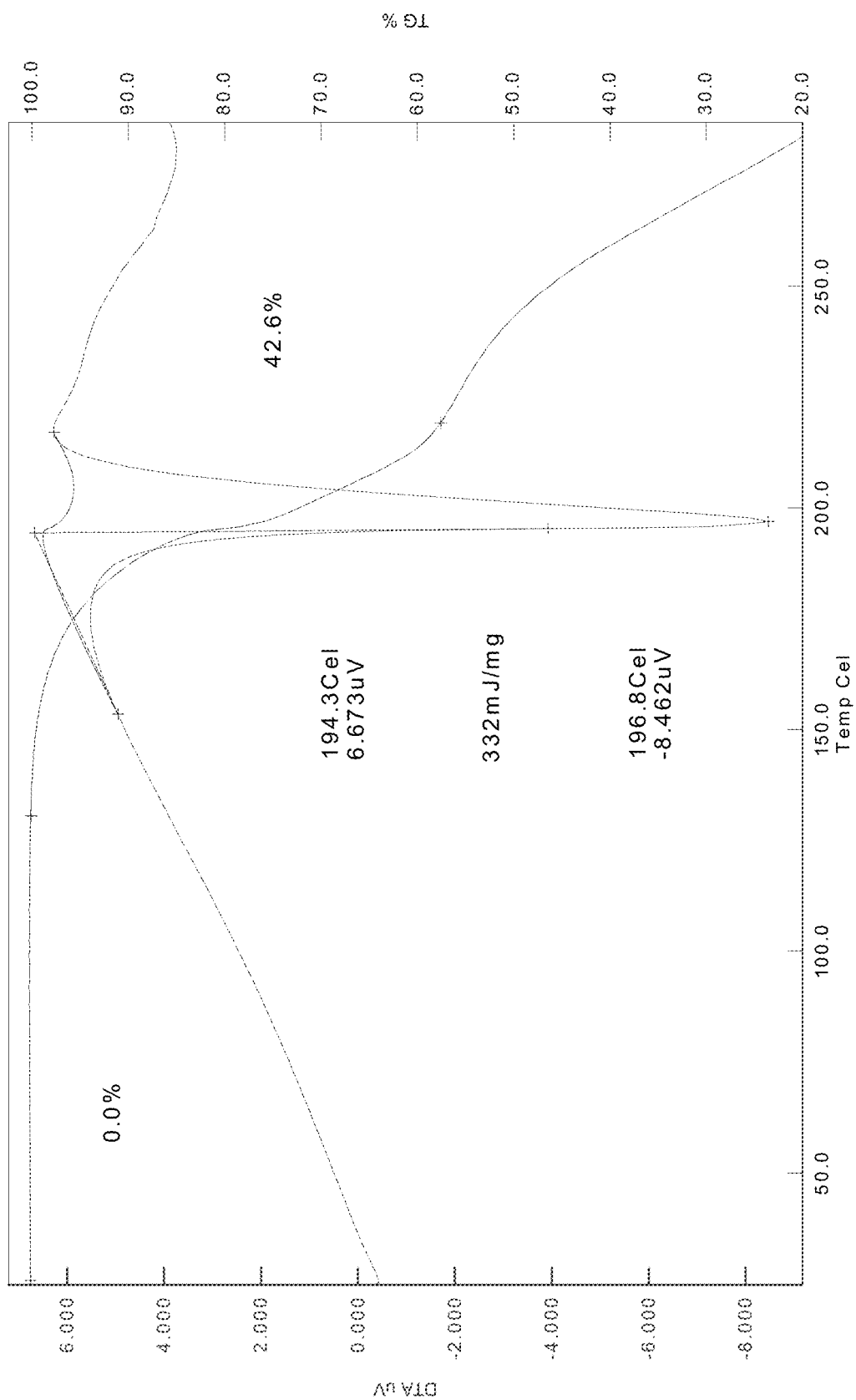
FIG. 24 depicts a DSC thermogram and TGA trace of Compound 5, Form B.

In some embodiments, Form B of Compound 5 is characterized by a differential scanning calorimetry (DSC) thermogram having the endothermic peak(s) as shown in FIG. 24. In some embodiments, Form B of Compound 5 has a DSC thermogram substantially the same as that shown in FIG. 24.

Methods for preparing Form B of Compound 5 are described infra.

In some embodiments, the present invention provides Compound 5:

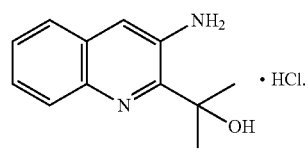

In some embodiments, the present invention provides Compound 5, wherein the compound is crystalline.

In some embodiments, the present invention provides Compound 5, wherein the compound is a crystalline solid substantially free of amorphous Compound 5.

In some embodiments, the present invention provides compound 5, wherein the compound is substantially free of impurities.

In some embodiments, the present invention provides Compound 5, wherein the compound has one or more peaks in its XRPD selected from those at about 13.9, about 15.8, and about 24.3 degrees 2-theta. In some such embodiments, the present invention provides Compound 5, wherein the compound has at least two peaks in its XRPD selected from those at about 13.9, about 15.8, and about 24.3 degrees 2-theta. In some such embodiments, the present invention provides Compound 5, wherein the compound is of Form A.

In some embodiments, the present invention provides Compound 5, wherein the compound has an XRPD substantially similar to that depicted in FIG. 21.

In some embodiments, the present invention provides Compound 5, wherein the compound has one or more peaks in its XRPD selected from those at about 10.2, about 17.0, and about 28.8 degrees 2-theta. In some such embodiments, the present invention provides Compound 5, wherein the compound has at least two peaks in its XRPD selected from those at about 10.2, about 17.0, and about 28.8 degrees 2-theta. In some such embodiments, the present invention provides Compound 5, wherein the compound is of Form B.

In some embodiments, the present invention provides Compound 5, wherein the compound has an XRPD substantially similar to that depicted in FIG. 23.

In some embodiments, the present invention provides a composition comprising Compound 5 and a pharmaceutically acceptable carrier or excipient.

In some embodiments, the present invention provides a method of inhibiting or preventing the accumulation of A2E in a patient comprising administering to the patient Compound 5 or composition thereof.

In some embodiments, the present invention provides a method of treating various conditions in a patient in which aldehyde toxicity is implicated in the pathogenesis, comprising administering of Compound 5 or composition thereof to the patient. In some such embodiments, the various conditions, in a patient, in which aldehyde toxicity is implicated in the pathogenesis may include dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents.

f. Compound 6—Oxalate Salts of Compound A

In some embodiments, the present invention provides an oxalate salt of Compound A, represented by Compound 6:

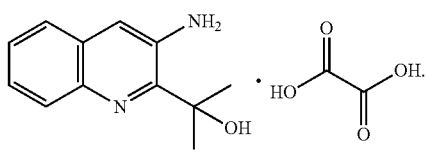

It will be appreciated by one of ordinary skill in the art that the oxalic acid and Compound A are ionically bonded to form Compound 6. It is contemplated that Compound 6 can exist in a variety of physical forms. For example, Compound 6 can be in solution, suspension, or in solid form. In certain embodiments, Compound 6 is in solid form. When Compound 6 is in solid form, the compound may be amorphous, crystalline, or a mixture thereof. Exemplary solid forms are described in more detail below.

In some embodiments, the present invention provides Compound 6 substantially free of impurities. As used herein, the term "substantially free of impurities" means that the compound contains no significant amount of extraneous matter. In some embodiments, the "impurities" can be determined by HPLC according to the procedures set forth in the Examples for the relevant solid forms of Compound 6. Such extraneous matter may include excess oxalic acid, excess Compound A, residual solvents, or any other impurities that may result from the preparation of, and/or isolation of, Compound 6.

In certain embodiments, at least about 95% by weight of Compound 6 is present. In still other embodiments of the invention, at least about 99% by weight of Compound 6 is present.

In some embodiments, Compound 6 is present in an amount of at least about 97, 97.5, 98.0, 98.5, 99, 99.5, 99.8 weight percent where the percentages are based on the total weight of the composition. In some embodiments, Compound 6 contains no more than about 3.0 area percent HPLC of total organic impurities and, in certain embodiments, no more than about 1.5 area percent HPLC total organic impurities relative to the total area of the HPLC chromatogram. In other embodiments, Compound 6 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 6 is also meant to include all tautomeric forms of Compound 6. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that Compound 6 can exist in at least two distinct polymorphic forms. In some embodiments, the present invention provides a polymorphic form of Compound 6 referred to herein as Form A. In some embodiments, the present invention provides a polymorphic form of Compound 6 referred to herein as Form B.

In certain embodiments, Compound 6 is a crystalline solid. In other embodiments, Compound 6 is a crystalline solid substantially free of amorphous Compound 6. As used herein, the term "substantially free of amorphous Compound 6" means that the compound contains no significant amount of amorphous Compound 6. In certain embodiments, at least about 95% by weight of crystalline Compound 6 is present. In still other embodiments of the invention, at least about 99% by weight of crystalline Compound 6 is present.

In some embodiments, Compound 6 is amorphous. In some embodiments, Compound 6 is amorphous, and is substantially free of crystalline Compound 6.

i. Form A of Compound 6

In some embodiments, Form A of Compound 6 has at least 1, 2, 3, 4, 5, or more spectral peak(s) selected from the peaks listed in Table 13 below. In some embodiments, the peak(s) with relatively highest intensity peak(s) are selected.

TABLE 13

XRPD Peak Positions for Form A of Compound 6

| Pos. [°2θ] | d-spacing [Å] | Rel. Int. [%] |
|---|---|---|
| 8.6 | 10.23 | 86.55 |
| 10.2 | 8.66 | 8.43 |
| 15.7 | 5.64 | 31.46 |
| 16.0 | 5.54 | 40.56 |
| 16.2 | 5.48 | 30.47 |
| 16.8 | 5.29 | 100.00 |
| 17.1 | 5.18 | 31.46 |
| 17.3 | 5.11 | 17.50 |
| 20.0 | 4.43 | 7.15 |
| 20.5 | 4.33 | 7.93 |
| 21.5 | 4.13 | 21.08 |
| 22.0 | 4.04 | 16.09 |
| 24.7 | 3.61 | 6.97 |
| 25.0 | 3.57 | 18.33 |
| 26.1 | 3.41 | 25.03 |
| 27.1 | 3.29 | 51.72 |
| 27.9 | 3.20 | 18.68 |
| 28.2 | 3.17 | 22.55 |
| 28.5 | 3.13 | 14.24 |
| 28.7 | 3.11 | 21.77 |

[1] In this and all subsequent tables, the position 2θ is within ± 0.2.

In some embodiments, Form A of Compound 6 is characterized in that it has one or more peaks in its X-ray powder diffraction pattern selected from those at about 8.6, about 16.8, and about 27.1 degrees 2-theta. In some embodiments, Form A of Compound 6 is characterized in that it has two or more peaks in its X-ray powder diffraction pattern selected from those at about 8.6, about 16.8, and about 27.1 degrees 2-theta. In some embodiments, Form A of Compound 6 is characterized in that it has all three peaks in its X-ray powder diffraction pattern selected from those at about 8.6, about 16.8, and about 27.1 degrees 2-theta. In some embodiments, Form A of Compound 6 is further characterized by additional 1, 2, 3, 4 or 5 peak(s) selected from Table 13.

Figure 25:
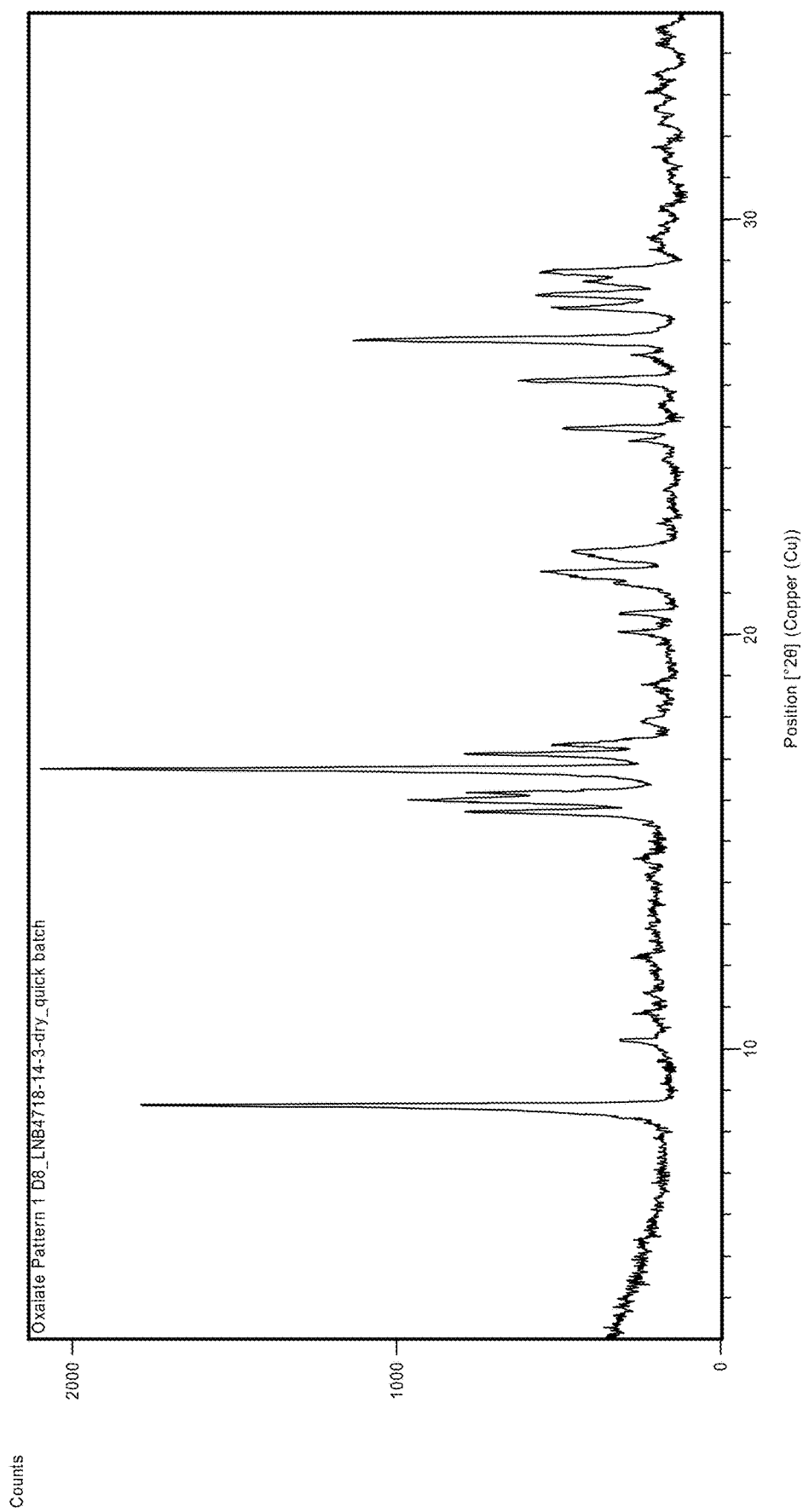
FIG. 25 depicts the XRPD pattern of Compound 6, Form A.

In certain embodiments, the X-ray powder diffraction pattern is substantially similar to the XRPD provided in FIG. 25.

In some embodiments, Form A of Compound 6 is characterized by a differential scanning calorimetry (DSC) thermogram having the endothermic peak(s) as shown in FIG.

26. In some embodiments, Form A of Compound 6 has a DSC thermogram substantially the same as that shown in FIG. 26.

Methods for preparing Form A of Compound 6 are described infra.

ii. Form B of Compound 6

In some embodiments, Form B of Compound 6 has at least 1, 2, 3, 4, 5, or more spectral peak(s) selected from the peaks listed in Table 14 below. In some embodiments, the peak(s) with relatively highest intensity peak(s) are selected.

TABLE 14

XRPD Peak Positions for Form B of Compound 6

| Pos. [°2θ] | d-spacing [Å] | Rel. Int. [%] |
| --- | --- | --- |
| 8.5 | 10.36 | 44.51 |
| 12.3 | 7.20 | 20.12 |
| 13.4 | 6.62 | 91.58 |
| 14.1 | 6.28 | 60.91 |
| 17.1 | 5.18 | 20.07 |
| 17.3 | 5.13 | 14.24 |
| 18.2 | 4.87 | 100.00 |
| 18.8 | 4.73 | 27.65 |
| 19.4 | 4.57 | 52.42 |
| 21.7 | 4.09 | 46.91 |
| 22.0 | 4.04 | 54.20 |
| 22.7 | 3.92 | 14.75 |
| 24.7 | 3.61 | 20.46 |
| 25.7 | 3.46 | 91.67 |
| 26.8 | 3.32 | 14.79 |
| 27.5 | 3.25 | 26.29 |
| 28.0 | 3.19 | 21.10 |
| 28.5 | 3.13 | 14.86 |
| 29.0 | 3.08 | 19.77 |
| 29.2 | 3.06 | 35.09 |

[1] In this and all subsequent tables, the position 2θ is within ± 0.2.

In some embodiments, Form B of Compound 6 is characterized in that it has one or more peaks in its X-ray powder diffraction pattern selected from those at about 13.4, about 18.2, and about 25.7 degrees 2-theta. In some embodiments, Form B of Compound 6 is characterized in that it has two or more peaks in its X-ray powder diffraction pattern selected from those at about 13.4, about 18.2, and about 25.7 degrees 2-theta. In some embodiments, Form B of Compound 6 is characterized in that it has all three peaks in its X-ray powder diffraction pattern at about 13.4, about 18.2 and about 25.7 degrees 2-theta. In some embodiments, Form B of Compound 6 is further characterized by additional 1, 2, 3, 4 or 5 peak(s) selected from Table 14.

Figure 27:
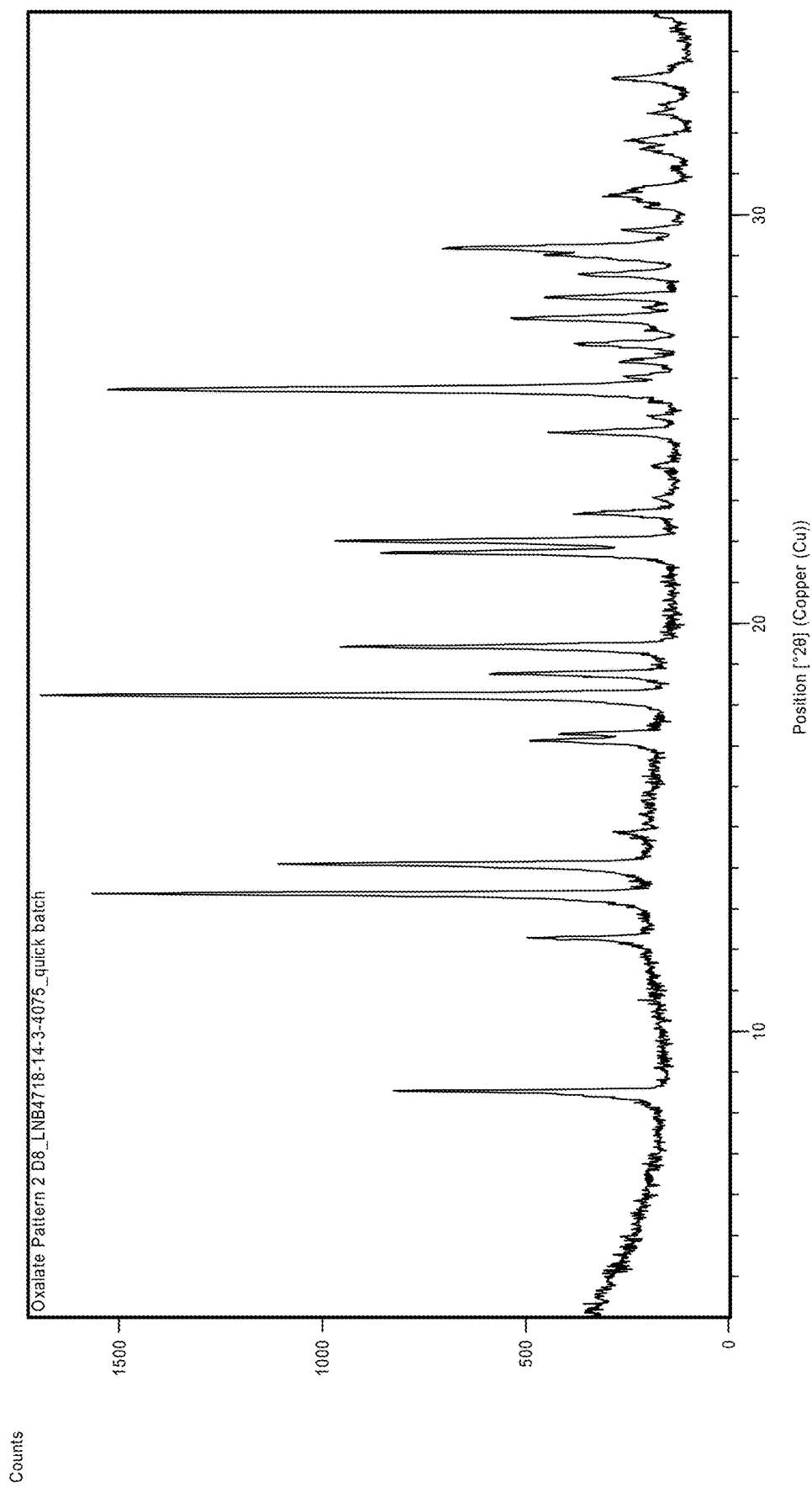
FIG. 27 depicts the XRPD pattern of Compound 6, Form B.

In certain embodiments, the X-ray powder diffraction pattern is substantially similar to the XRPD provided in FIG. 27.

Figure 28:
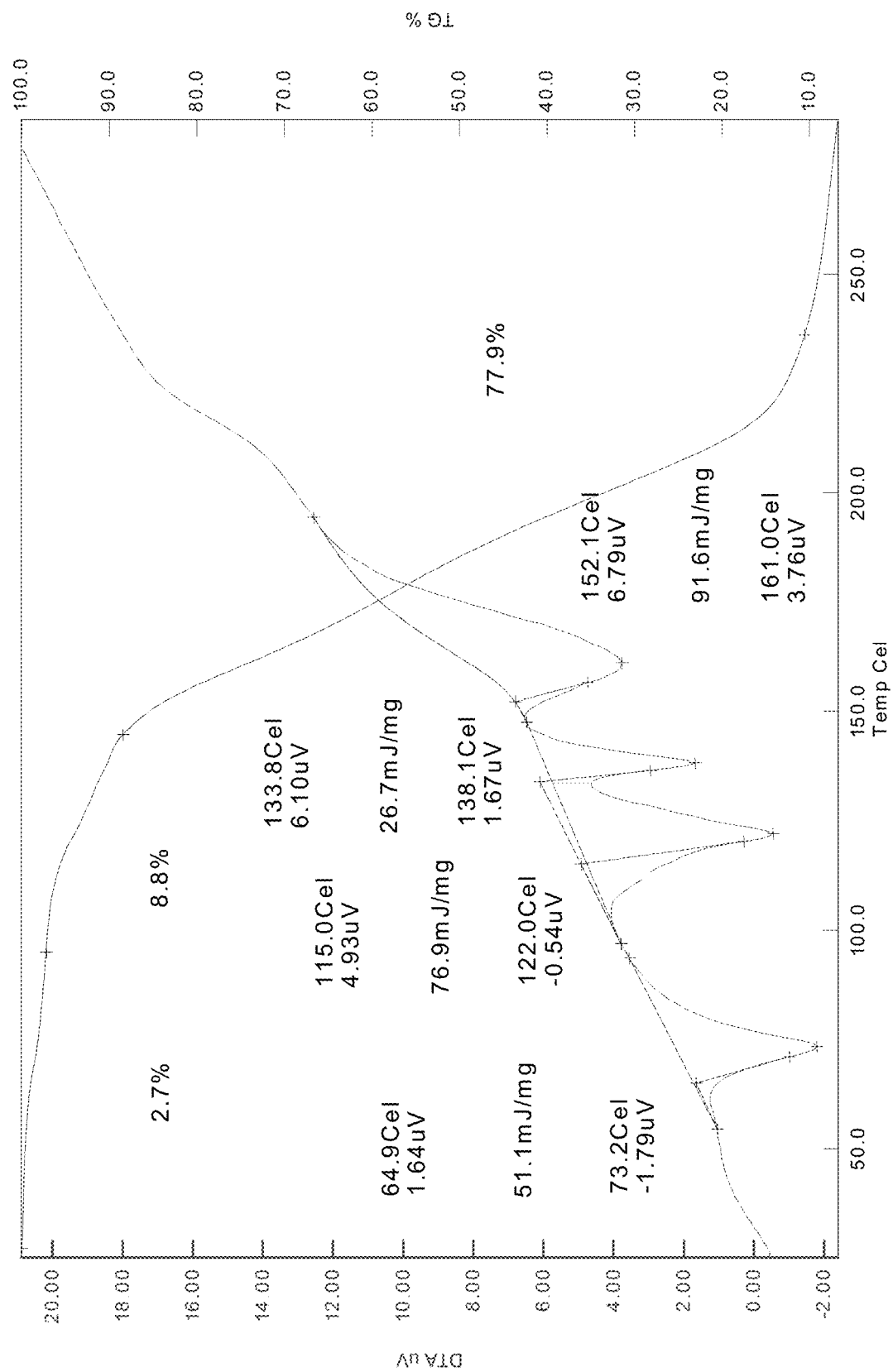
FIG. 28 depicts a DSC thermogram and TGA trace of Compound 6, Form B.

In some embodiments, Form B of Compound 6 is characterized by a differential scanning calorimetry (DSC) thermogram having the endothermic peak(s) as shown in FIG. 28. In some embodiments, Form B of Compound 6 has a DSC thermogram substantially the same as that shown in FIG. 28.

Methods for preparing Form B of Compound 6 are described infra.

In some embodiments, the present invention provides Compound 6:

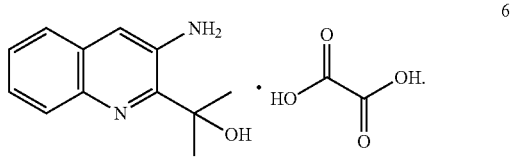

In some embodiments, the present invention provides Compound 6, wherein the compound is crystalline.

In some embodiments, the present invention provides Compound 6, wherein the compound is a crystalline solid substantially free of amorphous Compound 6.

In some embodiments, the present invention provides Compound 6, wherein the compound is substantially free of impurities.

In some embodiments, the present invention provides Compound 6, wherein the compound has one or more peaks in its XRPD selected from those at about 8.6, about 16.8, and about 27.1 degrees 2-theta. In some such embodiments, the present invention provides Compound 6, wherein the compound has at least two peaks in its XRPD selected from those at about 8.6, about 16.8, and about 27.1 degrees 2-theta. In some such embodiments, the present invention provides Compound 6, wherein the compound is of Form A.

In some embodiments, the present invention provides Compound 6, wherein the compound has an XRPD substantially similar to that depicted in FIG. 25.

In some embodiments, the present invention provides Compound 6, wherein the compound has one or more peaks in its XRPD selected from those at about 13.4, about 18.2, and about 25.7 degrees 2-theta. In some such embodiments, the present invention provides Compound 6, wherein the compound has at least two peaks in its XRPD selected from those at about 13.4, about 18.2, and about 25.7 degrees 2-theta. In some such embodiments, the present invention provides Compound 6, wherein the compound is of Form B.

In some embodiments, the present invention provides Compound 6, wherein the compound has an XRPD substantially similar to that depicted in FIG. 27.

In some embodiments, the present invention provides a composition comprising Compound 6 and a pharmaceutically acceptable carrier or excipient.

In some embodiments, the present invention provides a method of inhibiting or preventing the accumulation of A2E in a patient comprising administering to the patient Compound 6 or composition thereof.

In some embodiments, the present invention provides a method of treating various conditions in a patient in which aldehyde toxicity is implicated in the pathogenesis, comprising administering of Compound 6 or composition thereof to the patient. In some such embodiments, the various conditions, in a patient, in which aldehyde toxicity is implicated in the pathogenesis may include dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents.

g. Compound 7—Phosphate Salts of Compound A

In some embodiments, the present invention provides a phosphate salt of Compound A, represented by Compound 7:

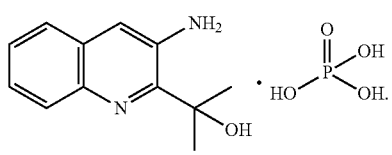

It will be appreciated by one of ordinary skill in the art that the phosphoric acid and Compound A are ionically bonded to form Compound 7. It is contemplated that Compound 7 can exist in a variety of physical forms. For example, Compound 7 can be in solution, suspension, or in solid form. In certain embodiments, Compound 7 is in solid form. When Compound 7 is in solid form, the compound may be amorphous, crystalline, or a mixture thereof. Exemplary solid forms are described in more detail below.

In some embodiments, the present invention provides Compound 7 substantially free of impurities. As used herein, the term "substantially free of impurities" means that the compound contains no significant amount of extraneous matter. In some embodiments, the "impurities" can be determined by HPLC according to the procedures set forth in the Examples for the relevant solid forms of Compound 7. Such extraneous matter may include excess phosphoric acid, excess Compound A, residual solvents, or any other impurities that may result from the preparation of, and/or isolation of, Compound 7.

In certain embodiments, at least about 95% by weight of Compound 7 is present. In still other embodiments of the invention, at least about 99% by weight of Compound 7 is present.

In some embodiments, Compound 7 is present in an amount of at least about 97, 97.5, 98.0, 98.5, 99, 99.5, 99.8 weight percent where the percentages are based on the total weight of the composition. In some embodiments, Compound 7 contains no more than about 3.0 area percent HPLC of total organic impurities and, in certain embodiments, no more than about 1.5 area percent HPLC total organic impurities relative to the total area of the HPLC chromatogram. In other embodiments, Compound 7 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 7 is also meant to include all tautomeric forms of Compound 7. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that Compound 7 can exist in at least two distinct polymorphic forms. In some embodiments, the present invention provides a polymorphic form of Compound 7 referred to herein as Form A. In some embodiments, the present invention provides a polymorphic form of Compound 7 referred to herein as Form B.

In certain embodiments, Compound 7 is a crystalline solid. In other embodiments, Compound 7 is a crystalline solid substantially free of amorphous Compound 7. As used herein, the term "substantially free of amorphous Compound 7" means that the compound contains no significant amount of amorphous Compound 7. In certain embodiments, at least about 95% by weight of crystalline Compound 7 is present. In still other embodiments of the invention, at least about 99% by weight of crystalline Compound 7 is present.

In some embodiments, Compound 7 is amorphous. In some embodiments, Compound 7 is amorphous, and is substantially free of crystalline Compound 7.

i. Form A of Compound 7

In some embodiments, Form A of Compound 7 has at least 1, 2, 3, 4, 5, or more spectral peak(s) selected from the peaks listed in Table 15 below. In some embodiments, the peak(s) with relatively highest intensity peak(s) are selected.

TABLE 15

XRPD Peak Positions for Form A of Compound 7

| Pos. [°2θ] | d-spacing [Å] | Rel. Int. [%] |
|---|---|---|
| 8.4 | 10.53 | 100.00 |
| 9.0 | 9.80 | 5.36 |
| 15.3 | 5.78 | 25.51 |
| 15.8 | 5.60 | 20.83 |
| 16.0 | 5.54 | 85.37 |
| 16.5 | 5.38 | 6.55 |
| 16.8 | 5.26 | 22.25 |
| 17.0 | 5.22 | 8.48 |
| 18.6 | 4.77 | 5.65 |
| 20.1 | 4.43 | 8.80 |
| 20.4 | 4.35 | 22.36 |
| 21.2 | 4.19 | 4.84 |
| 21.9 | 4.06 | 8.96 |
| 22.6 | 3.94 | 26.89 |
| 24.4 | 3.65 | 11.44 |
| 24.5 | 3.63 | 6.64 |
| 25.4 | 3.51 | 9.59 |
| 25.7 | 3.47 | 6.63 |
| 27.0 | 3.31 | 11.90 |
| 27.3 | 3.26 | 11.42 |

[1] In this and all subsequent tables, the position 2θ is within ± 0.2.

In some embodiments, Form A of Compound 7 is characterized in that it has one or more peaks in its X-ray powder diffraction pattern selected from those at about 8.4, about 16.0, and about 22.6 degrees 2-theta. In some embodiments, Form A of Compound 7 is characterized in that it has two or more peaks in its X-ray powder diffraction pattern selected from those at about 8.4, about 16.0, and about 22.6 degrees 2-theta. In some embodiments, Form A of Compound 7 is characterized in that it has all three peaks in its X-ray powder diffraction pattern at about 8.4, about 16.0, and about 22.6 degrees 2-theta. In some embodiments, Form A of Compound 7 is further characterized by additional 1, 2, 3, 4 or 5 peak(s) selected from Table 15.

Figure 29:
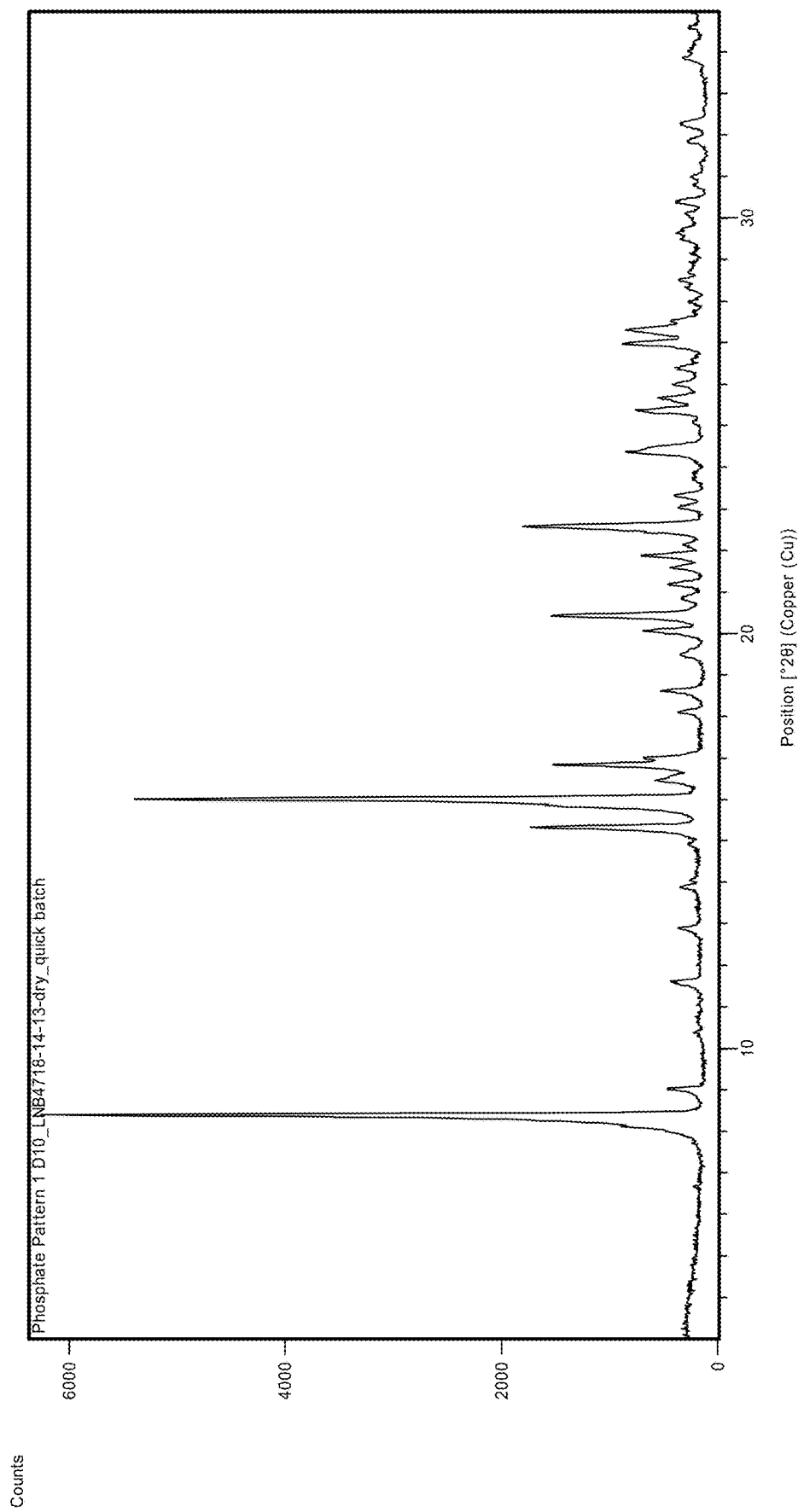
FIG. 29 depicts the XRPD pattern of Compound 7, Form A.

In certain embodiments, the X-ray powder diffraction pattern is substantially similar to the XRPD provided in FIG. 29.

In some embodiments, Form A of Compound 7 is characterized by a differential scanning calorimetry (DSC) thermogram having the endothermic peak(s) as shown in FIG.

30. In some embodiments, Form A of Compound 7 has a DSC thermogram substantially the same as that shown in FIG. 30.

Methods for preparing Form A of Compound 7 are described infra.

ii. Form B of Compound 7

In some embodiments, Form B of Compound 7 has at least 1, 2, 3, 4, 5, or more spectral peak(s) selected from the peaks listed in Table 16 below. In some embodiments, the peak(s) with relatively highest intensity peak(s) are selected.

TABLE 16

XRPD Peak Positions for Form B of Compound 7

| Pos. [°2θ] | d-spacing [Å] | Rel. Int. [%] |
| --- | --- | --- |
| 8.9 | 9.91 | 42.39 |
| 10.9 | 8.14 | 46.60 |
| 15.3 | 5.80 | 3.09 |
| 15.7 | 5.64 | 50.69 |
| 18.6 | 4.78 | 3.20 |
| 19.0 | 4.66 | 15.85 |
| 19.7 | 4.50 | 100.00 |
| 20.7 | 4.29 | 12.13 |
| 21.5 | 4.14 | 2.79 |
| 23.7 | 3.76 | 6.08 |
| 24.0 | 3.71 | 4.88 |
| 25.0 | 3.56 | 7.89 |
| 25.9 | 3.43 | 79.04 |
| 26.0 | 3.43 | 36.75 |
| 26.3 | 3.38 | 7.08 |
| 26.5 | 3.36 | 8.49 |
| 27.8 | 3.21 | 3.86 |
| 28.1 | 3.17 | 8.63 |
| 32.0 | 2.80 | 7.98 |
| 34.7 | 2.58 | 5.16 |

[1] In this and all subsequent tables, the position 2θ is within ± 0.2.

In some embodiments, Form B of Compound 7 is characterized in that it has one or more peaks in its X-ray powder diffraction pattern selected from those at about 15.7, about 19.7, and about 25.9 degrees 2-theta. In some embodiments, Form B of Compound 7 is characterized in that it has two or more peaks in its X-ray powder diffraction pattern selected from those at about 15.7, about 19.7, and about 25.9 degrees 2-theta. In some embodiments, Form B of Compound 7 is characterized in that it has all three peaks in its X-ray powder diffraction pattern at about 15.7, about 19.7, and about 25.9 degrees 2-theta. In some embodiments, Form B of Compound 7 is further characterized by additional 1, 2, 3, 4 or 5 peak(s) selected from Table 16.

Figure 31:
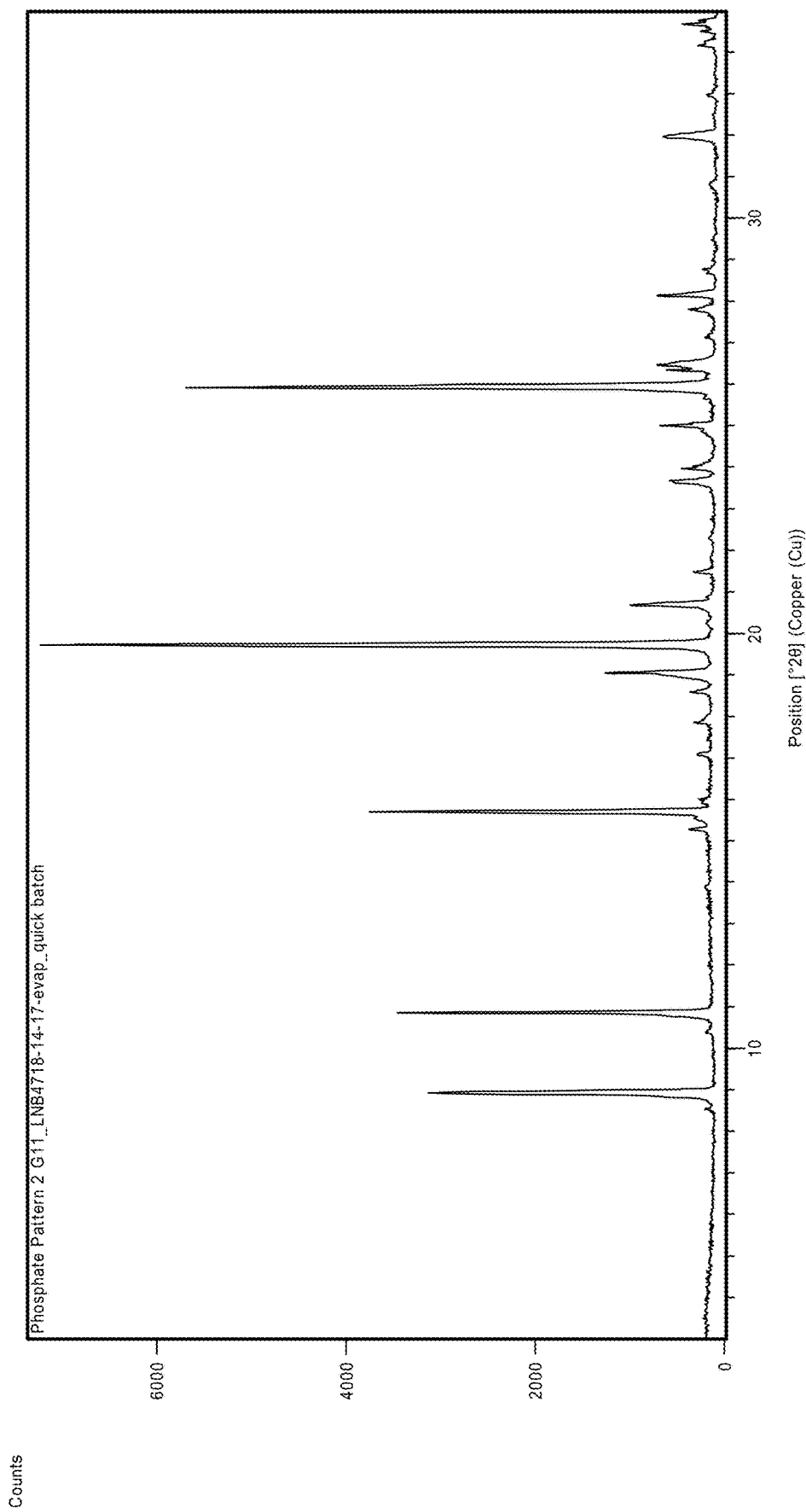
FIG. 31 depicts the XRPD pattern of Compound 7, Form B.

In certain embodiments, the X-ray powder diffraction pattern is substantially similar to the XRPD provided in FIG. 31.

Figure 32:
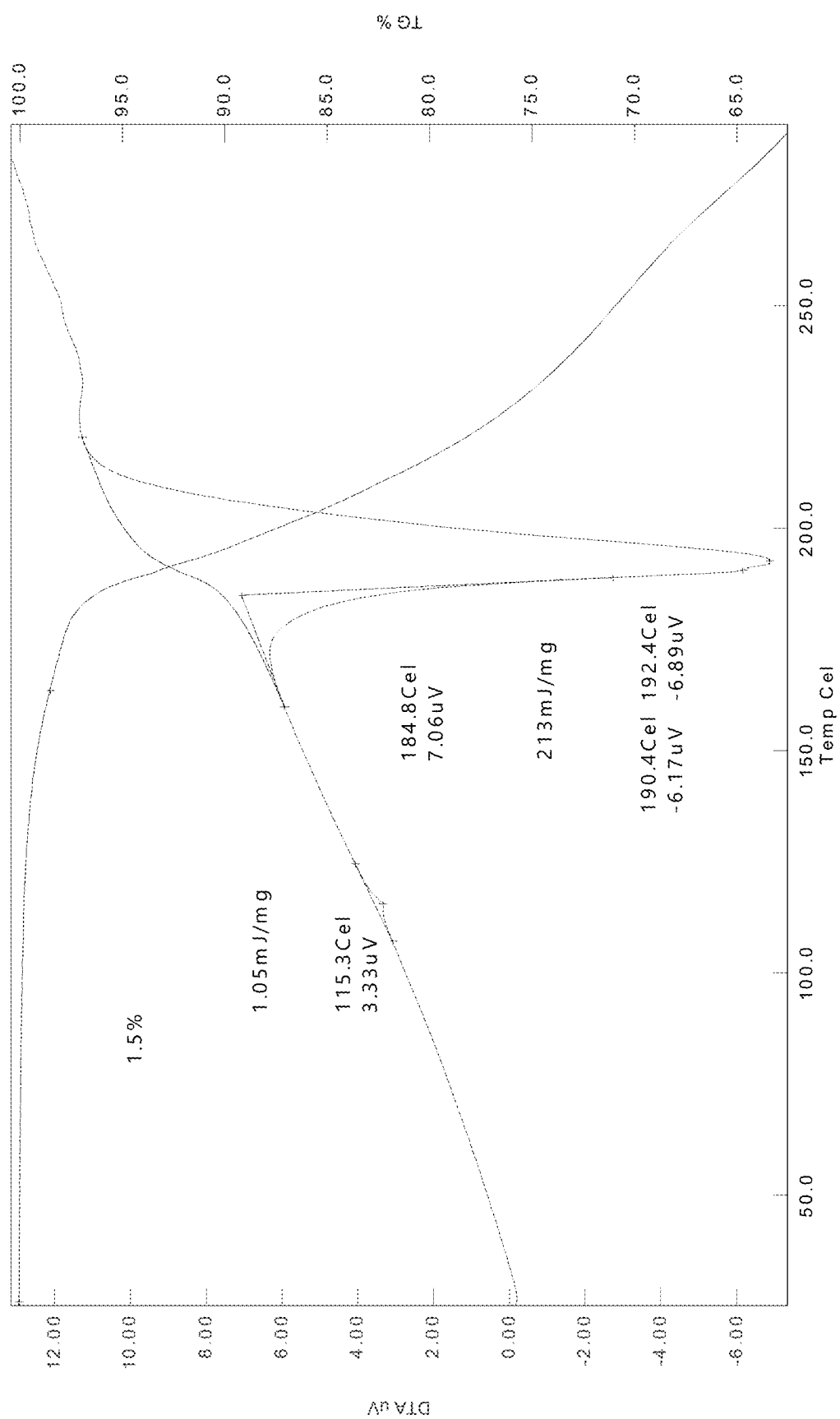
FIG. 32 depicts a DSC thermogram and TGA trace of Compound 7, Form B.

In some embodiments, Form B of Compound 7 is characterized by a differential scanning calorimetry (DSC) thermogram having the endothermic peak(s) as shown in FIG. 32. In some embodiments, Form B of Compound 7 has a DSC thermogram substantially the same as that shown in FIG. 32.

Methods for preparing Form B of Compound 7 are described infra.

In some embodiments, the present invention provides Compound 7:

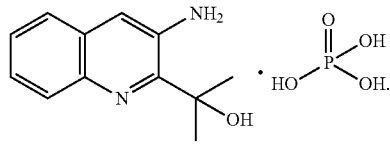

In some embodiments, the present invention provides Compound 7, wherein the compound is crystalline.

In some embodiments, the present invention provides Compound 7, wherein the compound is a crystalline solid substantially free of amorphous Compound 7.

In some embodiments, the present invention provides Compound 7, wherein the compound is substantially free of impurities.

In some embodiments, the present invention provides Compound 7, wherein the compound has one or more peaks in its XRPD selected from those at about 8.4, about 16.0, and about 22.6 degrees 2-theta. In some such embodiments, the present invention provides Compound 7, wherein the compound has at least two peaks in its XRPD selected from those at about 8.4, about 16.0, and about 22.6 degrees 2-theta. In some such embodiments, the present invention provides Compound 7, wherein the compound is of Form A.

In some embodiments, the present invention provides Compound 7, wherein the compound has an XRPD substantially similar to that depicted in FIG. 29.

In some embodiments, the present invention provides Compound 7, wherein the compound has one or more peaks in its XRPD selected from those at about 15.7, about 19.7, and about 25.9 degrees 2-theta. In some such embodiments, the present invention provides Compound 7, wherein the compound has at least two peaks in its XRPD selected from those at about 15.7, about 19.7, and about 25.9 degrees 2-theta. In some such embodiments, the present invention provides Compound 7, wherein the compound is of Form B.

In some embodiments, the present invention provides Compound 7, wherein the compound has an XRPD substantially similar to that depicted in FIG. 31.

In some embodiments, the present invention provides a composition comprising Compound 7 and a pharmaceutically acceptable carrier or excipient.

In some embodiments, the present invention provides a method of inhibiting or preventing the accumulation of A2E in a patient comprising administering to the patient Compound 7 or composition thereof.

In some embodiments, the present invention provides a method of treating various conditions in a patient in which aldehyde toxicity is implicated in the pathogenesis, comprising administering of Compound 7 or composition thereof to the patient. In some such embodiments, the various conditions, in a patient, in which aldehyde toxicity is implicated in the pathogenesis may include dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents.

h. Compound 8—Edisylate Salts of Compound A

In some embodiments, the present invention provides an edisylate salt of Compound A, represented by Compound 8:

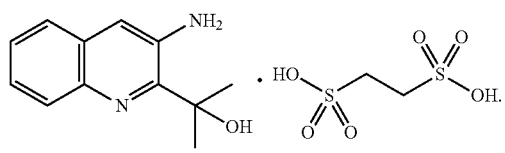

8

It will be appreciated by one of ordinary skill in the art that the ethanedisulfonic acid and Compound A are ionically bonded to form Compound 8. It is contemplated that Compound 8 can exist in a variety of physical forms. For example, Compound 8 can be in solution, suspension, or in solid form. In certain embodiments, Compound 8 is in solid form. When Compound 8 is in solid form, the compound may be amorphous, crystalline, or a mixture thereof. Exemplary solid forms are described in more detail below.

In some embodiments, the present invention provides Compound 8 substantially free of impurities. As used herein, the term "substantially free of impurities" means that the compound contains no significant amount of extraneous matter. In some embodiments, the "impurities" can be determined by HPLC according to the procedures set forth in the Examples for the relevant solid forms of Compound 8. Such extraneous matter may include excess camphorsulfonic acid, excess Compound A, residual solvents, or any other impurities that may result from the preparation of, and/or isolation of, Compound 8.

In certain embodiments, at least about 95% by weight of Compound 8 is present. In still other embodiments of the invention, at least about 99% by weight of Compound 8 is present.

In some embodiments, Compound 8 is present in an amount of at least about 97, 97.5, 98.0, 98.5, 99, 99.5, 99.8 weight percent where the percentages are based on the total weight of the composition. In some embodiments, Compound 8 contains no more than about 3.0 area percent HPLC of total organic impurities and, in certain embodiments, no more than about 1.5 area percent HPLC total organic impurities relative to the total area of the HPLC chromatogram. In other embodiments, Compound 8 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 8 is also meant to include all tautomeric forms of Compound 8. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that Compound 8 can exist in a variety of solid forms. Exemplary such forms include polymorphs such as those described herein.

In certain embodiments, Compound 8 is a crystalline solid. In other embodiments, Compound 8 is a crystalline solid substantially free of amorphous Compound 8. As used herein, the term "substantially free of amorphous Compound 8" means that the compound contains no significant amount of amorphous Compound 8.

In certain embodiments, at least about 95% by weight of crystalline Compound 8 is present. In still other embodiments of the invention, at least about 99% by weight of crystalline Compound 8 is present.

In some embodiments, Compound 8 is amorphous. In some embodiments, Compound 8 is amorphous, and is substantially free of crystalline Compound 8.

i. Form A of Compound 8

In some embodiments, Form A of Compound 8 has at least 1, 2, 3, 4, 5, or more spectral peak(s) selected from the peaks listed in Table 17 below. In some embodiments, the peak(s) with relatively highest intensity peak(s) are selected.

TABLE 17

| XRPD Peak Positions for Form A of Compound 8 | | |
|---|---|---|
| Pos. [°2θ] | d-spacing [Å] | Rel. Int. [%] |
| 5.5 | 15.92 | 81.49 |
| 5.9 | 14.85 | 32.07 |
| 11.6 | 7.63 | 54.99 |
| 13.3 | 6.63 | 19.70 |
| 15.3 | 5.80 | 23.29 |
| 16.6 | 5.34 | 24.55 |
| 18.3 | 4.84 | 23.15 |
| 19.7 | 4.50 | 39.02 |
| 20.4 | 4.35 | 29.26 |
| 21.0 | 4.23 | 20.88 |
| 21.2 | 4.19 | 85.55 |
| 21.3 | 4.18 | 100.00 |
| 21.6 | 4.12 | 72.17 |
| 21.8 | 4.08 | 30.93 |
| 22.1 | 4.02 | 35.85 |
| 22.6 | 3.93 | 58.76 |
| 22.9 | 3.89 | 60.71 |
| 23.3 | 3.82 | 27.50 |
| 23.9 | 3.73 | 32.90 |
| 26.9 | 3.31 | 37.85 |

[1] In this and all subsequent tables, the position 2θ is within ± 0.2.

In some embodiments, Form A of Compound 8 is characterized in that it has one or more peaks in its X-ray powder diffraction pattern selected from those at about 5.5, about 21.2, and about 21.3 degrees 2-theta. In some embodiments, Form A of Compound 8 is characterized in that it has two or more peaks in its X-ray powder diffraction pattern selected from those at about 5.5, about 21.2, and about 21.3 degrees 2-theta. In some embodiments, Form A of Compound 8 is characterized in that it has all three peaks in its X-ray powder diffraction pattern at about 5.5, about 21.2, and about 21.3 degrees 2-theta. In some embodiments, Form A of Compound 8 is further characterized by additional 1, 2, 3, 4 or 5 peak(s) selected from Table 17.

Figure 33:
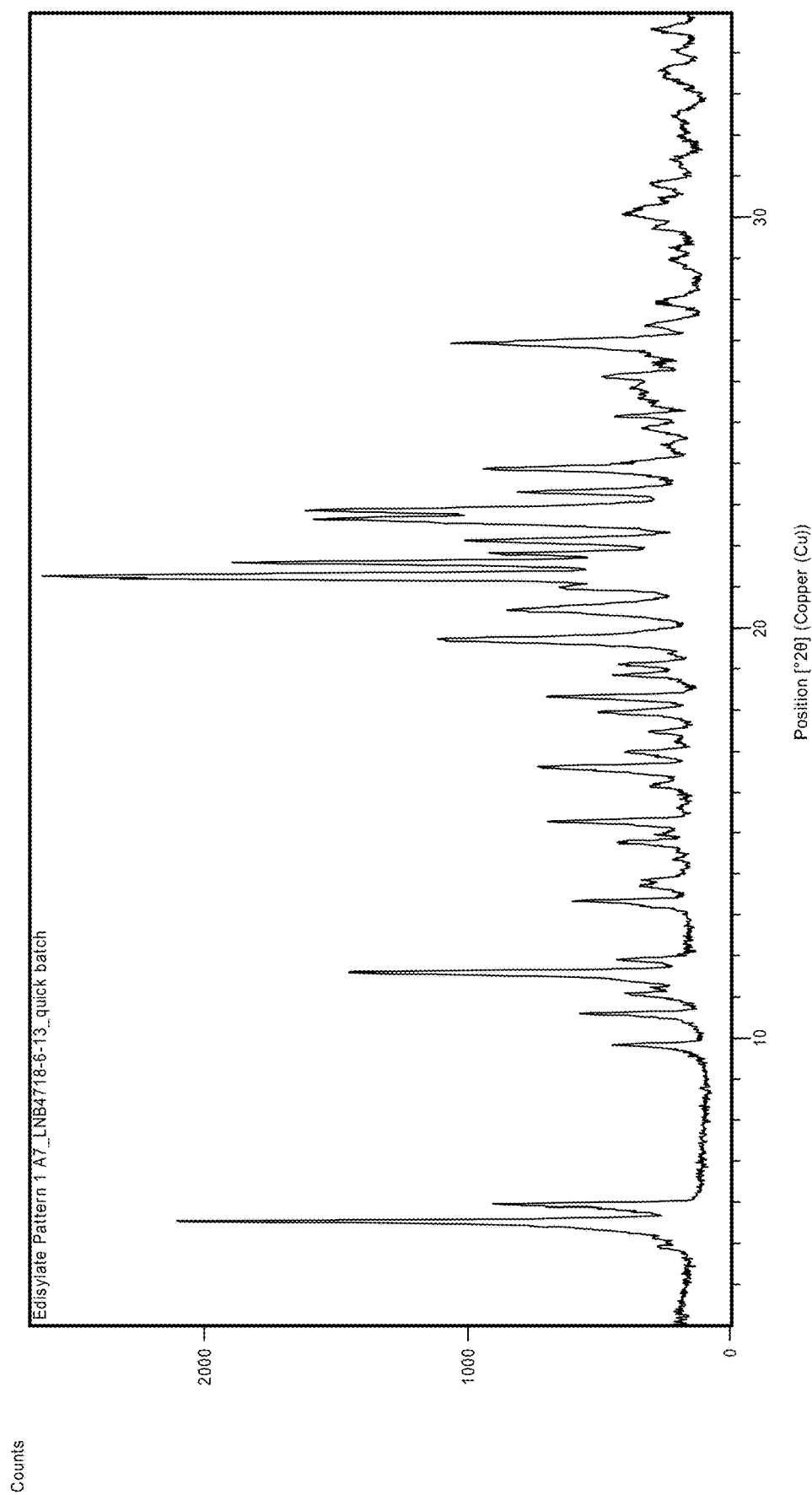
FIG. 33 depicts the XRPD pattern of Compound 8, Form A.

In certain embodiments, the X-ray powder diffraction pattern is substantially similar to the XRPD provided in FIG. 33.

Figure 34:
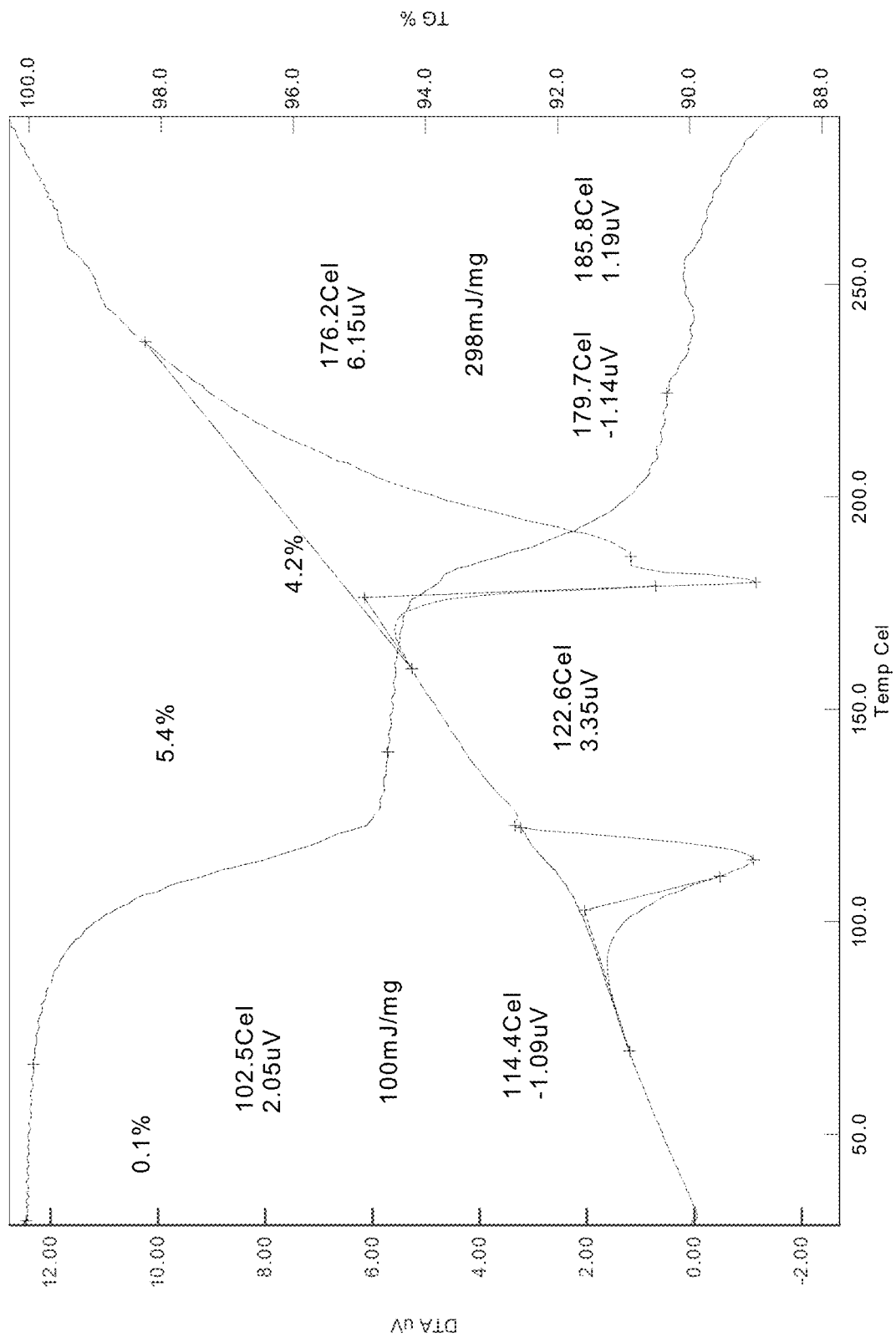
FIG. 34 depicts a DSC thermogram and TGA trace of Compound 8, Form A.

In some embodiments, Form A of Compound 8 is characterized by a differential scanning calorimetry (DSC) thermogram having the endothermic peak(s) as shown in FIG. 34. In some embodiments, Form A of Compound 8 has a DSC thermogram substantially the same as that shown in FIG. 34.

Methods for preparing Form A of Compound 8 are described infra.

In some embodiments, the present invention provides Compound 8:

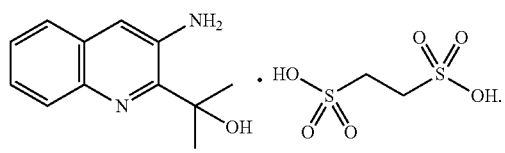

In some embodiments, the present invention provides Compound 8, wherein the compound is crystalline.

In some embodiments, the present invention provides Compound 8, wherein the compound is a crystalline solid substantially free of amorphous Compound 8.

In some embodiments, the present invention provides Compound 8, wherein the compound is substantially free of impurities.

In some embodiments, the present invention provides Compound 8, wherein the compound has one or more peaks in its XRPD selected from those at about 5.5, about 21.2, and about 21.3 degrees 2-theta. In some such embodiments, the present invention provides Compound 8, wherein the compound has at least two peaks in its XRPD selected from those at about 5.5, about 21.2, and about 21.3 degrees 2-theta. In some such embodiments, the present invention provides Compound 8, wherein the compound is of Form A.

In some embodiments, the present invention provides Compound 8, wherein the compound has an XRPD substantially similar to that depicted in FIG. 33.

In some embodiments, the present invention provides a composition comprising Compound 8 and a pharmaceutically acceptable carrier or excipient.

In some embodiments, the present invention provides a method of inhibiting or preventing the accumulation of A2E in a patient comprising administering to the patient Compound 8 or composition thereof.

In some embodiments, the present invention provides a method of treating various conditions in a patient in which aldehyde toxicity is implicated in the pathogenesis, comprising administering of Compound 8 or composition thereof to the patient. In some such embodiments, the various conditions, in a patient, in which aldehyde toxicity is implicated in the pathogenesis may include dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents.

i. Compound 9—Tartrate Salts of Compound A

In some embodiments, the present invention provides a tartrate salt of Compound A, represented by Compound 9:

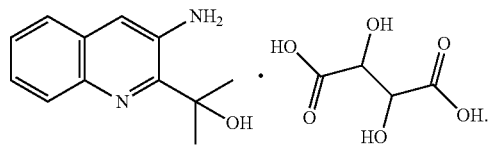

It will be appreciated by one of ordinary skill in the art that the tartaric acid and Compound A are ionically bonded to form Compound 9. It is contemplated that Compound 9 can exist in a variety of physical forms. For example, Compound 9 can be in solution, suspension, or in solid form. In certain embodiments, Compound 9 is in solid form. When Compound 9 is in solid form, the compound may be amorphous, crystalline, or a mixture thereof. Exemplary solid forms are described in more detail below.

In some embodiments, the present invention provides Compound 9 substantially free of impurities. As used herein, the term "substantially free of impurities" means that the compound contains no significant amount of extraneous matter. In some embodiments, the "impurities" can be determined by HPLC according to the procedures set forth in the Examples for the relevant solid forms of Compound 9. Such extraneous matter may include excess tartaric acid, excess Compound A, residual solvents, or any other impurities that may result from the preparation of, and/or isolation of, Compound 9.

In certain embodiments, at least about 95% by weight of Compound 9 is present. In still other embodiments of the invention, at least about 99% by weight of Compound 9 is present.

In some embodiments, Compound 9 is present in an amount of at least about 97, 97.5, 98.0, 98.5, 99, 99.5, 99.8 weight percent where the percentages are based on the total weight of the composition. In some embodiments, Compound 9 contains no more than about 3.0 area percent HPLC of total organic impurities and, in certain embodiments, no more than about 1.5 area percent HPLC total organic impurities relative to the total area of the HPLC chromatogram. In other embodiments, Compound 9 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 9 is also meant to include all tautomeric forms of Compound 9. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that Compound 9 can exist in at least three distinct polymorphic forms. In some embodiments, the present invention provides a polymorphic form of Compound 9 referred to herein as Form A. In some embodiments, the present invention provides a polymorphic form of Compound 9 referred to herein as Form B. In some embodiments, the present invention provides a polymorphic form of Compound 9 referred to herein as Form C.

In certain embodiments, Compound 9 is a crystalline solid. In other embodiments, Compound 9 is a crystalline solid substantially free of amorphous Compound 9. As used herein, the term "substantially free of amorphous Compound 9" means that the compound contains no significant amount of amorphous Compound 9. In certain embodiments, at least about 95% by weight of crystalline Compound 9 is present. In still other embodiments of the invention, at least about 99% by weight of crystalline Compound 9 is present.

In some embodiments, Compound 9 is amorphous. In some embodiments, Compound 9 is amorphous, and is substantially free of crystalline Compound 9.

i. Form A of Compound 9

In some embodiments, Form A of Compound 9 has at least 1, 2, 3, 4, 5, or more spectral peak(s) selected from the peaks listed in Table 18 below. In some embodiments, the peak(s) with relatively highest intensity peak(s) are selected.

TABLE 18

XRPD Peak Positions for Form A of Compound 9

| Pos. [°2θ] | d-spacing [Å] | Rel. Int. [%] |
|---|---|---|
| 7.8 | 11.34 | 29.77 |
| 9.1 | 9.73 | 55.11 |
| 12.1 | 7.33 | 20.74 |
| 13.1 | 6.77 | 24.11 |
| 14.7 | 6.03 | 71.27 |
| 15.6 | 5.68 | 46.57 |
| 15.8 | 5.61 | 100.00 |
| 17.2 | 5.15 | 71.16 |
| 17.3 | 5.12 | 51.86 |
| 17.9 | 4.97 | 26.22 |
| 18.2 | 4.87 | 43.60 |
| 20.4 | 4.34 | 22.29 |
| 21.3 | 4.18 | 49.85 |
| 21.7 | 4.09 | 37.11 |
| 23.2 | 3.83 | 36.55 |
| 24.3 | 3.66 | 33.80 |
| 24.5 | 3.63 | 36.53 |
| 26.9 | 3.31 | 36.98 |
| 27.6 | 3.23 | 17.21 |
| 28.1 | 3.17 | 17.48 |

[1] In this and all subsequent tables, the position 2θ is within ± 0.2.

In some embodiments, Form A of Compound 9 is characterized in that it has one or more peaks in its X-ray powder diffraction pattern selected from those at about 14.7, about 15.8, and about 17.2 degrees 2-theta. In some embodiments, Form A of Compound 9 is characterized in that it has two or more peaks in its X-ray powder diffraction pattern selected from those at about 14.7, about 15.8, and about 17.2 degrees 2-theta. In some embodiments, Form A of Compound 9 is characterized in that it has all three peaks in its X-ray powder diffraction pattern at about 14.7, about 15.8, and about 17.2 degrees 2-theta. In some embodiments, Form A of Compound 9 is further characterized by additional 1, 2, 3, 4 or 5 peak(s) selected from Table 18.

Figure 35:
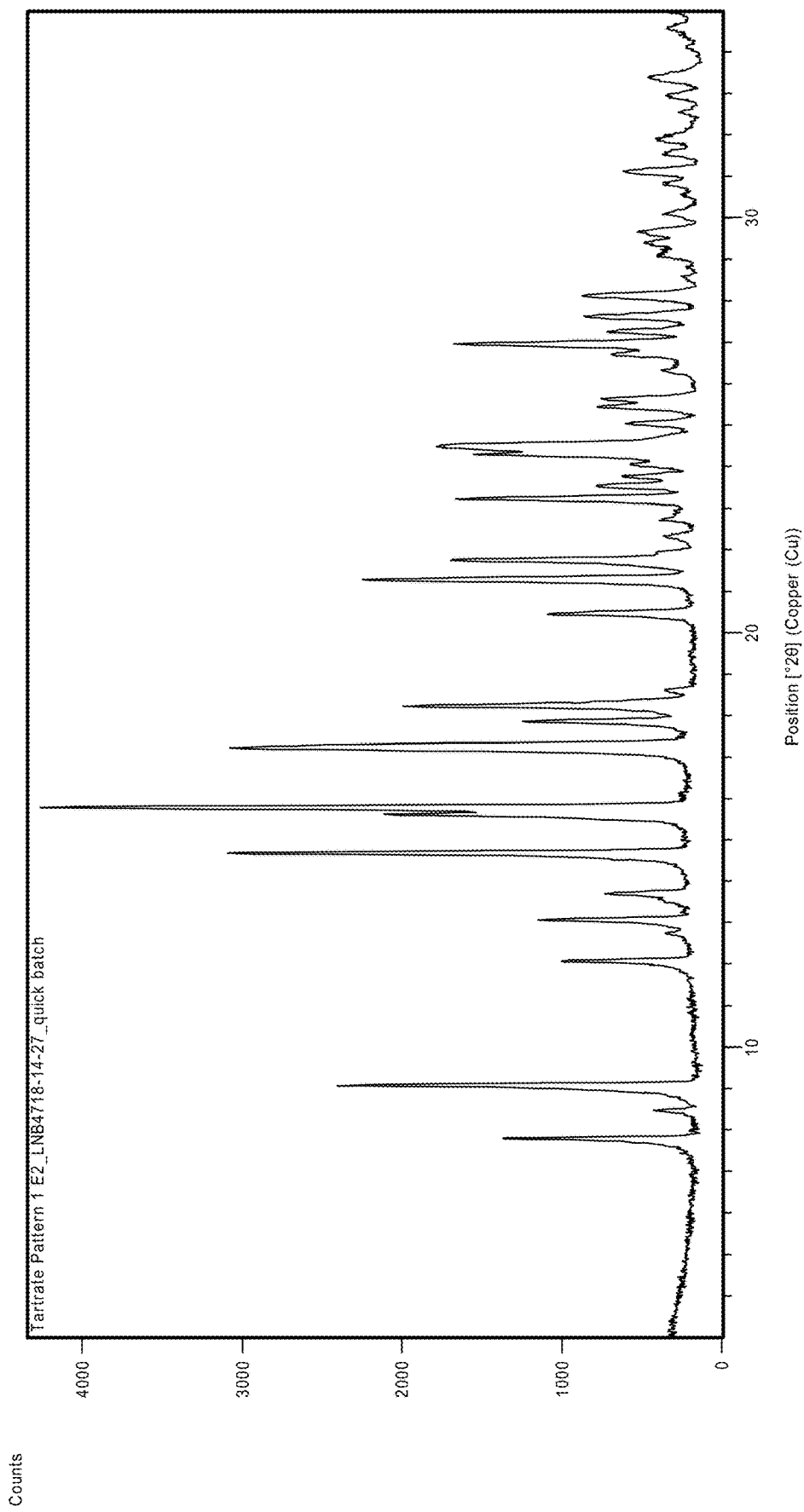
FIG. 35 depicts the XRPD pattern of Compound 9, Form A.

In certain embodiments, the X-ray powder diffraction pattern is substantially similar to the XRPD provided in FIG. 35.

Figure 36:
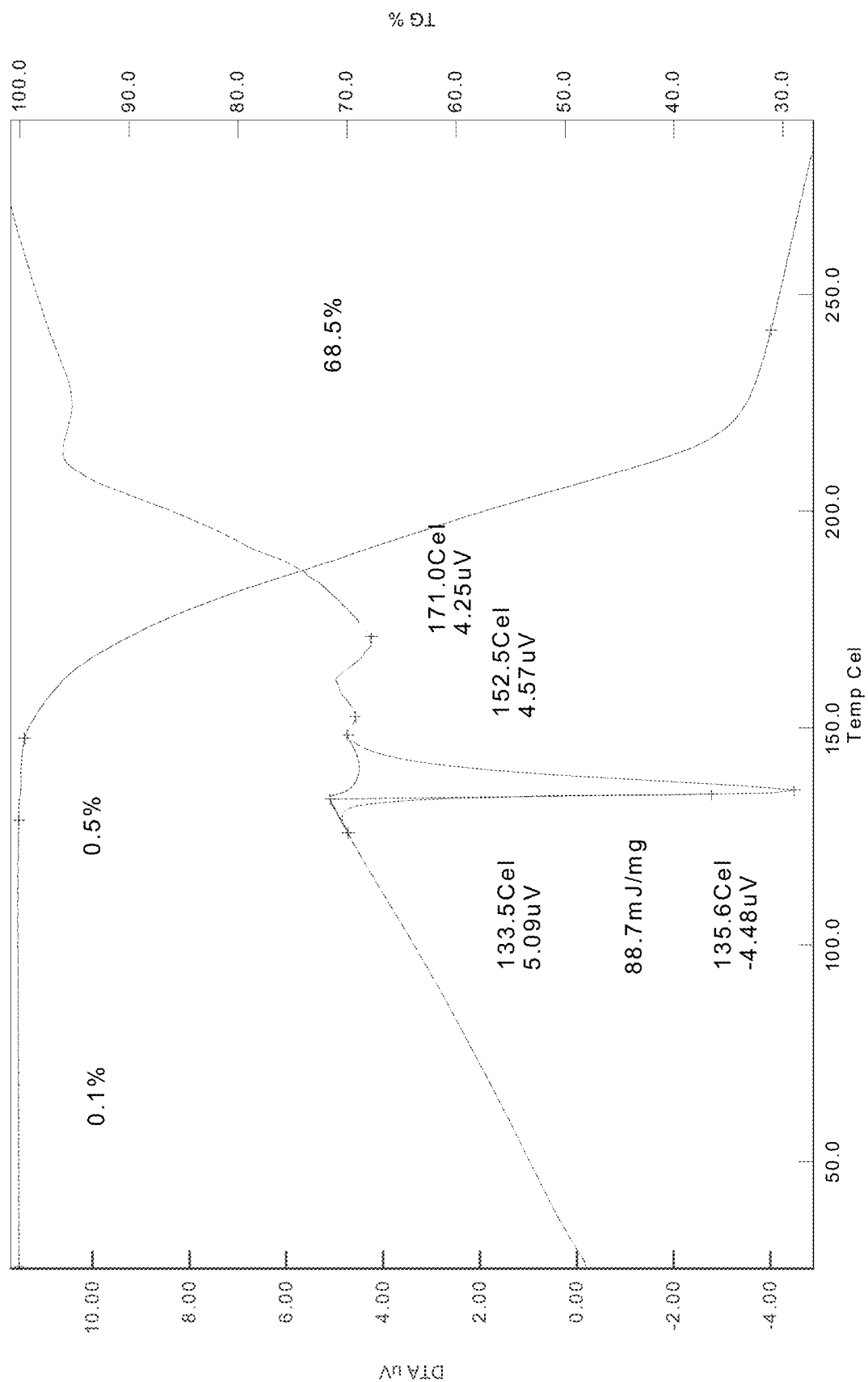
FIG. 36 depicts a DSC thermogram and TGA trace of Compound 9, Form A.

In some embodiments, Form A of Compound 9 is characterized by a differential scanning calorimetry (DSC) thermogram having the endothermic peak(s) as shown in FIG. 36. In some embodiments, Form A of Compound 9 has a DSC thermogram substantially the same as that shown in FIG. 36.

Methods for preparing Form A of Compound 9 are described infra.

ii. Form B of Compound 9

In some embodiments, Form B of Compound 9 has at least 1, 2, 3, 4, 5, or more spectral peak(s) selected from the peaks listed in Table 19 below. In some embodiments, the peak(s) with relatively highest intensity peak(s) are selected.

TABLE 19

XRPD Peak Positions for Form B of Compound 9

| Pos. [°2θ] | d-spacing [Å] | Rel. Int. [%] |
|---|---|---|
| 7.9 | 11.19 | 34.91 |
| 10.5 | 8.46 | 33.80 |
| 13.4 | 6.60 | 16.16 |
| 14.9 | 5.93 | 32.50 |
| 15.1 | 5.86 | 26.62 |
| 15.9 | 5.59 | 100.00 |
| 16.8 | 5.27 | 19.94 |
| 18.6 | 4.77 | 49.59 |
| 21.0 | 4.23 | 26.13 |
| 22.3 | 3.99 | 13.53 |
| 23.5 | 3.78 | 12.07 |
| 23.9 | 3.73 | 15.43 |
| 24.2 | 3.68 | 12.75 |
| 24.9 | 3.57 | 16.70 |
| 25.4 | 3.51 | 12.54 |
| 25.9 | 3.44 | 30.84 |
| 26.1 | 3.41 | 11.63 |
| 27.0 | 3.30 | 15.65 |
| 30.5 | 2.93 | 12.36 |
| 31.9 | 2.80 | 17.12 |

[1] In this and all subsequent tables, the position 2θ is within ± 0.2.

In some embodiments, Form B of Compound 9 is characterized in that it has one or more peaks in its X-ray powder diffraction pattern selected from those at about 7.9, about 15.9, and about 18.6 degrees 2-theta. In some embodiments, Form B of Compound 9 is characterized in that it has two or more peaks in its X-ray powder diffraction pattern selected from those at about 7.9, about 15.9, and about 18.6 degrees 2-theta. In some embodiments, Form B of Compound 9 is characterized in that it has all three peaks in its X-ray powder diffraction pattern at about 7.9, about 15.9, and about 18.6 degrees 2-theta. In some embodiments, Form B of Compound 9 is further characterized by additional 1, 2, 3, 4 or 5 peak(s) selected from Table 19.

Figure 37:
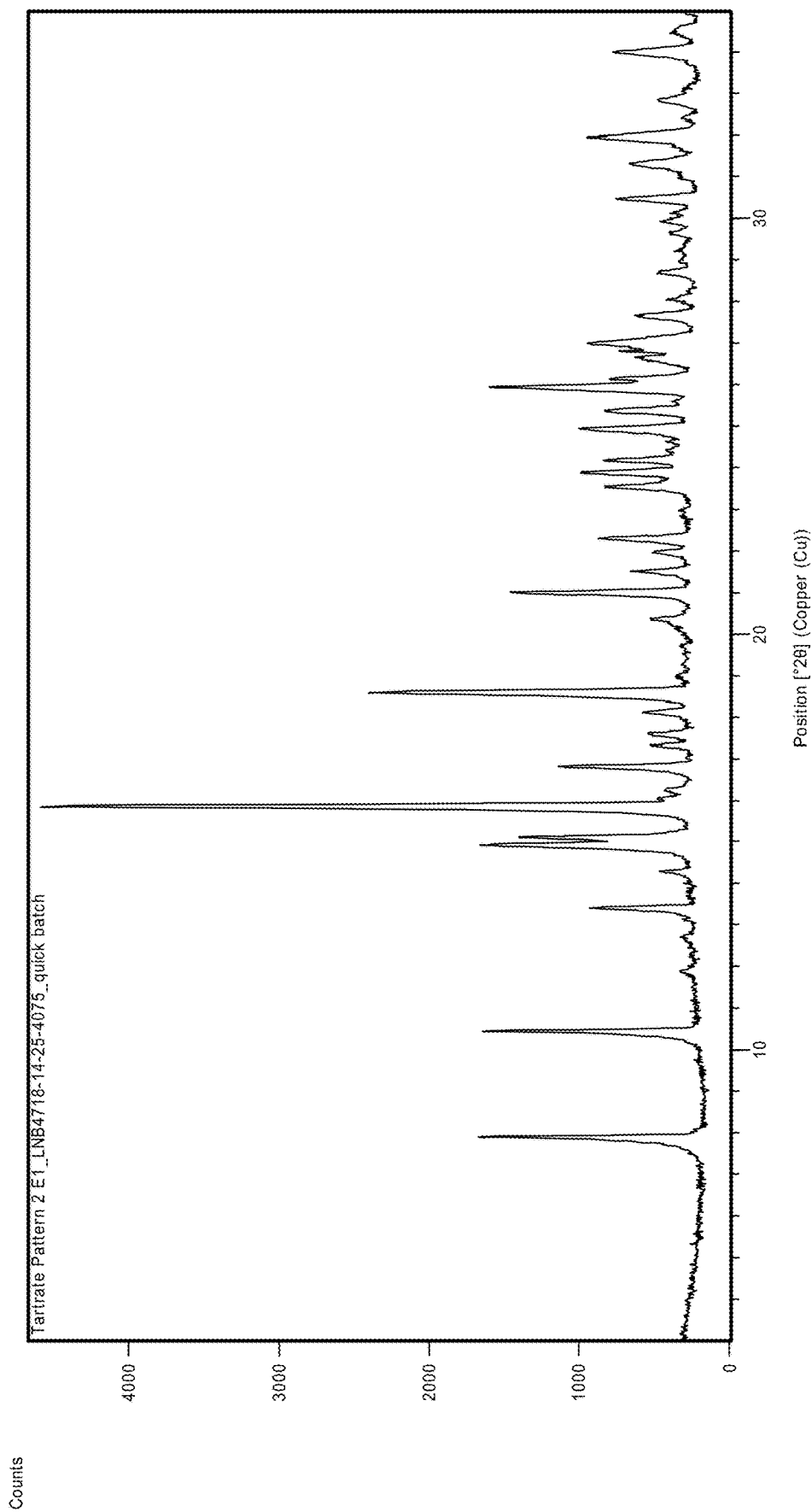
FIG. 37 depicts the XRPD pattern of Compound 9, Form B.

In certain embodiments, the X-ray powder diffraction pattern is substantially similar to the XRPD provided in FIG. 37.

Figure 38:
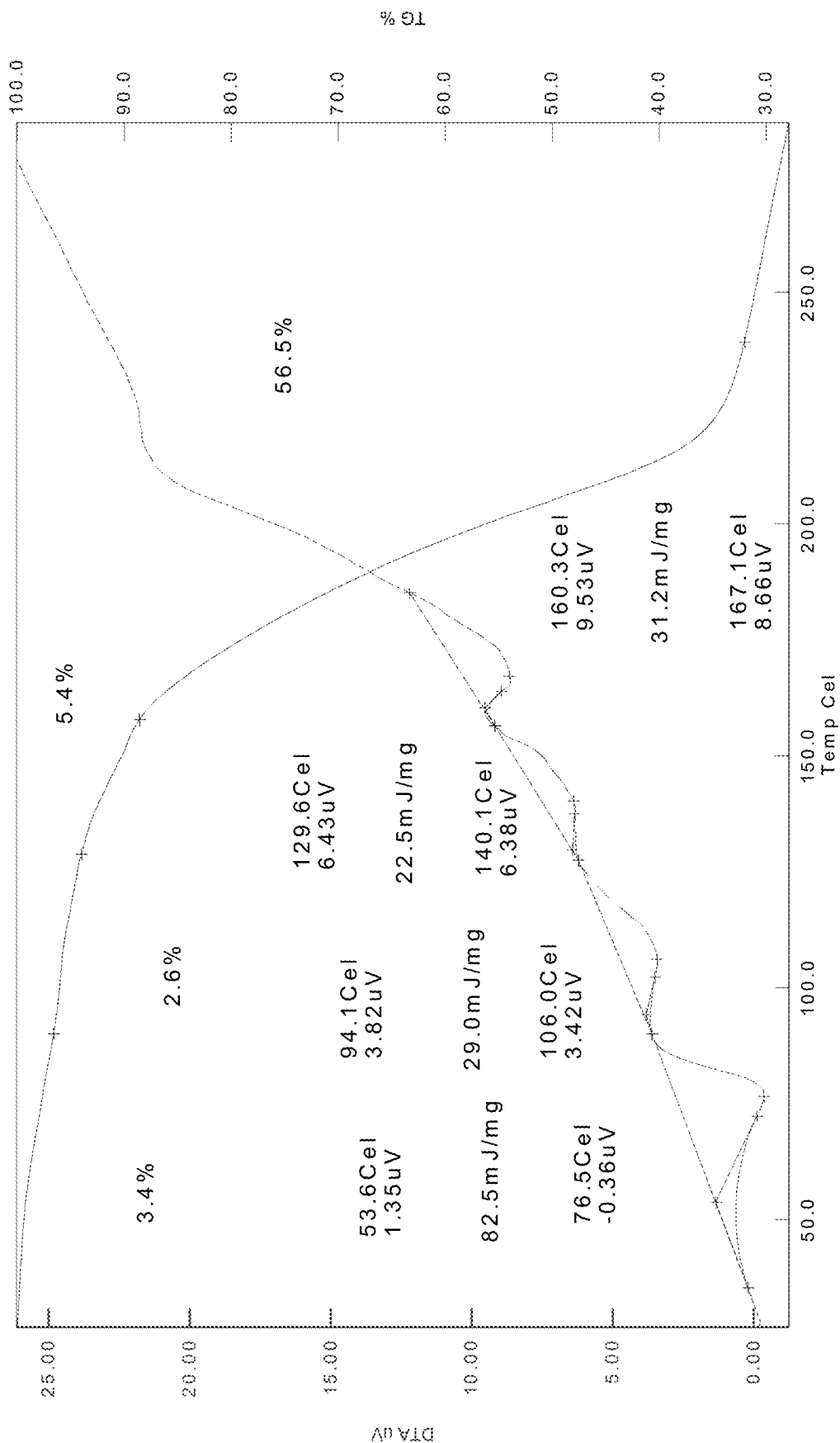
FIG. 38 depicts a DSC thermogram and TGA trace of Compound 9, Form B.

In some embodiments, Form B of Compound 9 is characterized by a differential scanning calorimetry (DSC) thermogram having the endothermic peak(s) as shown in FIG. 38. In some embodiments, Form B of Compound 9 has a DSC thermogram substantially the same as that shown in FIG. 38.

Methods for preparing Form B of Compound 9 are described infra.

iii. Form C of Compound 9

In some embodiments, Form C of Compound 9 has at least 1, 2, 3, 4, 5, or more spectral peak(s) selected from the peaks listed in Table 20 below. In some embodiments, the peak(s) with relatively highest intensity peak(s) are selected.

TABLE 20

XRPD Peak Positions for Form C of Compound 9

| Pos. [°2θ] | d-spacing [Å] | Rel. Int. [%] |
|---|---|---|
| 8.1 | 10.93 | 60.16 |
| 12.8 | 6.94 | 37.75 |

TABLE 20-continued

XRPD Peak Positions for Form C of Compound 9

| Pos. [°2θ] | d-spacing [Å] | Rel. Int. [%] |
|---|---|---|
| 14.3 | 6.19 | 76.70 |
| 14.9 | 5.94 | 70.38 |
| 15.3 | 5.81 | 48.03 |
| 16.2 | 5.47 | 43.15 |
| 16.9 | 5.24 | 90.44 |
| 17.4 | 5.11 | 82.49 |
| 18.7 | 4.74 | 34.87 |
| 19.7 | 4.50 | 35.12 |
| 21.5 | 4.14 | 29.37 |
| 23.7 | 3.75 | 41.77 |
| 23.8 | 3.75 | 39.15 |
| 24.3 | 3.67 | 100.00 |
| 24.8 | 3.58 | 35.49 |
| 25.1 | 3.54 | 21.92 |
| 25.5 | 3.49 | 45.37 |
| 25.7 | 3.46 | 33.87 |
| 27.0 | 3.30 | 22.91 |
| 27.2 | 3.28 | 20.85 |

[1] In this and all subsequent tables, the position 2θ is within ± 0.2.

In some embodiments, Form C of Compound 9 is characterized in that it has one or more peaks in its X-ray powder diffraction pattern selected from those at about 16.9, about 17.4, and about 24.3 degrees 2-theta. In some embodiments, Form C of Compound 9 is characterized in that it has two or more peaks in its X-ray powder diffraction pattern selected from those at about 16.9, about 17.4, and about 24.3 degrees 2-theta. In some embodiments, Form C of Compound 9 is characterized in that it has all three peaks in its X-ray powder diffraction pattern at about 16.9, about 17.4, and about 24.3 degrees 2-theta. In some embodiments, Form C of Compound 9 is further characterized by additional 1, 2, 3, 4 or 5 peak(s) selected from Table 20.

Figure 39:
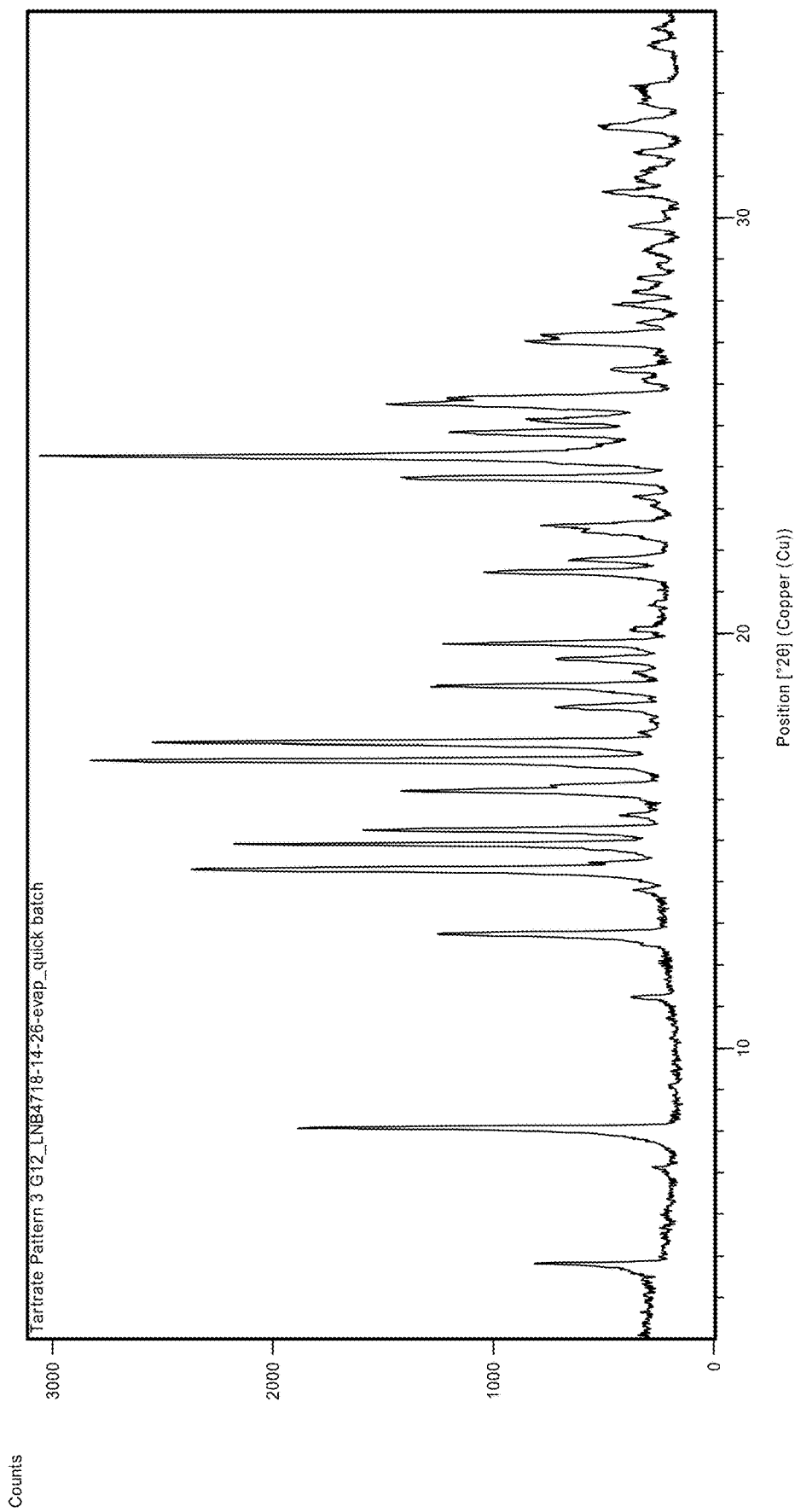
FIG. 39 depicts the XRPD pattern of Compound 9, Form C.

In certain embodiments, the X-ray powder diffraction pattern is substantially similar to the XRPD provided in FIG. 39.

Figure 40:
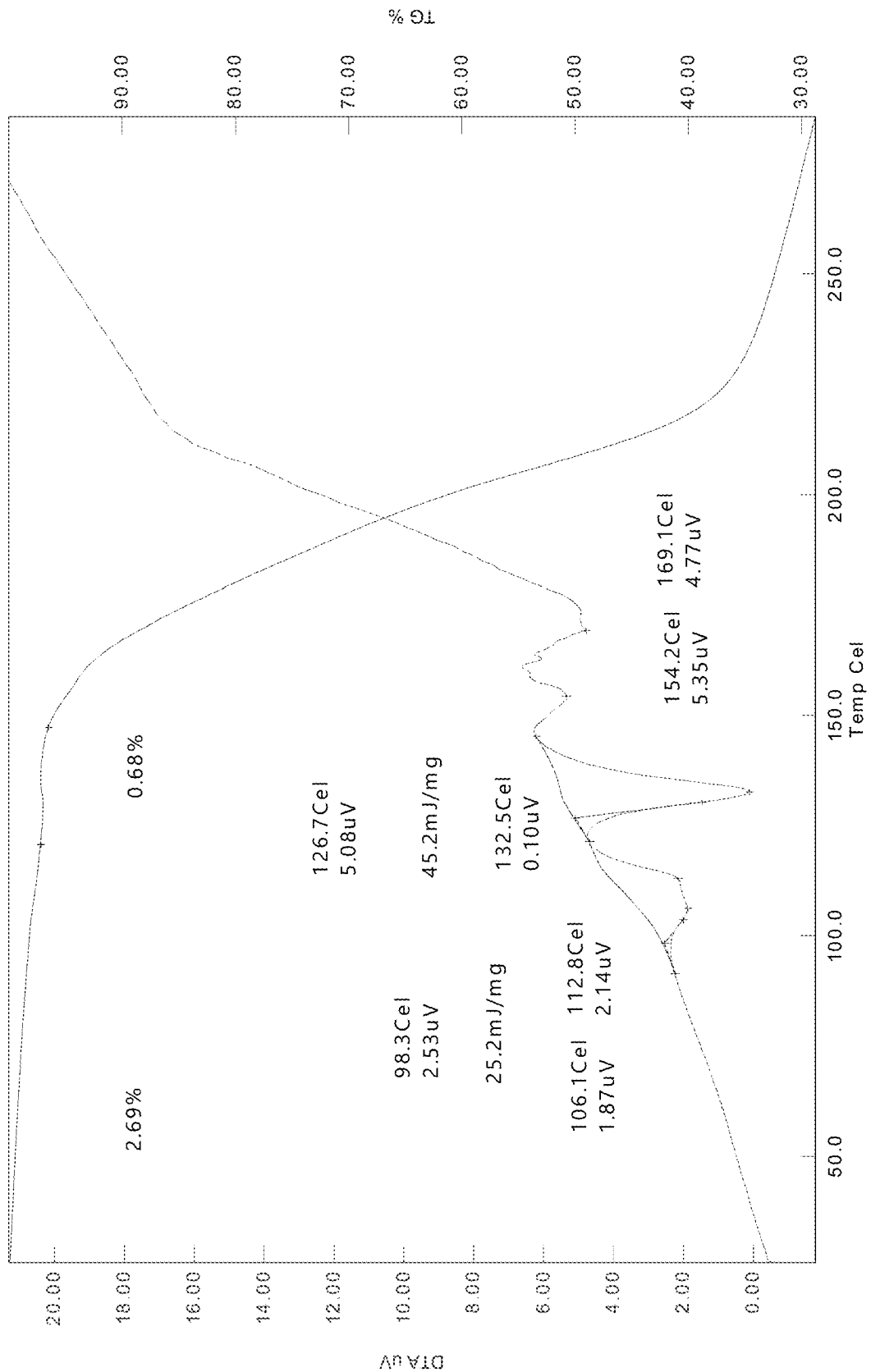
FIG. 40 depicts a DSC thermogram and TGA trace of Compound 9, Form C.

In some embodiments, Form C of Compound 9 is characterized by a differential scanning calorimetry (DSC) thermogram having the endothermic peak(s) as shown in FIG. 40. In some embodiments, Form C of Compound 9 has a DSC thermogram substantially the same as that shown in FIG. 40.

Methods for preparing Form C of Compound 9 are described infra.

In some embodiments, the present invention provides Compound 9:

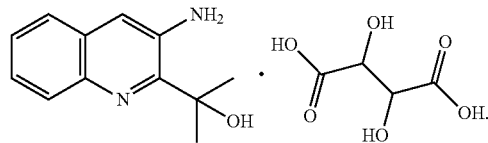

9

In some embodiments, the present invention provides Compound 9, wherein the compound is crystalline.

In some embodiments, the present invention provides Compound 9, wherein the compound is a crystalline solid substantially free of amorphous Compound 9.

In some embodiments, the present invention provides Compound 9, wherein the compound is substantially free of impurities.

In some embodiments, the present invention provides Compound 9, wherein the compound has one or more peaks in its XRPD selected from those at about 14.7, about 15.8, and about 17.2 degrees 2-theta. In some such embodiments, the present invention provides Compound 9, wherein the compound has at least two peaks in its XRPD selected from those at about 14.7, about 15.8, and about 17.2 degrees 2-theta. In some such embodiments, the present invention provides Compound 9, wherein the compound is of Form A.

In some embodiments, the present invention provides Compound 9, wherein the compound has an XRPD substantially similar to that depicted in FIG. 35.

In some embodiments, the present invention provides Compound 9, wherein the compound has one or more peaks in its XRPD selected from those at about 7.9, about 15.9, and about 18.6 degrees 2-theta. In some such embodiments, the present invention provides Compound 9, wherein the compound has at least two peaks in its XRPD selected from those at about 7.9, about 15.9, and about 18.6 degrees 2-theta. In some such embodiments, the present invention provides Compound 9, wherein the compound is of Form B.

In some embodiments, the present invention provides Compound 9, wherein the compound has an XRPD substantially similar to that depicted in FIG. 37.

In some embodiments, the present invention provides Compound 9, wherein the compound has one or more peaks in its XRPD selected from those at about 16.9, about 17.4, and about 24.3 degrees 2-theta. In some such embodiments, the present invention provides Compound 9, wherein the compound has at least two peaks in its XRPD selected from those at about 16.9, about 17.4, and about 24.3 degrees 2-theta. In some such embodiments, the present invention provides Compound 9, wherein the compound is of Form C.

In some embodiments, the present invention provides Compound 9, wherein the compound has an XRPD substantially similar to that depicted in FIG. 39.

In some embodiments, the present invention provides a composition comprising Compound 9 and a pharmaceutically acceptable carrier or excipient.

In some embodiments, the present invention provides a method of inhibiting or preventing the accumulation of A2E in a patient comprising administering to the patient Compound 9 or composition thereof.

In some embodiments, the present invention provides a method of treating various conditions in a patient in which aldehyde toxicity is implicated in the pathogenesis, comprising administering of Compound 9 or composition thereof to the patient. In some such embodiments, the various conditions, in a patient, in which aldehyde toxicity is implicated in the pathogenesis may include dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents.

j. Compound 10—Fumarate Salts of Compound A

In some embodiments, the present invention provides a fumarate salt of Compound A, represented by Compound 10:

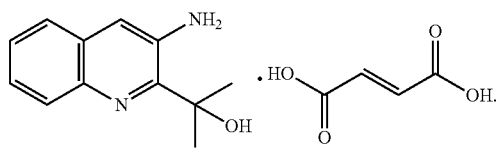

It will be appreciated by one of ordinary skill in the art that the fumaric acid and Compound A are ionically bonded to form Compound 10. It is contemplated that Compound 10 can exist in a variety of physical forms. For example, Compound 10 can be in solution, suspension, or in solid form. In certain embodiments, Compound 10 is in solid form. When Compound 10 is in solid form, the compound may be amorphous, crystalline, or a mixture thereof. Exemplary solid forms are described in more detail below.

In some embodiments, the present invention provides Compound 10 substantially free of impurities. As used herein, the term "substantially free of impurities" means that the compound contains no significant amount of extraneous matter. In some embodiments, the "impurities" can be determined by HPLC according to the procedures set forth in the Examples for the relevant solid forms of Compound 10. Such extraneous matter may include excess camphorsulfonic acid, excess Compound A, residual solvents, or any other impurities that may result from the preparation of, and/or isolation of, Compound 10.

In certain embodiments, at least about 95% by weight of Compound 10 is present. In still other embodiments of the invention, at least about 99% by weight of Compound 10 is present.

In some embodiments, Compound 10 is present in an amount of at least about 97, 97.5, 98.0, 98.5, 99, 99.5, 99.8 weight percent where the percentages are based on the total weight of the composition. In some embodiments, Compound 10 contains no more than about 3.0 area percent HPLC of total organic impurities and, in certain embodiments, no more than about 1.5 area percent HPLC total organic impurities relative to the total area of the HPLC chromatogram. In other embodiments, Compound 10 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 10 is also meant to include all tautomeric forms of Compound 10. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that Compound 10 can exist in a variety of solid forms. Exemplary such forms include polymorphs such as those described herein.

In certain embodiments, Compound 10 is a crystalline solid. In other embodiments, Compound 10 is a crystalline solid substantially free of amorphous Compound 10. As used herein, the term "substantially free of amorphous Compound 10" means that the compound contains no significant amount of amorphous Compound 10. In certain embodiments, at least about 95% by weight of crystalline Compound 10 is present. In still other embodiments of the invention, at least about 99% by weight of crystalline Compound 10 is present.

In some embodiments, Compound 10 is amorphous. In some embodiments, Compound 10 is amorphous, and is substantially free of crystalline Compound 10.

i. Form A of Compound 10

In some embodiments, Form A of Compound 10 has at least 1, 2, 3, 4, 5, or more spectral peak(s) selected from the peaks listed in Table 21 below. In some embodiments, the peak(s) with relatively highest intensity peak(s) are selected.

TABLE 21

| XRPD Peak Positions for Form A of Compound 10 | | |
|---|---|---|
| Pos. [°2θ] | d-spacing [Å] | Rel. Int. [%] |
| 9.1 | 9.74 | 23.60 |
| 12.2 | 7.25 | 18.09 |
| 12.8 | 6.91 | 67.46 |
| 15.2 | 5.83 | 20.06 |
| 16.1 | 5.50 | 79.76 |
| 16.3 | 5.43 | 39.82 |
| 17.1 | 5.18 | 11.22 |
| 18.2 | 4.87 | 14.84 |
| 18.7 | 4.75 | 27.53 |
| 20.0 | 4.45 | 11.79 |
| 20.3 | 4.38 | 80.52 |
| 21.3 | 4.17 | 26.34 |
| 22.8 | 3.90 | 19.27 |
| 24.1 | 3.69 | 100.00 |
| 24.5 | 3.64 | 20.16 |
| 25.9 | 3.44 | 73.88 |
| 27.8 | 3.21 | 21.59 |
| 27.8 | 3.21 | 17.81 |
| 28.7 | 3.10 | 47.36 |
| 29.4 | 3.04 | 12.43 |

[1] In this and all subsequent tables, the position 2θ is within ± 0.2.

In some embodiments, Form A of Compound 10 is characterized in that it has one or more peaks in its X-ray powder diffraction pattern selected from those at about 16.1, about 20.3, and about 24.1 degrees 2-theta. In some embodiments, Form A of Compound 10 is characterized in that it has two or more peaks in its X-ray powder diffraction pattern selected from those at about 16.1, about 20.3, and about 24.1 degrees 2-theta. In some embodiments, Form A of Compound 10 is characterized in that it has all three peaks in its X-ray powder diffraction pattern selected from those at about 16.1, about 20.3, and about 24.1 degrees 2-theta. In some embodiments, Form A of Compound 10 is further characterized by additional 1, 2, 3, 4 or 5 peak(s) selected from Table 21.

Figure 41:
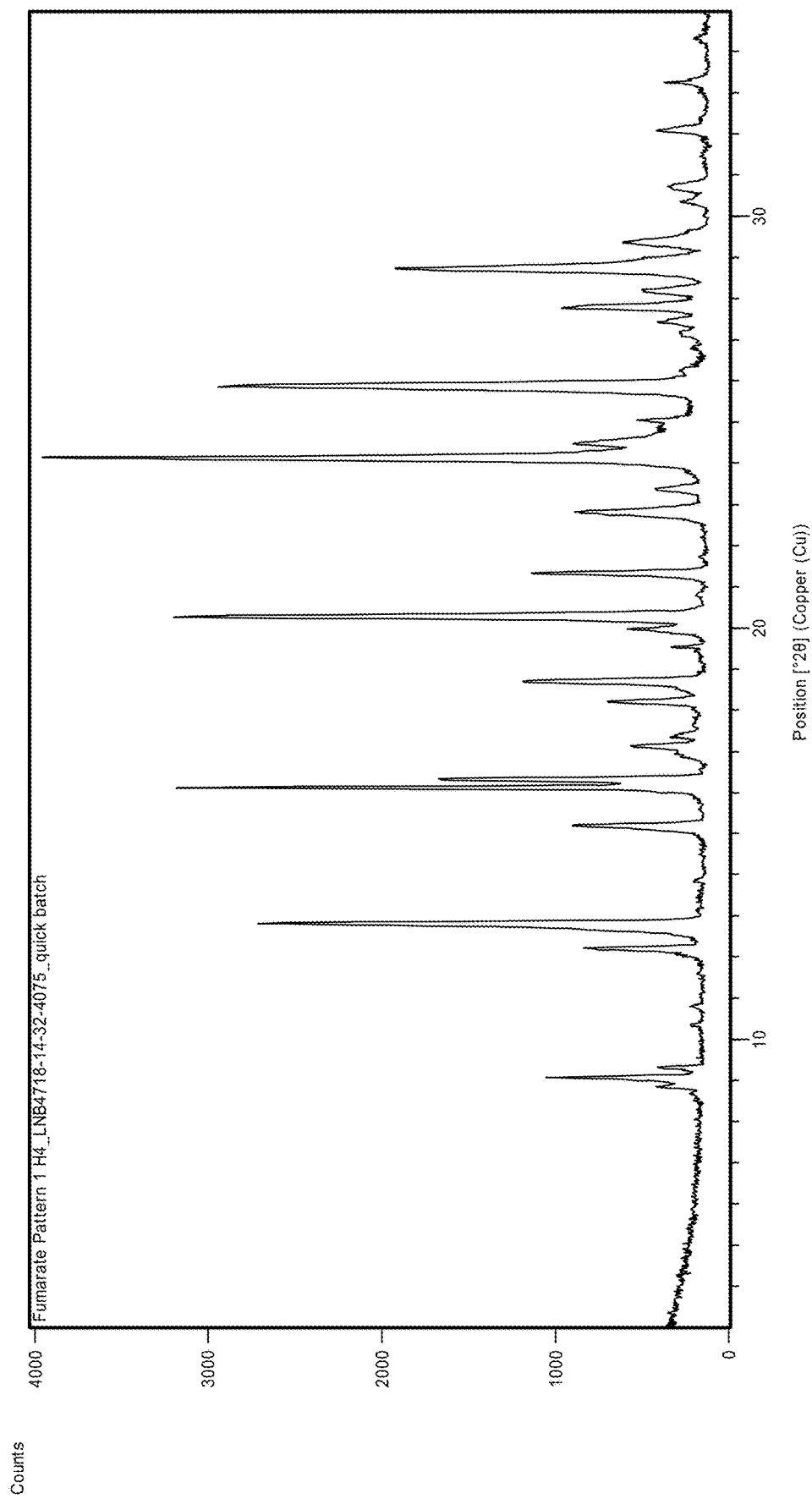
FIG. 41 depicts the XRPD pattern of Compound 10, Form A.

In certain embodiments, the X-ray powder diffraction pattern is substantially similar to the XRPD provided in FIG. 41.

Figure 42:
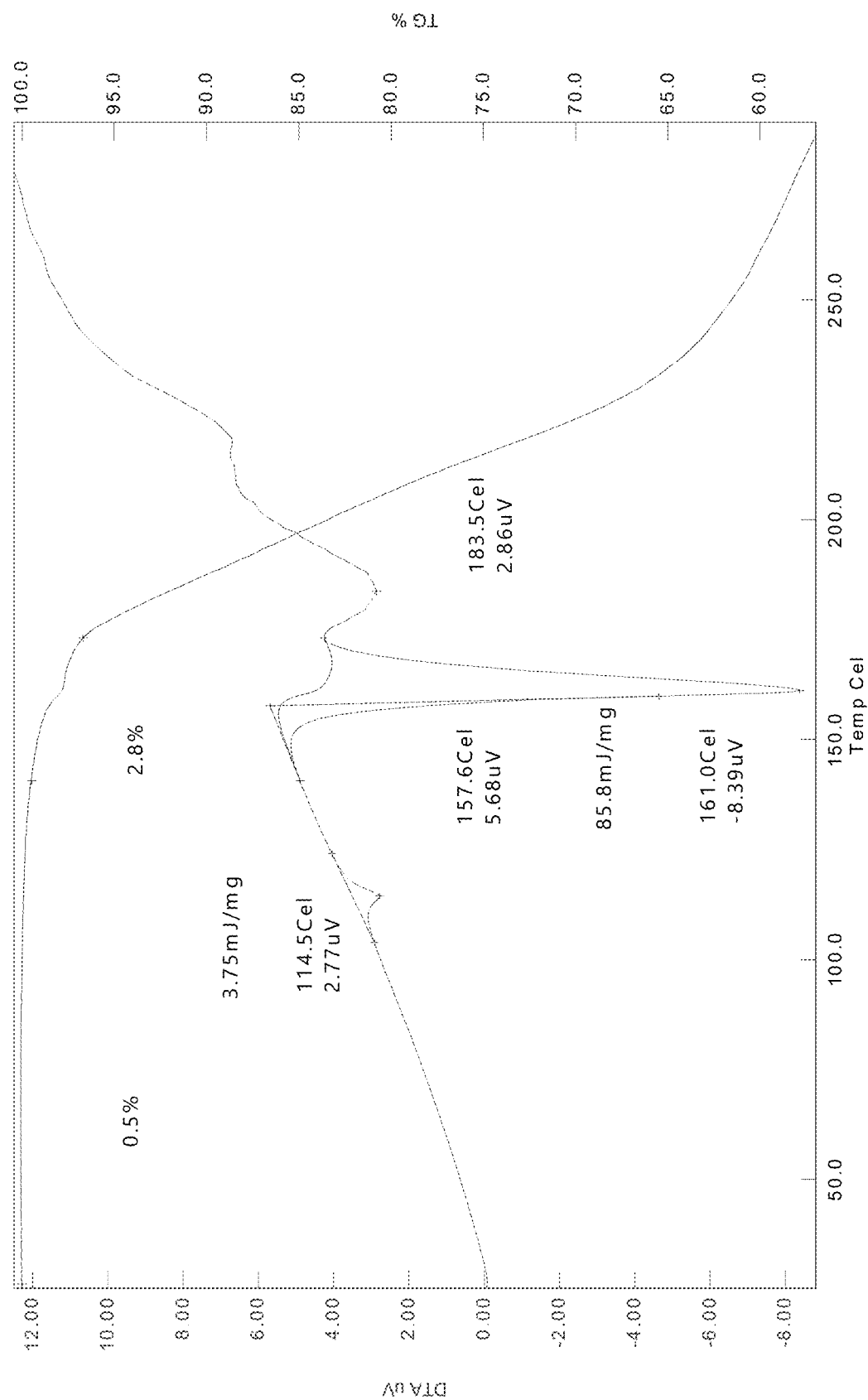
FIG. 42 depicts a DSC thermogram and TGA trace of Compound 10, Form A.

In some embodiments, Form A of Compound 10 is characterized by a differential scanning calorimetry (DSC) thermogram having the endothermic peak(s) as shown in FIG. 42. In some embodiments, Form A of Compound 10 has a DSC thermogram substantially the same as that shown in FIG. 42.

Methods for preparing Form A of Compound 10 are described infra.

In some embodiments, the present invention provides Compound 10:

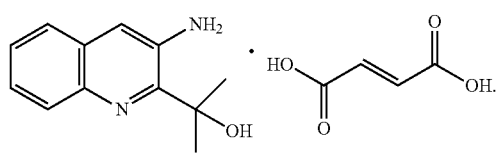

In some embodiments, the present invention provides Compound 10, wherein the compound is crystalline.

In some embodiments, the present invention provides Compound 10, wherein the compound is a crystalline solid substantially free of amorphous Compound 10.

In some embodiments, the present invention provides Compound 10, wherein the compound is substantially free of impurities.

In some embodiments, the present invention provides Compound 10, wherein the compound has one or more peaks in its XRPD selected from those at about 16.1, about 20.3, and about 24.1 degrees 2-theta. In some such embodiments, the present invention provides Compound 10, wherein the compound has at least two peaks in its XRPD selected from those at about 16.1, about 20.3, and about 24.1 degrees 2-theta. In some such embodiments, the present invention provides Compound 10, wherein the compound is of Form A.

In some embodiments, the present invention provides Compound 10, wherein the compound has an XRPD substantially similar to that depicted in FIG. 41.

In some embodiments, the present invention provides a composition comprising Compound 10 and a pharmaceutically acceptable carrier or excipient.

In some embodiments, the present invention provides a method of inhibiting or preventing the accumulation of A2E in a patient comprising administering to the patient Compound 10 or composition thereof.

In some embodiments, the present invention provides a method of treating various conditions in a patient in which aldehyde toxicity is implicated in the pathogenesis, comprising administering of Compound 10 or composition thereof to the patient. In some such embodiments, the various conditions, in a patient, in which aldehyde toxicity is implicated in the pathogenesis may include dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents.

k. Compound 11—Citrate Salts of Compound A

In some embodiments, the present invention provides a citrate salt of Compound A, represented by Compound 11:

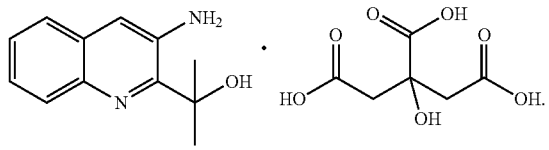

It will be appreciated by one of ordinary skill in the art that the citric acid and Compound A are ionically bonded to form Compound 11. It is contemplated that Compound 11 can exist in a variety of physical forms. For example, Compound 11 can be in solution, suspension, or in solid form. In certain embodiments, Compound 11 is in solid form. When Compound 11 is in solid form, the compound may be amorphous, crystalline, or a mixture thereof. Exemplary solid forms are described in more detail below.

In some embodiments, the present invention provides Compound 11 substantially free of impurities. As used herein, the term "substantially free of impurities" means that the compound contains no significant amount of extraneous matter. In some embodiments, the "impurities" can be determined by HPLC according to the procedures set forth in the Examples for the relevant solid forms of Compound 11. Such extraneous matter may include excess camphorsulfonic acid, excess Compound A, residual solvents, or any other impurities that may result from the preparation of, and/or isolation of, Compound 11.

In certain embodiments, at least about 95% by weight of Compound 11 is present. In still other embodiments of the invention, at least about 99% by weight of Compound 11 is present.

In some embodiments, Compound 11 is present in an amount of at least about 97, 97.5, 98.0, 98.5, 99, 99.5, 99.8 weight percent where the percentages are based on the total weight of the composition. In some embodiments, Compound 11 contains no more than about 3.0 area percent HPLC of total organic impurities and, in certain embodiments, no more than about 1.5 area percent HPLC total organic impurities relative to the total area of the HPLC chromatogram. In other embodiments, Compound 11 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 11 is also meant to include all tautomeric forms of Compound 11. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that Compound 11 can exist in a variety of solid forms. Exemplary such forms include polymorphs such as those described herein.

In certain embodiments, Compound 11 is a crystalline solid. In other embodiments, Compound 11 is a crystalline solid substantially free of amorphous Compound 11. As used herein, the term "substantially free of amorphous Compound 11" means that the compound contains no significant amount of amorphous Compound 11. In certain embodiments, at least about 95% by weight of crystalline Compound 11 is present. In still other embodiments of the invention, at least about 99% by weight of crystalline Compound 11 is present.

In some embodiments, Compound 11 is amorphous. In some embodiments, Compound 11 is amorphous, and is substantially free of crystalline Compound 11.

i. Form A of Compound 11

In some embodiments, Form A of Compound 11 has at least 1, 2, 3, 4, 5, or more spectral peak(s) selected from the peaks listed in Table 22 below. In some embodiments, the peak(s) with relatively highest intensity peak(s) are selected.

TABLE 22

XRPD Peak Positions for Form A of Compound 11

| Pos. [°2θ] | d-spacing [Å] | Rel. Int. [%] |
| --- | --- | --- |
| 9.4 | 9.42 | 61.29 |
| 11.4 | 7.75 | 96.94 |
| 12.5 | 7.06 | 62.91 |
| 16.3 | 5.44 | 56.18 |
| 16.6 | 5.35 | 65.57 |
| 16.7 | 5.31 | 100.00 |
| 16.8 | 5.29 | 63.93 |
| 17.3 | 5.11 | 58.06 |
| 20.2 | 4.39 | 31.17 |
| 21.7 | 4.08 | 81.57 |
| 22.4 | 3.97 | 28.43 |
| 22.6 | 3.94 | 42.06 |
| 22.9 | 3.87 | 95.44 |
| 24.1 | 3.68 | 19.63 |
| 26.7 | 3.33 | 15.33 |
| 31.0 | 2.88 | 22.79 |
| 31.4 | 2.84 | 37.81 |
| 31.5 | 2.84 | 27.73 |
| 34.6 | 2.59 | 33.00 |
| 34.7 | 2.58 | 22.31 |

[1] In this and all subsequent tables, the position 2θ is within ± 0.2.

In some embodiments, Form A of Compound 11 is characterized in that it has one or more peaks in its X-ray powder diffraction pattern selected from those at about 11.4, about 16.7, and about 22.9 degrees 2-theta. In some embodiments, Form A of Compound 11 is characterized in that it has two or more peaks in its X-ray powder diffraction pattern selected from those at about 11.4, about 16.7, and about 22.9 degrees 2-theta. In some embodiments, Form A of Compound 11 is characterized in that it has all three peaks in its X-ray powder diffraction pattern selected from those at about 11.4, about 16.7, and about 22.9 degrees 2-theta. In some embodiments, Form A of Compound 11 is further characterized by additional 1, 2, 3, 4 or 5 peak(s) selected from Table 22.

Figure 43:
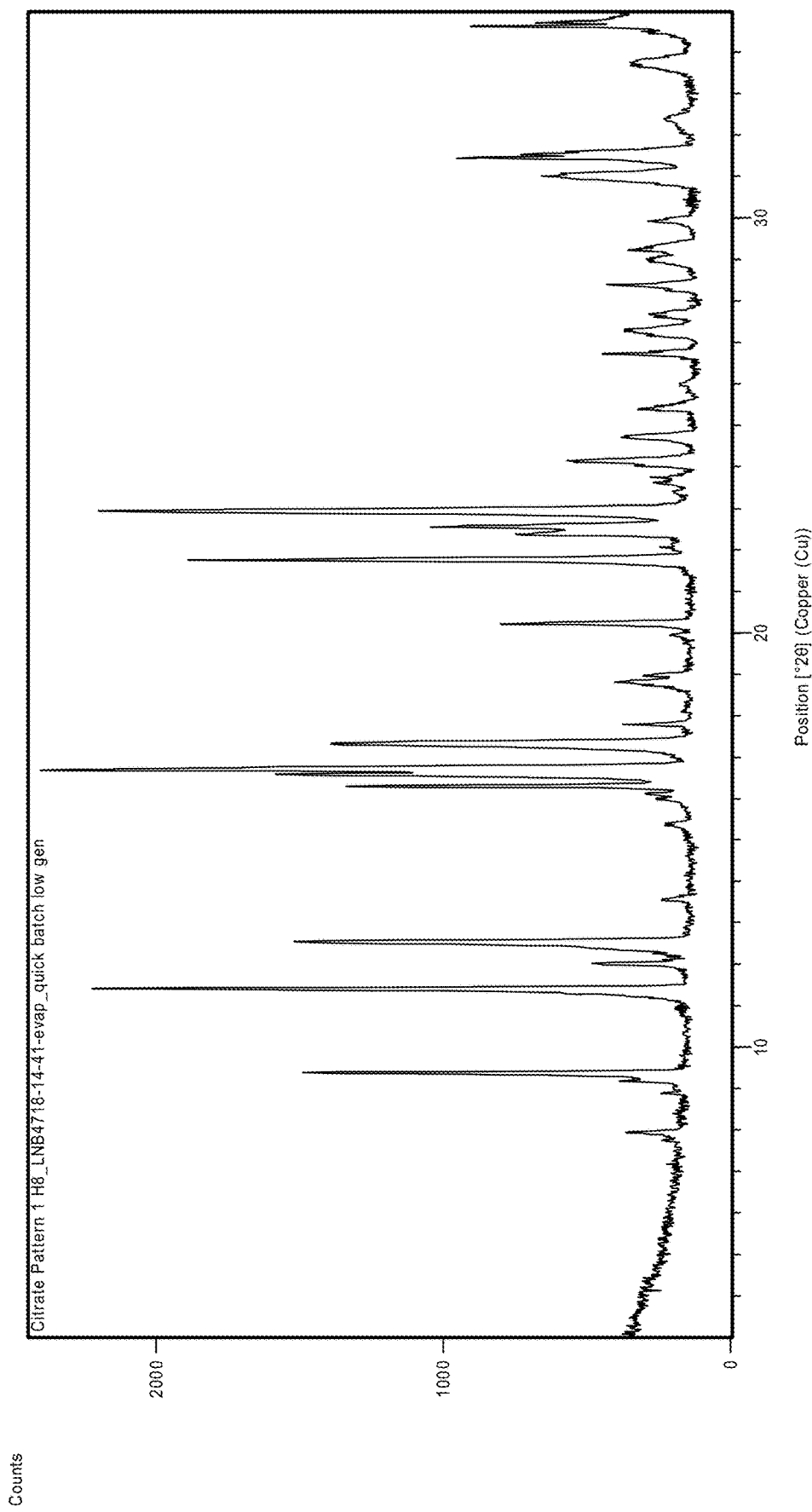
FIG. 43 depicts single crystal micrograph of Compound 11, Form A.

In certain embodiments, the X-ray powder diffraction pattern is substantially similar to the XRPD provided in FIG. 43.

Figure 44:
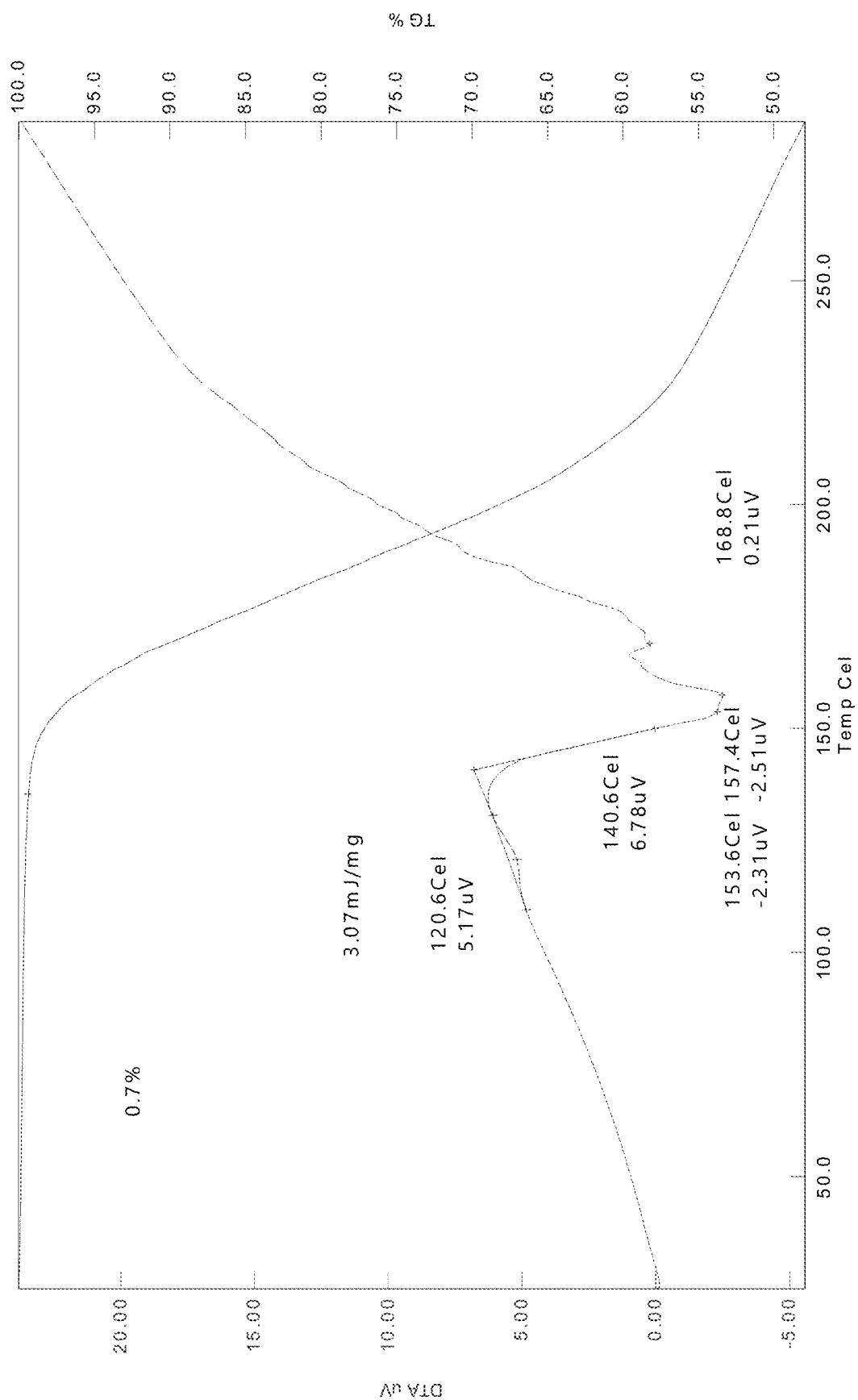
FIG. 44 depicts a DSC thermogram and TGA trace of Compound 11, Form A.

In some embodiments, Form A of Compound 11 is characterized by a differential scanning calorimetry (DSC) thermogram having the endothermic peak(s) as shown in FIG. 44. In some embodiments, Form A of Compound 11 has a DSC thermogram substantially the same as that shown in FIG. 44.

Methods for preparing Form A of Compound 11 are described infra.

In some embodiments, the present invention provides Compound 11:

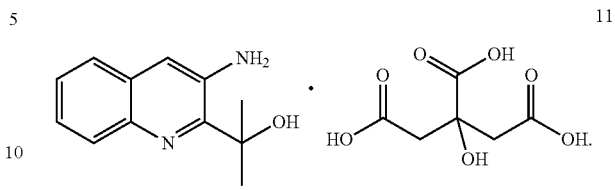

In some embodiments, the present invention provides Compound 11, wherein the compound is crystalline.

In some embodiments, the present invention provides Compound 11, wherein the compound is a crystalline solid substantially free of amorphous Compound 11.

In some embodiments, the present invention provides Compound 11, wherein the compound is substantially free of impurities.

In some embodiments, the present invention provides Compound 11, wherein the compound has one or more peaks in its XRPD selected from those at about 11.4, about 16.7, and about 22.9 degrees 2-theta. In some such embodiments, the present invention provides Compound 11, wherein the compound has at least two peaks in its XRPD selected from those at about 11.4, about 16.7, and about 22.9 degrees 2-theta. In some such embodiments, the present invention provides Compound 11, wherein the compound is of Form A.

In some embodiments, the present invention provides Compound 11, wherein the compound has an XRPD substantially similar to that depicted in FIG. 43.

In some embodiments, the present invention provides a composition comprising Compound 11 and a pharmaceutically acceptable carrier or excipient.

In some embodiments, the present invention provides a method of inhibiting or preventing the accumulation of A2E in a patient comprising administering to the patient Compound 11 or composition thereof.

In some embodiments, the present invention provides a method of treating various conditions in a patient in which aldehyde toxicity is implicated in the pathogenesis, comprising administering of Compound 11 or composition thereof to the patient. In some such embodiments, the various conditions, in a patient, in which aldehyde toxicity is implicated in the pathogenesis may include dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents.

In some embodiments, the present invention provides a compound selected from: Compound A, Form A; Compound 1, Form A; Compound 1, Form B; Compound 2, Form A; Compound 3, Form A; Compound 3, Form B; Compound 3, Form C; Compound 3, Form D; Compound 4, Form A; Compound 4, Form B; Compound 5, Form A; Compound 5, Form B; Compound 6, Form A; Compound 6, Form B; Compound 7, Form A; Compound 7, Form B; Compound 8, Form A; Compound 9, Form A; Compound 9, Form B; Compound 9, Form C; Compound 10, Form A; and Compound 11, Form A. In some such embodiments, the present invention provides a composition comprising one of the above compound forms and a pharmaceutically acceptable carrier or excipient. In some such embodiments, the present invention provides a method of treating one or more of the diseases, disorders, or conditions described herein.

II. General Methods of Providing a Salt Compound

Compound A is prepared according to Scheme 1, described infra.

Salt compounds of general formula X, which formula encompasses, inter alia, salt compounds 1 through 11, and/or particular forms thereof, are prepared from Compound A, according to the general scheme below.

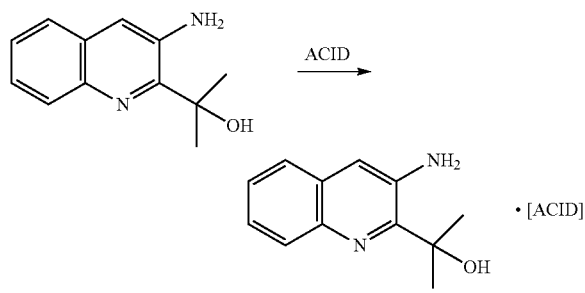

Compound a        Salt Compound X

For instance, each of compounds 1 through 11, and forms thereof, are prepared from Compound A by combining Compound A with an appropriate acid to form a salt of that acid. Thus, another aspect of the present invention provides a method for preparing compounds 1 through 11, and forms thereof.

As described generally above, in some embodiments, the present invention provides a method for preparing a salt compound of the general formula X:

Salt compound X

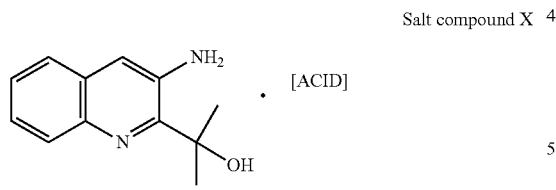

comprising step of:
combining Compound A:

Compound A

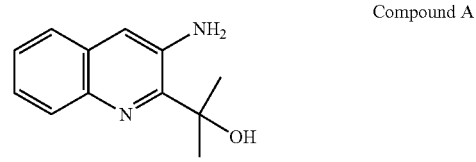

with a suitable acid and optionally a suitable solvent under conditions suitable for forming a salt compound of general formula X.

In some embodiments, a suitable acid is methanesulfonic acid. In some embodiments, the present invention provides a method of making a mesylate salt of Compound A. In certain embodiments, the mesylate salt of Compound A is Compound 1. In certain embodiments, the mesylate salt of Compound A is Form A of Compound 1. In certain embodiments, the mesylate salt of Compound A is Form B of Compound 1.

In some embodiments, a suitable acid is benzenesulfonic acid. In some embodiments, the present invention provides a method of making a besylate salt of Compound A. In certain embodiments, the besylate salt of Compound A is Compound 2. In certain embodiments, the besylate salt of Compound A is Form A of Compound 2.

In some embodiments, a suitable acid is sulfuric acid. In some embodiments, the present invention provides a method of making a sulfate salt of Compound A. In certain embodiments, the sulfate salt of Compound A is Compound 3. In certain embodiments, the sulfate salt of Compound A is Form A of Compound 3. In certain embodiments, the sulfate salt of Compound A is Form B of Compound 3. In certain embodiments, the sulfate salt of Compound A is Form C of Compound 3. In certain embodiments, the sulfate salt of Compound A is Form D of Compound 3.

In some embodiments, a suitable acid is p-toluenesulfonic acid. In some embodiments, the present invention provides a method of making a tosylate salt of Compound A. In certain embodiments, the tosylate salt of Compound A is Compound 4. In certain embodiments, the tosylate salt of Compound A is Form A of Compound 4. In certain embodiments, the tosylate salt of Compound A is Form B of Compound 4.

In some embodiments, a suitable acid is hydrochloric acid. In some embodiments, the present invention provides a method of making a hydrochloride salt of Compound A. In certain embodiments, the hydrochloric salt of Compound A is Compound 5. In certain embodiments, the hydrochloride salt of Compound A is Form A of Compound 5. In certain embodiments, the hydrochloride salt of Compound A is Form B of Compound 5.

In some embodiments, a suitable acid is oxalic acid. In some embodiments, the present invention provides a method of making an oxalate salt of Compound A. In certain embodiments, the oxalate salt of Compound A is Compound 6. In certain embodiments, the oxalate salt of Compound A is Form A of Compound 6. In certain embodiments, the oxalate salt of Compound A is Form B of Compound 6.

In some embodiments, a suitable acid is phosphoric acid. In some embodiments, the present invention provides a method of making a phosphate salt of Compound A. In certain embodiments, the phosphate salt of Compound A is Compound 7. In certain embodiments, the phosphate salt of Compound A is Form A of Compound 7. In certain embodiments, the phosphate salt of Compound A is Form B of Compound 7.

In some embodiments, a suitable acid is ethanedisulfonic acid. In some embodiments, the present invention provides a method of making an edisylate salt of Compound A. In certain embodiments, the edisylate salt of Compound A is Compound 8. In certain embodiments, the edisylate salt of Compound A is Form A of Compound 8.

In some embodiments, a suitable acid is tartaric acid. In some embodiments, the present invention provides a method of making a tartrate salt of Compound A. In certain embodiments, the tartrate salt of Compound A is Compound 9. In certain embodiments, the tartrate salt of Compound A is Form A of Compound 9. In certain embodiments, the tartrate salt of Compound A is Form B of Compound 9. In certain embodiments, the tartrate salt of Compound A is Form C of Compound 9.

In some embodiments, a suitable acid is fumaric acid. In some embodiments, the present invention provides a method of making a fumarate salt of Compound A. In certain embodiments, the fumarate salt of Compound A is Compound 10. In certain embodiments, the fumarate salt of Compound A is Form A of Compound 10.

In some embodiments, a suitable acid is citric acid. In some embodiments, the present invention provides a method of making a citrate salt of Compound A. In certain embodiments, the citrate salt of Compound A is Compound 11. In certain embodiments, the citrate salt of Compound A is Form A of Compound 11.

A suitable solvent may be any solvent system (e.g., one solvent or a mixture of solvents) in which Compound A and/or an acid are soluble or are at least partially soluble.

Examples of suitable solvents useful in the present invention include, but are not limited to protic solvents, aprotic solvents, polar aprotic solvent, or mixtures thereof. In certain embodiments, suitable solvents include an ether, an ester, an alcohol, a ketone, or a mixture thereof. In some embodiments, the solvent is one or more organic alcohols. In some embodiments, the solvent is chlorinated. In some embodiments, the solvent is an aromatic solvent.

In certain embodiments, a suitable solvent is methanol, ethanol, isopropanol, or acetone wherein the solvent is anhydrous or in combination with water or heptane. In some embodiments, suitable solvents include tetrahydrofuran, dimethylformamide, dimethylsulfoxide, glyme, diglyme, methyl t-butyl ether, t-butanol, n-butanol, and acetonitrile. In some embodiments, a suitable solvent is ethanol. In some embodiments, a suitable solvent is anhydrous ethanol. In some embodiments, the suitable solvent is MTBE.

In some embodiments, a suitable solvent is ethyl acetate. In some embodiments, a suitable solvent is a mixture of methanol and methylene chloride. In some embodiments, a suitable solvent is a mixture of acetonitrile and water. In certain embodiments, a suitable solvent is methyl acetate, isopropyl acetate, acetone, or tetrahydrofuran. In certain embodiments, a suitable solvent is diethylether. In certain embodiments, a suitable solvent is water. In certain embodiments, a suitable solvent is methyl ethyl ketone. In certain embodiments, a suitable solvent is toluene.

In some embodiments, the present invention provides a method for preparing a salt compound of the general formula X, comprising one or more steps of removing a solvent and adding a solvent. In some embodiments, an added solvent is the same as the solvent removed. In some embodiments, an added solvent is different from the solvent removed. Means of solvent removal are known in the synthetic and chemical arts and include, but are not limited to, any of those described herein and in the Exemplification.

In some embodiments, a method for preparing a salt compound of the general formula X comprises one or more steps of heating or cooling a preparation.

In some embodiments, a method for preparing a salt compound of the general formula X comprises one or more steps of agitating or stirring a preparation.

In some embodiments, a method for preparing a salt compound of the general formula X comprises a step of adding a suitable acid to a solution or slurry of Compound A.

In some embodiments, a method for preparing a salt compound of the general formula X comprises a step of heating.

In certain embodiments, a salt compound of formula X precipitates from the mixture. In another embodiment, a salt compound of formula X crystallizes from the mixture. In other embodiments, a salt compound of formula X crystallizes from solution following seeding of the solution (i.e., adding crystals of a salt compound of formula X to the solution).

A salt compound of formula X can precipitate out of the reaction mixture, or be generated by removal of part or all of the solvent through methods such as evaporation, distillation, filtration (ex. nanofiltration, ultrafiltration), reverse osmosis, absorption and reaction, by adding an anti-solvent such as heptane, by cooling or by different combinations of these methods.

As described generally above, a salt compound of formula X is optionally isolated. It will be appreciated that a salt compound of formula X may be isolated by any suitable physical means known to one of ordinary skill in the art. In certain embodiments, precipitated solid salt compound of formula X is separated from the supernatant by filtration. In other embodiments, precipitated solid salt compound of formula X is separated from the supernatant by decanting the supernatant.

In certain embodiments, a salt compound of formula X is separated from the supernatant by filtration.

In certain embodiments, an isolated salt compound of formula X is dried in air. In other embodiments, isolated salt compound of formula X is dried under reduced pressure, optionally at elevated temperature.

III. Pharmaceutically Acceptable Compositions

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder, the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention are administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues. Subcutaneous depot formulations are also prepared with hyaluronidase.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention can also be administered topically, such as directly to the eye, e.g., as an eye-drop or ophthalmic ointment. Eye drops typically comprise an effective amount of at least one compound of the invention and a carrier capable of being safely applied to an eye. For example, the eye drops are in the form of an isotonic solution, and the pH of the solution is adjusted so that there is no irritation of the eye. In many instances, the epithelial barrier interferes with penetration of molecules into the eye. Thus, most currently used ophthalmic drugs are supplemented with some form of penetration enhancer. These penetration enhancers work by loosening the tight junctions of the most superior epithelial cells (Burstein, Trans Ophthalmol Soc U K. 1985; 104(Pt 4): 402-9; Ashton et al., J Pharmacol Exp Ther., 1991; 259(2):719-24; Green et al., Am J Ophthalmol., 1971; 72(5): 897-905). The most commonly used penetration enhancer is benzalkonium chloride (Tang et al., J Pharm Sci., 1994, 83(1):85-90; Burstein et al., Invest Ophthalmol Vis Sci., 1980; 19(3): 308-13), which also works as preservative against microbial contamination. It is typically added to a final concentration of 0.01-0.05%.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

IV. Uses of Compounds and Pharmaceutically Acceptable Compositions Thereof

Certain compounds described herein are found to be useful in scavenging toxic aldehydes, such as MDA and 4-HNE. The compounds described herein undergo a Schiff base condensation with MDA, 4-HNE, or other toxic aldehydes, and form a complex with the aldehydes in an energetically favorable reaction, thus decreasing or eliminating aldehydes available for reaction with a protein, lipid, carbohydrate, or DNA. Importantly, compounds described herein can react with aldehydes to form a compound having a closed-ring structure that contains the aldehydes, thus trapping the aldehydes and preventing the aldehydes from being released back into the cellular milieu.

As used herein, the terms "treatment," "treat," and "treating" refer to reversing, alleviating, delaying the onset of, or inhibiting the progress of a disease, disorder, or condition, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent, delay or lessen the severity of their recurrence.

The invention relates to compounds described herein for the treatment, prevention, and/or reduction of a risk of disease, disorder, or condition in which aldehyde toxicity is implicated in the pathogenesis.

Examples of the diseases, disorders, or conditions in which aldehyde toxicity is implicated include an ocular disease, disorder, or condition, including, but not limited to, a corneal disease (e.g., dry eye syndrome, cataracts, keratoconus, bullous and other keratopathy, and Fuchs' endothelial dystrophy), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions associated with high aldehyde levels as a result of inflammation (e.g., uveitis, scleritis, ocular Stevens-Johnson Syndrome, ocular rosacea (with or without meibomian gland dysfunction)). In one example, the ocular disease, disorder, or condition is not macular degeneration, such as age-related macular degeneration ("AMD"), or Stargardt's disease. In a further example, the ocular disease, disorder, or condition is dry eye syndrome, ocular rosacea, or uveitis.

Examples of the diseases, disorders, conditions, or indications in which aldehyde toxicity is implicated also include non-ocular disorders, including psoriasis, topical (discoid) lupus, contact dermatitis, atopic dermatitis, allergic dermatitis, radiation dermatitis, acne vulgaris, Sjögren-Larsson Syndrome and other ichthyoses, solar elastosis/wrinkles, skin tone firmness, puffiness, eczema, smoke or irritant induced skin changes, dermal incision, a skin condition associated burn and/or wound, SLE, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, succinic semialdehyde dehydrogenase deficiency, multiple sclerosis, amyotrophic lateral sclerosis, diabetes, metabolic syndrome, age-related disorders, and fibrotic diseases. In a further example, the non-ocular disorder is a skin disease, disorder, or condition selected from contact dermatitis, atopic dermatitis, allergic dermatitis, and radiation dermatitis. In another example, the non-ocular disorder is a skin disease, disorder, or condition selected from Sjögren-Larsson Syndrome and a cosmetic indication associated burn and/or wound.

In a further example, the diseases, disorders, or conditions in which aldehyde toxicity is implicated are an age-related disorder. Examples of age-related diseases, disorders, or conditions include wrinkles, dryness, and pigmentation of the skin.

Examples of the diseases, disorders, or conditions in which aldehyde toxicity is implicated further include conditions associated with the toxic effects of blister agents or burns from alkali agents. The compounds described herein decrease or eliminate toxic aldehydes and thus treat, prevent, and/or reduce a risk of these diseases or disorders.

In one embodiment, the invention relates to the treatment, prevention, and/or reduction of a risk of an ocular disease, disorder, or condition in which aldehyde toxicity is implicated in the pathogenesis, comprising administering to a subject in need thereof a compound described herein. The ocular disease, disorder, or condition includes, but is not limited to, a corneal disease (e.g., dry eye syndrome, cataracts, keratoconus, bullous and other keratopathy, and Fuchs' endothelial dystrophy in the cornea), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions where inflammation leads to high aldehyde levels (e.g., uveitis, scleritis, ocular Stevens-Johnson Syndrome, ocular rosacea (with or without meibomian gland dysfunction)). The ocular disease, disorder, or condition does not include macular degeneration, such as AMD, or Stargardt's disease. In one illustration, in the ocular disease, disorder, or condition, the amount or concentration of MDA or 4-HNE is increased in the ocular tissues or cells. For example, the amount or concentration of aldehydes (e.g., MDA or 4-HNE) is increased at least 1.1-fold, 1.2-fold, 1.3-fold, 1.4-fold, 1.5-fold, 2-fold, 2.5-fold, 5-fold, 10-fold as compared to that in normal ocular tissues or cells. Compounds described herein, such as Compound 1, decrease aldehyde (e.g., MDA and 4-HNE) concentration in a time-dependent manner. The amount or concentration of aldehydes (e.g., MDA or 4-HNE) can be measured by methods or techniques known in the art, such as those described in Tukozkan et al., Furat Tip Dergisi., 2006; 11: 88-92.

In one class, the ocular disease, disorder, or condition is dry eye syndrome. In a second class, the ocular disease, disorder, or condition is a condition associated with PRK healing and other corneal healing. For example, the invention is directed to advancing PRK healing or other corneal healing, comprising administering to a subject in need thereof a compound described herein. In a third class, the ocular disease, disorder, or condition is an ocular condition associated with high aldehyde levels resulting from inflammation (e.g., uveitis, scleritis, ocular Stevens-Johnson Syndrome, and ocular rosacea (with or without meibomian gland dysfunction). In a fourth class, the ocular disease, disorder, or condition is keratoconus, cataracts, bullous and other keratopathy, Fuchs' endothelial dystrophy, ocular cicatricial pemphigoid, or allergic conjunctivitis. The compound described herein may be administered topically or systemically, as described herein below.

In a second embodiment, the invention relates to the treatment, prevention, and/or reduction of a risk of a skin disorder or condition or a cosmetic indication, in which aldehyde toxicity is implicated in the pathogenesis, comprising administering to a subject in need thereof a compound described herein. The skin disorder or condition includes, but is not limited to, psoriasis, scleroderma, topical (discoid) lupus, contact dermatitis, atopic dermatitis, allergic dermatitis, radiation dermatitis, acne vulgaris, and Sjögren-Larsson Syndrome and other ichthyosis, and the cosmetic indication is solar elastosis/wrinkles, skin tone firmness, puffiness, eczema, smoke or irritant induced skin changes, dermal incision, or a skin condition associated burn and/or wound. In some embodiments, the invention relates to age-related diseases, disorders, or conditions of the skin, as described herein.

Various skin disorders or conditions, such as atopic dermatitis, topical (discoid) lupus, psoriasis and scleroderma, are characterized by high MDA and 4-HNE levels (Niwa et al., Br J Dermatol., 2003; 149:248-254; Akturk et al., J Eur Acad Dermatol Venereol., 2012; 26(7):833-7; Tikly et al., Clin Rheumatol., 2006; 25:320-324). In addition, ichthyosis characteristic of the Sjögren-Larsson Syndrome (SLS) originates from accumulation of fatty aldehydes, which disrupts the normal function and secretion of lamellar bodies (LB), leading to intercellular lipid deposits in the stratum corneum (SC) and a defective water barrier in the skin layer (Rizzo et al., Arch Dermatol Res., 2010; 302:443-451). The enzyme that metabolizes aldehydes (fatty aldehyde dehydrogenase) is dysfunctional in SLS patients. Thus, compounds that decrease or eliminate aldehydes, such as the compounds described herein, can be used to treat, prevent, and/or reduce a risk of skin disorders or conditions in which aldehyde toxicity is implicated in the pathogenesis, such as those described herein. Furthermore, with an improvement to the water barrier and prevention of aldehyde-mediated inflammation (including fibrosis and elastosis (Chairpotto et al., Biofactors, 2005; 24(1-4):229-36), many cosmetic indications, such as solar elastosis/wrinkles, skin tone, firmness (puffiness), eczema, smoke or irritant induced skin changes and dermal incision cosmesis, and skin conditions associated with burn and/or wound can be treated using the method of the invention.

In one class, the skin disease, disorder, or condition is psoriasis, scleroderma, topical (discoid) lupus, contact dermatitis, atopic dermatitis, allergic dermatitis, radiation dermatitis, acne vulgaris, or Sjögren-Larsson Syndrome and other ichthyoses. In one exemplification, the skin disease, disorder, or condition is contact dermatitis, atopic dermatitis, allergic dermatitis, radiation dermatitis, or Sjögren-Larsson Syndrome and other ichthyoses. In a second class, the cosmetic indication is solar elastosis/wrinkles, skin tone firmness, puffiness, eczema, smoke or irritant induced skin changes, dermal incision, or a skin condition associated with burn and/or wound.

In a third embodiment, the invention relates to the treatment, prevention, and/or reduction of a risk of a condition associated with the toxic effects of blister agents or burns from alkali agents in which aldehyde toxicity is implicated in the pathogenesis, comprising administering to a subject in need thereof a compound described herein.

Blister agents include, but are not limited to, sulfur mustard, nitrogen mustard, and phosgene oxime. Toxic or injurious effects of blister agents include pain, irritation, and/or tearing in the skin, eye, and/or mucous, and conjunctivitis and/or corneal damage to the eye. Sulfur mustard is the compound bis(2-chlorethyl) sulfide. Nitrogen mustard includes the compounds bis(2-chlorethyl)ethylamine, bis(2-chlorethyl)methylamine, and tris(2-chlorethyl)amine. Sulfur mustard or its analogs can cause an increase in oxidative stress, and in particular 4-HNE levels, and by depleting the antioxidant defense system and thereby increasing lipid peroxidation, may induce an oxidative stress response and thus increase aldehyde levels (Jafari et al., Clinical Toxicology, 2010; 48:184-192; Pal et al., Free Radic Biol Med., 2009; 47(11):1640-1651). Increased activities of antioxidant enzymes may be a compensatory response to reactive oxygen species generated by the sulfur mustard. Antioxidants, such as silibinin, when applied topically, attenuate skin injury induced from exposure to sulfur mustard or its analogs (Jafari et al., Clinical Toxicology, 2010; 48:184-192; Tewari-Singh et al., PLOS ONE, 2012; 7(9):e46149). Further, intervention to reduce free radical species was an effective treatment, post-exposure, for phosgene-induced lung injury (Sciuto et al., Inhalation Toxicology, 2004; 16:565-580). Thus, compounds that decrease or eliminate aldehydes, such as compounds described herein, can be used to treat, prevent, and/or reduce the risk of a condition associated with the toxic effects of blister agents, such as sulfur mustard, nitrogen mustard, and phosgene oxime.

Alkali agents include, but are not limited to, lime, lye, ammonia, and drain cleaners. Compounds that reduce or eliminate aldehydes, such as compounds described herein, can be used to treat, prevent, and/or reduce a risk of a condition associated with burns from an alkali agent.

In a fourth embodiment, the invention relates to the treatment, prevention, and/or reduction of a risk of an autoimmune, immune-mediated, inflammatory, cardiovascular, or neurological disease, disorder, or condition, or metabolic syndrome, or diabetes, in which aldehyde toxicity is implicated in the pathogenesis, comprising administering to a subject in need thereof a compound described herein. The autoimmune or immune-mediated disease, disorder, or condition includes, but is not limited to, lupus, scleroderma, asthma, chronic obstructive pulmonary disease (COPD), and rheumatoid arthritis. The inflammatory disease, disorder, or condition includes, but is not limited to, rheumatoid arthritis, inflammatory bowel disease (e.g., Crohn's disease and ulcerative colitis), sepsis, and fibrosis (e.g., renal, hepatic, pulmonary, and cardiac fibrosis). The cardiovascular disease, disorder, or condition includes, but is not limited to, atherosclerosis and ischemic-reperfusion injury. The neurological disease, disorder, or condition includes, but is not limited to, Parkinson's disease, Alzheimer's disease, succinic semialdehyde dehydrogenase, deficiency, multiple sclerosis, amyotrophic lateral sclerosis, and the neurological aspects of Sjögren-Larsson Syndrome (cognitive delay and spasticity).

A skilled person would understand that the disease, disorder, or condition listed herein may involve more than one pathological mechanism. For example, a disease, disorder, or condition listed herein may involve dysregulation in the immunological response and inflammatory response. Thus, the above categorization of a disease, disorder, or condition is not absolute, and the disease, disorder, or condition may be considered an immunological, an inflammatory, a cardiovascular, a neurological, and/or metabolic disease, disorder, or condition.

Individuals with deficiencies in aldehyde dehydrogenase are found to have high aldehyde levels and increased risk of Parkinson's disease (Fitzmaurice et al., Proc Natl Acad Sci USA, 2013; 110(2):636-41) and Alzheimer's disease (Kamino et al., Biochem Biophys Res Commun., 2000; 273: 192-196). In Parkinson's disease, aldehydes specifically interfere with dopamine metabolism (Reed, Free Radic Biol Med, 2011; 51:1302; Zarkovic, Mol Aspects Med, 2003; 24:293-303; Khan et al., Brain Res, 2007; 1145:150-156). In addition, aldehydes levels are elevated in multiple sclerosis, amyotrophic lateral sclerosis, autoimmune diseases such as lupus, rheumatoid arthritis, SLE, psoriasis, scleroderma, and fibrotic diseases, and increased levels of 4-HNE, MDA, glyoxal, and methylglyoxal are implicated in the progression of atherosclerosis and diabetes (Aldini et al., J Cell Mol Med., 2011; 15:1339-1354; Wang et al., Arthritis Rheum., 2010; 62:2064-2072; Amara et al., Clin Exp Immunol, 1995; 101:233238; Hassan et al., Int J Rheum Dis., 2011; 14:325-321; Akturk et al., J Eur Acad Dermatol Venereol., 2012; 26(7):833-7; Tikly et al., Clin Rheumatol., 2006, 25:320-324; Albano et al., Gut, 2005; 54: 987-993; Pozzi et al., J Am Soc Nephrol., 2009; 20(10): 2119-2125; Lankin et al., Curr Aging Sci., 2017; 10:18-25; Samosonov et al., Oxid Med Cell Longev., 2017; 2017:1625130). MDA is further implicated in the increased formation of foam cells leading to atherosclerosis (Leibundgut et al., Curr Opin in Pharmacol., 2013; 13:168-179). Also, aldehyde-related toxicity plays an important role in the pathogenesis of many inflammatory lung diseases, such as asthma and chronic obstructive pulmonary disease (COPD) (Bartoli et al., Mediators Inflamm., 2011; 2011:891752). Thus, compounds that decrease or eliminate aldehydes, such as compounds described herein, can be used to treat, prevent, and/or reduce a risk of an autoimmune, immune-mediated, inflammatory, cardiovascular, or neurological disease, disorder, or condition, or metabolic syndrome, or diabetes. For example, compounds described herein prevent aldehyde-mediated cell death in neurons. Further, compounds described herein downregulate a broad spectrum of pro-inflammatory cytokines and/or upregulate anti-inflammatory cytokines, which indicates that compounds described herein are useful in treating inflammatory diseases, such as multiple sclerosis and amyotrophic lateral sclerosis.

As discussed above, a disclosed composition may be administered to a subject in order to treat or prevent macular degeneration and other forms of retinal disease whose etiology involves the accumulation of A2E and/or lipofuscin. Other diseases, disorders, or conditions characterized by the accumulation A2E may be similarly treated.

In one embodiment, a compound that reduces the formation of A2E is administered to a subject. For example, the compound may compete with PE for reaction with trans-RAL, thereby reducing the amount of A2E formed. In another embodiment, a compound that prevents the accumulation of A2E is administered to a subject. For example, the compound competes so successfully with PE for reaction with trans-RAL, no A2E is formed.

Individuals to be treated fall into three groups: (1) those who are clinically diagnosed with macular degeneration or other forms of retinal disease, whose disease etiology involves the accumulation of A2E and/or lipofuscin on the basis of visual deficits (including but not limited to dark adaptation, contrast sensitivity and acuity) as determined by visual examination and/or electroretinography, and/or retinal health as indicated by fundoscopic examination of retinal and RPE tissue for drusen accumulations, tissue atrophy and/or lipofuscin fluorescence; (2) those who are pre-symptomatic for macular degenerative disease but thought to be at risk based on abnormal results in any or all of the same measures; and (3) those who are pre-symptomatic but thought to be at risk genetically based on family history of macular degenerative disease and/or genotyping results showing one or more alleles or polymorphisms associated with the disease. The compositions are administered topically or systemically at one or more times per month, week or day. Dosages may be selected to avoid side effects, if any, on visual performance in dark adaptation. Treatment is continued for a period of at least one, three, six, or twelve or more months. Patients may be tested at one, three, six, or twelve months or longer intervals to assess safety and efficacy. Efficacy is measured by examination of visual performance and retinal health as described above.

In one embodiment, a subject is diagnosed as having symptoms of macular degeneration, and then a disclosed compound is administered. In another embodiment, a subject may be identified as being at risk for developing macular degeneration (risk factors include a history of smoking, age, female gender, and family history), and then a disclosed compound is administered. In another embodiment, a subject may have dry AMD in both eyes, and then a disclosed compound is administered. In another embodiment, a subject may have wet AMD in one eye but dry AMD in the other eye, and then a disclosed compound is administered. In yet another embodiment, a subject may be diagnosed as having Stargardt's disease and then a disclosed compound is administered. In another embodiment, a subject is diagnosed as having symptoms of other forms of retinal disease in which the etiology involves the accumulation of A2E and/or lipofuscin, and then the compound is administered. In another embodiment, a subject may be identified as being at risk for developing other forms of retinal disease in which the etiology involves the accumulation of A2E and/or lipofuscin, and then the disclosed compound is administered. In some embodiments, a compound is administered prophylactically. In some embodiments, a subject has been diagnosed as having the disease before retinal damage is apparent. For example, a subject is found to carry a gene mutation for ABCA4 and is diagnosed as being at risk for Stargardt's disease before any ophthalmologic signs are manifest, or a subject is found to have early macular changes indicative of macular degeneration before the subject is aware of any effect on vision. In some embodiments, a human subject may know that he or she is in need of the macular generation treatment or prevention.

In some embodiments, a subject may be monitored for the extent of macular degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

In some embodiments, the disclosed methods may be combined with other methods for treating or preventing macular degeneration or other forms of retinal disease in which the etiology involves the accumulation of A2E and/or lipofuscin, such as photodynamic therapy. For example, a patient may be treated with more than one therapy for one or more diseases, disorders or conditions. For example, a patient may have one eye afflicted with dry form AMD, which is treated with a compound of the invention, and the other eye afflicted with wet form AMD, which is treated with, e.g., photodynamic therapy.

In some embodiments, a compound for treating or preventing macular degeneration or other forms of retinal disease in which the etiology involves the accumulation of A2E and/or lipofuscin may be administered chronically. The compound may be administered daily, more than once daily, twice a week, three times a week, weekly, biweekly, monthly, bimonthly, semi-annually, annually, and/or biannually.

Sphingosine 1-phosphate, a bioactive signaling molecule with diverse cellular functions, is irreversibly degraded by the endoplasmic reticulum enzyme sphingosine 1-phosphate lyase, generating trans-2-hexadecenal and phosphoethanolamine. It has been demonstrated that trans-2-hexadecenal causes cytoskeletal reorganization, detachment, and apoptosis in multiple cell types via a JNK-dependent pathway (see, Upadhyaya et al., Biochem Biophys Res Commun., 2012; 424(1):18-21). These findings and the known chemistry of related α,β-unsaturated aldehydes raise the possibility that trans-2-hexadecenal interact with additional cellular components. It was shown that it reacts readily with deoxyguanosine and DNA to produce the diastereomeric cyclic 1,N(2)-deoxyguanosine adducts 3-(2-deoxy-β-d-erythro-pentofuranosyl)-5,6,7,8-tetrahydro-8R-hydroxy-6R-tridecylpyrimido[1,2-a]purine-10(3H)one and 3-(2-deoxy-β-d-erythro-pentofuranosyl)-5,6,7,8-tetrahydro-8S-hydroxy-6S-tridecylpyrimido[1,2-a]purine-10(3H)one. These findings demonstrate that trans-2-hexadecenal produced endogenously by sphingosine 1-phosphate lyase react directly with DNA, forming aldehyde-derived DNA adducts with potentially mutagenic consequences.

Succinic semialdehyde dehydrogenase deficiency (SSADHD), also known as 4-hydroxybutyric aciduria or gamma-hydroxybutyric aciduria, is the most prevalent autosomal-recessively inherited disorder of GABA metabolism (Vogel et al., J Inherit Metab Dis., 2013; 36(3):401-410), manifests a phenotype of developmental delay and hypotonia in early childhood, and severe expressive language impairment and obsessive-compulsive disorder in adolescence and adulthood. Epilepsy occurs in half of patients, usually as generalized tonic-clonic seizures although sometimes absence and myoclonic seizures occur (Pearl et al., Dev Med Child Neurol., 2015; 57(7): 611-617). Greater than two-thirds of patients manifest neuropsychiatric problems (i.e., ADHD, OCD, and aggression) in adolescence and adulthood, which can be disabling. Metabolically, there is accumulation of the major inhibitory neurotransmitter, GABA, and gamma-hydroxybutyrate (GHB), a neuromodulatory monocarboxylic acid (Snead et al., N Engl J Med., 2005; 352:2721-32). In addition, several other intermediates specific to this disorder have been detected both in patients and the corresponding murine model. Vigabatrin (VGB; γ-vinyl-GABA), an irreversible inhibitor of GABA-transaminase, is a logical choice for treatment of SSADH deficiency because it prevents the conversion of GABA to GHB by inhibiting GABA transaminase. Outcomes have been mixed, and in some patients treatment has led to deterioration (Good, J AAPOS, 2011; 15:411-412; Pellock et al., Acta Neurol Scand., 2011; 124 (Suppl. 192):83-91; Escalera et al., An Pediatr (Barc)., 2010; 72(2):128-32; Casarano et al., JIMD Reports, 2012; 2:119-23; 119-23; Matern et al., J Inher Metab Dis., 1996; 19:313-328; Al-Essa et al., Brain Develop., 2000; 22:127-131). Targeted therapy for SSADH deficiency remains elusive and interventions palliative.

As discussed above, the compounds of the disclosure are used to treat inflammatory disorders. In some embodiments, the compounds are administered in a therapeutically effective amount to a subject to treat a systemic inflammatory disorder. In some embodiments, the systemic inflammatory disorder is non-alcoholic fatty liver disease (NAFLD), non-alcoholic steatohepatitis (NASH), inflammatory bowel disease (IBD), Crohn's disease, ulcerative colitis (UC), psoriasis, IBS (irritable bowel syndrome or spastic colon), ankylosing spondylitis, osteoporosis, rheumatoid arthritis (RA), psoriatic arthritis, chronic obstructive pulmonary disease (COPD), interstitial lung disease (including idiopathic pulmonary fibrosis), atherosclerosis, psoriatic arthritis, pulmonary arterial hypertension, pyridoxine-dependent epilepsy, atopic dermatitis, rosacea, multiple sclerosis (MS), systemic lupus erythematosus (SLE), lupus nephritis, sepsis, eosinophilic esophagitis, chronic kidney disease (CKD), fibrotic renal disease, chronic eosinophilic pneumonia, extrinsic allergic alveolitis, pre-eclampsia, endometriosis, polycystic ovary syndrome (PCOS), reduced female fertility, reduced sperm viability and motility, or cyclophosphamide-induced hemorrhagic cystitis.

In some embodiments, the compounds of the disclosure are used to treat a systemic disease, disorder, or condition. In some embodiments, the systemic disease, disorder, or condition is light chain deposition disease, IgA nephropathy, end stage renal disease, gout, pseudogout, diabetic nephropathy, diabetic neuropathy, traumatic brain injury, noise-induced hearing loss, Alzheimer's Disease, Parkinson's Disease, Huntington Disease, amyotrophic lateral sclerosis, primary biliary cirrhosis, primary sclerosing cholangitis, uterine leiomyoma, sarcoidosis, or chronic kidney disease. In some embodiments, the compounds of the disclosure are administered in an effective amount to treat non-alcoholic fatty liver disease (NAFLD).

In some embodiments, the compounds of the disclosure are administered in an effective amount to treat non-alcoholic steatohepatitis (NASH).

In some embodiments, the compounds of the disclosure are administered in an effective amount to treat inflammatory bowel disease (IBD).

In some embodiments, the compounds of the disclosure are administered in an effective amount to treat Crohn's disease.

In some embodiments, the compounds of the disclosure are administered in an effective amount to treat ulcerative colitis (UC).

In some embodiments, the compounds of the disclosure are administered in an effective amount to treat psoriasis.

In some embodiments, the compounds of the disclosure are administered in an effective amount to treat IBS (irritable bowel syndrome) or spastic colon.

In some embodiments, the compounds of the disclosure are administered in an effective amount to treat ankylosing spondylitis.

In some embodiments, the compounds of the disclosure are administered in an effective amount to treat osteoporosis.

In some embodiments, the compounds of the disclosure are administered in an effective amount to treat rheumatoid arthritis (RA).

In some embodiments, the compounds of the disclosure are administered in an effective amount to treat psoriatic arthritis.

In some embodiments, the compounds of the disclosure are administered in an effective amount to treat chronic obstructive pulmonary disease (COPD).

In some embodiments, the compounds of the disclosure are administered in an effective amount to treat interstitial lung disease (including idiopathic pulmonary fibrosis).

In some embodiments, the compounds of the disclosure are administered in an effective amount to treat atherosclerosis.

In some embodiments, the compounds of the disclosure are administered in an effective amount to treat psoriatic arthritis.

In some embodiments, the compounds of the disclosure are administered in an effective amount to treat pulmonary arterial hypertension.

In some embodiments, the compounds of the disclosure are administered in an effective amount to treat pyridoxine-dependent epilepsy.

In some embodiments, the compounds of the disclosure are administered in an effective amount to treat atopic dermatitis.

In some embodiments, the compounds of the disclosure are administered in an effective amount to treat rosacea.

In some embodiments, the compounds of the disclosure are administered in an effective amount to treat multiple sclerosis (MS).

In some embodiments, the compounds of the disclosure are administered in an effective amount to treat systemic lupus erythematosus (SLE).

In some embodiments, the compounds of the disclosure are administered in an effective amount to treat lupus nephritis.

In some embodiments, the compounds of the disclosure are administered in an effective amount to treat sepsis.

In some embodiments, the compounds of the disclosure are administered in an effective amount to treat eosinophilic esophagitis.

In some embodiments, the compounds of the disclosure are administered in an effective amount to treat chronic kidney disease (CKD).

In some embodiments, the compounds of the disclosure are administered in an effective amount to treat fibrotic renal disease.

In some embodiments, the compounds of the disclosure are administered in an effective amount to treat chronic eosinophilic pneumonia.

In some embodiments, the compounds of the disclosure are administered in an effective amount to treat extrinsic allergic alveolitis.

In some embodiments, the compounds of the disclosure are administered in an effective amount to treat pre-eclampsia.

In some embodiments, the compounds of the disclosure are administered in an effective amount to treat endometriosis.

In some embodiments, the compounds of the disclosure are administered in an effective amount to treat polycystic ovary syndrome (PCOS).

In some embodiments, the compounds of the disclosure are administered in an effective amount to treat reduced female fertility.

In some embodiments, the compounds of the disclosure are administered in an effective amount to treat reduced sperm viability and motility.

In some embodiments, the compounds of the disclosure are administered in an effective amount to treat cyclophosphamide-induced hemorrhagic cystitis.

In some embodiments, the inflammatory disorder is an ocular inflammatory disorder. In some embodiments, the ocular inflammatory disorder is diabetic macular edema (DME), atopic keratoconjunctivitis (AKC), vernal keratoconjunctivitis (VKC), age-related macular degeneration (AMD), dry eye disease (DED), allergic conjunctivitis (AC), dry eye disease with allergic conjunctivitis, noninfectious anterior uveitis, posterior uveitis, pan-uveitis, post-surgical ocular pain and inflammation.

In some embodiments, the compound of the disclosure is administered in an effective amount for the prevention of corneal fibrosis after radial keratotomy, prevention of corneal fibrosis after trauma or exposure to vesicants, or prevention of corneal fibrosis after infection.

In some embodiments, the compounds of the disclosure are administered in an effective amount to treat diabetic macular edema (DME). In some embodiments, the diabetic macular edema for treatment is non-clinically significant macular edema (Non-CSME). In some embodiments, the diabetic macular edema for treatment is clinically significant macular edema (CSME).

In some embodiments, the compounds of the disclosure are administered in an effective amount to treat uveitis, including pan-uveitis, anterior uveitis, posterior uveitis, and non-infectious uveitis, which are ocular disorders that can be secondary to a primary underlying disorder. Some of the disorders with which uveitis is sometimes associated are Behçet's syndrome, ankylosing spondylitis, Lyme disease, sarcoidosis, and psoriasis. Uveitis is an inflammation of the iris, ciliary body, and choroid. It is associated with blurred vision; seeing dark, floating spots ("floaters"); eye pain; redness of the eye; and sensitivity to light (photophobia). A standard course of therapy for uveitis is a topical corticosteroid, and in some instances, a dilator such cyclopentolate, or an immunomodulatory agent.

In some embodiments, the compounds of the disclosure are administered in an effective amount to treat non-alcoholic steatohepatitis (NASH), inflammatory bowel disease (IBD), Crohn's disease, ulcerative colitis (UC) or psoriasis.

In some embodiments, the compounds of the disclosure are administered in an effective amount to treat atopic keratoconjunctivitis (AKC) or vernal keratoconjunctivitis (VKC).

In some embodiments, the compounds of the disclosure are administered in an effective amount to treat age-related macular degeneration (AMD).

In some embodiments, the compounds of the disclosure are administered in an effective amount to treat dry eye disease (DED).

In some embodiments, the compounds of the disclosure are administered in an effective amount to treat allergic conjunctivitis (AC).

In some embodiments, the compounds of the disclosure are administered in an effective amount to treat dry eye disease with allergic conjunctivitis.

In some embodiments, the compounds of the disclosure are administered in an effective amount to treat post-surgical ocular pain and inflammation.

In some embodiments, the compounds of the disclosure are administered in an effective amount for prevention of corneal fibrosis after radial keratotomy.

In some embodiments, the compounds of the disclosure are administered in an effective amount for prevention of corneal fibrosis after trauma.

In some embodiments, the compounds of the disclosure are administered in an effective amount for prevention of corneal fibrosis after infection.

In some embodiments, the compounds of the disclosure are administered in an effective amount to treat non-alcoholic fatty liver disease (NAFLD).

In some embodiments, the compounds of the disclosure are administered in an effective amount for treatment and/or prevention of light chain deposition disease.

In some embodiments, the compounds of the disclosure are administered in an effective amount for treatment and/or prevention of IgA nephropathy.

In some embodiments, the compounds of the disclosure are administered in an effective amount for treatment and/or prevention of end stage renal disease.

In some embodiments, the compounds of the disclosure are administered in an effective amount for treatment and/or prevention of gout.

In some embodiments, the compounds of the disclosure are administered in an effective amount for treatment and/or prevention of pseudogout.

In some embodiments, the compounds of the disclosure are administered in an effective amount for treatment and/or prevention of diabetic nephropathy.

In some embodiments, the compounds of the disclosure are administered in an effective amount for treatment and/or prevention of diabetic neuropathy.

In some embodiments, the compounds of the disclosure are administered in an effective amount for treatment and/or prevention of traumatic brain injury.

In some embodiments, the compounds of the disclosure are administered in an effective amount for treatment and/or prevention of noise-induced hearing loss.

In some embodiments, the compounds of the disclosure are administered in an effective amount for treatment and/or prevention of Alzheimer's Disease, In some embodiments, the compounds of the disclosure are administered in an effective amount for treatment and/or prevention of Parkinson's disease.

In some embodiments, the compounds of the disclosure are administered in an effective amount for treatment and/or prevention of Huntington Disease.

In some embodiments, the compounds of the disclosure are administered in an effective amount for treatment and/or prevention of amyotrophic lateral sclerosis.

In some embodiments, the compounds of the disclosure are administered in an effective amount for treatment and/or prevention of primary biliary cirrhosis.

In some embodiments, the compounds of the disclosure are administered in an effective amount for treatment and/or prevention of primary sclerosing cholangitis.

In some embodiments, the compounds of the disclosure are administered in an effective amount for treatment and/or prevention of uterine leiomyoma.

In some embodiments, the compounds of the disclosure are administered in an effective amount for treatment and/or prevention of sarcoidosis.

In some embodiments, the compounds of the disclosure are administered in an effective amount for treatment and/or prevention of chronic kidney disease.

V. Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided compound, or composition thereof, is administered in combination with another therapeutic agent.

An additional therapeutic agent may be administered separately from a provided combination therapy, as part of a multiple dosage regimen. Alternatively, those agents may be part of a single dosage form, mixed together with a compound of this invention in a single composition. If administered as part of a multiple dosage regimen, the two active agents may be submitted simultaneously, sequentially or within a period of time from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound as described herein and one or more additional therapeutic agents. The therapeutic agent may be administered together with a compound as described herein or may be administered prior to or following administration of a compound as described herein. Suitable therapeutic agents are described in further detail below. In certain embodiments, a compound as described herein may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound as described herein may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In some embodiments, the present invention provides a method of treating a disorder as described herein, comprising administering a provided compound or composition thereof, in combination with an additional therapeutic agent. In some embodiments, the additional therapeutic is standard of care for the disorder being treated.

As used herein the term "standard of care" refers to treatment that is accepted by medical experts as a proper treatment for a certain type of disease and that is widely used by healthcare professionals. Also known as best practice, standard medical care, and standard therapy. One of ordinary skill in the art would recognize the standard of care treatment protocol for treatment of the disorders described herein.

In another embodiment, the present invention provides a method of treating an inflammatory disease, disorder or condition by administering to a patient in need thereof a compound as described herein and one or more additional therapeutic agents. Such additional therapeutic agents may be small molecules or recombinant biologic agents and include, for example, anti-inflammatory agents selected from non-steroidal anti-inflammatory drugs (NTHES) such as aspirin, ibuprofen, naproxen, etodolac (Lodine®) and celecoxib, colchicine (Colcrys®), corticosteroids such as prednisone, prednisolone, methylprednisolone, hydrocortisone, and the like methotrexate (Rheumatrex®), "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), or "anti-IL-6" agents such as tocilizumab (Actemra®), diclofenac, cortisone, hyaluronic acid (Synvisc® or Hyalgan®).

In some embodiments, the present invention provides a method of treating allergic conjunctivitis in a patient in need thereof comprising administering to the patient a provided compound or composition thereof in combination with an additional therapeutic agent useful for treating allergy or at least one allergy-related symptom. In some embodiments, the additional therapeutic agent is an anti-histamine. In some embodiments, the anti-histamine is selected from fexofenadine (Allegra), terfenadine (Seldane), triprolidine (Zymine), brompheniramine (Lodrane), chlorpheniramine (Chlor-Trimeton), cetirizine, diphenhydramine, carbinoxamine, promethazine, loratedine (Claritin), desloratadine (Clarinex), cetirizine (Zyrtec), clemastine (Allerhist), levocetirizine (Xyzal), or hydroxyzine (Atarax).

In some embodiments, the additional therapeutic agent is an anti-allergy agent. Such anti-allergy agents are well known in the art and include anti-inflammatory nasal sprays, eye drops, nasal decongestants (e.g., oxymetazoline, phenylephrine, or pseudoephedrine), and immunotherapy (e.g., allergy shots). Such agents include mast cell inhibitors (e.g., cromolyn sodium) and leukotriene inhibitors (e.g., Singulair). In some embodiments, the additional therapeutic is cetirizine (e.g., Zerviate, a cetirizine ophthalmic solution).

In some embodiments, the second therapeutic agent is a leukotriene inhibitor, non-steroidal anti-inflammatory drug (NTHE), steroid, tyrosine kinase inhibitor, receptor kinase inhibitor, modulator of nuclear receptor family of transcription factor, Hsp90 inhibitor, adenosine receptor ($A_{2A}$) agonist, disease modifying antirheumatic drugs (DMARDS), phosphodiesterase (PDE) inhibitor, neutrophil elastase inhibitor, modulator of Axl receptor tyrosine kinase, or combinations thereof.

In some embodiments, the second therapeutic agent is a leukotriene inhibitor. In some embodiments, the leukotriene inhibitor is montelukast, zafirlukast, pranlukast, zileuton, or combinations thereof.

In some embodiments, the second therapeutic agent is an NTHE. In some embodiments, the NTHE is acetylsalicylic acid, diflunisal, salsalate, ibuprofen, dexibuprofen, naloxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, phenylbutazone, mefenamic acid, meclofenamic acid, flufenamic acid, tolfenamic acid, celecoxib or combinations thereof.

In some embodiments, the second therapeutic agent is a steroid. In some embodiments, the steroid is prednisone, prednisolone, methylprednisone, triacmcinolone, betamethasone, dexamethasone, and prodrugs thereof.

In some embodiments, the second therapeutic agent is a tyrosine kinase inhibitor. In some embodiments, the tyrosine kinase inhibitor is an inhibitor of the following kinases, including, among others, JAK, Syk, JNK/SAPK, MAPK, PI-3K, or Ripk2. In some embodiments, the tyrosine kinase inhibitor is ruxolitinib, tofacitinib, oclactinib, filgotinib, ganotinib, lestaurtinib, momelotinib, pacritinib, upadacitinib, peficitinib, fedratinib, bentamapimod, D-JNKI-1 (XG-102, AM-111), ponatinib, WEHI-345, OD36, GSK583, idelalisib, copanlisib, taselisib, duvelisib, alpelisib, umbralisib, dactolisib, CUDC-907, entospletinib, fostamatinib, or combinations thereof.

In some embodiments, the second therapeutic agent is a receptor kinase inhibitor, including among others, an inhibitor of EGFR or HER2. In some embodiments, the receptor kinase inhibitor is gefitinib, erlotinib, neratinib, lapatinib, cetuximab, panitumumab, vandetanib, necitumumab, osimertinib, trastuzumab, neratinib, lapatinib, pertuzumab, or combinations thereof.

In some embodiments, the second therapeutic agent is a modulator of nuclear receptor family of transcription factors, including, among others, and inhibitor of PPAR, RXR, FXR, or LXR. In some embodiments, the inhibitor is pioglitazone, bexarotene, obeticholic acid, ursodeoxycholic acid, fexaramine, hypocholamide, or combinations thereof.

In some embodiments, the second therapeutic agent is an Hsp90 inhibitor. In some embodiments, the Hsp90 inhibitor is ganetespib, 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010, or combinations thereof.

In some embodiments, the second therapeutic agent is an adenosine receptor (AA) agonist. In some embodiments, the adenosine receptor agonist is, among others, disclosed in U.S. Pat. No. 9,067,963, which is incorporated herein by reference. In some embodiments, the adenosine receptor agonist is LNC-3050, LNC-3015, LNC-3047, LNC-3052, or combinations thereof.

In some embodiments, the second therapeutic agent is a disease-modifying antirheumatic drug (DMARD). In some embodiments, the DMARD is, among others, tocilizumab, certolizumab, etanercept, adalimumab, anakinra, abatacept, infliximab, rituximab, golimumab, uteskinumab, or combinations thereof.

In some embodiments, the second therapeutic agent is a phosphodiesterase (PDE) inhibitor. In some embodiments, the phosphodiesterase inhibitor is apremilast, crisaborole, piclimilast, drotaverine, ibudulast, roflumilast, sildenafil, tadalafil, vardenafil, or combinations thereof.

In some embodiments, the second therapeutic agent is a neutrophil elastase inhibitor. In some embodiments, the neutrophil elastase inhibitor is, among others, sivelestat.

In some embodiments, the second therapeutic agent is a modulator of Axl receptor tyrosine kinase. In some embodiments, the modulator of Axl receptor tyrosine kinase is bemcentinib (BGB324 or R428), TP-0903, LY2801653, amuvatinib (MP-470), bosutinib (SKI-606), MGCD 265, ASP2215, cabozantinib (XL184), foretinib (GSK1363089/XL880), or SGI-7079. In some embodiments, the modulator of Axl receptor tyrosine kinase is a monoclonal antibody targeting AXL (e.g., YW327.6S2) or an AXL decoy receptor (e.g., GL2I.T), or glesatinib, merestinib, or a dual Flt3-Axl inhibitor such as gilteritinib.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1: General Procedures

XRPD analysis was carried out on a PANalytical X'pert pro, scanning the samples between 3 and 35°2θ. The material was gently ground to release any agglomerates and loaded onto a multi-well plate with Kapton or Mylar polymer film to support the sample. The multi-well plate was then placed into the diffractometer and analyzed using Cu K radiation (α1 λ=1.54060 Å; α2=1.54443 Å; β=1.39225 Å; α1:α2 ratio=0.5) running in transmission mode (step size 0.0130°2θ) using 40 kV/40 mA generator settings.

Polarised Light Microscopy (PLM) analysis was carried out using an Olympus BX50 polarising microscope, equipped with a Motic camera and image capture software (Motic Images Plus 2.0) to determine the presence of crystallinity (birefringence). All images were recorded using the 20× objective, unless otherwise stated.

Thermo-gravimetric analysis (TGA) data were collected as follows. Approximately, 5 mg of material was weighed into an open aluminium pan and loaded into a simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 cm³/min.

Differential scanning calorimetry (DSC) data were collected as follows. Approximately 5 mg of material was weighed into an aluminium DSC pan and sealed non-hermetically with a pierced aluminium lid. The sample pan was then loaded into a Seiko DSC6200 (equipped with a cooler) cooled and held at 20° C. Once a stable heat-flow response was obtained, the sample and reference were heated to an upper temperature limit at a scan rate of 10° C./min and the resulting heat flow response monitored. Nitrogen was used as the purge gas, at a flow rate of 50 cm³/min. The following heating profiles were used during the secondary polymorph screen:

Compound 5, Form A—20° C. to 200° C., 200° C. to 20° C. and 20° C. to 250° C.;

Compound 7, Form A—20° C. to 160° C., 160° C. to 20° C. and 20° C. to 250° C.;

Compound 9, Form A—20° C. to 200° C.; and

Compound 10, Form A—20° C. to 220° C.

Proton Nuclear Magnetic Resonance (¹H NMR) spectra were collected on a Bruker AVIIIHD spectrometer equipped with a DCH cryoprobe operating at 50012 MHz for protons. Experiments were performed in deuterated dimethyl sulfoxide and each sample was prepared to ca. 10 mM concentration.

Dynamic Vapour Sorption (DVS) data were collected as follows. Approximately, 10-20 mg of sample was placed into a mesh vapour sorption balance pan and loaded into a DVS Intrinsic dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Gravimetric Vapour Sorption (GVS) data were collected as follows. Approximately 10-20 mg of sample was placed into a mesh vapor sorption balance pan and loaded into an IGASorp Moisture Sorption Analyser balance by Hiden Analytical. The sample was subjected to a ramping profile from 40-90% relative humidity (RH) at 10% increments, maintaining the sample at each step until a stable weight had been achieved (98% step completion, minimum step length 30 minutes, maximum step length 60 minutes) at 25° C. After completion of the sorption cycle, the sample was dried using the same procedure to 0% RH, and finally taken back to the starting point of 40% RH. Two cycles were performed. The weight change during the sorption/desorption cycles were plotted, allowing for the hygroscopic nature of the sample to be determined.

Variable temperature X-ray powder diffraction (VT-XRPD) analysis was carried out on a Philips X'Pert Pro Multipurpose diffractometer equipped with a temperature chamber. The samples were scanned between 4 and 35.99°2θ using Cu K radiation (α1 λ=1.54060 Å; α2=1.54443 Å; β=1.39225 Å; α1:α2 ratio=0.5) running in Bragg-Brentano geometry (step size 0.008°2θ) using 40 kV/40 mA generator settings. Measurements were performed at 25° C., 60° C., 140° C. and 25° C. for Compound 5, Form A.

Charged Aerosol Detection (CAD) data were collected as follows. Counterion content was measured using the following instrument parameters: Column—ACE Hillic-N 100×2.1 mm, 3 um, LC/213; Column Temperature—30° C.; Nebulizer Temperature—35° C.; Flow Rate—0.5 mL/min;

Mobile Phase A—pH 7 ammonium formate; Diluent—Acetonitrile:water (90:10); and Gradient program—Isocratic.

High Performance Liquid Chromatography-Ultraviolet Detection (HPLC-UV) for free-base forms were carried out using the following instrument parameters: Column—ACE Excel 3 C18-AR 75×4.6 mm×3 μm; Column Temperature—35° C.; Autosampler Temperature—Ambient; UV wavelength—240 nm; Injection Volume—3 μL; Flow Rate—1 mL/min; Mobile Phase A—0.1% TFA in water, and Mobile Phase B—0.1% TFA in Acetonitrile. The gradient program used for the free-base forms is shown below in Table 23.

TABLE 23

Gradient Program for Free-base Forms.

| Time (minutes) | Solvent B [%] |
| --- | --- |
| 0 | 5 |
| 0.5 | 5 |
| 10.5 | 95 |
| 12.5 | 95 |
| 12.75 | 5 |
| 15 | 5 |

High Performance Liquid Chromatography-Ultraviolet Detection (HPLC-UV) for free-base forms were carried out using the following instrument parameters: Column—ACE Excel 3 C18-AR 75×4.6 mm×3 μm; Column Temperature—35° C.; Autosampler Temperature—Ambient; UV wavelength—240 nm; Injection Volume—3 μL; Flow Rate—1 mL/min; Mobile Phase A—0.1% TFA in water, and Mobile Phase B—0.1% TFA in Acetonitrile. The gradient program used for the free-base forms is shown below in Table 24.

TABLE 24

Gradient Program for Free-base Forms.

| Time (minutes) | Solvent B [%] |
| --- | --- |
| 0 | 5 |
| 0.5 | 5 |
| 10.5 | 95 |
| 12.5 | 95 |
| 12.75 | 5 |
| 15 | 5 |

High Performance Liquid Chromatography-Ultraviolet Detection (HPLC-UV) for free-base forms was carried out using the following instrument parameters: Column—ACE Excel 3 C18-AR 75×4.6 mm×3 μm; Column Temperature—35° C.; Autosampler Temperature—Ambient; UV wavelength—240 nm; Injection Volume—3 μL; Flow Rate—1 mL/min; Mobile Phase A—0.1% TFA in water, and Mobile Phase B—0.1% TFA in Acetonitrile. The gradient program used for the free-base forms is shown below in Table 25.

TABLE 25

Gradient Program for Free-base Forms.

| Time (minutes) | Solvent B [%] |
| --- | --- |
| 0 | 5 |
| 0.5 | 5 |
| 10.5 | 95 |
| 12.5 | 95 |
| 12.75 | 5 |
| 15 | 5 |

High Performance Liquid Chromatography-Ultraviolet Detection (HPLC-UV) for salt forms was carried out using the following instrument parameters: Column—ACE Excel 3 C18-AR 75×4.6 mm×3 μm; Column Temperature—30° C.; Autosampler Temperature—Ambient; UV wavelength—275 nm; Injection Volume—6 μL; Flow Rate—1 mL/min; Mobile Phase A—0.1% TFA in water, and Mobile Phase B—0.1% TFA in Acetonitrile. The gradient program used for the salt forms is shown below in Table 26.

TABLE 26

Gradient Program for Salt Forms.

| Time (minutes) | Solvent B [%] |
| --- | --- |
| 0 | 5 |
| 10 | 95 |
| 12.5 | 95 |
| 12.75 | 5 |
| 15 | 5 |

Liquid Chromatography-Mass Spectrometry (LC-MS) data was carried out using the following instrument parameters: Column—ACE Excel 3 Super C18, 75 mm×4.6 mm, 3 μm; Mobile Phase A—0.1% Formic Acid in Deionised water; Mobile Phase B—0.1% Formic Acid in Acetonitrile; Diluent—Acetonitrile; Flow Rate—1.0 mL/min; Runtime—20 minutes; Column Temperature—30° C.; Injection Volume—10 μL; Needle Wash—Acetonitrile, Vial position #100; and PDA Range—190-400 nm. The gradient program used is shown below in Table 27.

TABLE 27

Gradient Program for LC-MS Analysis.

| Time (minutes) | Solvent B (%) |
| --- | --- |
| 0.00 | 5 |
| 12.00 | 95 |
| 15.00 | 95 |
| 15.10 | 5 |
| 20.00 | 5 |

Both +ve and −ve ESI were used and the tune method used the following parameters: Capillary temp—200° C.; Sheath Gas Flow—20.0; Source Voltage—4.50 kV; Source Current—80.00 uA; Capillary Voltage—8.0 V; and Tube Lens Offset—40.00 V.

Example 2: Polymorph Screenings

1. Free-base Primary Polymorph Screenings

Based on solubility screen results, a primary polymorph screen using an initial set of 28 solvents, as shown in Table 28, was performed as follows: A). To 28×2 mL vials, approximately 10 mg of the received Compound A was added; B). The solids were then slurried in the solvents (volumes shown in Table 28) and placed in an incubator/shaker to temperature cycle between ambient and 40° C. in 4 hour cycles for 72 hours; C). Any solids recovered were analyzed by XRPD.

TABLE 28

Solvents Selected for Initial Primary Polymorph Screen

| | Solvent | Solvent Added |
|---|---|---|
| 1 | 1,2-Dimethoxyethane | 50 μL |
| 2 | 1,4-Dioxane | 50 μL |
| 3 | 2-Butanone (MEK) | 50 μL |
| 4 | 2-Ethoxyethanol | 100 μL |
| 5 | 2-Methyl THF | 50 μL |
| 6 | Methanol:water (40:60 v/v %) | 500 μL |
| 7 | Methanol:water (95:5 v/v %) | 100 μL |
| 8 | Acetone | 100 μL |
| 9 | Acetonitrile | 50 μL |
| 10 | Anisole | 140 μL |
| 11 | Dichloromethane | 90 μL |
| 12 | Dimethylacetamide | 50 μL |
| 13 | Dimethylformamide | 50 μL |
| 14 | Dimethylsulfoxide | 50 μL |
| 15 | Ethanol | 50 μL |
| 16 | Ethyl Acetate | 50 μL |
| 17 | Isopropyl Acetate | 100 μL |
| 18 | Methanol | 50 μL |
| 19 | Methylisobutyl ketone | 100 μL |
| 20 | Nitromethane | 250 μL |
| 21 | N-Methylpyrrolidone | 50 μL |
| 22 | Propan-1-ol | 100 μL |
| 23 | Propan-2-ol | 250 μL |
| 24 | t-Butylmethyl Ether | 95 μL |
| 25 | Tetrahydrofuran | 50 μL |
| 26 | Toluene | 330 μL |
| 27 | Water | 500 μL |
| 28 | Acetic Acid | 100 μL |

Evaporation: The procedure for temperature cycling was repeated for the evaporation samples. After temperature cycling, the samples were un-caped and left to evaporate at ambient temperature for a minimum of 72 hours. Once fully evaporated, any solids present were analyzed in the first instance by XRPD. The vials were left evaporating for a total of 3 weeks with any observations noted throughout this time.

Crash Cooling to 2° C.: The procedure for temperature cycling was repeated for the crash cooling samples. After temperature cycling the samples were capped and crash cooled to 2° C. and left to stand. The samples were held at this temperature for a minimum of 72 hours. When sufficient solid was noted, the samples were separated and the solids analyzed by XRPD in the first instance. Samples which did not return solid were stored at 2° C. for up to 2 weeks.

Crash Cooling to −18° C.: The procedure for temperature cycling was repeated for the crash cooling samples. After temperature cycling the samples were capped and crash cooled to −18° C. and left to stand. The samples were held at this temperature for a minimum of 72 hours. When sufficient solid was noted the samples were separated and the solids analyzed by XRPD in the first instance. Samples which did not return solid were stored at −18° C. for up to 2 weeks.

Anti-Solvent Addition: Anti-solvent addition was carried out using the solvents heptane, hexane and water. The contents of the samples were checked after addition and again after 24 hours at ambient conditions. The samples were then transferred to the fridge for 24 hours at 2° C. Observations were made post addition and 48 hours by XRPD.

The primary polymorph screen used 28 solvents and 5 experimental conditions with time points of 48 hours and 2 weeks. Solids were recovered from the majority of solvent systems through evaporation and anti-solvent addition post temperature cycling. All solids recovered were identified as Compound A Form A by XRPD.

2. Free-base Secondary Polymorph Screenings

Following the initial polymorph screen, a second screen was carried out using an additional 11, more unusual, solvent systems with a time point of 4 days. Such solvents were ethylene carbonate, propylene carbonate, DMI (dimethylethylene urea), DMPU (dimethylpropylene urea), cyrene (dihydrolevoglucosenone), ethyl lactate, cyclopentyl methyl ether, dimethyl carbonate, ethylene glycol, 2-dimethylaminoethanol and polyethylene glycol. Solids were recovered from 5 of the evaporation samples and 5 of the crash cooling to 2° C. samples. All solids recovered were identified as Compound A Form A by XRPD.

3. Primary Salt Screening

Salt screens were carried out in two batches of 7 counterions. Approximately 860 mg of the Compound A was added to a 20 mL scintillation vial and dissolved in 10 mL of DCM, concentration of 86 mg/mL. The stock solution was then dispensed into 43 vials (20 mg of Compound A) and the DCM allowed to evaporate. An additional control sample was analyzed by XRPD to confirm Compound A Form A was still present. 1M stock solutions of each counterion were prepared in either THF or ethanol, as shown in Table 29. Fumaric acid was added as neat counterion due to low solubility. 1.05 equivalents of each counterion was added at room temperature and observations made.

TABLE 29

Solvents Used to make Acid Stock Solutions

| Counterion | Solvent used for 1M Stock Solution |
|---|---|
| Hydrochloric acid | THF |
| Sulfuric acid 98% | THF |
| 1-2-Ethanedisulfonic acid | Ethanol |
| p-Toluenesulfonic acid | Ethanol |
| Methanesulfonic acid | THF |
| Naphthalene-2-sulfonic acid | Ethanol |
| Benzenesulfonic acid | THF |
| Oxalic acid | THF |
| Maleic acid | THF |
| Phosphoric acid | THF |
| Ethanesulfonic acid | THF |
| L-Tartaric acid | THF |
| Fumaric acid | Neat addition |
| Citric acid | THF |

All samples were then temperature cycled using the following procedure: a) heat to 40° C., hold for 4 hours; b) cooled to room temperature, hold for 4 hours; and c) repeat for ca. 72 hours.

All samples displaying solutions had the lids removed from the vials and were allowed to evaporate at ambient temperature. Samples with solid material had the mother liquor removed and the solids analyzed by XRPD. The mother liquor was transferred to a new sample vial and stored at 5° C. to allow for further precipitation. The solids on the XRPD plate were allowed to dry at ambient before re-analysis by XRPD. The analyzed solids on the XRPD plate were exposed to 40° C./75% RH conditions for 24 hours before analysis by XRPD.

4. Secondary Salt Screening

Compound 5, Form B, Compound 7, Form A, Compound 9, Form A, and Compound 10, Form A were scaled up as described below.

Example 3: General Preparation of Compound A—Scheme 1

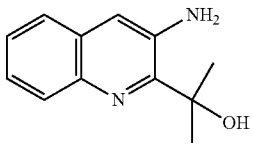

Compound A was prepared according to the steps and intermediates shown below in Scheme 1.

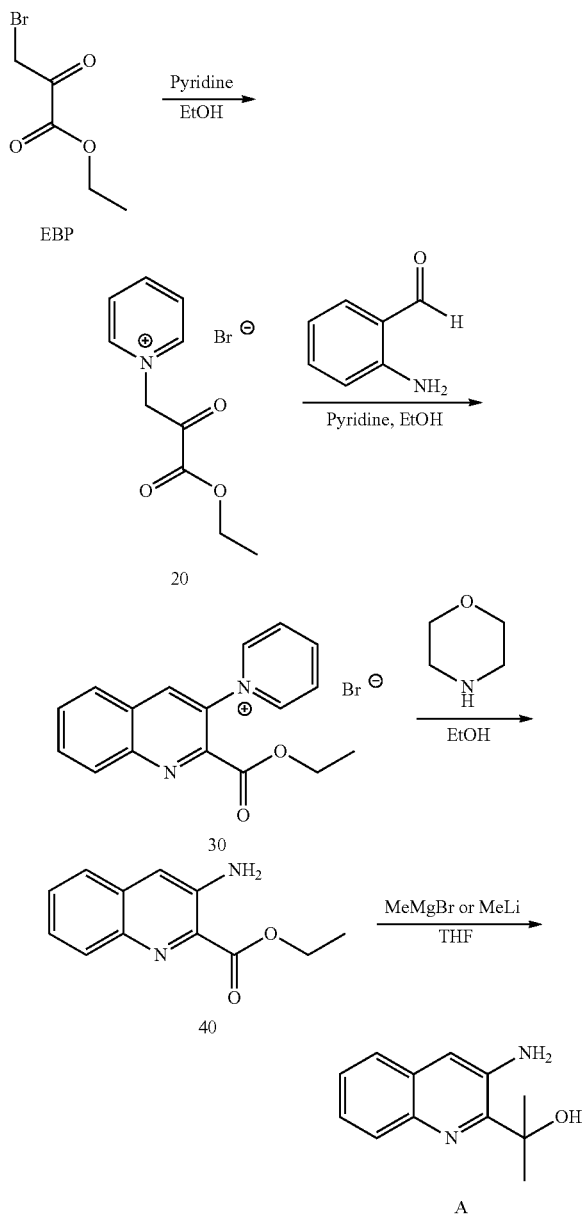

The synthesis of Compound A may be accomplished in four steps from commercially available ethyl bromopyruvate (EBP). Reaction of EBP with pyridine yields Compound 20. Compound 20 may be reacted without isolation with 2-aminobenzaldehyde to form Compound 30, which may be treated, without isolation, with morpholine to provide Compound 40 as an isolable solid. Compound 40 may then be treated with methylmagnesiumbromide (MeMgBr) in either tetrahydrofuran or 2-methyltetrahydrofuran to provide Compound A as a light-yellow solid. Alternatively, Compound 40 may be treated with methyllithium (MeLi) in either diethyl ether or dimethoxymethane to provide Compound A.

Step 1—Synthesis of Ethyl 3-aminoquinoline-2-carboxylate (Compound 40)

An 80 L jacketed glass reactor was charged with ethanol (10 L) and pyridine (10.45 kg, 132.08 moles). The resulting mixture was heated to 40° C.±5° C. and ethyl bromopyruvate (EBP) (16.1 kg, 82.55 moles) was added over 2 hours, maintaining the internal temperature at 40° C.±5° C. during the addition. The batch was heated to 65° C.±5° C. for at least 2 hours. In a separate vessel, 2-amino benzaldehyde (5.0 kg, 41.27 moles) was dissolved in ethanol (15.0 L). The resulting solution of 2-amino benzaldehyde was added to the reaction mixture (20) over 1 hour maintaining the internal temperature at 65° C.±5° C. The reaction mixture was heated to 80° C.±5° C. and stirred for a minimum of 1.5 hours. The batch (30) was cooled to 70° C.±5° C. and morpholine (19.77 kg, 227.01 moles) was added over 2 hours maintaining the internal temperature at 70° C.±5° C. The batch was warmed to 75° C.±5° C. and maintained at this temperature until complete by HPLC analysis (typically 1 hour). The reaction mixture was cooled to 20° C.±5° C. and water (20 L) was added. The batch was cooled to 0° C.±5° C. and maintained at this temperature for a minimum of 30 minutes. The resulting solid was collected by vacuum filtration and rinsed with water (12.5 L). The resulting solid was dried under vacuum at 35° C.±5° C. till constant weight was achieved. This crude product was slurried in heptanes (11.5 L) and ethanol (5.0 L) and heated to 70° C.±5° C. for a minimum of 1 hour. The slurry was cooled to 0° C.±5° C. and the resulting yellow solid was collected by vacuum filtration. The cake was washed with heptanes (7.5 L) and conditioned on the filter until liquids ceased to elute. The solid was transferred to trays and dried in a vacuum oven at 35° C.±5° C. to constant weight, providing Compound 40 as a yellow solid (5.71 kg, 64%).

Step 2a—Synthesis of 2-(3-Aminoquinolin-2-yl)propan-2-ol (Compound A) with MeMgBr To a 1 L 3 neck round bottom flask equipped with temperature probe, mechanical stirrer, condenser and an addition funnel, was charged methylmagnesium bromide (3.4 molar solution in 2-MeTHF, 88.23 mL, 300 mmol). The solution was cooled to −2° C. to −5° C. A suspension of Compound 40 (10.8 g, 50 mmol) in THF (100 mL) (Compound 40 was not completely soluble) was added dropwise to the reaction mixture via a peristaltic pump in such a way that the temperature of the reaction mixture was kept below 2° C. After complete addition of the solution, the temperature of the reaction was slowly raised to room temperature and the reaction mixture was stirred overnight. The mixture was cooled to 0° C. and quenched by addition of sat. aq. ammonium chloride (50 mL) and the solution was stirred for 30 minutes. The phases were separated. 20 mL of acetic acid was added to the aqueous layer to make it homogeneous and this was then extracted with DCM (2×100 mL). The combined organic layers were concentrated, and the oily residue was dissolved in DCM (200 mL) and filtered through a silica gel plug. The plug was washed with DCM (2×50 mL). The organics were extracted with 2 M aq. sulfuric acid. (Note: If solids are present water can be added to dissolve solids). The aqueous layer was washed with DCM (2×50 mL) and the pH of the aqueous layer was then adjusted to pH 7 with 50% aqueous NaOH solution. The aqueous layer was then extracted with ethyl acetate (200 mL) and concentrated with solvent swapping to heptanes to give a pale-yellow solid which was collected by filtration, the cake was washed with heptanes. The solids were recrystallized by dissolving in the minimum amount of ethyl acetate at reflux and the solution was treated with heptanes until cloud point. The mixture was then allowed to cool to room temperature and the product was collected by filtration and dried under vacuum (35° C., 10 mmHg) to obtain Compound A (6.75 g, 62%), as a pale-yellow solid which homogenous by NMR and HPLC analysis.

Step 2b—Synthesis of
2-(3-Aminoquinolin-2-yl)propan-2-ol (Compound A) with MeLi

A 100 L jacketed glass reactor was charged with methyl lithium (3.1 M in dimethoxymethane) (18.47 kg, 66.59 moles). The batch was cooled to −20° C.±5° C. and a solution of Compound 40 (2.4 kg, 5.55 moles) in THF (47.0 L) was charged to the reactor maintaining the internal temperature at −20±5° C. The resulting mixture was stirred at −20° C.±5° C. until complete reaction by HPLC analysis (typically 2 hours). The reaction mixture was quenched by addition of a solution of 2 N hydrochloric acid (1.2 L) in THF (1.2 L), while maintaining the internal temperature at <5° C. by rate of addition. 2N hydrochloric acid (28.0 L) was added to the reactor maintaining the internal temperature in the range of −5° C. to +5° C. The aqueous phase was separated, and the organic phase was concentrated to dryness using a rotary evaporator with a bath temperature of 45° C.±5° C. The resulting crude product was treated with methyl tert-butylether (7.5 L) and warmed to 45° C. to obtain complete dissolution. The solution was charged to a 50 L jacketed glass reactor and water (7.2 L) was added. The resulting mixture was stirred for 15 minutes at 20° C. and the aqueous phase was separated. The organic phase was concentrated using a rotary evaporator to dryness. The resulting solid was treated with methyl tert-butylether (3.5 L) to obtain a solution which was then treated with heptanes (9.5 L). After agitation for a minimum of 30 minutes the resulting solid is collected by filtration to provide Compound A as an orange solid (943 g, 42%).

Synthesis of 2-(3-Aminoquinolin-2-yl) propan-2-ol (Compound A) from 2-(3-amino-6-chloroquinolin-2-yl) propan-2-ol A 500 mL round bottomed flask was charged with 2-(3-amino-6-chloroquinolin-2-yl) propan-2-ol (prepared using procedures described in U.S. Pat. No. 9,687,481 B2) (19.0 g, 80.5 mmol), triethylamine (24.44 g, 241.5 mmol) and 10% palladium on carbon (1.9 g, 10 wt %) were combined in ethyl acetate (190 mL). The resulting mixture was exposed to a hydrogen atmosphere (1 atmosphere pressure) and stirred for 4 hours when deemed complete by HPLC analysis. The catalyst was removed by filtration and the ethyl acetate solution was washed with water and dried over anhydrous sodium sulfate. The solution was concentrated to approximately 3 volumes of ethyl acetate. Heptanes (300 mL) were added and the resulting precipitated solid was collected by vacuum filtration and the cake was washed with heptane (40 mL) and conditioned on the filter until liquids ceased to elute. The solid was dried in a vacuum oven at 35° C. to provide Compound A (15.3 g, 94%) as a pale-yellow solid.

Example 4: General Preparation of Compound A—Alternate

Compound A was alternatively prepared according to the steps and intermediates shown above in Scheme 1, and described below.

Step 1—Synthesis of Ethyl
3-aminoquinoline-2-carboxylate (Compound 40)

To a 1 L 3-neck round bottom flask equipped with temperature probe, mechanical stirrer, condenser and an addition funnel, was charged ethanol (60 mL) and pyridine (17.72 mL, 220 mmol) and the resulting solution was stirred under nitrogen. To this solution was added ethyl bromopyruvate (25.2 mL, 200 mmol) dropwise. The reaction mixture was heated to 65° C.±5° C. for 2 hours. 2-Aminobenzaldehyde (12.1 g, 100 mmol) was added in portions to the reaction mixture. The resultant mixture was heated to 80° C. for 90 minutes. The reaction mixture was then cooled to 70° C. and morpholine (47.5 mL, 550 mmol) was added. The temperature of the reaction mixture was raised to 75° C. and heated at this temperature for 1 hour. At this point the reaction was complete by LCMS analysis. The reaction mixture was cooled to 0° C. and water (50 mL) was added. The resulting slurry was stirred for 30 minutes at 20° C. Solids were removed by filtration and the cake was air dried. The brown solid was re-suspended in heptane (70 mL) and ethanol (30 mL) and heated to reflux for 1 h. The flask was then cooled in ice bath and the product was isolated by filtration and dried under vacuum (35° C., 10 mm Hg) to obtain 12.6 g of Compound 40 (58% yield) as a tan solid.

Step 2a—Synthesis of
2-(3-Aminoquinolin-2-yl)propan-2-ol (Compound A) with MeMgBr To a 1 L 3 neck round bottom flask equipped with temperature probe, mechanical stirrer, condenser and an addition funnel, was charged methylmagnesium bromide (3.4 molar solution in 2-MeTHF, 88.23 mL, 300 mmol). The solution was cooled to −2° C. to −5° C. A suspension of Compound 40 (10.8 g, 50 mmol) in THF (100 mL) (Compound 40 was not completely soluble) was added dropwise to the reaction mixture via a peristaltic pump in such a way that the temperature of the reaction mixture was kept below 2° C. After complete addition of the solution, the temperature of the reaction was slowly raised to room temperature and the reaction mixture was stirred overnight. The mixture was cooled to 0° C. and quenched by addition of sat. aq. ammonium chloride (50 mL) and the solution was stirred for 30 minutes. The phases were separated. 20 mL of acetic acid was added to the aqueous layer to make it homogeneous and this was then extracted with DCM (2×100 mL). The combined organic layers were concentrated and the oily residue was dissolved in DCM (200 mL) and filtered through a silica gel plug. The plug was washed with DCM (2×50 mL). The organics were extracted with 2 M aq. sulfuric acid. (Note: If solids are present water can be added to dissolve solids). The aqueous layer was washed with DCM (2×50 mL) and the pH of the aqueous layer was then adjusted to pH 7 with 50% aqueous NaOH solution. The aqueous layer was then extracted with ethyl acetate (200 mL) and concentrated with solvent swapping to heptanes to give a pale yellow solid which was collected by filtration, the cake was washed with heptanes. The solids were recrystallized by dissolving in the minimum amount of ethyl acetate at reflux and the solution was treated with heptanes until cloud point. The mixture was then allowed to cool to room temperature and the product was collected by filtration and dried under vacuum (35° C., 10 mmHg) to obtain Compound A (6.75 g, 62%), as a pale yellow solid which homogenous by NMR and HPLC analysis.

Step 2b—Synthesis of 2-(3-Aminoquinolin-2-yl)propan-2-ol (Compound A) with MeLi

To a 1 L 3 neck round bottom flask equipped with temperature probe, mechanical stirrer, condenser and an addition funnel To a 100 L reactor equipped with temperature probe, mechanical stirrer, and condenser was charged methyl lithium (3.0 molar solution in diethoxymethane, 10.741 L, 33.3 mol). The solution was cooled to −20±5° C. A solution of Compound 40 (1.2 kg, 5.55 mol) in anhydrous THF (24.0 L) was added dropwise to the reaction mixture at −20±5° C. The reaction mixture was aged at −20±5° C. overnight. After stirring for 16 hours at −20±5° C., the mixture was quenched by dropwise addition of 20% HCl (17.8 L, 15 volumes). The pH was dropped to 2.5. The phases were separated and the aqueous layer was basified with saturated NaHCO$_3$ solution (18.0 L, 15 volumes), and extracted with MTBE (30.0 L, 25 volumes). The organic layer was distilled to 3 volumes and passed through silica gel (2 wt. %) and the silica gel plug was washed with 20 volumes of 1:1 MTBE/heptanes. The batch was distilled down to 3 vol and the resulting slurry was heated to 60±5° C. for 2 h, then diluted with 0.5 volumes of MTBE and cooled to 15±5° C. over 4 h and aged at this temperature for 18 hours. The slurry was then filtered and the filter cake was washed with 2 volumes of heptanes and dried to constant weight in a vacuum oven at 35±5° C. at 10 mmHg to give Compound A as a pale yellow solid (471 g, 42% yield) with 95% (AUC) HPLC purity.

Example 4: Preparation of Free Base Form A of Compound A

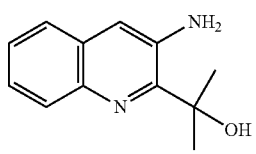

A

Compound A is prepared according to the procedures described in Example A or Example B, supra.
1. Form A of Compound A
Form A of Compound A was prepared as described above for the polymorph screens.

Table 1, supra, is reproduced below and sets forth the X-ray diffraction peaks observed for Form A of Compound A.

TABLE 1

XRPD Peak Positions for Form A of Compound A

| Pos. [°2Th.] | d-spacing [Å] | Rel. Int. [%] |
|---|---|---|
| 9.3 | 9.55 | 4.35 |
| 10.4 | 8.49 | 81.69 |
| 10.9 | 8.15 | 9.83 |
| 12.1 | 7.33 | 8.44 |
| 13.7 | 6.48 | 6.51 |
| 13.9 | 6.35 | 21.39 |
| 16.0 | 5.54 | 31.73 |
| 17.1 | 5.18 | 52.98 |
| 17.5 | 5.07 | 100 |
| 17.6 | 5.03 | 41.77 |
| 17.7 | 5.01 | 49.62 |
| 18.3 | 4.84 | 16.55 |
| 18.6 | 4.78 | 68.6 |
| 19.7 | 4.53 | 43.7 |
| 20.3 | 4.38 | 51.66 |
| 20.9 | 4.25 | 70.46 |
| 21.3 | 4.17 | 1.67 |
| 21.8 | 4.08 | 4.36 |
| 22.2 | 4.0 | 4.18 |
| 22.5 | 3.96 | 2.83 |
| 23.4 | 3.81 | 11.17 |
| 24.2 | 3.67 | 13.97 |
| 24.4 | 3.65 | 11.26 |
| 24.9 | 3.58 | 5.29 |
| 25.6 | 3.48 | 2.46 |
| 26.1 | 3.41 | 12.02 |
| 26.4 | 3.37 | 19.22 |
| 26.6 | 3.35 | 14.25 |
| 27.4 | 3.26 | 3.65 |
| 27.9 | 3.20 | 5.23 |
| 28.2 | 3.17 | 4.55 |
| 28.7 | 3.11 | 7.49 |
| 29.0 | 3.08 | 1.59 |
| 29.6 | 3.02 | 2.61 |
| 30.2 | 2.96 | 12.62 |
| 30.8 | 2.91 | 4.75 |
| 31.3 | 2.86 | 3.27 |
| 32.3 | 2.77 | 5.82 |
| 32.7 | 2.74 | 2.93 |
| 33.3 | 2.69 | 4.66 |
| 33.6 | 2.66 | 1.56 |
| 34.1 | 2.63 | 5.84 |
| 34.6 | 2.59 | 2.15 |

[1] In this and all subsequent tables, the position 2θ is within ±0.2.

FIG. 1 depicts an XRPD pattern of Form A of Compound A.

FIG. 2 depicts a DSC thermogram and TGA trace of Form A of Compound A.

Example 5: Preparation of Forms A and B of Compound 1

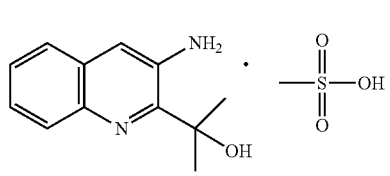

1

1. Form A of Compound 1

Form A of Compound 1 was prepared as described above. Table 2, supra, is reproduced below and sets forth the X-ray diffraction peaks observed for Form A of Compound 1.

TABLE 2

| \multicolumn{3}{c|}{XRPD Peak Positions for Form A of Compound 1} |
| Pos. [°2θ] | d-spacing [Å] | Rel. Int. [%] |
| --- | --- | --- |
| 9.7 | 9.10 | 21.52 |
| 10.4 | 8.51 | 23.71 |
| 12.2 | 7.25 | 12.22 |
| 13.7 | 6.47 | 43.53 |
| 14.5 | 6.09 | 5.00 |
| 14.8 | 5.99 | 12.51 |
| 16.8 | 5.28 | 7.23 |
| 17.2 | 5.14 | 10.42 |
| 17.8 | 5.00 | 9.84 |
| 18.0 | 4.93 | 69.59 |
| 19.8 | 4.48 | 7.43 |
| 20.9 | 4.26 | 11.84 |
| 22.2 | 4.01 | 28.47 |
| 22.8 | 3.90 | 4.34 |
| 24.6 | 3.63 | 14.88 |
| 26.5 | 3.36 | 100.00 |
| 27.8 | 3.21 | 5.39 |
| 28.3 | 3.15 | 14.34 |
| 29.3 | 3.05 | 11.60 |
| 33.2 | 2.70 | 5.33 |

[1] In this and all subsequent tables, the position 2θ is within ±0.2.

FIG. 3 depicts an XRPD pattern of Form A of Compound 1.

FIG. 4 depicts a DSC thermogram and TGA trace of Form A of Compound 1.

2. Form B of Compound 1

Form B of Compound 1 was prepared as described above. Table 3, supra, is reproduced below and sets forth the X-ray diffraction peaks observed for Form B of Compound 1.

TABLE 3

| \multicolumn{3}{c|}{XRPD Peak Positions for Form B of Compound 1} |
| Pos. [°2θ] | d-spacing [Å] | Rel. Int. [%] |
| --- | --- | --- |
| 8.4 | 10.52 | 29.49 |
| 11.5 | 7.72 | 13.76 |
| 13.0 | 6.80 | 40.87 |
| 14.6 | 6.08 | 23.63 |
| 15.8 | 5.60 | 23.94 |
| 17.9 | 4.94 | 100.00 |
| 19.4 | 4.58 | 8.37 |
| 20.9 | 4.24 | 23.67 |
| 21.2 | 4.19 | 11.35 |
| 21.8 | 4.07 | 17.53 |
| 22.4 | 3.98 | 15.58 |
| 23.6 | 3.77 | 9.23 |
| 25.6 | 3.48 | 8.32 |
| 25.6 | 3.48 | 8.81 |
| 26.2 | 3.40 | 33.35 |
| 26.2 | 3.40 | 32.56 |
| 27.2 | 3.28 | 12.44 |
| 27.9 | 3.20 | 16.72 |
| 28.0 | 3.18 | 17.35 |
| 31.9 | 2.80 | 11.58 |

[1] In this and all subsequent tables, the position 2θ is within ±0.2.

FIG. 5 depicts an XRPD pattern of Form B of Compound 1.

FIG. 6 depicts a DSC thermogram and TGA trace of Form B of Compound 1.

Example 6—Preparation of Form A of Compound 2

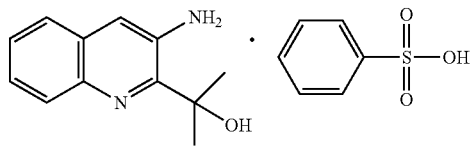

1. Form A of Compound 2

Form A of Compound 2 was prepared as described above. Table 4, supra, is reproduced below and sets forth the X-ray diffraction peaks observed for Form A of Compound 2.

TABLE 4

| \multicolumn{3}{c|}{XRPD Peak Positions for Form A of Compound 2} |
| Pos. [°2θ] | d-spacing [Å] | Rel. Int. [%] |
| --- | --- | --- |
| 11.2 | 7.89 | 80.98 |
| 13.4 | 6.60 | 55.12 |
| 13.6 | 6.51 | 37.52 |
| 15.0 | 5.90 | 65.91 |
| 15.1 | 5.85 | 55.93 |
| 16.9 | 5.26 | 33.60 |
| 18.1 | 4.91 | 41.70 |
| 19.7 | 4.50 | 23.90 |
| 20.4 | 4.36 | 40.50 |
| 21.9 | 4.05 | 19.49 |
| 22.5 | 3.95 | 17.69 |
| 22.8 | 3.90 | 16.92 |
| 23.7 | 3.76 | 83.16 |
| 25.1 | 3.54 | 100.00 |
| 25.2 | 3.54 | 59.31 |
| 26.4 | 3.38 | 88.05 |
| 26.6 | 3.35 | 31.34 |
| 27.0 | 3.30 | 19.68 |
| 27.5 | 3.24 | 34.38 |
| 27.6 | 3.24 | 24.82 |

[1] In this and all subsequent tables, the position 2θ is within ±0.2.

FIG. 7 depicts an XRPD pattern of Form A of Compound 2.

FIG. 8 depicts a DSC thermogram and TGA trace of Form A of Compound 2.

Example 7: Preparation of Forms A, B, C and D of Compound 3

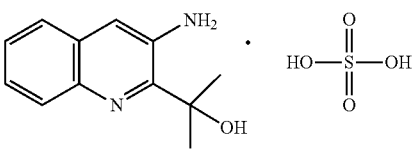

1. Form A of Compound 3

Form A of Compound 3 was prepared as described above. Table 5, supra, is reproduced below and sets forth the X-ray diffraction peaks observed for Form A of Compound 3.

TABLE 5

XRPD Peak Positions for Form A of Compound 3

| Pos. [°2θ] | d-spacing [Å] | Rel. Int. [%] |
|---|---|---|
| 8.6 | 10.33 | 11.59 |
| 13.2 | 6.69 | 99.09 |
| 13.5 | 6.56 | 11.90 |
| 14.4 | 6.17 | 17.80 |
| 14.7 | 6.03 | 14.16 |
| 17.7 | 5.01 | 84.48 |
| 18.6 | 4.78 | 21.33 |
| 19.2 | 4.63 | 22.31 |
| 19.8 | 4.49 | 44.88 |
| 21.6 | 4.11 | 30.97 |
| 22.2 | 4.01 | 51.90 |
| 24.3 | 3.66 | 17.55 |
| 25.3 | 3.53 | 11.98 |
| 27.1 | 3.28 | 100.00 |
| 27.2 | 3.28 | 80.05 |
| 27.7 | 3.22 | 11.34 |
| 28.0 | 3.18 | 12.49 |
| 28.9 | 3.09 | 20.40 |
| 29.0 | 3.07 | 28.49 |
| 29.7 | 3.01 | 13.66 |

[1] In this and all subsequent tables, the position 2θ is within ±0.2.

FIG. 9 depicts an XRPD pattern of Form A of Compound 3.

FIG. 10 depicts a DSC thermogram and TGA trace of Form A of Compound 3.

2. Form B of Compound 3

Form B of Compound 3 was prepared as described above.

Table 6, supra, is reproduced below and sets forth the X-ray diffraction peaks observed for Form B of Compound 3.

TABLE 6

XRPD Peak Positions for Form B of Compound 3

| Pos. [°2θ] | d-spacing [Å] | Rel. Int. [%] |
|---|---|---|
| 9.9 | 8.93 | 29.22 |
| 10.1 | 8.73 | 23.13 |
| 12.6 | 7.04 | 23.63 |
| 13.3 | 6.68 | 68.31 |
| 15.8 | 5.61 | 28.48 |
| 17.5 | 5.08 | 38.70 |
| 17.7 | 5.01 | 100.00 |
| 18.6 | 4.77 | 31.45 |
| 19.2 | 4.62 | 25.63 |
| 19.8 | 4.49 | 57.57 |
| 20.1 | 4.41 | 62.25 |
| 20.2 | 4.40 | 43.73 |
| 20.9 | 4.25 | 32.58 |
| 21.6 | 4.11 | 65.94 |
| 22.2 | 4.00 | 50.49 |
| 23.3 | 3.81 | 62.22 |
| 24.3 | 3.65 | 20.78 |
| 25.5 | 3.49 | 20.30 |
| 27.1 | 3.28 | 79.55 |
| 29.1 | 3.07 | 38.25 |

[1] In this and all subsequent tables, the position 2θ is within ±0.2.

FIG. 11 depicts an XRPD pattern of Form B of Compound 3.

FIG. 12 depicts a DSC thermogram and TGA trace of Form B of Compound 3.

3. Form C of Compound 3

Form C of Compound 3 was prepared as described above.

Table 7, supra, is reproduced below and sets forth the X-ray diffraction peaks observed for Form C of Compound 3.

TABLE 7

XRPD Peak Positions for Form C of Compound 3

| Pos. [°2θ] | d-spacing [Å] | Rel. Int. [%] |
|---|---|---|
| 8.8 | 10.00 | 6.39 |
| 12.2 | 7.25 | 4.36 |
| 12.7 | 6.99 | 3.87 |
| 13.0 | 6.83 | 1.66 |
| 13.2 | 6.69 | 3.22 |
| 16.5 | 5.38 | 20.50 |
| 16.6 | 5.34 | 24.05 |
| 16.8 | 5.28 | 61.67 |
| 16.9 | 5.26 | 100.00 |
| 17.7 | 5.01 | 5.02 |
| 18.5 | 4.80 | 4.27 |
| 19.1 | 4.65 | 2.23 |
| 19.8 | 4.47 | 49.51 |
| 21.6 | 4.12 | 1.47 |
| 22.1 | 4.01 | 2.18 |
| 22.8 | 3.90 | 1.74 |
| 23.9 | 3.73 | 3.74 |
| 25.5 | 3.49 | 3.12 |
| 27.1 | 3.29 | 5.11 |
| 34.1 | 2.63 | 2.17 |

[1] In this and all subsequent tables, the position 2θ is within ±0.2.

FIG. 13 depicts an XRPD pattern of Form C of Compound 3.

FIG. 14 depicts a DSC thermogram and TGA trace of Form C of Compound 3.

4. Form D of Compound 3

Form D of Compound 3 was prepared as described above.

Table 8, supra, is reproduced below and sets forth the X-ray diffraction peaks observed for Form D of Compound 3.

TABLE 8

XRPD Peak Positions for Form D of Compound 3

| Pos. [°2θ] | d-spacing [Å] | Rel. Int. [%] |
|---|---|---|
| 9.1 | 9.67 | 23.98 |
| 12.3 | 7.17 | 20.98 |
| 12.4 | 7.12 | 27.62 |
| 13.1 | 6.74 | 12.41 |
| 15.0 | 5.90 | 15.13 |
| 15.4 | 5.75 | 12.18 |
| 15.5 | 5.72 | 12.65 |
| 16.2 | 5.47 | 100.00 |
| 18.3 | 4.84 | 48.40 |
| 19.9 | 4.46 | 21.99 |
| 20.2 | 4.40 | 38.48 |
| 20.4 | 4.35 | 14.01 |
| 20.6 | 4.31 | 34.56 |
| 21.4 | 4.16 | 14.48 |
| 25.7 | 3.47 | 17.18 |
| 25.8 | 3.45 | 25.53 |
| 27.0 | 3.30 | 30.53 |
| 28.0 | 3.19 | 13.39 |
| 28.7 | 3.11 | 22.90 |
| 29.1 | 3.07 | 12.07 |

[1] In this and all subsequent tables, the position 2θ is within ±0.2.

FIG. 15 depicts an XRPD pattern of Form D of Compound 3.

FIG. 16 depicts a DSC thermogram and TGA trace of Form D of Compound 3.

Example 8: Preparation of Forms A and B of Compound 4

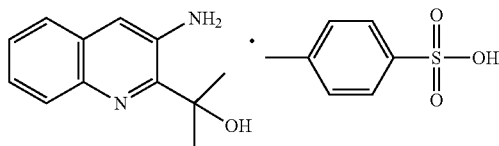

1. Form A of Compound 4

Form A of Compound 4 was prepared as described above. Table 9, supra, is reproduced below and sets forth the X-ray diffraction peaks observed for Form A of Compound 4.

TABLE 9

XRPD Peak Positions for Form A of Compound 4

| Pos. [°2θ] | d-spacing [Å] | Rel. Int. [%] |
|---|---|---|
| 8.7 | 10.21 | 43.02 |
| 13.1 | 6.78 | 34.27 |
| 13.3 | 6.64 | 10.07 |
| 13.6 | 6.52 | 21.56 |
| 15.1 | 5.87 | 8.78 |
| 15.9 | 5.58 | 9.30 |
| 16.3 | 5.43 | 16.59 |
| 17.4 | 5.09 | 7.17 |
| 18.7 | 4.75 | 5.78 |
| 20.0 | 4.45 | 22.49 |
| 20.2 | 4.40 | 22.35 |
| 20.5 | 4.33 | 9.60 |
| 21.8 | 4.08 | 24.01 |
| 22.0 | 4.04 | 9.51 |
| 22.4 | 3.97 | 24.66 |
| 22.9 | 3.88 | 18.07 |
| 23.5 | 3.79 | 4.96 |
| 24.2 | 3.68 | 100.00 |
| 26.5 | 3.36 | 21.60 |
| 28.7 | 3.11 | 9.24 |

[1] In this and all subsequent tables, the position 2θ is within ± 0.2.

FIG. 17 depicts an XRPD pattern of Form A of Compound 4.

FIG. 18 depicts a DSC thermogram and TGA trace of Form A of Compound 4.

2. Form B of Compound 4

Form B of Compound 4 was prepared as described above. Table 10, supra, is reproduced below and sets forth the X-ray diffraction peaks observed for Form B of Compound 4.

TABLE 10

XRPD Peak Positions for Form B of Compound 4

| Pos. [°2θ] | d-spacing [Å] | Rel. Int. [%] |
|---|---|---|
| 8.7 | 10.17 | 11.38 |
| 8.8 | 10.01 | 28.41 |
| 13.3 | 6.64 | 100.00 |
| 13.8 | 6.42 | 9.72 |
| 14.1 | 6.26 | 26.86 |
| 15.6 | 5.67 | 21.68 |
| 19.2 | 4.62 | 7.20 |
| 20.1 | 4.42 | 32.77 |
| 20.3 | 4.38 | 16.46 |
| 20.5 | 4.33 | 29.77 |
| 21.9 | 4.05 | 62.53 |

TABLE 10-continued

XRPD Peak Positions for Form B of Compound 4

| Pos. [°2θ] | d-spacing [Å] | Rel. Int. [%] |
|---|---|---|
| 22.2 | 4.00 | 14.46 |
| 22.4 | 3.96 | 17.84 |
| 23.4 | 3.80 | 33.85 |
| 23.8 | 3.73 | 30.33 |
| 24.1 | 3.69 | 7.52 |
| 25.9 | 3.43 | 50.89 |
| 26.7 | 3.34 | 10.18 |
| 27.2 | 3.28 | 9.55 |
| 28.5 | 3.13 | 22.60 |

[1] In this and all subsequent tables, the position 2θ is within ± 0.2.

FIG. 19 depicts an XRPD pattern of Form B of Compound 4.

FIG. 20 depicts a DSC thermogram and TGA trace of Form B of Compound 4.

Example 9: Preparation of Forms A and B of Compound 5

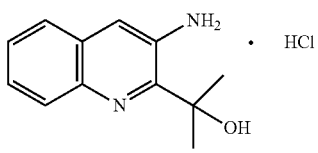

1. Form A of Compound 5

Form A of Compound 5 was prepared as described above. Table 11, supra, is reproduced below and sets forth the X-ray diffraction peaks observed for Form A of Compound 5.

TABLE 11

XRPD Peak Positions for Form A of Compound 5

| Pos. [°2θ] | d-spacing [Å] | Rel. Int. [%] |
|---|---|---|
| 10.0 | 8.85 | 13.64 |
| 10.2 | 8.64 | 33.20 |
| 12.7 | 6.97 | 40.44 |
| 13.9 | 6.37 | 79.47 |
| 15.8 | 5.61 | 100.00 |
| 18.2 | 4.86 | 33.01 |
| 18.5 | 4.80 | 39.33 |
| 20.4 | 4.35 | 15.26 |
| 20.8 | 4.27 | 14.96 |
| 21.7 | 4.09 | 27.67 |
| 23.3 | 3.82 | 35.73 |
| 24.3 | 3.66 | 94.78 |
| 24.8 | 3.59 | 18.42 |
| 25.5 | 3.50 | 36.21 |
| 28.0 | 3.19 | 48.63 |
| 28.5 | 3.13 | 17.72 |
| 28.8 | 3.10 | 27.58 |
| 30.0 | 2.98 | 12.41 |
| 30.3 | 2.95 | 57.23 |
| 31.9 | 2.80 | 19.17 |

[1] In this and all subsequent tables, the position 2θ is within ± 0.2.

FIG. 21 depicts an XRPD pattern of Form A of Compound 5.

Figure 22:
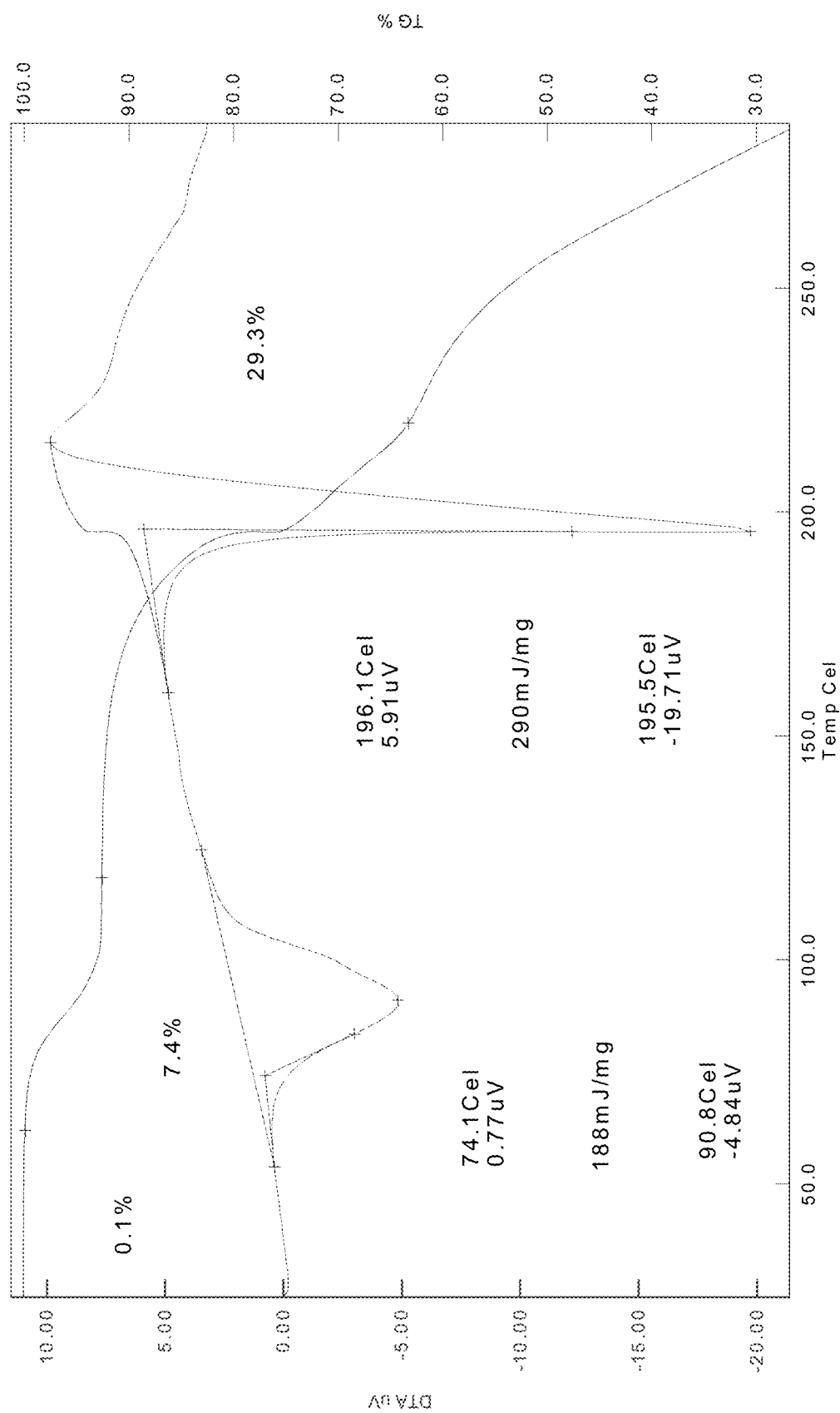
FIG. 22 depicts a DSC thermogram and TGA trace of Compound 5, Form A.

FIG. 22 depicts a DSC thermogram and TGA trace of Form A of Compound 5.

2. Form B of Compound 5

Form B of Compound 5 was prepared as described above. Form B of Compound 5 was scaled-up as follows.

Approximately 500 mg of the Compound A Form A was added to a 20 mL scintillation vial and dissolved in ethyl acetate (6.74 mL) to produce a concentration of 75 mg/mL. To the solution was added 1.05 equivalents of HCl and precipitation was observed on the sides of the vial. The sample was then temperature-cycled by using an incubator shaker and the following temperature profile: a) heating to 40° C., hold for 4 hours; b) cooled to room temperature, hold for 4 hours; and c) repeat for ca. 72 hours.

The solids were isolated by filtration using a Buchner flask and funnel and dried at 40° C. for 5 hours. The solid material was analyzed by XRPD, PLM, TG/DTA, DSC, DVS/GVS, FT-IR, NMR, HPLC and CAD.

Table 12, supra, is reproduced below and sets forth the X-ray diffraction peaks observed for Form B of Compound 5.

TABLE 12

XRPD Peak Positions for Form B of Compound 5

| Pos. [°2θ] | d-spacing [Å] | Rel. Int. [%] |
|---|---|---|
| 10.0 | 8.86 | 28.40 |
| 10.2 | 8.71 | 100.00 |
| 11.2 | 7.90 | 11.02 |
| 15.4 | 5.75 | 25.60 |
| 17.0 | 5.21 | 75.77 |
| 17.5 | 5.06 | 16.26 |
| 19.1 | 4.65 | 12.93 |
| 19.9 | 4.47 | 32.12 |
| 20.1 | 4.42 | 7.00 |
| 22.6 | 3.93 | 6.96 |
| 23.5 | 3.79 | 12.62 |
| 23.7 | 3.75 | 15.34 |
| 24.2 | 3.67 | 25.53 |
| 24.3 | 3.66 | 42.05 |
| 26.4 | 3.38 | 23.72 |
| 28.3 | 3.15 | 28.13 |
| 28.8 | 3.10 | 42.83 |
| 28.9 | 3.10 | 21.99 |
| 29.7 | 3.01 | 11.83 |
| 30.5 | 2.93 | 7.93 |

[1] In this and all subsequent tables, the position 2θ is within ± 0.2.

FIG. 23 depicts an XRPD pattern of Form B of Compound 5.

FIG. 24 depicts a DSC thermogram and TGA trace of Form B of Compound 5.

Example 10: Preparation of Forms A and B of Compound 6

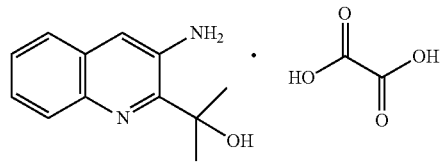

1. Form A of Compound 6

Form A of Compound 6 was prepared as described above. Table 13, supra, is reproduced below and sets forth the X-ray diffraction peaks observed for Form A of Compound 6.

TABLE 13

XRPD Peak Positions for Form A of Compound 6

| Pos. [°2θ] | d-spacing [Å] | Rel. Int. [%] |
|---|---|---|
| 8.6 | 10.23 | 86.55 |
| 10.2 | 8.66 | 8.43 |
| 15.7 | 5.64 | 31.46 |
| 16.0 | 5.54 | 40.56 |
| 16.2 | 5.48 | 30.47 |
| 16.8 | 5.29 | 100.00 |
| 17.1 | 5.18 | 31.46 |
| 17.3 | 5.11 | 17.50 |
| 20.0 | 4.43 | 7.15 |
| 20.5 | 4.33 | 7.93 |
| 21.5 | 4.13 | 21.08 |
| 22.0 | 4.04 | 16.09 |
| 24.7 | 3.61 | 6.97 |
| 25.0 | 3.57 | 18.33 |
| 26.1 | 3.41 | 25.03 |
| 27.1 | 3.29 | 51.72 |
| 27.9 | 3.20 | 18.68 |
| 28.2 | 3.17 | 22.55 |
| 28.5 | 3.13 | 14.24 |
| 28.7 | 3.11 | 21.77 |

[1] In this and all subsequent tables, the position 2θ is within ± 0.2.

FIG. 25 depicts an XRPD pattern of Form A of Compound 6.

Figure 26:
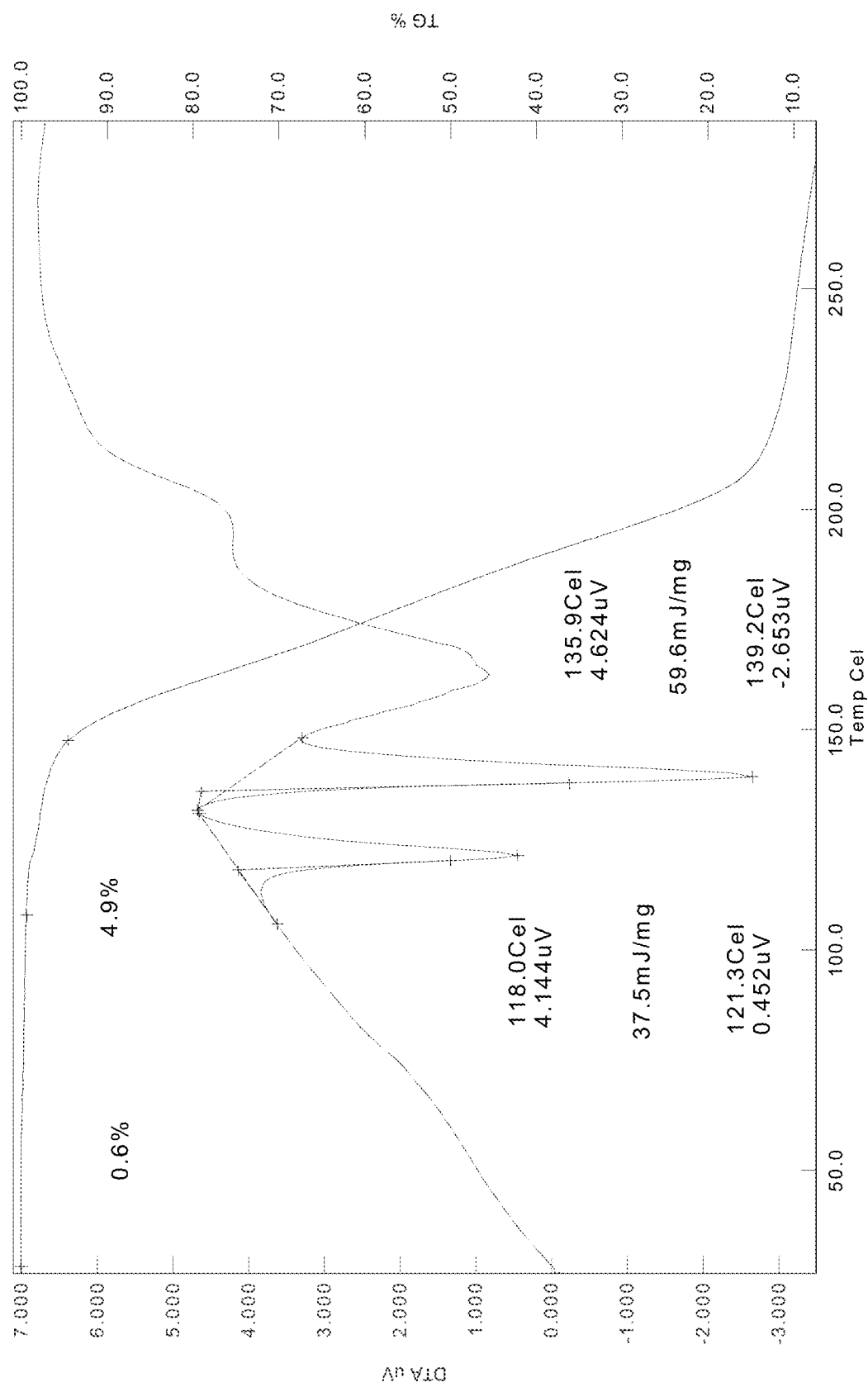
FIG. 26 depicts a DSC thermogram and TGA trace of Compound 6, Form A.

FIG. 26 depicts a DSC thermogram and TGA trace of Form A of Compound 6.

2. Form B of Compound 6

Form B of Compound 6 was prepared as described above.

Table 14, supra, is reproduced below and sets forth the X-ray diffraction peaks observed for Form B of Compound 6.

TABLE 14

XRPD Peak Positions for Form B of Compound 6

| Pos. [°2θ] | d-spacing [Å] | Rel. Int. [%] |
|---|---|---|
| 8.6 | 10.23 | 86.55 |
| 10.2 | 8.66 | 8.43 |
| 15.7 | 5.64 | 31.46 |
| 16.0 | 5.54 | 40.56 |
| 16.2 | 5.48 | 30.47 |
| 16.8 | 5.29 | 100.00 |
| 17.1 | 5.18 | 31.46 |
| 17.3 | 5.11 | 17.50 |
| 20.0 | 4.43 | 7.15 |
| 20.5 | 4.33 | 7.93 |
| 21.5 | 4.13 | 21.08 |
| 22.0 | 4.04 | 16.09 |
| 24.7 | 3.61 | 6.97 |
| 25.0 | 3.57 | 18.33 |
| 26.1 | 3.41 | 25.03 |
| 27.1 | 3.29 | 51.72 |
| 27.9 | 3.20 | 18.68 |
| 28.2 | 3.17 | 22.55 |
| 28.5 | 3.13 | 14.24 |
| 28.7 | 3.11 | 21.77 |

[1] In this and all subsequent tables, the position 2θ is within ± 0.2.

FIG. 27 depicts an XRPD pattern of Form B of Compound 6.

FIG. 28 depicts a DSC thermogram and TGA trace of Form B of Compound 6.

Example 11: Preparation of Forms A and B of Compound 7

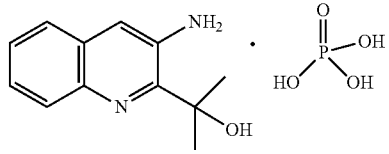

1. Form A of Compound 7

Form A of Compound 7 was prepared as described above. Form A of Compound 7 was scaled-up as follows.

Approximately 500 mg of the Compound A Form A was added to a 20 mL scintillation vial and dissolved in ethyl acetate (6.897 mL) to produce a concentration of 75 mg/mL. To the solution was added 1.05 equivalents of phosphoric acid and a gummy/oily precipitate was observed. The sample was then temperature-cycled by using an incubator shaker and the following temperature profile: a) heating to 40° C., hold for 4 hours; b) cooled to room temperature, hold for 4 hours; and c) repeat for ca. 72 hours.

The solids were isolated by filtration using a Buchner flask and funnel and dried at 40° C. for 5 hours. The solid material was analyzed by XRPD, PLM, TG/DTA, DSC, DVS/GVS, FT-IR, NMR, HPLC and CAD.

Table 15, supra, is reproduced below and sets forth the X-ray diffraction peaks observed for Form A of Compound 7.

TABLE 15

XRPD Peak Positions for Form A of Compound 7

| Pos. [°2θ] | d-spacing [Å] | Rel. Int. [%] |
|---|---|---|
| 8.4 | 10.53 | 100.00 |
| 9.0 | 9.80 | 5.36 |
| 15.3 | 5.78 | 25.51 |
| 15.8 | 5.60 | 20.83 |
| 16.0 | 5.54 | 85.37 |
| 16.5 | 5.38 | 6.55 |
| 16.8 | 5.26 | 22.25 |
| 17.0 | 5.22 | 8.48 |
| 18.6 | 4.77 | 5.65 |
| 20.1 | 4.43 | 8.80 |
| 20.4 | 4.35 | 22.36 |
| 21.2 | 4.19 | 4.84 |
| 21.9 | 4.06 | 8.96 |
| 22.6 | 3.94 | 26.89 |
| 24.4 | 3.65 | 11.44 |
| 24.5 | 3.63 | 6.64 |
| 25.4 | 3.51 | 9.59 |
| 25.7 | 3.47 | 6.63 |
| 27.0 | 3.31 | 11.90 |
| 27.3 | 3.26 | 11.42 |

[1] In this and all subsequent tables, the position 2θ is within ± 0.2.

FIG. 29 depicts an XRPD pattern of Form A of Compound 7.

Figure 30:
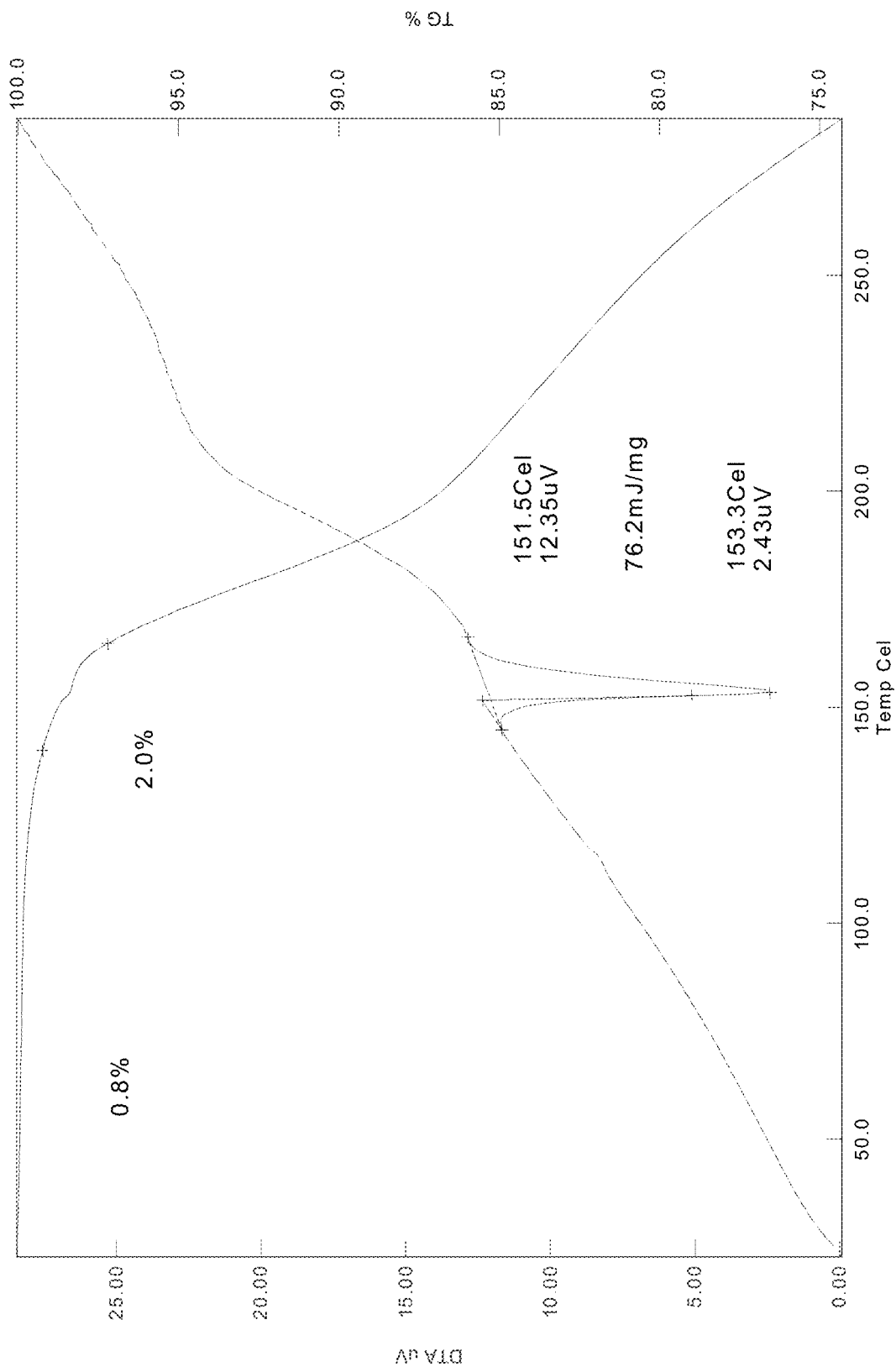
FIG. 30 depicts a DSC thermogram and TGA trace of Compound 7, Form A.

FIG. 30 depicts a DSC thermogram and TGA trace of Form A of Compound 7.

2. Form B of Compound 7

Approximately Form B of Compound 7 was prepared as described above.

Table 16, supra, is reproduced below and sets forth the X-ray diffraction peaks observed for Form B of Compound 7.

TABLE 16

XRPD Peak Positions for Form B of Compound 7

| Pos. [°2θ] | d-spacing [Å] | Rel. Int. [%] |
|---|---|---|
| 8.9 | 9.91 | 42.39 |
| 10.9 | 8.14 | 46.60 |
| 15.3 | 5.80 | 3.09 |
| 15.7 | 5.64 | 50.69 |
| 18.6 | 4.78 | 3.20 |
| 19.0 | 4.66 | 15.85 |
| 19.7 | 4.50 | 100.00 |
| 20.7 | 4.29 | 12.13 |
| 21.5 | 4.14 | 2.79 |
| 23.7 | 3.76 | 6.08 |
| 24.0 | 3.71 | 4.88 |
| 25.0 | 3.56 | 7.89 |
| 25.9 | 3.43 | 79.04 |
| 26.0 | 3.43 | 36.75 |
| 26.3 | 3.38 | 7.08 |
| 26.5 | 3.36 | 8.49 |
| 27.8 | 3.21 | 3.86 |
| 28.1 | 3.17 | 8.63 |
| 32.0 | 2.80 | 7.98 |
| 34.7 | 2.58 | 5.16 |

[1] In this and all subsequent tables, the position 2θ is within ± 0.2.

FIG. 31 depicts an XRPD pattern of Form B of Compound 7.

FIG. 32 depicts a DSC thermogram and TGA trace of Form B of Compound 7.

Example 12: Preparation of Form A of Compound 8

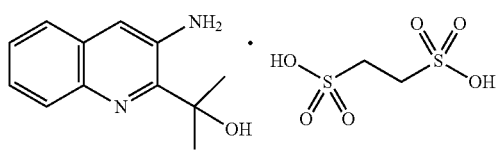

1. Form A of Compound 8

Form A of Compound 8 was prepared as described above.

Table 17, supra, is reproduced below and sets forth the X-ray diffraction peaks observed for Form A of Compound 8.

TABLE 17

XRPD Peak Positions for Form A of Compound 8

| Pos. [°2θ] | d-spacing [Å] | Rel. Int. [%] |
|---|---|---|
| 8.9 | 9.91 | 42.39 |
| 10.9 | 8.14 | 46.60 |
| 15.3 | 5.80 | 3.09 |
| 15.7 | 5.64 | 50.69 |
| 18.6 | 4.78 | 3.20 |
| 19.0 | 4.66 | 15.85 |
| 19.7 | 4.50 | 100.00 |
| 20.7 | 4.29 | 12.13 |
| 21.5 | 4.14 | 2.79 |
| 23.7 | 3.76 | 6.08 |
| 24.0 | 3.71 | 4.88 |
| 25.0 | 3.56 | 7.89 |
| 25.9 | 3.43 | 79.04 |
| 26.0 | 3.43 | 36.75 |
| 26.3 | 3.38 | 7.08 |
| 26.5 | 3.36 | 8.49 |
| 27.8 | 3.21 | 3.86 |
| 28.1 | 3.17 | 8.63 |

TABLE 17-continued

XRPD Peak Positions for Form A of Compound 8

| Pos. [°2θ] | d-spacing [Å] | Rel. Int. [%] |
|---|---|---|
| 32.0 | 2.80 | 7.98 |
| 34.7 | 2.58 | 5.16 |

[1] In this and all subsequent tables, the position 2θ is within ± 0.2.

FIG. 33 depicts an XRPD pattern of Form A of Compound 8.

FIG. 34 depicts a DSC thermogram and TGA trace of Form A of Compound 8.

Example 13: Preparation of Forms A, B and C of Compound 9

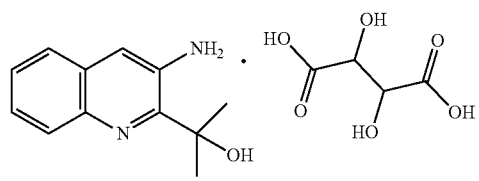

9

1. Form A of Compound 9

Form A of Compound 9 was prepared as described above. Form A of Compound 9 was scaled-up as follows.

Approximately 500 mg of the Compound A Form A was added to a 20 mL scintillation vial and dissolved in ethyl acetate (6.723 mL) to produce a concentration of 75 mg/mL. To the solution was added 1.05 equivalents of L-tartaric acid and a precipitate was observed on the sides of the vial. The sample was then temperature-cycled by using an incubator shaker and the following temperature profile: a) heating to 40° C., hold for 4 hours; b) cooled to room temperature, hold for 4 hours; and c) repeat for ca. 72 hours.

The solids were isolated by filtration using a Buchner flask and funnel and dried at 40° C. for 5 hours. The solid material was analyzed by XRPD, PLM, TG/DTA, DSC, DVS/GVS, FT-IR, NMR, HPLC and CAD.

Table 18, supra, is reproduced below and sets forth the X-ray diffraction peaks observed for Form A of Compound 9.

TABLE 18

XRPD Peak Positions for Form A of Compound 9

| Pos. [°2θ] | d-spacing [Å] | Rel. Int. [%] |
|---|---|---|
| 7.8 | 11.34 | 29.77 |
| 9.1 | 9.73 | 55.11 |
| 12.1 | 7.33 | 20.74 |
| 13.1 | 6.77 | 24.11 |
| 14.7 | 6.03 | 71.27 |
| 15.6 | 5.68 | 46.57 |
| 15.8 | 5.61 | 100.00 |
| 17.2 | 5.15 | 71.16 |
| 17.3 | 5.12 | 51.86 |
| 17.9 | 4.97 | 26.22 |
| 18.2 | 4.87 | 43.60 |
| 20.4 | 4.34 | 22.29 |
| 21.3 | 4.18 | 49.85 |
| 21.7 | 4.09 | 37.11 |
| 23.2 | 3.83 | 36.55 |
| 24.3 | 3.66 | 33.80 |

TABLE 18-continued

XRPD Peak Positions for Form A of Compound 9

| Pos. [°2θ] | d-spacing [Å] | Rel. Int. [%] |
|---|---|---|
| 24.5 | 3.63 | 36.53 |
| 26.9 | 3.31 | 36.98 |
| 27.6 | 3.23 | 17.21 |
| 28.1 | 3.17 | 17.48 |

[1] In this and all subsequent tables, the position 2θ is within ± 0.2.

FIG. 35 depicts an XRPD pattern of Form A of Compound 9.

FIG. 36 depicts a DSC thermogram and TGA trace of Form A of Compound 9.

2. Form B of Compound 9

Form B of Compound 9 was prepared as described above. Table 19, supra, is reproduced below and sets forth the X-ray diffraction peaks observed for Form B of Compound 9.

TABLE 19

XRPD Peak Positions for Form B of Compound 9

| Pos. [°2θ] | d-spacing [Å] | Rel. Int. [%] |
|---|---|---|
| 7.9 | 11.19 | 34.91 |
| 10.5 | 8.46 | 33.80 |
| 13.4 | 6.60 | 16.16 |
| 14.9 | 5.93 | 32.50 |
| 15.1 | 5.86 | 26.62 |
| 15.9 | 5.59 | 100.00 |
| 16.8 | 5.27 | 19.94 |
| 18.6 | 4.77 | 49.59 |
| 21.0 | 4.23 | 26.13 |
| 22.3 | 3.99 | 13.53 |
| 23.5 | 3.78 | 12.07 |
| 23.9 | 3.73 | 15.43 |
| 24.2 | 3.68 | 12.75 |
| 24.9 | 3.57 | 16.70 |
| 25.4 | 3.51 | 12.54 |
| 25.9 | 3.44 | 30.84 |
| 26.1 | 3.41 | 11.63 |
| 27.0 | 3.30 | 15.65 |
| 30.5 | 2.93 | 12.36 |
| 31.9 | 2.80 | 17.12 |

[1] In this and all subsequent tables, the position 2θ is within ± 0.2.

FIG. 37 depicts an XRPD pattern of Form B of Compound 9.

FIG. 38 depicts a DSC thermogram and TGA trace of Form B of Compound 9.

3. Form C of Compound 9

Form C of Compound 9 was prepared as described above. Table 20, supra, is reproduced below and sets forth the X-ray diffraction peaks observed for Form C of Compound 9.

TABLE 20

XRPD Peak Positions for Form C of Compound 9

| Pos. [°2θ] | d-spacing [Å] | Rel. Int. [%] |
|---|---|---|
| 8.1 | 10.93 | 60.16 |
| 12.8 | 6.94 | 37.75 |
| 14.3 | 6.19 | 76.70 |
| 14.9 | 5.94 | 70.38 |
| 15.3 | 5.81 | 48.03 |
| 16.2 | 5.47 | 43.15 |
| 16.9 | 5.24 | 90.44 |
| 17.4 | 5.11 | 82.49 |
| 18.7 | 4.74 | 34.87 |

TABLE 20-continued

XRPD Peak Positions for Form C of Compound 9

| Pos. [°2θ] | d-spacing [Å] | Rel. Int. [%] |
|---|---|---|
| 19.7 | 4.50 | 35.12 |
| 21.5 | 4.14 | 29.37 |
| 23.7 | 3.75 | 41.77 |
| 23.8 | 3.75 | 39.15 |
| 24.3 | 3.67 | 100.00 |
| 24.8 | 3.58 | 35.49 |
| 25.1 | 3.54 | 21.92 |
| 25.5 | 3.49 | 45.37 |
| 25.7 | 3.46 | 33.87 |
| 27.0 | 3.30 | 22.91 |
| 27.2 | 3.28 | 20.85 |

[1] In this and all subsequent tables, the position 2θ is within ± 0.2.

FIG. 39 depicts an XRPD pattern of Form C of Compound 9.

FIG. 40 depicts a DSC thermogram and TGA trace of Form C of Compound 9.

Example 14: Preparation of Form A of Compound 10

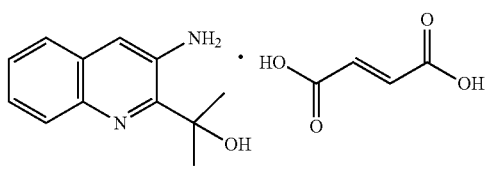

1. Form A of Compound 10

Form A of Compound 10 was prepared as described above. Form A of Compound 10 was scaled-up as follows.

Approximately 500 mg of the Compound A Form A was added to a 20 mL scintillation vial and dissolved in ethyl acetate (6.723 mL) to produce a concentration of 75 mg/mL. To the solution was added 1.05 equivalents of fumaric acid dissolved in 9 mL of ethanol and a clear solution was observed upon addition. The sample was then allowed to evaporate at ambient temperature. The large crystals produced were gently ground before analysis by XRPD, PLM, TG/DTA, DSC, DVS/GVS, FT-IR, NMR and HPLC.

Table 21, supra, is reproduced below and sets forth the X-ray diffraction peaks observed for Form A of Compound 10.

TABLE 21

XRPD Peak Positions for Form A of Compound 10

| Pos. [°2θ] | d-spacing [Å] | Rel. Int. [%] |
|---|---|---|
| 9.1 | 9.74 | 23.60 |
| 12.2 | 7.25 | 18.09 |
| 12.8 | 6.91 | 67.46 |
| 15.2 | 5.83 | 20.06 |
| 16.1 | 5.50 | 79.76 |
| 16.3 | 5.43 | 39.82 |
| 17.1 | 5.18 | 11.22 |
| 18.2 | 4.87 | 14.84 |
| 18.7 | 4.75 | 27.53 |
| 20.0 | 4.45 | 11.79 |
| 20.3 | 4.38 | 80.52 |
| 21.3 | 4.17 | 26.34 |
| 22.8 | 3.90 | 19.27 |
| 24.1 | 3.69 | 100.00 |
| 24.5 | 3.64 | 20.16 |
| 25.9 | 3.44 | 73.88 |
| 27.8 | 3.21 | 21.59 |
| 27.8 | 3.21 | 17.81 |
| 28.7 | 3.10 | 47.36 |
| 29.4 | 3.04 | 12.43 |

[1] In this and all subsequent tables, the position 2θ is within ± 0.2.

FIG. 41 depicts an XRPD pattern of Form A of Compound 10.

FIG. 42 depicts a DSC thermogram and TGA trace of Form A of Compound 10.

Example 15: Preparation of Form A of Compound 11

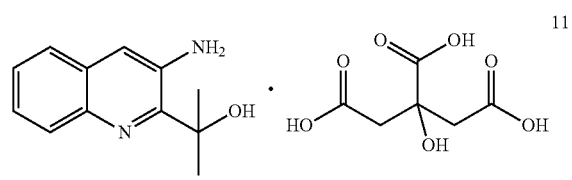

1. Form A of Compound 11

Form A of Compound 11 was prepared as described above.

Table 22, supra, is reproduced below and sets forth the X-ray diffraction peaks observed for Form A of Compound 11.

TABLE 22

XRPD Peak Positions for Form A of Compound 11

| Pos. [°2θ] | d-spacing [Å] | Rel. Int. [%] |
|---|---|---|
| 9.4 | 9.42 | 61.29 |
| 11.4 | 7.75 | 96.94 |
| 12.5 | 7.06 | 62.91 |
| 16.3 | 5.44 | 56.18 |
| 16.6 | 5.35 | 65.57 |
| 16.7 | 5.31 | 100.00 |
| 16.8 | 5.29 | 63.93 |
| 17.3 | 5.11 | 58.06 |
| 20.2 | 4.39 | 31.17 |
| 21.7 | 4.08 | 81.57 |
| 22.4 | 3.97 | 28.43 |
| 22.6 | 3.94 | 42.06 |
| 22.9 | 3.87 | 95.44 |
| 24.1 | 3.68 | 19.63 |
| 26.7 | 3.33 | 15.33 |
| 31.0 | 2.88 | 22.79 |
| 31.4 | 2.84 | 37.81 |
| 31.5 | 2.84 | 27.73 |
| 34.6 | 2.59 | 33.00 |
| 34.7 | 2.58 | 22.31 |

[1] In this and all subsequent tables, the position 2θ is within ± 0.2.

FIG. 43 depicts an XRPD pattern of Form A of Compound 11.

FIG. 44 depicts a DSC thermogram and TGA trace of Form A of Compound 11.

Example 16: Single Crystal Studies of Compound A

Single crystal studies of Compound A produced a monoclinic P2₁ unit cell with the parameters shown below in Table 30. The unit cell was observed to be asymmetric and to contain four complete Compound A formula units, with hydrogen bonding association between the molecules.

TABLE 30

Unit Cell Parameters for Single Crystal of Compound A

| | |
|---|---|
| a | 6.5547(3) Å |
| b | 32.5447(12) Å |
| c | 10.0239(4) Å |
| V | 2109.93(15) Å³ |
| $R_{int}$ | 6.66% |
| α | 90° |
| β | 99.342(4)° |
| γ | 90° |
| Z | 8 |
| Z' | 4 |
| $R_1(I > 2\sigma(I))$ | 5.74% |
| GooF (S) | 1.078 |
| $wR_2$ (all data) | 10.55% |
| ρ(calc) | 1.273 g/cm³ |

Figure 45:
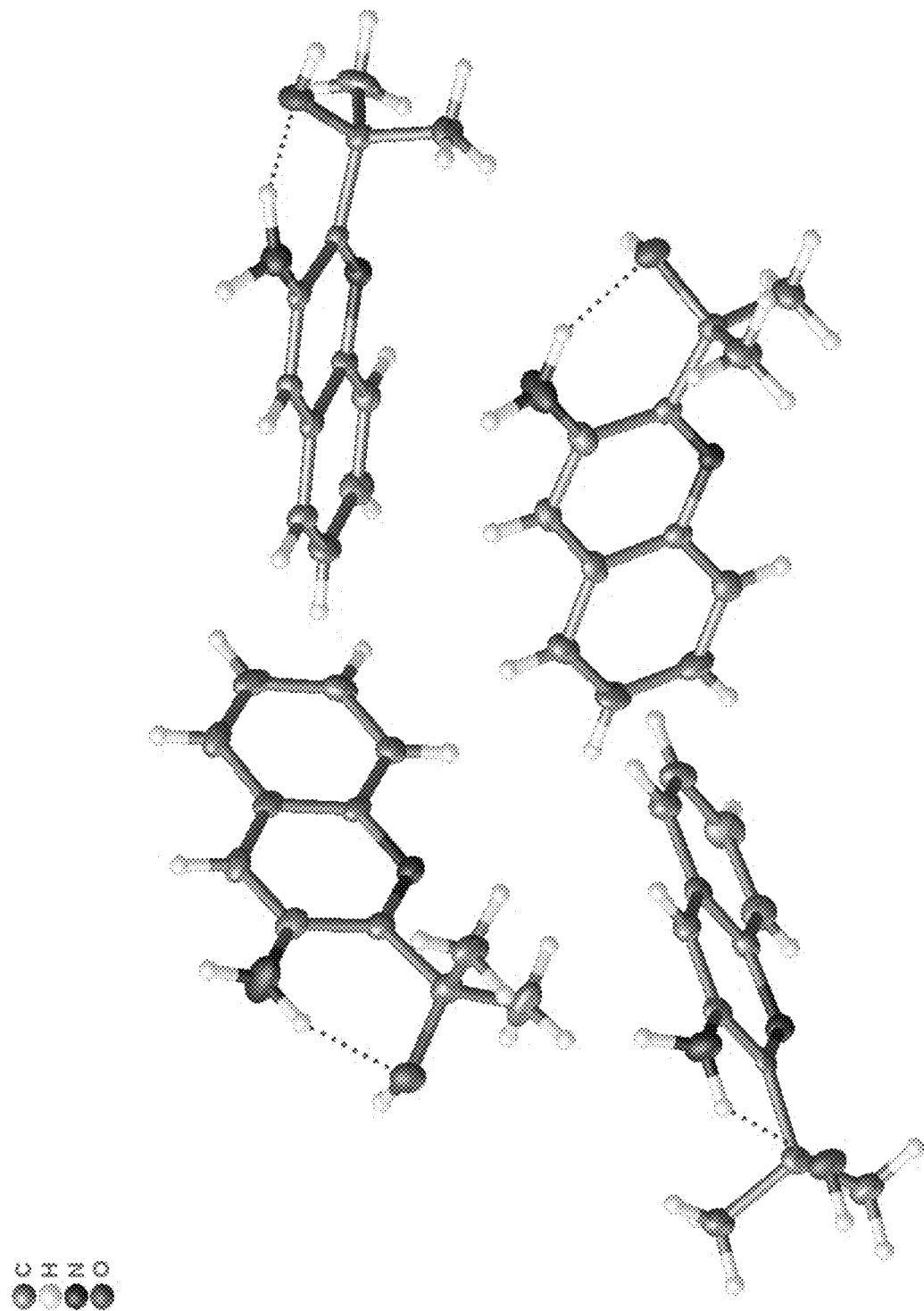
FIG. 45 depicts a unit cell of Compound A.

FIG. 45 depicts a unit cell of Compound A.

Figure 46:
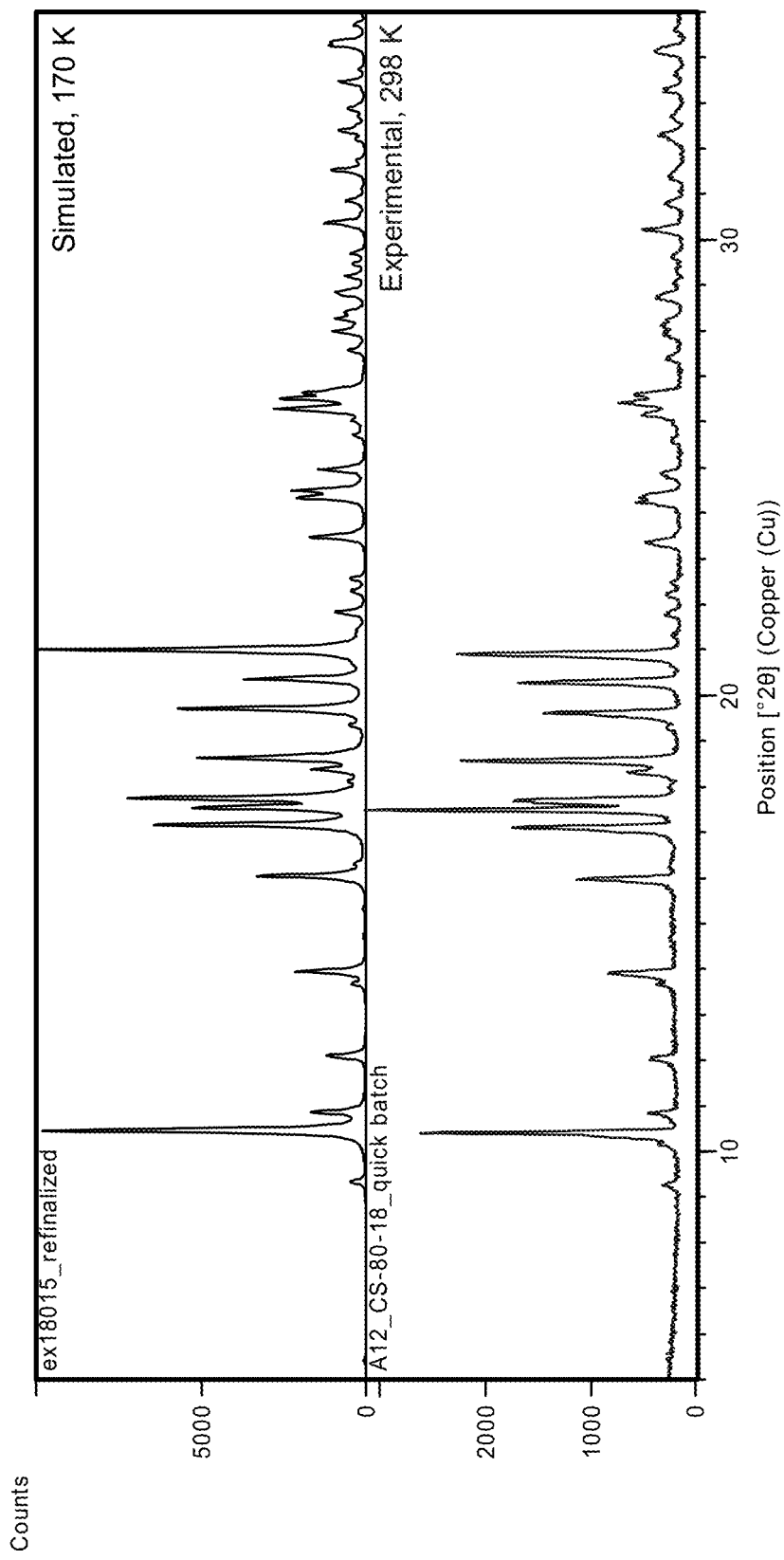
FIG. 46 depicts simulated and experimental XRPD patterns of Compound A.

FIG. 46 depicts simulated and experimental XRPD patterns of Compound A.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A solid form of Compound 5:

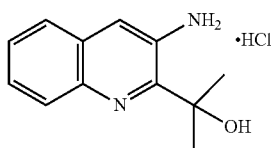

of Form A having one or more peaks in its X-ray powder diffraction (XRPD) pattern selected from those at 13.9±0.2, 15.8±0.2, and 24.3±0.2 degrees 2-theta; or of Form B having one or more peaks in its XRPD selected from those 10.2±0.2, 17.0±0.2, and 28.8±0.2 degrees 2-theta.

2. The solid form according to claim 1, wherein said solid form is crystalline.

3. The solid form according to claim 1, wherein said solid form is a crystalline solid substantially free of amorphous compound 5.

4. The solid form according to claim 1, wherein said solid form is substantially free of impurities.

5. The solid form according to claim 1, having at least two peaks in its XRPD selected from those at 13.9±0.2, 15.8±0.2 and 24.3±0.2 degrees 2-theta.

6. The solid form according to claim 5, wherein the compound is of Form A.

7. The solid form according to claim 1, having an XRPD substantially similar to that depicted in FIG. 21.

8. The solid form according to claim 1, having at least two peaks in its XRPD selected from those at 10.2±0.2, 17.0±0.2 and 28.8±0.2 degrees 2-theta.

9. The solid form according to claim 8, wherein the compound is of Form B.

10. The solid form according to claim 1, having an XRPD substantially similar to that depicted in FIG. 23.

11. A pharmaceutical composition comprising the solid form according to claim 1 and a pharmaceutically acceptable carrier, excipient, or vehicle.

12. A method of treating a condition in a patient in which aldehyde toxicity is implicated in the pathogenesis, comprising administering to the patient a solid form according to claim 1 or composition thereof, wherein:
(a) the condition is an ocular disease, disorder or condition selected from dry eye, cataracts, keratoconus, Fuchs' endothelial dystrophy in the cornea, uveitis, allergic conjunctivitis, ocular cicatricial pemphigoid, advancing photorefractive keratectomy (PRK) healing or other corneal healing, and ocular rosacea with or without meibomian gland dysfunction;
(b) the condition is a skin disease, disorder or condition selected from psoriasis, scleroderma, topical (discoid) lupus, contact dermatitis, atopic dermatitis, allergic dermatitis, radiation dermatitis, acne vulgaris, and Sjögren-Larsson Syndrome and other ichthyoses;
(c) the condition is a cosmetic indication selected from solar elastosis/wrinkles, skin tone firmness, puffiness, eczema, smoke or irritant induced skin changes, and dermal incision; or
(d) the condition is selected from lupus, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, succinic semialdehyde dehydrogenase deficiency, multiple sclerosis, amyotrophic lateral sclerosis, and renal, hepatic, pulmonary, or cardiac fibrosis.

13. The method according to claim 12, further comprising administering to the patient an additional therapeutic agent.

14. A solid form of a compound selected from the group consisting of:

Compound A

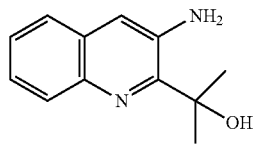

of Form A, wherein Form A has one or more peaks in its XRPD selected from those at 10.4±0.2, 17.1±0.2, 17.5±0.2, 18.6±0.2, 20.3±0.2, and 20.9±0.2 degrees 2-theta;

Compound 1

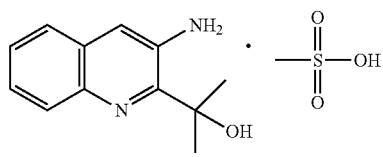

of Form A, wherein Form A has one or more peaks in its XRPD selected from those at 9.7±0.2, 10.4±0.2, 13.7±0.2, 18.0±0.2, 22.2±0.2 and 26.5±0.2 degrees 2-theta or Form B, wherein Form B has one or more peaks in its XRPD selected from those at 8.4±0.2, 13.0±0.2, 15.8±0.2, 17.9±0.2, 20.9±0.2, and 26.2±0.2 degrees 2-theta;

Compound 2

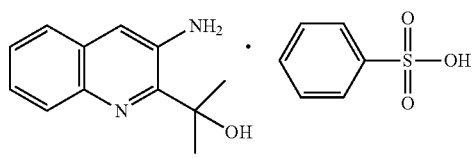

2 of Form A, wherein Form A has one or more peaks in its XRPD selected from those at 11.2±0.2, 15.0±0.2, 23.7±0.2, 25.1±0.2, 25.2±0.2, and 26.4±0.2 degrees 2-theta;

Compound 3

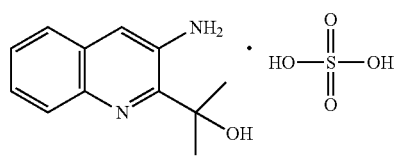

3 of Form A, wherein Form A has one or more peaks in its XRPD selected from those at 13.2±0.2, 17.7±0.2, 19.8±0.2, 22.2±0.2, 27.1±0.2, and 27.2±0.2 degrees 2-theta, or Form B, wherein Form B has one or more peaks in its XRPD selected from those at 13.3±0.2, 17.7±0.2, 20.1±0.2, 21.6±0.2, 23.3±0.2, and 27.1±0.2 degrees 2-theta, or Form C, wherein Form C has one or more peaks in its XRPD selected from those at 8.8±0.2, 16.5±0.2, 16.6±0.2, 16.8±0.2, 16.9±0.2, and 19.8±0.2 degrees 2-theta, or Form D, wherein Form D has one or more peaks in its XRPD selected from those at 12.4±0.2, 16.2±0.2, 18.3±0.2, 20.2±0.2, 20.6±0.2, and 27.0±0.2 degrees 2-theta;

Compound 4

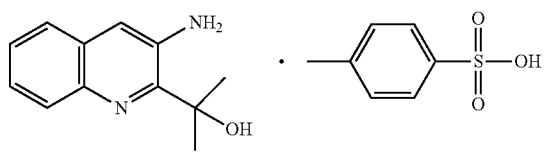

4 of Form A, wherein Form A has one or more peaks in its XRPD selected from those at 8.7±0.2, 13.1±0.2, 20.0±0.2, 21.8±0.2, 22.4±0.2, and 24.2±0.2 degrees 2-theta or Form B, wherein Form B has one or more peaks in its XRPD selected from those at 13.3±0.2, 20.1±0.2, 21.9±0.2, 23.4±0.2, 23.8±0.2, and 25.9±0.2 degrees 2-theta;

Compound 6

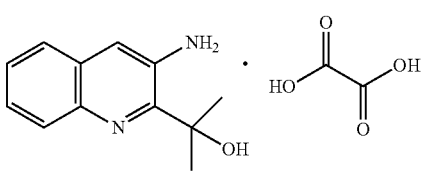

6 of Form A, wherein Form A has one or more peaks in its XRPD selected from those at 8.6±0.2, 15.7±0.2, 16.0±0.2, 16.8±0.2, 17.1±0.2, and 27.1±0.2 degrees 2-theta or Form B, wherein Form B has one or more peaks in its XRPD selected from those at 13.4±0.2, 14.1±0.2, 18.2±0.2, 19.4±0.2, 22.0±0.2, and 25.7±0.2 degrees 2-theta;

Compound 7

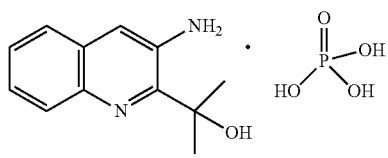

7 of Form A, wherein Form A has one or more peaks in its XRPD selected from those at 8.4±0.2, 15.3±0.2, 16.0±0.2, 16.8±0.2, 20.4±0.2, and 22.6±0.2 degrees 2-theta or Form B, wherein Form B has one or more peaks in its XRPD selected from those at 8.9±0.2, 10.9±0.2, 15.7±0.2, 19.7±0.2, 25.9±0.2, and 26.0±0.2 degrees 2-theta;

Compound 8

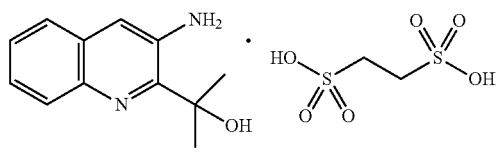

8 of Form A, wherein Form A has one or more peaks in its XRPD selected from those at 5.5±0.2, 21.2±0.2, 21.3±0.2, 21.6±0.2, 22.6±0.2, and 22.9±0.2 degrees 2-theta;

Compound 9

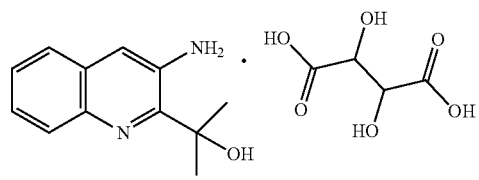

9 of Form A, wherein Form A has one or more peaks in its XRPD selected from those at 9.1±0.2, 14.7±0.2, 15.8±0.2, 17.2±0.2, 17.3±0.2, and 21.3±0.2 degrees 2-theta, or Form B, wherein Form B has one or more peaks in its XRPD selected from those at 7.9±0.2, 10.5±0.2, 14.9±0.2, 15.9±0.2, 18.6±0.2, and 25.9±0.2 degrees 2-theta, or Form C, wherein Form C has one or more peaks in its XRPD selected from those at 8.1±0.2, 14.3±0.2, 14.9±0.2, 16.9±0.2, 17.4±0.2, and 24.3±0.2 degrees 2-theta;

Compound 10

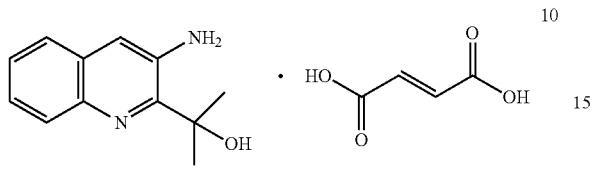

10 of Form A, wherein Form A has one or more peaks in its XRPD selected from those at 12.8±0.2, 16.1±0.2, 20.3±0.2, 24.1±0.2, 25.9±0.2, and 28.7±0.2 degrees 2-theta; and Compound 11

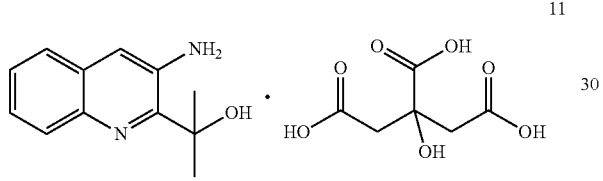

11 of Form A, wherein Form A has one or more peaks in its XRPD selected from those at 11.4±0.2, 16.6±0.2, 16.7±0.2, 16.8±0.2, 21.7±0.2, and 22.9±0.2 degrees 2-theta.

15. A pharmaceutical composition comprising a compound according to claim 14, and a pharmaceutically acceptable carrier, excipient, or vehicle.

16. A method of treating a condition in a patient in which aldehyde toxicity is implicated in the pathogenesis, comprising administering to the patient a solid form according to claim 14 or composition thereof, wherein:
(a) the condition is an ocular disease, disorder or condition selected from dry eye, cataracts, keratoconus, Fuchs' endothelial dystrophy in the cornea, uveitis, allergic conjunctivitis, ocular cicatricial pemphigoid, advancing photorefractive keratectomy (PRK) healing or other corneal healing, and ocular rosacea with or without meibomian gland dysfunction;
(b) the condition is a skin disease, disorder or condition selected from psoriasis, scleroderma, topical (discoid) lupus, contact dermatitis, atopic dermatitis, allergic dermatitis, radiation dermatitis, acne vulgaris, and Sjögren-Larsson Syndrome and other ichthyoses;
(c) the condition is a cosmetic indication selected from solar elastosis/wrinkles, skin tone firmness, puffiness, eczema, smoke or irritant induced skin changes, and dermal incision; or
(d) the condition is selected from lupus, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, succinic semialdehyde dehydrogenase deficiency, multiple sclerosis, amyotrophic lateral sclerosis, and renal, hepatic, pulmonary, or cardiac fibrosis.

17. The method according to claim 16, further comprising administering to the patient an additional therapeutic agent.

18. A method for preparing solid form of a compound of formula X:

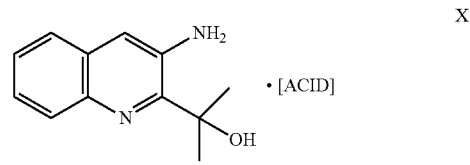

X comprising steps of:
combining A:

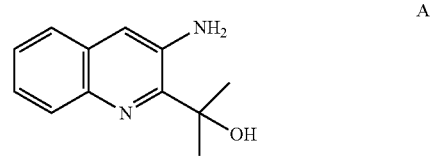

A with a suitable acid and optionally a suitable solvent under conditions for forming the solid form of the compound of formula X, wherein:
(a) the suitable acid is methanesulfonic acid thereby forming a mesylate salt of Compound A and optionally crystallizing the mesylate salt to Form A, wherein Form A has one or more peaks in its XRPD selected from those at 9.7±0.2, 10.4±0.2, 13.7±0.2, 18.0±0.2, 22.2±0.2 and 26.5±0.2 degrees 2-theta or Form B, wherein Form B has one or more peaks in its XRPD selected from those at 8.4±0.2, 13.0±0.2, 15.8±0.2, 17.9±0.2, 20.9±0.2, and 26.2±0.2 degrees 2-theta;
(b) the suitable acid is benzenesulfonic acid thereby forming a besylate salt of Compound A and optionally crystallizing the besylate salt to Form A, wherein Form A has one or more peaks in its XRPD selected from those at 11.2±0.2, 15.0±0.2, 23.7±0.2, 25.1±0.2, 25.2±0.2, and 26.4±0.2 degrees 2-theta;
(c) the suitable acid is sulfuric acid thereby forming a sulfate salt of Compound A an optionally crystallizing the sulfate salt to Form A, wherein Form A has one or more peaks in its XRPD selected from those at 13.2±0.2, 17.7±0.2, 19.8±0.2, 22.2±0.2, 27.1±0.2, and 27.2±0.2 degrees 2-theta, or Form B, wherein Form B has one or more peaks in its XRPD selected from those at 13.3±0.2, 17.7±0.2, 20.1±0.2, 21.6±0.2, 23.3±0.2, and 27.1±0.2 degrees 2-theta, or Form C, wherein Form C has one or more peaks in its XRPD selected from those at 8.8±0.2, 16.5±0.2, 16.6±0.2, 16.8±0.2, 16.9±0.2, and 19.8±0.2 degrees 2-theta, or Form D, wherein Form D has one or more peaks in its XRPD selected from those at 12.4±0.2, 16.2±0.2, 18.3±0.2, 20.2±0.2, 20.6±0.2, and 27.0±0.2 degrees 2-theta;
(d) the suitable acid is p-toluenesulfonic acid thereby forming a tosylate salt of Compound A and optionally crystallizing the tosylate salt to Form A, wherein Form A has one or more peaks in its XRPD selected from those at 8.7±0.2, 13.1±0.2, 20.0±0.2, 21.8±0.2, 22.4±0.2, and 24.2±0.2 degrees 2-theta or Form B, wherein Form B has one or more peaks in its XRPD selected from those at 13.3±0.2, 20.1±0.2, 21.9±0.2, 23.4±0.2, 23.8±0.2, and 25.9±0.2 degrees 2-theta;

(e) the suitable acid is hydrochloric acid thereby forming a hydrochloride salt of Compound A and optionally crystallizing the hydrochloride salt to Form A, wherein Form A has one or more peaks in its XRPD pattern selected from those at 13.9±0.2, 15.8±0.2, and 24.3±0.2 degrees 2-theta or Form B, wherein Form B has one or more peaks in its XRPD selected from those 10.2±0.2, 17.0±0.2, and 28.8±0.2 degrees 2-theta;

(f) the suitable acid is oxalic acid thereby forming an oxalate salt of Compound A and optionally crystallizing the oxalate salt to Form A, wherein Form A has one or more peaks in its XRPD selected from those at 8.6±0.2, 15.7±0.2, 16.0±0.2, 16.8±0.2, 17.1±0.2, and 27.1±0.2 degrees 2-theta or Form B, wherein Form B has one or more peaks in its XRPD selected from those at 13.4±0.2, 14.1±0.2, 18.2±0.2, 19.4±0.2, 22.0±0.2, and 25.7±0.2 degrees 2-theta;

(g) the suitable acid is phosphoric acid thereby forming a phosphate salt of Compound A and optionally crystallizing the phosphate salt to Form A, wherein Form A has one or more peaks in its XRPD selected from those at 8.4±0.2, 15.3±0.2, 16.0±0.2, 16.8±0.2, 20.4±0.2, and 22.6±0.2 degrees 2-theta or Form B, wherein Form B has one or more peaks in its XRPD selected from those at 8.9±0.2, 10.9±0.2, 15.7±0.2, 19.7±0.2, 25.9±0.2, and 26.0±0.2 degrees 2-theta;

(h) the suitable acid is ethanedisulfonic acid thereby forming an edisylate salt of Compound A and optionally crystallizing the edisylate salt to Form A, wherein Form A has one or more peaks in its XRPD selected from those at 5.5±0.2, 21.2±0.2, 21.3±0.2, 21.6±0.2, 22.6±0.2, and 22.9±0.2 degrees 2-theta;

(i) the suitable acid is tartaric acid thereby forming a tartrate salt of Compound A and optionally recrystallizing the tartrate salt to Form A, wherein Form A has one or more peaks in its XRPD selected from those at 9.1±0.2, 14.7±0.2, 15.8±0.2, 17.2±0.2, 17.3±0.2, and 21.3±0.2 degrees 2-theta, or Form B, wherein Form B has one or more peaks in its XRPD selected from those at 7.9±0.2, 10.5±0.2, 14.9±0.2, 15.9±0.2, 18.6±0.2, and 25.9±0.2 degrees 2-theta, or Form C, wherein Form C has one or more peaks in its XRPD selected from those at 8.1±0.2, 14.3±0.2, 14.9±0.2, 16.9±0.2, 17.4±0.2, and 24.3±0.2 degrees 2-theta;

(j) the suitable acid is fumaric acid thereby forming a fumarate salt of Compound A and optionally recrystallizing the fumarate salt to Form A, wherein Form A has one or more peaks in its XRPD selected from those at 12.8±0.2, 16.1±0.2, 20.3±0.2, 24.1±0.2, 25.9±0.2, and 28 7±0 2 degrees 2-theta; or (k) the suitable acid is citric acid thereby forming a citrate salt of Compound A and optionally recrystallizing the citrate salt to Form A, wherein Form A has one or more peaks in its XRPD selected from those at 11.4±0.2, 16.6±0.2, 16.7±0.2, 16.8±0.2, 21.7±0.2, and 22.9±0.2 degrees 2-theta.

19. The solid form of claim 14, wherein the solid form is of Compound A:

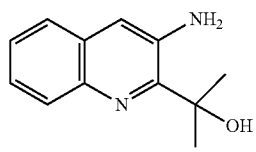

A of Form A, wherein Form A has one or more peaks in its XRPD selected from those at 10.4±0.2, 17.1±0.2, 17.5±0.2, 18.6±0.2, 20.3±0.2, and 20.9±0.2 degrees 2-theta.

20. A pharmaceutical composition comprising a compound according to claim 19, and a pharmaceutically acceptable carrier, excipient, or vehicle.

21. A method of treating a condition in a patient in which aldehyde toxicity is implicated in the pathogenesis, comprising administering to the patient a solid form according to claim 19 or composition thereof, wherein:

(a) the condition is an ocular disease, disorder or condition selected from dry eye, cataracts, keratoconus, Fuchs' endothelial dystrophy in the cornea, uveitis, allergic conjunctivitis, ocular cicatricial pemphigoid, advancing photorefractive keratectomy (PRK) healing or other corneal healing, and ocular rosacea with or without meibomian gland dysfunction;

(b) the condition is a skin disease, disorder or condition selected from psoriasis, scleroderma, topical (discoid) lupus, contact dermatitis, atopic dermatitis, allergic dermatitis, radiation dermatitis, acne vulgaris, and Sjögren-Larsson Syndrome and other ichthyoses;

(c) the condition is a cosmetic indication selected from solar elastosis/wrinkles, skin tone firmness, puffiness, eczema, smoke or irritant induced skin changes, and dermal incision;

(d) the condition is selected from lupus, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, succinic semialdehyde dehydrogenase deficiency, multiple sclerosis, amyotrophic lateral sclerosis, and renal, hepatic, pulmonary, or cardiac fibrosis.

* * * * *